(12) United States Patent
Liang et al.

(10) Patent No.: US 12,378,249 B2
(45) Date of Patent: Aug. 5, 2025

(54) ISOQUINOLINE COMPOUNDS AND USES THEREOF

(71) Applicant: Genentech, Inc., South San Francisco, CA (US)

(72) Inventors: Jun Liang, South San Francisco, CA (US); Sushant Malhotra, South San Francisco, CA (US); Rohan V. Mendonca, South San Francisco, CA (US); Naomi Rajapaksa, South San Francisco, CA (US); Michael Siu, South San Francisco, CA (US); Craig Stivala, South San Francisco, CA (US); John C. Tellis, South San Francisco, CA (US); BinQing Wei, South San Francisco, CA (US); Bryan K. Chan, South San Francisco, CA (US); Joy Alison Drobnick, South San Francisco, CA (US); Lewis J. Gazzard, South San Francisco, CA (US); Timothy Heffron, South San Francisco, CA (US); Graham Jones, Harlow (GB); Michael Lainchbury, Harlow (GB); Andrew Madin, Harlow (GB); Eileen Mary Seward, Harlow (GB); Matthew W. Cartwright, Harlow (GB); Emanuela Gancia, Harlow (GB); David Favor, Shanghai (CN); Kin Chiu Fong, Shanghai (CN); Andrew Good, Shanghai (CN); Yonghan Hu, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 1232 days.

(21) Appl. No.: 17/156,387

(22) Filed: Jan. 22, 2021

(65) Prior Publication Data
US 2021/0253580 A1 Aug. 19, 2021

Related U.S. Application Data

(63) Continuation of application No. PCT/US2019/043123, filed on Jul. 23, 2019.

(30) Foreign Application Priority Data

Jul. 24, 2018 (WO) ................ PCT/CN2018/096780

(51) Int. Cl.
| | | |
|---|---|---|
| C07D 487/04 | (2006.01) | |
| A61P 37/04 | (2006.01) | |
| C07D 401/12 | (2006.01) | |
| C07D 401/14 | (2006.01) | |
| C07D 405/14 | (2006.01) | |
| C07D 487/14 | (2006.01) | |
| C07D 498/04 | (2006.01) | |
| C07D 498/14 | (2006.01) | |

(Continued)

(52) U.S. Cl.
CPC ............ *C07D 487/04* (2013.01); *A61P 37/04* (2018.01); *C07D 401/12* (2013.01); *C07D 401/14* (2013.01); *C07D 405/14* (2013.01); *C07D 487/14* (2013.01); *C07D 498/04* (2013.01); *C07D 498/14* (2013.01); *C07D 513/04* (2013.01); *C07D 519/00* (2013.01)

(58) Field of Classification Search
None
See application file for complete search history.

(56) References Cited

U.S. PATENT DOCUMENTS

| | | |
|---|---|---|
| 4,590,273 A | 5/1986 | Konz et al. |
| 7,863,291 B2 | 1/2011 | Cook, II et al. |

(Continued)

FOREIGN PATENT DOCUMENTS

| | | |
|---|---|---|
| CN | 107266421 A | 10/2017 |
| PL | 176081 B1 | 4/1999 |

(Continued)

OTHER PUBLICATIONS

Bartmann, W. et al., "Synthesis of di- and tetraalkyl-3-piperazinoisoquinolines and related compounds as potential antidepressant agents" Journal of Heterocyclic Chemistry 24(3):677-82 ( 1987).

(Continued)

*Primary Examiner* — Jeffrey S Lundgren
*Assistant Examiner* — Michael J Schmitt
(74) *Attorney, Agent, or Firm* — Genentech, Inc.

(57) ABSTRACT

Isoquinoline compounds of formula (I):

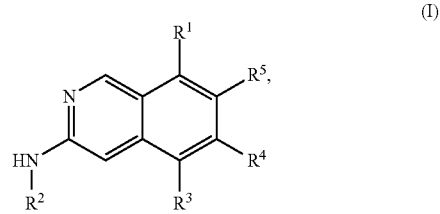

variations thereof, and their use as inhibitors of HPK1 (hematopoietic kinase 1) are described. The compounds are useful in treating HPK1-dependent disorders and enhancing an immune response. Also described are methods of inhibiting HPK1, methods of treating HPK1-dependent disorders, methods for enhancing an immune response, and methods for preparing the isoquinoline compounds.

25 Claims, No Drawings

(51) Int. Cl.
*C07D 513/04* (2006.01)
*C07D 519/00* (2006.01)

(56) References Cited

U.S. PATENT DOCUMENTS

| | | |
|---|---|---|
| 8,309,577 B2 | 11/2012 | Cook, II et al. |
| 8,461,339 B2 | 6/2013 | Boyle et al. |
| 8,530,468 B2 | 9/2013 | Collins et al. |
| 2006/0156485 A1 | 7/2006 | Lim et al. |
| 2010/0081671 A1 | 4/2010 | Plettenburg et al. |
| 2010/0331328 A1 | 12/2010 | Collins et al. |
| 2011/0245248 A1 | 10/2011 | Plettenburg et al. |
| 2013/0096119 A1 | 4/2013 | Bur et al. |
| 2014/0066453 A1 | 3/2014 | Blake et al. |
| 2018/0072719 A1 | 3/2018 | Ye et al. |
| 2018/0072720 A1 | 3/2018 | Vechorkin et al. |
| 2020/0108075 A1 | 4/2020 | Liang et al. |

FOREIGN PATENT DOCUMENTS

| | | | |
|---|---|---|---|
| WO | 2000/071508 A2 | 11/2000 | |
| WO | 2000/071508 A3 | 11/2000 | |
| WO | 2000/071510 A2 | 11/2000 | |
| WO | 2000/071510 A3 | 11/2000 | |
| WO | 2005/032468 A2 | 4/2005 | |
| WO | 2005/032468 A3 | 4/2005 | |
| WO | 2005/035503 A1 | 4/2005 | |
| WO | 2006/048248 A2 | 5/2006 | |
| WO | 2006/048248 A3 | 5/2006 | |
| WO | 2006/048251 A1 | 5/2006 | |
| WO | 2007/000240 A1 | 1/2007 | |
| WO | 2007/053346 A1 | 5/2007 | |
| WO | 2007/071348 A1 | 6/2007 | |
| WO | 2007/084391 A2 | 7/2007 | |
| WO | 2007/125405 A3 | 11/2007 | |
| WO | WO-2007125405 A2 * | 11/2007 | ........... C07D 239/84 |
| WO | 2008/077554 A1 | 7/2008 | |
| WO | 2008/119569 A1 | 10/2008 | |
| WO | 2009/000558 A1 | 12/2008 | |
| WO | 2009/023193 A1 | 2/2009 | |
| WO | 2009/103966 A1 | 8/2009 | |
| WO | 2009/131926 A1 | 10/2009 | |
| WO | WO-2010007374 A1 * | 1/2010 | ........... C07D 401/12 |
| WO | 2011/073845 A1 | 6/2011 | |
| WO | 2011/075607 A1 | 6/2011 | |
| WO | 2011/121555 A1 | 10/2011 | |
| WO | 2012/056372 A1 | 5/2012 | |
| WO | 2012/080284 A2 | 6/2012 | |
| WO | 2012/080284 A3 | 6/2012 | |
| WO | 2012/137099 A1 | 10/2012 | |
| WO | 2012/177725 A1 | 12/2012 | |
| WO | 2012/177728 A1 | 12/2012 | |
| WO | 2013/003315 A2 | 1/2013 | |
| WO | 2013/169793 A2 | 11/2013 | |
| WO | 2013/169793 A3 | 11/2013 | |
| WO | 2014/036015 A1 | 3/2014 | |
| WO | 2014/037751 A1 | 3/2014 | |
| WO | 2014/043296 A1 | 3/2014 | |
| WO | 2014/123900 A1 | 8/2014 | |
| WO | 2015/003166 A1 | 1/2015 | |
| WO | 2016/014674 A1 | 1/2016 | |
| WO | 2016/046530 A1 | 3/2016 | |
| WO | 2016/205942 A1 | 12/2016 | |
| WO | 2017/069980 A1 | 4/2017 | |
| WO | 2017/106556 A1 | 6/2017 | |
| WO | 2017/152821 A1 | 9/2017 | |
| WO | 2017/155765 A1 | 9/2017 | |
| WO | 2017/158388 A1 | 9/2017 | |
| WO | 2017/189823 A2 | 11/2017 | |
| WO | 2017/189829 A1 | 11/2017 | |
| WO | 2018/065768 A1 | 4/2018 | |
| WO | 2018/102366 A1 | 6/2018 | |
| WO | 2018/119263 A1 | 6/2018 | |
| WO | 2018/136700 A1 | 7/2018 | |
| WO | 2018/182051 A1 | 10/2018 | |
| WO | 2018/183418 A1 | 10/2018 | |
| WO | 2018/183964 A1 | 10/2018 | |
| WO | 2018/231745 A1 | 12/2018 | |
| WO | 2019/079626 A1 | 4/2019 | |
| WO | 2019/084497 A1 | 5/2019 | |
| WO | 2019/155066 A1 | 8/2019 | |
| WO | 2020/023560 A1 | 1/2020 | |
| WO | 2020/072627 A1 | 4/2020 | |
| WO | 2020/072695 A1 | 4/2020 | |

OTHER PUBLICATIONS

Collins, I., et al., CAS Registry Database, 1184844-45-8, CAPLUS Accession No. 2009:1042183Document No. 151:289187, Entitled: Bicyclylaryl-aryl-amine compounds, their preparation, and their use as CHKI kinase inhibitors for treating proliferative diseases, pp. 1-3 (2009).

Di Bartolo, V., et al., "A novel pathway down-modulating T cell activation involves HPK-1-dependent recruitment of 14-3-3 proteins on SLP-76" J Exp Med 204(3):681-691 (Mar. 19, 2007).

Dong, X. et al., "QSAR study of Akt/protein kinase B (PKB) inhibitors using support vector machine" Eur J Med Chem 44(10):4090-4097 (Oct. 1, 2009).

International Preliminary Report on Patentability (IPRP) for PCT/US2019/043123: pp. 1-8, issued on Jan. 26, 2021.

International Search Report for PCT/US2019/043123: pp. 1-15, mailed on Sep. 20, 2019.

Johnson, C.N. et al., "Structure-Based Design of Type II Inhibitors Applied to Maternal Embryonic Leucine Zipper Kinase" ACS Med Chem Lett 6(1):31-36 (Jan. 8, 2015).

Lasserre, R., et al., "Release of serine/threonine-phosphorylated adaptors from signaling microclusters down-regulates T cell activation" J Cell Biol 195(5):839-853 (Nov. 28, 2011).

Liang, J. et al., "Identification of an imidazopyridine scaffold to generate potent and selective TYK2 inhibitors that demonstrate activity in an in vivo psoriasis model" Bioorganic & Medicinal Chemistry Letters 27(18):4370-4376 ( 2017).

Lu, B. et al., "Discovery of EBI-907: A highly potent and orally active B-RafV600E inhibitor for the treatment of melanoma and associated cancers" Bioorg Med Chem Lett 26(3):819-823 (Feb. 1, 2016).

Ma, X. et al., "Identification of New FLT3 Inhibitors That Potently Inhibit AML Cell Lines via an Azo Click-It/Staple-It Approach" ACS Med Chem Lett 8(5):492-497 (Apr. 14, 2017).

Panchaud, P. et al., "Discovery and Optimization of Isoquinoline Ethyl Ureas as Antibacterial Agents" J Med Chem 60(9):3755-3775 (May 11, 2017).

Yule, I.A. et al., "Pyridine-3-carboxamide-6-yl-ureas as novel inhibitors of bacterial DNA gyrase: Structure based design, synthesis, SAR and antimicrobial activity" Eur J Med Chem 86:31-38 (Oct. 30, 2014).

Zdrojewski, T. et al., "A general approach to 3-aminoisoquinoline, its N-mono- and N,N-disubstituted derivatives" Tetrahedron 51(45):12439-12444 (Nov. 6, 1995).

Zeng, Q. et al., "Azole-based inhibitors of AKT/PKB for the treatment of cancer" Bioorg Med Chem Lett 20(5):1559-1564 (Mar. 1, 2010).

Zhu, G. et al., "Isoquinoline-pyridine-based protein kinase B/Akt antagonists: SAR and in vivo antitumor activity" Bioorg Med Chem Lett 16(12):3150-3155 (Jun. 15, 2006).

U.S. Appl. No. 16/921,297, filed Jul. 6, 2020, Bryan Chan et al., Isoquinolines as Inhibitors of HPK1.

U.S. Appl. No. 17/220,307, filed Apr. 1, 2021, Jun Liang et al., Isoquinoline Compounds for the Treatment of Cancer.

* cited by examiner

ISOQUINOLINE COMPOUNDS AND USES THEREOF

CROSS REFERENCE TO RELATED APPLICATIONS

This application is a continuation of International Patent Application No. PCT/US2019/043123, filed Jul. 23, 2019, which claims the benefit of International Patent Application No. PCT/CN2018/096780, filed Jul. 24, 2018, the contents of which are incorporated herein by reference in their entireties.

FIELD OF THE INVENTION

The present disclosure relates to isoquinoline compounds that are inhibitors of HPK1, compositions containing these compounds, and methods for enhancing an immune response and treating HPK1-dependent disorders such as cancer.

BACKGROUND OF THE INVENTION

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY OF THE INVENTION

Disclosed are isoquinoline compounds that are inhibitors of HPK1, compositions containing these compounds, and methods for enhancing an immune response and treating HPK1-dependent disorders such as cancer.

In one aspect, provided is a compound of Formula (I), or any variation thereof, or a salt thereof (e.g., a pharmaceutically acceptable salt thereof), as detailed herein. Also provided is a pharmaceutical composition comprising a compound of Formula (I), or any variation thereof detailed herein, or a pharmaceutically acceptable salt thereof, and a pharmaceutically acceptable carrier or excipient.

In another aspect, provided is a method for inhibiting HPK1, comprising contacting HPK1 in a subject with an effective amount of the compound of Formula (I), or any variation thereof detailed herein, or a pharmaceutically acceptable salt thereof. Also provided is a method for enhancing an immune response in a subject in need thereof, comprising administering to the subject an effective amount of the compound of Formula (I), or any variation thereof detailed herein, or a pharmaceutically acceptable salt thereof.

Further provided is a method for treating a HPK11-dependent disorder, comprising administering to a subject in need thereof an effective amount of the compound of Formula (I), or any variation thereof detailed herein, or a pharmaceutically acceptable salt thereof. In some embodiments, the subject is a human. In some embodiments, the HPK11-dependent disorder is a cancer, for example, colorectal cancer, melanoma, non-small cell lung cancer, ovarian cancer, breast cancer, pancreatic cancer, a hematological malignancy, and a renal cell carcinoma. In some embodiments, the method further comprises administering a chemotherapeutic agent to the subject.

Also provided is a compound of Formula (I), or any variation thereof detailed herein, or a pharmaceutically acceptable salt thereof, for use in a method of inhibiting HPK1, enhancing an immune response, or treating a HPK11-dependent disorder such as cancer.

Also provided is use of a compound of Formula (I), or any variation thereof detailed herein, or a pharmaceutically acceptable salt thereof, in a method detailed herein (e.g., treatment of a HPK1T-dependent disorder such as cancer.

Also provided is use of a compound of Formula (I), or any variation thereof detailed herein, or a pharmaceutically acceptable salt thereof, for the manufacture of a medicament for use in a method detailed herein (e.g., treatment of a HPK1-dependent disorder such as cancer.

Also provided is a kit for treating a HPK1-dependent disorder, the kit comprising a pharmaceutical composition comprising a the compound of Formula (I), or any variation thereof detailed herein, or a pharmaceutically acceptable salt thereof; and instructions for use.

In another aspect, provided is a method of making a compound of Formula (I) or any variation thereof. Also provided are compound intermediates useful in synthesis of a compound of Formula (I), or any variation thereof.

DETAILED DESCRIPTION OF THE INVENTION

Disclosed herein, are compounds of Formula (I), or variations thereof such as Formula (IA), (IB) and (IC), and pharmaceutical compositions thereof that are inhibitors or modulators of HPK1 (hematopoietic progenitor kinase 1). As such, the compounds and compositions are useful in treating diseases and disorders mediated by HPK1. An example of a method of treating is in the case of a subject who is suffering from cancer. The compounds can be used not only to combat cancer, but can also advantageously be used to enhance an immune response in a subject in need thereof.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). The alkenyl group may be in "cis" or "trans" configurations, or alternatively in "E" or "Z" configurations. Particular alkenyl groups are those having 2 to 20 carbon atoms (a "$C_{2-20}$ alkenyl"), having a 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Example of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula C≡C) having the number of carbon atoms designated (i.e., $C_{2-10}$ means two to ten carbon atoms). Particular alkynyl groups are those having 2 to 20 carbon atoms (a "$C_{2-20}$ alkynyl"), having a 2 to 8 carbon atoms (a "$C_{2-8}$ alkynyl"), having 2 to 6 carbon atoms (a "$C_{2-6}$ alkynyl"), having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_{1-6}$ alkylene"), 1 to 5 carbon atoms (a "$C_{1-5}$ alkylene"), having 1 to 4 carbon atoms (a "$C_{1-4}$ alkylene"), or 1 to 3 carbon atoms (a "$C_{1-3}$ alkylene"). Examples of alkylene include, but are not limited to, groups such as methylene (—CH$_2$—), ethylene (—CH$_2$—CH$_2$—), propylene (—CH$_2$—CH$_2$—CH$_2$—), butylene (—CH$_2$—CH$_2$—CH$_2$—CH$_2$—), and the like.

"Cycloalkyl" as used herein refers to non-aromatic, saturated or unsaturated cyclic univalent hydrocarbon structures having the number of carbon atoms designated (i.e., $C_{3-10}$ means three to ten carbon atoms). Cycloalkyl can consist of one ring, such as cyclohexyl, or multiple rings, such as adamantly, but excludes aryl groups. A cycloalkyl comprising more than one ring may be fused, spiro, or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_{3-8}$ cycloalkyl"), or having 3 to 6 carbon atoms (a "$C_{3-6}$ alkynyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Aryl" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular (i.e., ring) carbon atoms (a "$C_{6-14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic cyclic group having a single ring or multiple condensed rings, and having from 1 to 14 annular (i.e., ring) carbon atoms and from 1 to 6 annular (i.e., ring) heteroatoms, such as nitrogen, phosphorus, sulfur or oxygen, and the like. A heterocycle comprising more than one ring may be fused, spiro or bridged, or any combination thereof. In fused ring systems, one or more may be fused rings can be cycloalkyl. Particular heterocyclyl groups are 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to 5 annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur.

"Halo" or Halogen" refers to fluoro, chloro, bromo and/or iodo. "Haloalkyl" refers to an alkyl group substituted with one or more halogen that may be the same or different. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.

"Oxo" refers to the moiety =O.

"Geminal" refers to the relationship between two moieties that are attached to the same atom. For example, in the residue —CH$_2$—CR$^x$R$^y$—, R$^x$ and R$^y$ are geminal and R$^x$ may be referred to as a geminal R group to R$^y$.

"Vicinal" refers to the relationship between two moieties that are attached to adjacent atoms. For example, in the residue —CHR$^x$—CHR$^y$—, R$^x$ and R$^y$ are vicinal and R$^x$ may be referred to as a vicinal R group to R$^y$.

"Optionally substituted" unless otherwise specified means that a group may be unsubstituted or substituted by one or more (e.g., 1, 2, 3, 4 or 5) of the substituents listed for that group in which the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4 or 1 to 5 substituents.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK11 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK11 activity of about 5% to about 25%, about 25% to about 50%, about 50% to about 75%, or about 75% to 100%. In some embodiments, inhibit means a decrease in HPK11 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK11 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the IC$_{50}$ of the antagonist for the target is about 90%, 80%, 70%, 60%, 50%, 40%, 30%, 20%, 10%, 5%, 1%, 0.1%, 0.01%, 0.001% or less of the IC$_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the IC$_{50}$ of the HPK1 antagonist for HPK1 is about 90%, 80%, 70%, 60%, 50%, 40%, 30%, 20%, 10%, 0.1%, 0.01%, 0.001%, or less of the IC$_{50}$ of the HPK1 antagonist for another serine/threonine kinase or other type of kinase (e.g., tyrosine kinase).

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), preventing or delaying the spread (e.g., metastasis) or the disease, delay or slowing the progression of the disease, ameliorating the disease state, providing a remission (whether partial or total) of the disease, decreasing the dose of one or more medications required to treat the disease, enhancing effect of another medication, delaying the progression of the disease, increasing the quality of life, and/or prolonging survival. Also encompassed by "treatment" is a reduction of pathological consequence of cancer. The methods of the invention contemplate any one or more of these aspects of treatment.

As used here, "delaying" the development of cancer means to defer, hinder, slow, retard, stabilize, and/or postpone development of the disease. This delay can be of varying lengths of time, depending on the history of the disease and/or subject being treated. As is evident to one skilled in the art, a sufficient or significant delay can, in effect, encompass prevention, in that the subject does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams, mammography, imaging, or biopsy. Development may also refer to disease progression that may be initially undetectable and includes occurrence, recurrence, and onset.

As used herein, an "at risk" subject is a subject who is at risk of developing cancer. A subject "at risk" may or may not have detectable disease, and may or may not have displayed detectable disease prior to the treatment methods described herein. "At risk" denotes that a subject has one or more so-called risk factors, which are measurable parameters that correlate with development or cancer, which are described herein. A subject having one or more of these risk factors has a higher probability of developing cancer than a subject without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances.

As used herein, the term "effective amount" intends such amount of a compound of the invention which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial results may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells;) (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

A "prophylactically effective amount" refers to an amount of a compound, or pharmaceutically acceptable salt thereof, sufficient to prevent or reduce the severity of one or more future symptoms of cancer when administered to a subject who is susceptible and/or who may develop cancer. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotype presenting during future development of the disease).

It is understood that an effective amount of a compound or pharmaceutically acceptable salt thereof, including a prophylactically effective amount, may be given to a subject in the adjuvant setting, which refers to a clinical setting in which a subject has had a history of cancer, and generally (but not necessarily) has been responsive to therapy, which includes, but is not limited to, surgery (e.g., surgical resection), radiotherapy, and chemotherapy. However, because of their history of the cancer, these subjects are considered at risk of developing cancer. Treatment or administration in the "adjuvant setting" refers to a subsequent mode of treatment.

As used herein, "unit dosage form refers to physically discrete units, suitable as unit dosages, each unit containing predetermined quantity of active ingredient calculated to produce the desired therapeutic effect in association with the required pharmaceutical carrier or excipient. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time.

Controlled release formulation can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable' or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

In some embodiments, the salts of the compounds of the invention are pharmaceutically acceptable salts. "Pharmaceutically acceptable salts" are those salts which retain at least some of the biological activity of the free (non-salt) compound and which can be administered as drugs or pharmaceuticals to a subject. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include e.g. calcium carbonate, dextrose, fructose dc (dc—"directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g. dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc. In some cases, the terms "excipient" and "carrier" are used interchangeably.

The term "subject" or "patient" refers to animals such as mammals, including, but not limited to, primates (e.g., humans), cows, sheep, goats, horses, dogs, cats, rabbits, rats, mice and the like. In certain embodiments, the subject is a human or a human patient.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or biologic useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma11 and calicheamicin omega11 (see, e.g., Nicolaou et al., *Angew. Chem Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chlorambucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON@); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON@(toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-α, IFN-β, IFN-γ), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEPTIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO®, Amgen), pertuzumab (PERJETA®, Genentech), obinutuzumab (GAZYVA®, Genentech), nivolumab (OPDIVO®,) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Compounds

The compounds disclosed herein are compounds of Formula (I), or salts (e.g., pharmaceutically acceptable salts), solvates (e.g., hydrates), prodrugs, metabolites, or derivatives thereof. These compounds are useful inhibitors of HPK1.

In one aspect, provided is a compound of Formula (I):

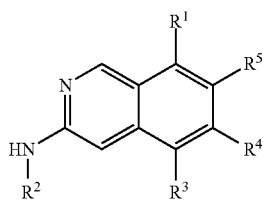

(I)

or a salt (e.g., a pharmaceutically acceptable salt), solvate (e.g., hydrate), prodrug, metabolites or derivative thereof, wherein:

$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;

$R^2$ is a 5- to 14-membered heteroaryl optionally substituted with $R^{10}$;

$R^3$ is hydrogen, halogen, cyano, $C_{1-6}$ alkyl, $C_{3-8}$ cycloalkyl, 3- to 14-membered heterocyclyl, or —OR$^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;

$R^4$ is $C_{1-6}$ alkyl, $C_{2-6}$ alkenyl, $C_{2-6}$ alkynyl, $C_{3-9}$ cycloalkyl, $C_{6-14}$ aryl, 5- to 14-membered heteroaryl, 3- to 14-membered heterocyclyl, halogen, cyano, —C(O)R$^6$, —C(O)OR$^7$, —C(O)NR$^{8a}$R$^{8b}$, —OR$^7$, —OC(O)R$^6$, —OC(O)NR$^{8a}$R$^{8b}$, —SR$^7$, —S(O)R$^9$, —S(O)$_2$R$^9$, —S(O)$_2$NR$^{8a}$R$^{8b}$, —P(O)R$^{9a}$R$^{9b}$, —NR$^{8a}$R$^{8b}$, —N(R$^8$)C(O)R$^6$, —N(R$^8$)C(O)OR$^7$, —N(R$^8$)C(O)NR$^{8a}$R$^{8b}$, —N(R$^8$)S(O)$_2$R$^9$, or —N(R$^8$)S(O)$_2$NR$^{8a}$R$^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;

$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)R$^6$, —C(O)OR$^7$, —C(O)NR$^{8a}$R$^{8b}$, —OR$^7$, —OC(O)R$^6$, —OC(O)NR$^{8a}$R$^{8b}$, —SR$^7$, —S(O)R$^9$, —S(O)$_2$R$^9$, —S(O)$_2$NR$^{8a}$R$^{8b}$, —P(O)R$^{9a}$R$^{9b}$, —NR$^{8a}$R$^{8b}$, —N(R$^8$)C(O)R$^6$, —N(R$^8$)C(O)OR$^7$, —N(R$^8$)C(O)NR$^{8a}$R$^{8b}$, —N(R$^8$)S(O)$_2$R$^9$, or —N(R$^8$)S(O)$_2$NR$^{8a}$R$^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;

each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;

each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;

each $R^8$ is independently hydrogen or $C_{1-6}$ alkyl;

each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$; or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;

each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;

each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or $—O—C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;

or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, $—C(O)R^a$, $—C(O)OR^b$, $—C(O)NR^cR^d$, $—OR^b$, $—OC(O)R^a$, $—OC(O)NR^cR^d$, $—SR^b$, $—S(O)R^e$, $—S(O)_2R^e$, $—S(O)(=NH)R^e$, $—S(O)_2NR^cR^d$, $—NR^cR^d$, $—N(R^f)C(O)R^a$, $—N(R^f)C(O)OR^b$, $—N(R^f)C(O)NR^cR^d$, $—N(R^f)S(O)_2R^e$, $—N(R^f)S(O)_2NR^cR^d$, or $—P(O)R^gR^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^1$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or $—O—C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, $—C(O)R^{a1}$, $—C(O)OR^{b1}$, $—C(O)NR^{c1}R^{d1}$, $—OR^{b1}$, $—OC(O)R^{a1}$, $—OC(O)NR^{c1}R^{d1}$, $—SR^{b1}$, $—S(O)R^{e1}$, $—S(O)_2R^{e1}$, $—S(O)_2NR^{c1}R^{d1}$, $—NR^{c1}R^{d1}$, $—N(R^{f1})C(O)R^{a1}$, $—N(R^{f1})C(O)OR^{b1}$, $—N(R^{f1})C(O)NR^{c1}R^{d1}$, $—N(R^{f1})S(O)_2R^{e1}$, $—N(R^{f1})S(O)_2NR^{c1}R^{d1}$, or $—P(O)R^{g1}R^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^e$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or $—O—C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^2$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^f$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^h$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

In some embodiments, the compound is other than a compound in Table 1X and salts thereof. In some embodiments, the compound herein, such as a compound of Formula (I), is other than a compound selected from one or more of Compound Nos. 1x-63x in Table 1X and salts thereof. In some embodiments, the compound herein, such as a compound of Formula (I), is other than a compound selected from one or more of Compound Nos. 1x-62x in Table 1X and salts thereof. In some embodiments, the compound herein, such as a compound of Formula (I), is other than Compound No. 63x and salts thereof. In some embodiments, the compounds of the disclosure, and methods of using the compounds detailed herein, encompass any of the compounds of Formula (I), including those listed Table 1X and salts thereof.

TABLE 1X

| No. | Name |
|---|---|
| 1x | 2H-Isoindole-2-carboxylic acid, 1,3-dihydro-4-[[6-[(methylamino)carbonyl]-3-isoquinolinyl]amino]-, 1,1-dimethylethyl ester |
| 2x | 6-Isoquinolinecarboxamide, 3-[(2-cyano-2,3-dihydro-1H-isoindol-4-yl)amino]-N-methyl- |
| 3x | 3-Isoquinolinamine, N-1,3-benzodioxol-5-yl-6-(4-piperidinyloxy)- |
| 4x | 3-Isoquinolinamine, N-(2,2-difluoro-1,3-benzodioxol-4-yl)-6-(4-piperidinyloxy)- |
| 5x | 3-Isoquinolinamine, 6-(4-piperidinyloxy)-N-(2,2,3,3-tetrafluoro-2,3-dihydro-1,4-benzodioxin-6-yl)- |
| 6x | 3-Isoquinolinamine, N-(2,2-difluoro-1,3-benzodioxol-5-yl)-6-(4-piperidinyloxy)- |
| 7x | 3-Isoquinolinamine, N-(2,3-dihydro-1,4-benzodioxin-6-yl)-6-(4-piperidinyloxy)- |
| 8x | 2H-1-Benzopyran-2-one, 3,4-dihydro-4-(methoxymethyl)-7-[[6-(4-piperidinyloxy)-3-isoquinolinyl]amino]- |
| 9x | 6-Isoquinolinecarboxamide, 3-[(1,3-dimethyl-1H-pyrazol-5-yl)amino]-N-[(3S,4R)-4-(4-methoxyphenyl)-1-methyl-3-pyrrolidinyl]- |
| 10x | 6-Isoquinolinecarboxamide, 3-[(1,3-dimethyl-1H-pyrazol-5-yl)amino]-N-[(3S,4R)-4-(4-methoxyphenyl)-1-(phenylmethyl)-3-pyrrolidinyl]- |
| 11x | 6-Isoquinolinecarboxamide, N-[(3S,4R)-4-(4-methoxyphenyl)-1-(phenylmethyl)-3-pyrrolidinyl]-3-[(1-methyl-1H-pyrazol-5-yl)amino]- |
| 12x | 6-Isoquinolinecarboxamide, N-[(1R)-1-(3-chloro-4-fluorophenyl)propyl]-3-[(1-methyl-1H-pyrazol-5-yl)amino]- |
| 13x | 6-Isoquinolinecarboxamide, N-[(S)-(3-fluoro-4-methoxyphenyl)(1-methyl-1H-pyrazol-4-yl)methyl]-3-[(1-methyl-1H-pyrazol-5-yl)amino]- |
| 14x | 6-Isoquinolinecarboxamide, N-[(S)-(4-chloro-3-fluorophenyl)(1-methyl-1H-pyrazol-4-yl)methyl]-3-[(1-methyl-1H-pyrazol-5-yl)amino]- |
| 15x | 6-Isoquinolinecarboxamide, N-[(1S)-1-(4-chloro-3-fluorophenyl)-2-hydroxyethyl]-3-[(1-methyl-1H-pyrazol-5-yl)amino]- |
| 16x | 6-Isoquinolinecarboxamide, N-[(1R)-1-(4-chloro-3-fluorophenyl)propyl]-3-[(1-methyl-1H-pyrazol-5-yl)amino]- |
| 17x | 6-Isoquinolinecarboxylic acid, 3-[(1-methyl-1H-pyrazol-5-yl)amino]- |

TABLE 1X-continued

| No. | Name |
|---|---|
| 18x | 6-Isoquinolinecarboxamide, N-[(1S)-1-(3-fluoro-4-methoxyphenyl)-2-hydroxyethyl]-3-[(1-methyl-1H-pyrazol-5-yl)amino]- |
| 19x | 6-Isoquinolinecarboxamide, N-[(S)-(4-chloro-3-fluorophenyl)(1-methyl-1H-pyrazol-4-yl)methyl]-3-[(1,3-dimethyl-1H-pyrazol-5-yl)amino]- |
| 20x | 6-Isoquinolinecarboxamide, N-[(1R)-1-(4-chloro-3-fluorophenyl)propyl]-3-[(1,3-dimethyl-1H-pyrazol-5-yl)amino]- |
| 21x | 6-Isoquinolinecarboxamide, N-[(1S)-1-(4-chloro-3-fluorophenyl)-2-hydroxyethyl]-3-[(1,3-dimethyl-1H-pyrazol-5-yl)amino]- |
| 22x | 6-Isoquinolinecarboxamide, 3-[(1,3-dimethyl-1H-pyrazol-5-yl)amino]-N-[(S)-(3-fluoro-4-methoxyphenyl)(1-methyl-1H-pyrazol-4-yl)methyl]- |
| 23x | 6-Isoquinolinecarboxylic acid, 3-[(1,3-dimethyl-1H-pyrazol-5-yl)amino]- |
| 24x | 6-Isoquinolinecarboxylic acid, 3-[(1,3-dimethyl-1H-pyrazol-5-yl)amino]-, methyl ester |
| 25x | 3-Isoquinolinamine, 6-bromo-N-(1,3-dimethyl-1H-pyrazol-5-yl)- |
| 26x | 6-Isoquinolinecarboxamide, 3-[(1,3-dimethyl-1H-pyrazol-5-yl)amino]-N-[(1S)-1-(3-fluoro-4-methoxyphenyl)-2-hydroxyethyl]- |
| 27x | 3-Isoquinolinamine, 6-(4-piperidinyloxy)-N-(1,3,5-trimethyl-1H-pyrazol-4-yl)- |
| 28x | 1H-Pyrazole-1-ethanol, 4-[3-[[2-methoxy-6-(4-morpholinyl)-3-pyridinyl]amino]-6-isoquinolinyl]-α,α-dimethyl- |
| 29x | 1H-Pyrazole-1-ethanol, 4-[3-[[5-(1,2-dimethyl-1H-imidazol-5-yl)-3-methoxy-2-pyridinyl]amino]-6-isoquinolinyl]-a,a-dimethyl- |
| 30x | 1H-Pyrazole-1-ethanol, 4-[3-[[6-(1,2-dimethyl-1H-imidazol-5-yl)-2-methoxy-3-pyridinyl]amino]-6-isoquinolinyl]-α,α-dimethyl- |
| 31x | 3-Isoquinolinamine, 6-(1H-pyrazol-4-yl)-N-[4-(1-pyrrolidinylmethyl)-2-pyridinyl]- |
| 32x | 6-Isoquinolinecarboxamide, N-[(1R)-1-(3-chloro-4-fluorophenyl)propyl]-3-[(2-methyl-4-pyridinyl)amino]- |
| 33x | 6-Isoquinolinecarboxamide, N-[(S)-(4-chloro-3-fluorophenyl)(1-methyl-1H-pyrazol-4-yl)methyl]-3-[(2-methyl-4-pyridinyl)amino]- |
| 34x | 6-Isoquinolinecarboxamide, N-[(S)-(3-fluoro-4-methoxyphenyl)(1-methyl-1H-pyrazol-4-yl)methyl]-3-[(2-methyl-4-pyridinyl)amino]- |
| 35x | 6-Isoquinolinecarboxylic acid, 3-[(2-methyl-4-pyridinyl)amino]- |
| 36x | 6-Isoquinolinecarboxylic acid, 3-[(2-methyl-4-pyridinyl)amino]-, methylester |
| 37x | 3-Isoquinolinamine, 6-bromo-N-(2-methyl-4-pyridinyl)- |
| 38x | 6-Isoquinolinecarboxamide, N-[(1S)-1-(4-chloro-3-fluorophenyl)-2-hydroxyethyl]-3-[(2-methyl-4-pyridinyl)amino]- |
| 39x | 3-Isoquinolinamine, 6-methoxy-N-[4-(1-pyrrolidinylmethyl)-2-pyridinyl]- |
| 40x | 3-Isoquinolinamine, 6,7-dimethoxy-N-[4-(1-pyrrolidinylmethyl)-2-pyridinyl]- |
| 41x | 3-Isoquinolinamine, 6,7-difluoro-N-[4-(1-pyrrolidinylmethyl)-2-pyridinyl]- |
| 42x | 3-Isoquinolinamine, 6-chloro-8-methyl-N-[4-(1-pyrrolidinylmethyl)-2-pyridinyl]- |
| 43x | 3-Isoquinolinamine, 6-chloro-N-[4-(1-pyrrolidinylmethyl)-2-pyridinyl]- |
| 44x | 3-Isoquinolinamine, N-(4,6-dimethyl-2-pyridinyl)-6-(4-piperidinyloxy)- |
| 45x | 3-Isoquinolinamine, N-(4-methyl-3-pyridinyl)-6-(4-piperidinyloxy)- |
| 46x | 3-Isoquinolinamine, N-(6-fluoro-3-pyridinyl)-6-(4-piperidinyloxy)- |
| 47x | 3-Isoquinolinamine, N-(2-methyl-4-pyridinyl)-6-(4-piperidinyloxy)- |
| 48x | 3-Isoquinolinamine, N-(6-methoxy-3-pyridinyl)-6-(4-piperidinyloxy)- |
| 49x | 3-Isoquinolinamine, 6-(4-piperidinyloxy)-N-4-pyridinyl- |
| 50x | 3-Isoquinolinamine, 6-(4-piperidinyloxy)-N-3-pyridinyl- |
| 51x | 3-Isoquinolinamine, 6-(4-piperidinyloxy)-N-2-pyridinyl- |
| 52x | 3-Isoquinolinamine, N-(4-methyl-2-pyridinyl)-6-(4-piperidinyloxy)- |
| 53x | 3-Isoquinolinamine, N-(5-methyl-2-pyridinyl)-6-(4-piperidinyloxy)- |
| 54x | 3-Isoquinolinamine, N-(6-methyl-2-pyridinyl)-6-(4-piperidinyloxy)- |
| 55x | 3-Isoquinolinamine, N-(2,6-dimethyl-4-pyrimidinyl)-6-(4-piperidinyloxy)- |
| 56x | 3-Isoquinolinamine, 6-(4-piperidinyloxy)-N-4-pyrimidinyl- |
| 57x | 3-Isoquinolinamine, 6-(4-piperidinyloxy)-N-2-pyrimidinyl- |
| 58x | 2-Pyrazinecarbonitrile, 5-[(6-chloro-3-isoquinolinyl)amino]- |
| 59x | 2-Pyrazinecarbonitrile, 5-[(6,8-dimethoxy-3-isoquinolinyl)amino]- |
| 60x | Carbamic acid, N-[cis-4-[[3-(2-pyrazinylamino)-6-isoquinolinyl]oxy]cyclohexyl]-, 1,1-dimethylethyl ester |
| 61x | 3-Isoquinolinamine, 6-[(cis-4-aminocyclohexyl)oxy]-N-2-pyrazinyl- |
| 62x | 3-Isoquinolinamine, 6-(4-piperidinyloxy)-N-2-pyrazinyl- |
| 63x | 2-Propenamide, N-[3-[[6-[1-(2,6-dichloro-3,5-dimethoxyphenyl)-1-hydroxyethyl]-3-isoquinolinyl]amino]-1-methyl-1H-pyrazol-4-yl]- |

In one aspect, provided is a compound of Formula (I), or a salt (e.g., a pharmaceutically acceptable salt), solvate (e.g., hydrate), prodrug, metabolites or derivative thereof, wherein $R^1$, $R^3$, $R^4$ and $R^5$ are as defined above, and $R^2$ is a monocyclic 5- or 6-membered heteroaryl optionally substituted with 1, 2, 3 or 4 substituents independently selected from $R^{10}$. In one variation, the compound is other than a compound selected from one or more of Compound Nos. 9x-62x in Table 1X and salts thereof. In one variation, the compound is other than a compound selected from one or more of Compound Nos. 9x-63x in Table 1X and salts thereof. In some embodiments, $R^2$ is a 5-membered heteroaryl optionally substituted with 1, 2, 3 or 4 substituents independently selected from $R^{10}$, provided that $R^2$ is other than a pyrazolyl or a substituted pyrazolyl. In some embodiments, $R^2$ is a 5-membered heteroaryl optionally substituted with 1, 2, 3 or 4 substituents independently selected from $R^{10}$, provided that $R^2$ is other than a compound selected from one or more of Compound Nos. 9x-27x in Table 1X and salts thereof. In some embodiments, $R^2$ is a 5-membered heteroaryl optionally substituted with 1, 2, 3 or 4 substituents independently selected from $R^{10}$, provided that $R^2$ is other than a compound selected from one or more of Compound Nos. 9x-27x and 63x in Table 1X and salts thereof.

In one aspect, provided is a compound of Formula (I), or a salt (e.g., a pharmaceutically acceptable salt), solvate (e.g., hydrate), prodrug, metabolites or derivative thereof, wherein $R^1$, $R^3$, $R^4$ and $R^5$ are as defined above, and $R^2$ is a polycyclic heteroaryl having the formula (a) or (b):

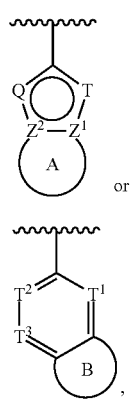

wherein the wavy line represents the attachment point to the parent structure,

Q is $CR^{20}$, $NR^{21}$, N, O or S;

T is N or $CR^{22}$;

$Z^1$ and $Z^2$ are independently N or C, provided at least one of $Z^1$ and $Z^2$ is C;

$T^1$, $T^2$ and $T^3$ are independently N or $CR^{23}$;

ring A and ring B are independently a $C_{5-8}$ cycloalkyl or a 5- to 8-membered heterocycle having at least 3 ring-forming carbon atoms and 1, 2 or 3 ring-forming heteroatoms independently selected from the group consisting of N, P, O and S; wherein the $C_{5-8}$ cycloalkyl and the 5- to 8-membered heterocycle are independently optionally substituted with 1, 2, 3, 4 or 5 substituents independently selected from $R^{10}$; and wherein two substituents of the $C_{5-8}$ cycloalkyl or the 5- to 8-membered heterocycle, where present, optionally taken together form a spiro, fused or bridged cycloalkyl (e.g., $C_{3-6}$ cycloalkyl) optionally substituted with 1, 2, 3 or 4 substituents independently selected from $R^{10}$ or a sprio, fused or bridged heterocyclyl (e.g., 3- to 6-membered heterocyclyl) optionally substituted with 1, 2, 3 or 4 substituents independently selected from $R^{10}$; and $R^{20}$, $R^{21}$, $R^{22}$ and $R^{23}$ are each independently hydrogen or $R^{10}$.

In some embodiments, ring A or ring B is $C_{5-8}$ cycloalkyl optionally substituted with $R^{10}$. In some embodiments, ring A or ring B is a 5- to 8-membered heterocycle (e.g., having at least 3 ring-forming carbon atoms and 1, 2 or 3 ring-forming heteroatoms independently selected from the group consisting of N, P, O and S) optionally substituted with $R^{10}$. In some embodiments, two germinal substituents of the $C_{5-8}$ cycloalkyl or the 5- to 8-membered heterocycle, where present, optionally taken together with the atom to which they are attached form a spiro $C_{3-6}$ cycloalkyl optionally substituted with 1, 2, 3 or 4 substituents independently selected from $R^{10}$ or a sprio 3- to 6-membered heterocyclyl optionally substituted with 1, 2, 3 or 4 substituents independently selected from $R^{10}$. In some embodiments, two vicinal substituents of the $C_{5-8}$ cycloalkyl or the 5- to 8-membered heterocycle, where present, optionally taken together with the atoms to which they are attached form a fused 5- or 6-membered heteroaryl optionally substituted with 1, 2, 3 or 4 substituents independently selected from $R^{10}$ or a fused 5- or 6-membered heterocyclyl optionally substituted with 1, 2, 3 or 4 substituents independently selected from $R^{10}$.

In some embodiments of the compound of Formula (I), or a salt (e.g., a pharmaceutically acceptable salt), solvate (e.g., hydrate), prodrug, metabolites or derivative thereof, wherein $R^1$, $R^3$, $R^4$ and $R^5$ are as defined above, and $R^2$ is a polycyclic heteroaryl having the formula (a):

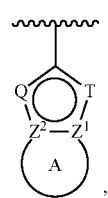

wherein the wavy line represents the attachment point to the parent structure, Q, T, $Z^1$, $Z^2$, and ring A are as defined above.

In some embodiments of the compound of Formula (I), or a salt (e.g., a pharmaceutically acceptable salt), solvate (e.g., hydrate), prodrug, metabolites or derivative thereof, wherein $R^1$, $R^3$, $R^4$ and $R^5$ are as defined above, and $R^2$ is a polycyclic heteroaryl having the formula (b):

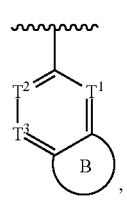

wherein the wavy line represents the attachment point to the parent structure, $T^1$, $T^2$, $T^3$, and ring B are as defined above. In some embodiments, at least one of $T^1$, $T^2$ and $T^3$ is N. In one variation, the compound is other than a compound selected from one or more of Compound Nos. 1x-8x in Table 1X and salts thereof. In another variation, provided that $R^4$ is other than methylaminocarbonyl [i.e., —C(O)NHMe] and piperidin-4-yloxy.

In one aspect, provided is a compound of Formula (I):

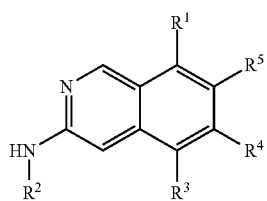

or a salt (e.g., a pharmaceutically acceptable salt) thereof, wherein:

$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;

$R^2$ is (i) or (ii):

(i) a monocyclic 5- or 6-membered heteroaryl optionally substituted with 1, 2, 3 or 4 substituents independently selected from $R^{10}$; or
(ii) a polycyclic heteroaryl having the formula (a) or (b):

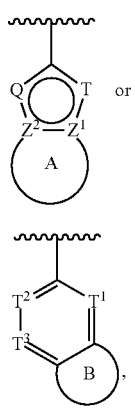

wherein the wavy line represents the attachment point to the parent structure,
Q is $CR^{20}$, $NR^{21}$, N, O or S;
T is N or $CR^{22}$;
$Z^1$ and $Z^2$ are independently N or C, provided at least one of $Z^1$ and $Z^2$ is C;
$T^1$, $T^2$ and $T^3$ are independently N or $CR^{23}$;
ring A and ring B are independently a $C_{5-8}$ cycloalkyl or a 5- to 8-membered heterocycle having at least 3 ring-forming carbon atoms and 1, 2 or 3 ring-forming heteroatoms independently selected from the group consisting of N, P, O and S(ring-forming atom counts including atoms designated as $Z^1$ and $Z^2$); wherein the $C_{5-8}$ cycloalkyl and the 5- to 8-membered heterocycle are independently optionally substituted with 1, 2, 3, 4 or 5 substituents independently selected from $R^{10}$; and wherein two substituents of the $C_{5-8}$ cycloalkyl or the 5- to 8-membered heterocycle, where present, optionally taken together form a spiro, fused or bridged cycloalkyl (e.g., $C_{3-6}$ cycloalkyl) optionally substituted with 1, 2, 3 or 4 substituents independently selected from $R^{10}$ or a sprio, fused or bridged heterocyclyl (e.g., 3- to 6-membered heterocyclyl) optionally substituted with 1, 2, 3 or 4 substituents independently selected from $R^{10}$;
$R^{20}$, $R^{21}$, $R^{22}$ and $R^{23}$ are each independently hydrogen or $R^{10}$.
$R^3$ is hydrogen, halogen, cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;
$R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R')C(O)R^6$, —$N(R')C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;
$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R')C(O)R^6$, —$N(R')C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;
each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;
each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;
each $R^8$ is independently hydrogen or $C_{1-6}$ alkyl;
each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;
or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;
each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;
each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;
or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;
each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^c$$R^d$, —O$R^b$, —OC(O)$R^a$, —OC(O)N$R^c$$R^d$, —S$R^b$, —S(O)$R^e$, —S(O)$_2$$R^e$, —S(O)(=NH)$R^e$, —S(O)$_2$N$R^c$$R^d$, —N$R^c$$R^d$, —N($R^f$)C(O)$R^a$, —N($R^f$)C(O)O$R^b$, —N($R^f$)C(O)N$R^c$$R^d$, —N($R^f$)S(O)$_2$$R^e$, —N($R^f$)S(O)$_2$N$R^c$$R^d$, or —P(O)$R^g$$R^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}$$R^{d1}$, —O$R^{b1}$, —OC(O)$R^{a1}$, —OC(O)N$R^{c1}$$R^{d1}$, —S$R^{b1}$, —S(O)$R^{e1}$, —S(O)$_2$$R^{e1}$, —S(O)$_2$N$R^{c1}$$R^{d1}$, —N$R^{c1}$$R^{d1}$, —N($R^{f1}$)C(O)$R^{a1}$, —N($R^{f1}$)C(O)O$R^{b1}$, —N($R^{f1}$)C(O)N$R^{c1}$$R^{d1}$, —N($R^{f1}$)S(O)$_2$$R^{e1}$, —N($R^{f1}$)S(O)$_2$N$R^{c1}$$R^{d1}$, or —P(O)$R^{g1}$$R^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}$$R^{d2}$, —O$R^{b2}$, —OC(O)$R^{a2}$, —OC(O)N$R^{c2}$$R^{d2}$, —S(O)$_2$$R^{e2}$, —S(O)$_2$N$R^{c2}$$R^{d2}$, —N$R^{c2}$$R^{d2}$, —N($R^f$)C(O)$R^{a2}$, —N($R^f$)C(O)O$R^{b2}$, —N($R^f$)C(O)N$R^{c2}$$R^{d2}$, —N($R^2$)S(O)$_2$$R^{e2}$, —N($R^f$)S(O)$_2$N$R^{c2}$$R^{d2}$, or —P(O)$R^{g2}$$R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than a compound in Table 1X and salts thereof.

In one aspect, provided is a compound of Formula (IA):

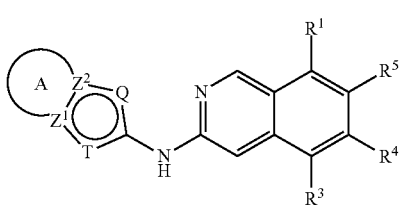

(IA)

or a salt (e.g., a pharmaceutically acceptable salt) thereof, wherein:

$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;

Q is $CR^{20}$, $NR^{21}$, N, O or S;

T is N or $CR^{22}$;

$Z^1$ and $Z^2$ are independently N or C, provided at least one of $Z^1$ and $Z^2$ is C;

ring A is a $C_{5-8}$ cycloalkyl or a 5- to 8-membered heterocycle having at least 3 ring-forming carbon atoms and 1, 2 or 3 ring-forming heteroatoms independently selected from the group consisting of N, P, O and S; wherein the $C_{5-8}$ cycloalkyl and the 5- to 8-membered heterocycle are independently optionally substituted with 1, 2, 3, 4 or 5 substituents independently selected from $R^{10}$; and wherein two substituents of the $C_{5-8}$ cycloalkyl or the 5- to 8-membered heterocycle, where present, optionally taken together form a spiro, fused or bridged cycloalkyl (e.g., $C_{3-6}$ cycloalkyl) optionally substituted with 1, 2, 3 or 4 substituents independently selected from $R^{10}$ or a sprio, fused or bridged heterocyclyl (e.g., 3- to 6-membered heterocyclyl) optionally substituted with 1, 2, 3 or 4 substituents independently selected from $R^{10}$;

$R^{20}$, $R^{21}$ and $R^{22}$ are each independently hydrogen or $R^{10}$.

$R^3$ is hydrogen, halogen, cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;

$R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)$R^6$, —C(O)O$R^7$, —C(O)N$R^{8a}R^{8b}$, —O$R^7$, —OC(O)$R^6$, —OC(O)N$R^{8a}R^{8b}$, —S$R^7$, —S(O)$R^9$, —S(O)$_2R^9$, —S(O)$_2$N$R^{8a}R^{8b}$, —P(O)$R^{9a}R^{9b}$, —N$R^{8a}R^{8b}$, —N($R^8$)C(O)$R^6$, —N($R^8$)C(O)O$R^7$, —N($R^8$)C(O)N$R^{8a}R^{8b}$, —N($R^8$)S(O)$R^9$, or —N($R^8$)S(O)$_2$N$R^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;

$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)$R^6$, —C(O)O$R^7$, —C(O)N$R^{8a}R^{8b}$, —O$R^7$, —OC(O)$R^6$, —OC(O)N$R^{8a}R^{8b}$, —S$R^7$, —S(O)$R^9$, —S(O)$_2R^9$, —S(O)$_2$N$R^{8a}R^{8b}$, —P(O)$R^{9a}R^{9b}$, —N$R^{8a}R^{8b}$, —N($R^8$)C(O)$R^6$, —N(RI)C(O)O$R^7$, —N($R^8$)C(O)N$R^{8a}R^{8b}$, —N($R^8$)S(O)$_2R^9$, or —N($R^8$)S(O)$_2$N$R^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;

each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;

each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;

each $R^8$ is independently hydrogen or $C_{1-6}$ alkyl;

each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;

or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;

each $R^9$ is independently $C_{1-6}$ alkyl, $C_{3-9}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;

each $R^{9a}$ and $R^{9b}$ is independently $C_{1-6}$ alkyl, $C_{3-9}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;

or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-9}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^c R^d$, —O$R^b$, —OC(O)$R^a$, —OC(O)N$R^c R^d$, —S$R^b$, —S(O)$R^e$, —S(O)$_2 R^e$, —S(O)(=NH)$R^e$, —S(O)$_2$N$R^c R^d$, —N$R^c R^d$, —N($R^f$)C(O)$R^a$, —N($R^f$)C(O)O$R^b$, —N($R^f$)C(O)N$R^c R^d$, —N($R^f$)S(O)$_2 R^e$, —N($R^f$)S(O)$_2$N$R^c R^d$, or —P(O)$R^g R^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1} R^{d1}$, —O$R^{b1}$, —OC(O)$R^{a1}$, —OC(O)N$R^{c1} R^{d1}$, —S$R^{b1}$, —S(O)$R^{e1}$, —S(O)$_2 R^{e1}$, —S(O)$_2$N$R^{c1} R^{d1}$, —N$R^{c1} R^{d1}$, —N($R^{f1}$)C(O)$R^{a1}$, —N($R^{f1}$)C(O)O$R^{b1}$, —N($R^{f1}$)C(O)N$R^{c1} R^{d1}$, —N($R^{f1}$)S(O)$_2 R^{e1}$, —N($R^{f1}$)S(O)$_2$N$R^{c1} R^{d1}$, or —P(O)$R^{g1} R^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

In one aspect, provided is a compound of Formula (IB):

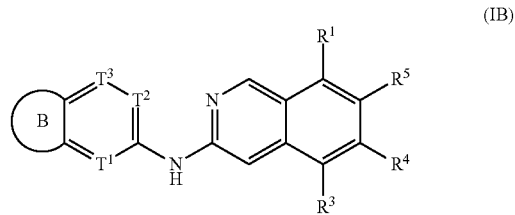

(IB)

or a salt (e.g., a pharmaceutically acceptable salt) thereof, wherein:

$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;

$T^1$, $T^2$ and $T^3$ are independently N or C$R^{23}$;

ring B is a $C_{5-8}$ cycloalkyl or a 5- to 8-membered heterocycle having at least 3 ring-forming carbon atoms and 1, 2 or 3 ring-forming heteroatoms independently selected from the group consisting of N, P, O and S; wherein the $C_{5-8}$ cycloalkyl and the 5- to 8-membered heterocycle are independently optionally substituted with 1, 2, 3, 4 or 5 substituents independently selected from $R^{10}$; and wherein two substituents of the $C_{5-8}$ cycloalkyl or the 5- to 8-membered heterocycle, where present, optionally taken together form a spiro, fused or bridged cycloalkyl (e.g., $C_{3-6}$ cycloalkyl) optionally substituted with 1, 2, 3 or 4 substituents independently selected from $R^{10}$ or a sprio, fused or bridged heterocyclyl (e.g., 3- to 6-membered heterocyclyl) optionally substituted with 1, 2, 3 or 4 substituents independently selected from $R^{10}$;

$R^{23}$ is hydrogen or $R^{10}$;

$R^3$ is hydrogen, halogen, cyano, $C_{1-6}$ alkyl, $C_{3-8}$ cycloalkyl, 3- to 14-membered heterocyclyl, or —O$R^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;

$R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)$R^6$, —C(O)O$R^7$, —C(O)N$R^{8a}R^{8b}$, —O$R^7$, —OC(O)$R^6$, —OC(O)N$R^{8a}R^{8b}$, —S$R^7$, —S(O)$R^9$, —S(O)$_2R^9$, —S(O)$_2$N$R^{8a}R^{8b}$, —P(O)$R^{9a}R^{9b}$, —N$R^{8a}R^{8b}$, —N($R^8$)C(O)$R^6$, —N($R^8$)C(O)O$R^7$, —N($R^8$)C(O)N$R^{8a}R^{8b}$, —N($R^8$)S(O)$_2R^9$, or —N($R^8$)S(O)$_2$N$R^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;

$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)R$^6$, —C(O)OR$^7$, —C(O)NR$^{8a}$R$^{8b}$, —OR$^7$, —OC(O)R$^6$, —OC(O)NR$^{8a}$R$^{8b}$, —SR$^7$, —S(O)R$^9$, —S(O)$_2$R$^9$, —S(O)$_2$NR$^{8a}$R$^{8b}$, —P(O)R$^{9a}$R$^{9b}$, —NR$^{8a}$R$^{8b}$, —N(R$^8$)C(O)R$^6$, —N(R$^8$)C(O)OR$^7$, —N(R$^8$)C(O)NR$^{8a}$R$^{8b}$, —N(R$^8$)S(O)$_2$R$^9$, or —N(R$^8$)S(O)$_2$NR$^{8a}$R$^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of R$^5$ are each optionally substituted with 1, 2, 3, 4 or 5 substituents independently selected from R$^{10}$;

each R$^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of R$^6$ are each optionally substituted with 1, 2, 3, 4 or 5 substituents independently selected from R$^{10}$;

each R$^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of R$^7$ are each optionally substituted with 1, 2, 3, 4 or 5 substituents independently selected from R$^{10}$;

each R$^8$ is independently hydrogen or $C_{1-6}$ alkyl;

each R$^{8a}$ and R$^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of R$^{8a}$ and R$^{8b}$ are each optionally substituted with 1, 2, 3, 4 or 5 substituents independently selected from R$^{10}$;

or R$^{8a}$ and R$^{8b}$ are taken together with the nitrogen atom to which they are attached to form a 4- to 12-membered heterocyclyl optionally substituted with 1, 2, 3, 4 or 5 substituents independently selected from R$^{10}$;

each R$^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of R$^9$ are each optionally substituted with 1, 2, 3, 4 or 5 substituents independently selected from R$^{10}$;

each R$^{9a}$ and R$^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of R$^{9a}$ and R$^{9b}$ are each optionally substituted with 1, 2, 3, 4 or 5 substituents independently selected from R$^{10}$;

or R$^{9a}$ and R$^{9b}$ are taken together with the phosphorus atom to which they are attached to form a 4- to 12-membered heterocyclyl optionally substituted with 1, 2, 3, 4 or 5 substituents independently selected from R$^{10}$;

each R$^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —OC(O)R$^a$, —OC(O)NR$^c$R$^d$, —SR$^b$, —S(O)R$^e$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, —N(R$^f$)S(O)$_2$NR$^c$R$^d$, or —P(O)R$^g$R$^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of R$^{10}$ are each optionally substituted with 1, 2, 3 or 4 substituents independently selected from R$^{11}$;

each R$^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of R$^a$ are each optionally substituted with 1, 2, 3 or 4 substituents independently selected from R$^{11}$;

each R$^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of R$^b$ are each optionally substituted with 1, 2, 3 or 4 substituents independently selected from R$^{11}$;

each R$^c$ and R$^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of R$^c$ and R$^d$ are each optionally substituted with 1, 2, 3 or 4 substituents independently selected from R$^{11}$;

or R$^c$ and R$^d$ are taken together with the nitrogen atom to which they are attached to form a 4- to 12-membered heterocyclyl optionally substituted with 1, 2, 3 or 4 substituents independently selected from R$^{11}$;

each R$^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of R$^e$ are each optionally substituted with 1, 2, 3 or 4 substituents independently selected from R$^{11}$;

each R$^f$ is independently hydrogen or $C_{1-6}$ alkyl;

each R$^g$ and R$^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of R$^g$ and R$^h$ are each optionally substituted with 1, 2, 3 or 4 substituents independently selected from R$^{11}$;

or R$^g$ and R$^h$ are taken together with the phosphorus atom to which they are attached to form a 4- to 12-membered heterocyclyl optionally substituted with 1, 2, 3 or 4 substituents independently selected from R$^{11}$;

each R$^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)R$^{a1}$, —C(O)OR$^{b1}$, —C(O)NR$^{c1}$R$^{d1}$, —OR$^{b1}$, —OC(O)R$^{a1}$, —OC(O)NR$^{c1}$R$^{d1}$, —SR$^{b1}$, —S(O)R$^{e1}$, —S(O)$_2$R$^{e1}$, —S(O)$_2$NR$^{c1}$R$^{d1}$, —NR$^{c1}$R$^{d1}$, —N(R$^{f1}$)C(O)R$^{a1}$, —N(R$^{f1}$)C(O)OR$^{b1}$, —N(R$^{f1}$)C(O)NR$^{c1}$R$^{d1}$, —N(R$^{f1}$)S(O)$_2$R$^{e1}$, —N(R$^{f1}$)S(O)$_2$NR$^{c1}$R$^{d1}$, or —P(O)R$^{g1}$R$^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocylyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_1$-6 alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than Compound Nos. 1x-8x in Table 1X and salts thereof.

In one aspect, provided is a compound of Formula (IC):

(IC)

or a salt (e.g., a pharmaceutically acceptable salt) thereof, wherein:

$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;

$R^2$ is a monocyclic 5- or 6-membered heteroaryl optionally substituted with 1, 2, 3 or 4 substituents independently selected from $R^{10}$;

$R^3$ is hydrogen, halogen, cyano, $C_{1-6}$ alkyl, $C_{3-8}$ cycloalkyl, 3- to 14-membered heterocyclyl, or —O$R^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;

$R^4$ is $C_{1-6}$ alkyl, $C_{2-6}$ alkenyl, $C_{2-6}$ alkynyl, $C_{3-9}$ cycloalkyl, $C_{6-14}$ aryl, 5- to 14-membered heteroaryl, 3- to 14-membered heterocyclyl, halogen, cyano, —C(O)$R^6$, —C(O)O$R^7$, —C(O)N$R^{8a}R^{8b}$, —O$R^7$, —OC(O)$R^6$, —OC(O)N$R^{8a}R^{8b}$, —S$R^7$, —S(O)$R^9$, —S(O)$_2R^9$, —S(O)$_2$N$R^{8a}R^{8b}$, —P(O)$R^{9a}R^{9b}$, —N$R^{8a}R^{8b}$, —N($R^8$)C(O)$R^6$, —N(RI)C(O)O$R^7$, —N($R^8$)C(O)N$R^{8a}R^{8b}$, —N($R^8$)S(O)$_2R^9$, or —N($R^8$)S(O)$_2$N$R^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;

$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)$R^6$, —C(O)O$R^7$, —C(O)N$R^{8a}R^{8b}$, —O$R^7$, —OC(O)$R^6$, —OC(O)N$R^{8a}R^{8b}$, —S$R^7$, —S(O)$R^9$, —S(O)$_2R^9$, —S(O)$_2$N$R^{8a}R^{8b}$, —P(O)$R^{9a}R^{9b}$, —N$R^{8a}R^{8b}$, —N($R^8$)C(O)$R^6$, —N($R^8$)C(O)O$R^7$, —N($R^8$)C(O)N$R^{8a}R^{8b}$, —N($R^8$)S(O)$_2R^9$, or —N($R^8$)S(O)$_2$N$R^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;

each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;

each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;

each $R^8$ is independently hydrogen or $C_{1-6}$ alkyl;

each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;

or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;

each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;

each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;

or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$, —O$R^b$, —OC(O)$R^a$, —OC(O)N$R^cR^d$, —S$R^b$, —S(O)$R^e$, —S(O)$_2R^e$, —S(O)(=NH)$R^e$, —S(O)$_2$N$R^cR^d$, —N$R^cR^d$, —N($R^f$)C(O)$R^a$, —N($R^f$)C(O)O$R^b$, —N($R^f$)C(O)N$R^cR^d$, —N($R^f$)S(O)$_2R^e$, —N($R^f$)S(O)$_2$N$R^cR^d$, or —P(O)$R^gR^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e1}$, —S(O)$_2$N$R^{c1}R^{d1}$, —N$R^{c1}R^{d1}$, —N($R^{f1}$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, —N($R^{f1}$)S(O)$_2$N$R^{c1}R^{d1}$, or —P(O)$R^{g1}R^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^e$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^k$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than Compound Nos. 9x-62x in Table 1X and salts thereof.

In some embodiments, the compound is of Formula (IC), provided that the compound is other than Compound Nos. 9x-63x in Table 1X and salts thereof.

In some embodiments, the compound is of the Formula (I), or variations thereof such as Formula (IA), (IB) and (IC), or a salt (e.g., a pharmaceutically acceptable salt) thereof, wherein $R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen. In some embodiments, $R^1$ is hydrogen, fluoro, chloro, $C_{3-4}$ cycloalkyl, $C_{1-6}$ alkyl, $C_{1-6}$ haloalkyl, —O($C_{1-6}$ alkyl) or —O($C_{1-6}$ haloalkyl). In one variation, $R^1$ is hydrogen, fluoro, chloro, or $C_{1-6}$ alkyl (e.g., methyl). In another variation, $R^1$ is hydrogen, fluoro, or methyl. In another variation, $R^1$ is hydrogen.

In some embodiments, the compound is of the Formula (I), or variations thereof such as Formula (IA), (IB) and (IC), or a salt (e.g., a pharmaceutically acceptable salt) thereof, wherein $R^3$ is hydrogen, halogen, cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$. In some embodiments, $R^3$ is hydrogen, fluoro, chloro, cyano, hydroxyl, $C_{3-4}$ cycloalkyl, $C_{1-6}$ alkyl, $C_{1-6}$ haloalkyl, —O($C_{1-6}$ alkyl) or —O($C_{1-6}$ haloalkyl). In one variation, $R^3$ is hydrogen, fluoro, cyano, or $C_{1-6}$ alkyl (e.g., methyl). In another variation, $R^3$ is hydrogen or fluoro. In another variation, $R^3$ is hydrogen.

In some embodiments, the compound is of the Formula (I), or variations thereof such as Formula (IA), (IB) and (IC), or a salt (e.g., a pharmaceutically acceptable salt) thereof, wherein $R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R^8)C(O)R^6$, —$N(R^8)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$. In some embodiments, $R^5$ is hydrogen, halogen, cyano, $C_{1-6}$ alkyl, $C_{3-8}$ cycloalkyl, 3- to 14-membered heterocyclyl, —$OR^7$, —$NR^{8a}R^{8b}$, or —$N(R^8)C(O)R^6$; wherein the $C_{1-6}$ alkyl, $C_{3-8}$ cycloalkyl and 3- to 14-membered heterocyclyl of $R^5$ are each optionally substituted with 1, 2, 3, 4 or 5 substituents independently selected from $R^{10}$. In some embodiments, $R^5$ is hydrogen, fluoro, chloro, cyano, hydroxyl, $C_{3-4}$ cycloalkyl, $C_{1-6}$ alkyl, $C_{1-6}$ haloalkyl, —O($C_{1-6}$ alkyl) or —O($C_{1-6}$ haloalkyl). In one variation, $R^5$ is hydrogen, fluoro, cyano, or $C_{1-6}$ alkyl. In another variation, $R^5$ is hydrogen, fluoro, or cyano. In another variation, $R^5$ is hydrogen.

It is intended and understood that each and every variation of $R^1$, $R^3$ and $R^5$ described for the Formula (I), (IA), (IB) or (IC) may be combined, the same as if each and every combination is specifically and individually described. For example, in some embodiments, $R^1$ is hydrogen, fluoro, chloro, or $C_{1-6}$ alkyl (e.g., methyl); $R^3$ is hydrogen or fluoro; and $R^5$ is hydrogen, fluoro, or cyano. In one variation, $R^1$ is hydrogen, fluoro, or methyl; $R^3$ is hydrogen; and $R^5$ is hydrogen.

In some embodiments, the compound is of the Formula (I), or variations thereof such as Formula (IA), (IB) and (IC), or a salt (e.g., a pharmaceutically acceptable salt) thereof, wherein $R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R^8)C(O)R^6$, —$N(RI)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

In some embodiments, $R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —$C(O)R^6$, —$C(O)OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R^8)C(O)R^6$, —$N(R^8)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

In some embodiments, $R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, cyano, —$C(O)R^6$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R^8)C(O)R^6$, —$N(R^8)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

In some embodiments, $R^4$ is

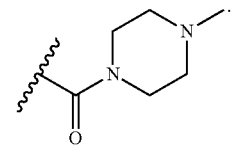 [SMILES: *C(=O)N1CCN(C)CC1]

In some embodiments, $R^4$ is $C_{3-8}$ cycloalkyl, $C_{6-14}$ aryl, 5- to 14-membered heteroaryl or 3- to 14-membered heterocyclyl; wherein the $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

In some embodiments, $R^4$ is $C_{6-10}$ aryl, 5- to 10-membered heteroaryl or 5- to 6-membered heterocyclyl; wherein the $C_{6-10}$ aryl, 5- to 10-membered heteroaryl and 5- to 6-membered heterocyclyl of $R^4$ are each optionally substituted with 1, 2, 3, 4 or 5 substituents independently selected from $R^{10}$.

In some embodiments, $R^4$ is

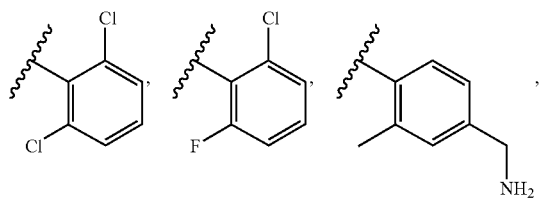

-continued

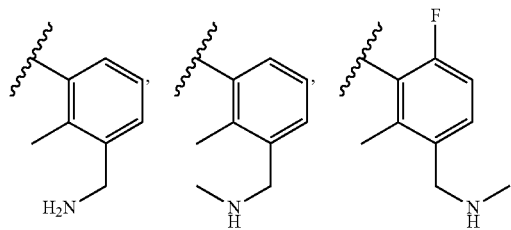

In some embodiments, $R^4$ is

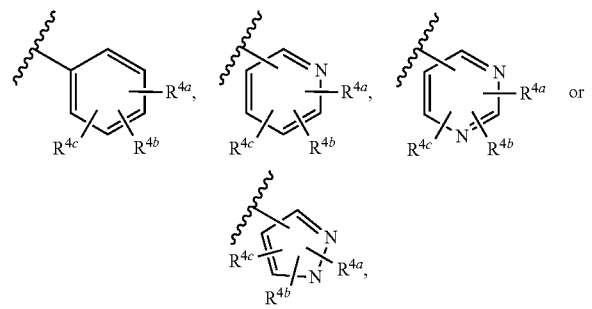

wherein the wavy line represents the attachment point to the parent structure, $R^{4a}$, $R^{4b}$ and $R^{4c}$ are each independently hydrogen or $R^{10}$, or two vicinal $R^{4(a-c)}$ are taken together with the atoms to which they are attached form a fused 5- or 6-membered heteroaryl optionally substituted with 1, 2, 3 or 4 substituents independently selected from $R^{10}$ or a fused 5- or 6-membered heterocyclyl optionally substituted with 1, 2, 3 or 4 substituents independently selected from $R^{10}$.

In one variation, $R^4$ is

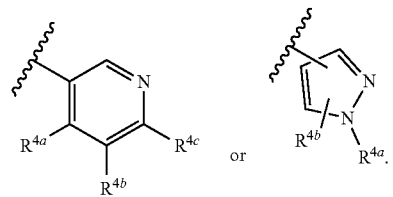

In one variation, $R^4$ is 5- to 10-membered heteroaryl optionally substituted with 1, 2, 3, 4 or 5 substituents independently selected from $R^{10}$.

In some embodiments, $R^4$ is

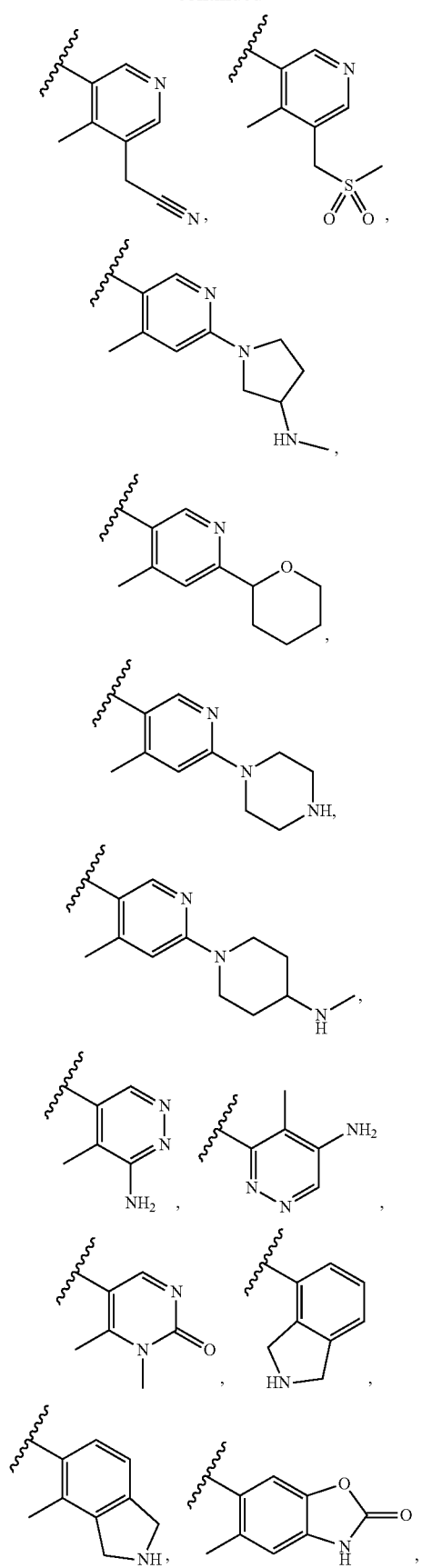
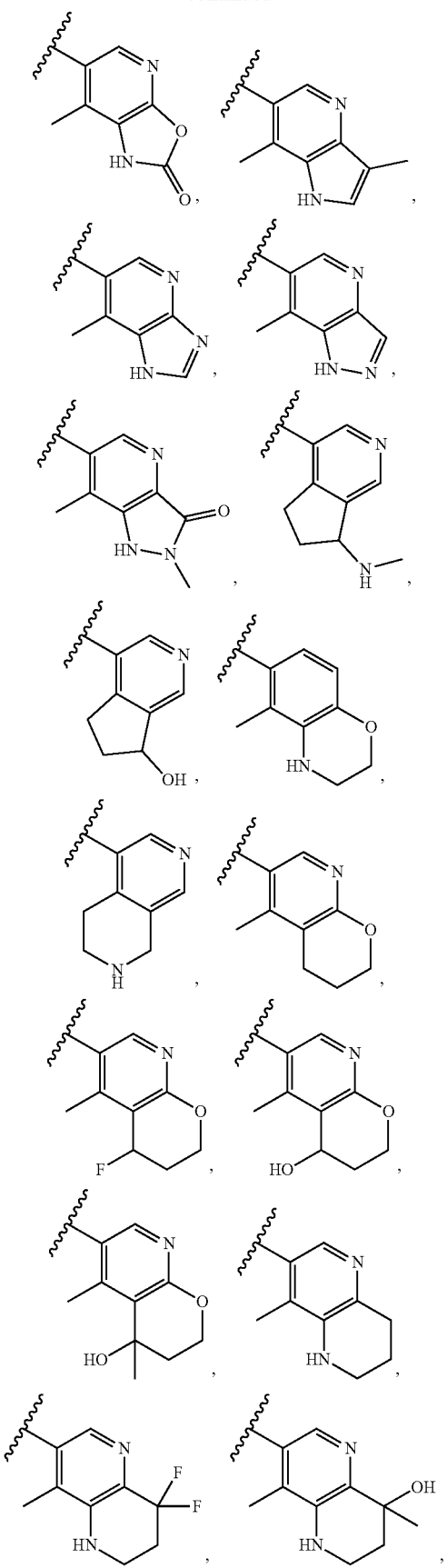

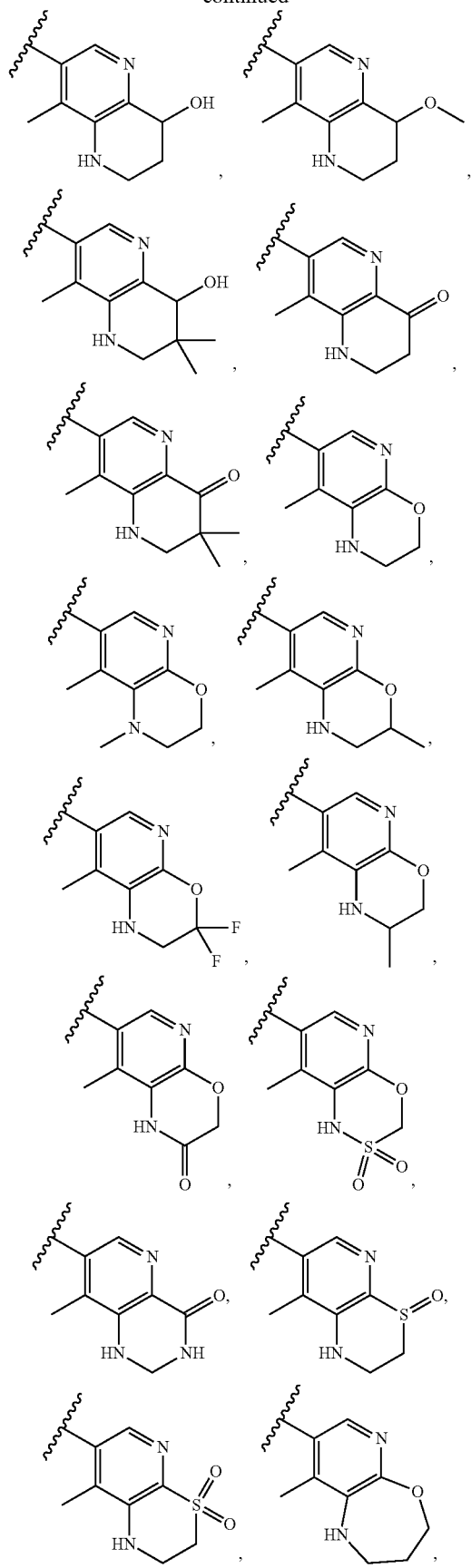
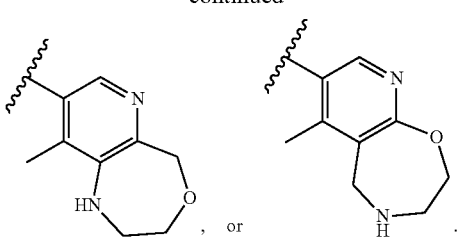
In one variation, $R^4$ is
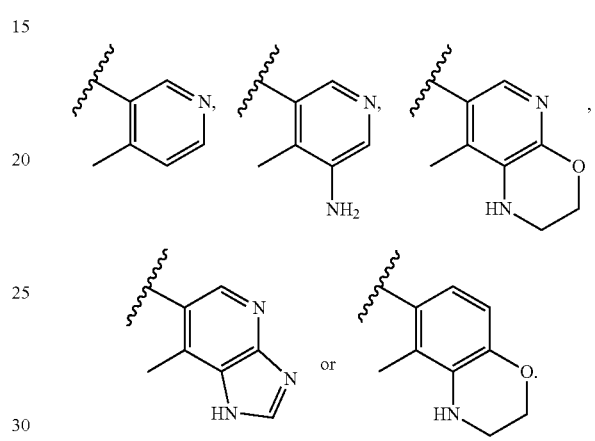
In another variation, R is selected from the group consisting of:
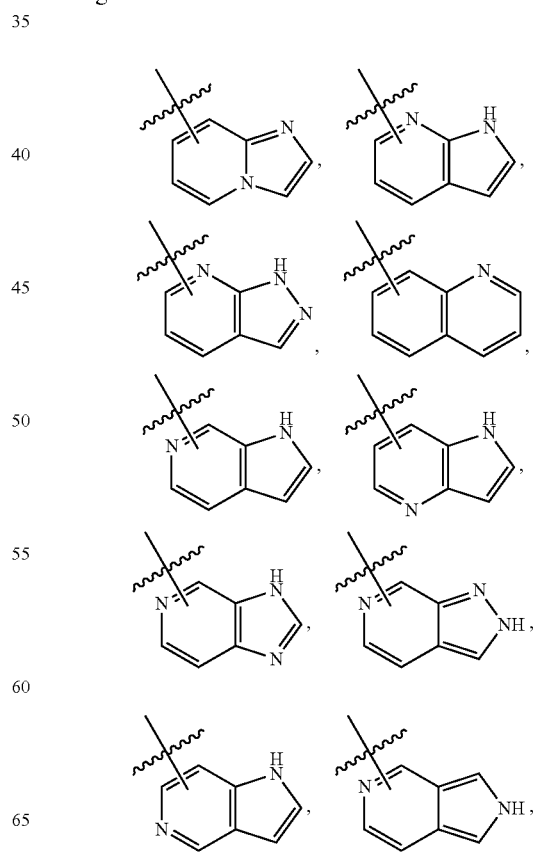

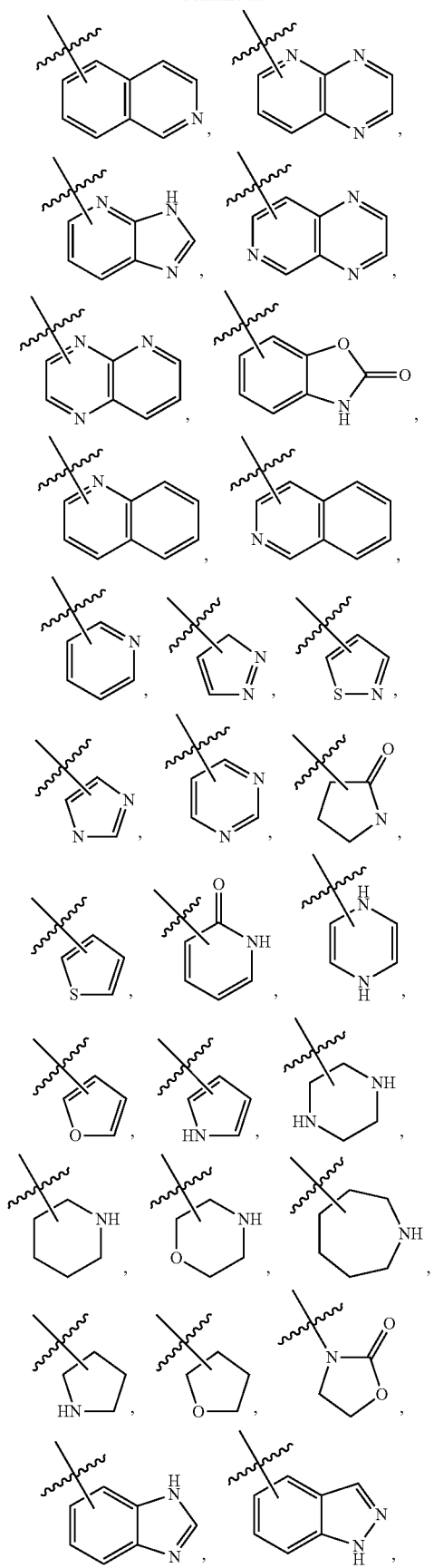
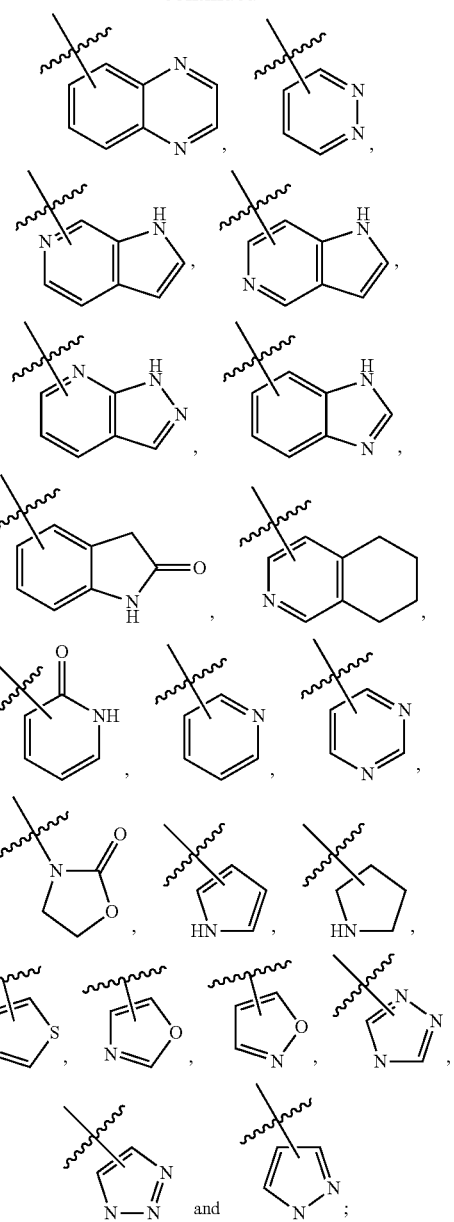

each of which can be optionally substituted with 1, 2, 3, 4 or 5 substituents independently selected from $R^{10}$.

It is intended and understood that each and every variation of $R^1$, $R^3$ and $R^5$, or a combination thereof, described for the Formula (I), (IA), (IB) or (IC) may be combined with each and every variation of $R^4$ described for the Formula (I), (IA), (IB) or (IC), the same as if each and every combination is specifically and individually described. For example, in some embodiments, $R^1$ is hydrogen, fluoro, chloro, or $C_{1-6}$ alkyl (e.g., methyl); $R^3$ is hydrogen or fluoro; $R^5$ is hydrogen, fluoro, or cyano; and $R^4$ is $C_{6-10}$ aryl, 5- to 10-membered heteroaryl or 5- to 6-membered heterocyclyl; wherein the $C_{6-10}$ aryl, 5- to 10-membered heteroaryl and 5- to 6-membered heterocyclyl of $R^4$ are each optionally substituted with 1, 2, 3, 4 or 5 substituents independently selected from $R^{10}$. In one variation, $R^1$ is hydrogen, fluoro, or methyl; $R^3$ is hydrogen; $R^5$ is hydrogen; and $R^4$ is

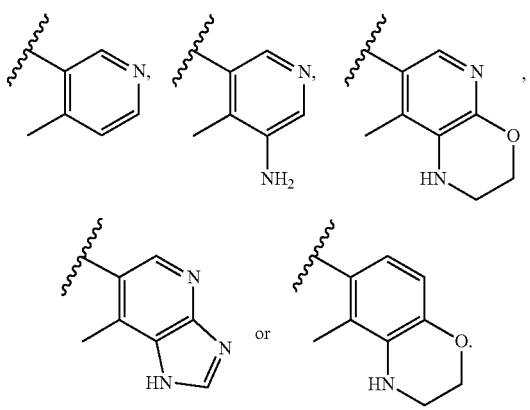

In some embodiments, the compound is of the Formula (I), or variations thereof such as Formula (IA), (IB) and (IC) where applicable, or a salt (e.g., a pharmaceutically acceptable salt) thereof, wherein $R^2$ is a 5- to 14-membered heteroaryl optionally substituted with $R^{10}$. In some embodiments, $R^2$ is a monocyclic 5- or 6-membered heteroaryl optionally substituted with 1, 2, 3 or 4 substituents independently selected from $R^{10}$. In some embodiments, $R^2$ is a polycyclic heteroaryl having the formula (a) or (b):

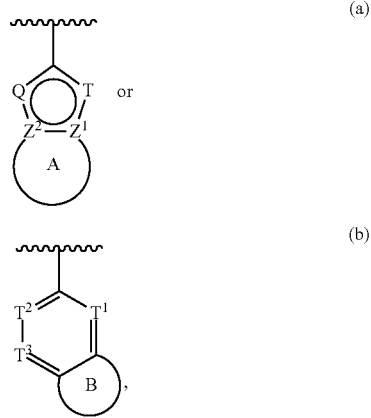

wherein the wavy line represents the attachment point to the parent structure.

In some embodiments, the compound is of the Formula (I), or a salt (e.g., a pharmaceutically acceptable salt) thereof, wherein $R^2$ is a polycyclic heteroaryl having the formula (a):

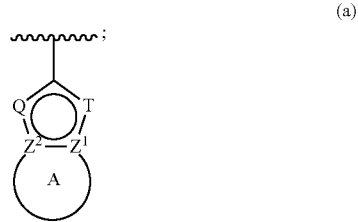

or the compound is of the Formula (IA):

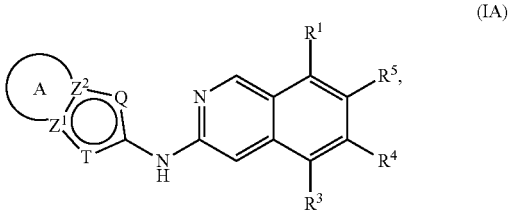

or a salt (e.g., a pharmaceutically acceptable salt) thereof, wherein Q, T, $Z^1$, $Z^2$ and ring A are as described herein.

In some embodiments, Q is $CR^{20}$, $NR^{21}$, N, O or S; T is N or $CR^{22}$; $Z^1$ and $Z^2$ are independently N or C, provided at least one of $Z^1$ and $Z^2$ is C; ring A is a 5- to 8-membered heterocycle having at least 3 ring-forming carbon atoms and 1, 2 or 3 ring-forming heteroatoms independently selected from the group consisting of N, P, O and S, wherein the 5- to 8-membered heterocycle is optionally substituted with 1, 2, 3, 4 or 5 substituents independently selected from $R^{10}$, and two germinal substituents of the 5- to 8-membered heterocycle, where present, optionally taken together with the atom to which they are attached form a spiro $C_{3-6}$ cycloalkyl optionally substituted with 1, 2, 3 or 4 substituents independently selected from $R^{10}$ or a sprio 3- to 6-membered heterocyclyl optionally substituted with 1, 2, 3 or 4 substituents independently selected from $R^{10}$, or two vicinal substituents of the 5- to 8-membered heterocycle, where present, optionally taken together with the atoms to which they are attached form a fused 5- or 6-membered heteroaryl optionally substituted with 1, 2, 3 or 4 substituents independently selected from $R^{10}$ or a fused 5- or 6-membered heterocyclyl optionally substituted with 1, 2, 3 or 4 substituents independently selected from $R^{10}$; and $R^{20}$, $R^{21}$ and $R^{22}$ are each independently hydrogen or $R^{10}$. In one variation, $R^{20}$, $R^{21}$ and $R^{22}$ are each independently hydrogen, halogen, hydroxyl, —O($C_{1-6}$ alkyl), cyano, $C_{1-6}$ alkyl or $C_{1-6}$ haloalkyl.

In some embodiments, Q is $CR^{20}$. In some embodiments, Q is $NR^{21}$, O or S. In some embodiments, Q is $NR^{21}$. In some embodiments, Q is S. In some embodiments, T is N. In some embodiments, T is $NR^{22}$. In some embodiments, $Z^1$ is N and $Z^2$ is C. In some embodiments, $Z^1$ is C and $Z^2$ is C. In some embodiments, $Z^1$ is C and $Z^2$ is N. In one variation, Q is $CR^{20}$; T is N; $Z^1$ is N and $Z^2$ is C. In some embodiments, Q is $NR^{21}$; T is N; $Z^1$ is C and $Z^2$ is C. In some embodiments, Q is S; T is N; $Z^1$ is C and $Z^2$ is C. In one variation, $R^{20}$, $R^{21}$ and $R^{22}$ are each independently hydrogen, halogen, hydroxyl, —O($C_{1-6}$ alkyl), cyano, $C_{1-6}$ alkyl (e.g., methyl), or $C_{1-6}$ haloalkyl (e.g., —$CF_3$). In one variation, $R^{20}$ is hydrogen or methyl. In one variation, $R^{20}$ is hydrogen. In one variation, $R^{21}$ is hydrogen. In one variation, $R^{22}$ is hydrogen.

In some of these embodiments, $R^2$ in the Formula (I) or the moiety of formula (a) in the Formula (IA) is:

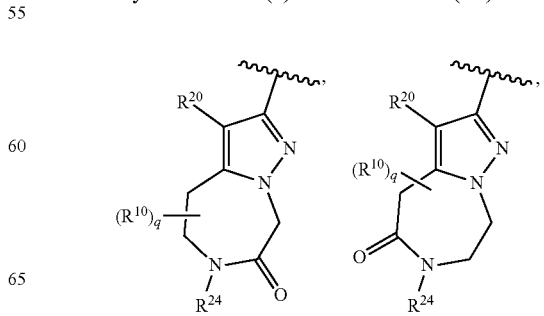

-continued

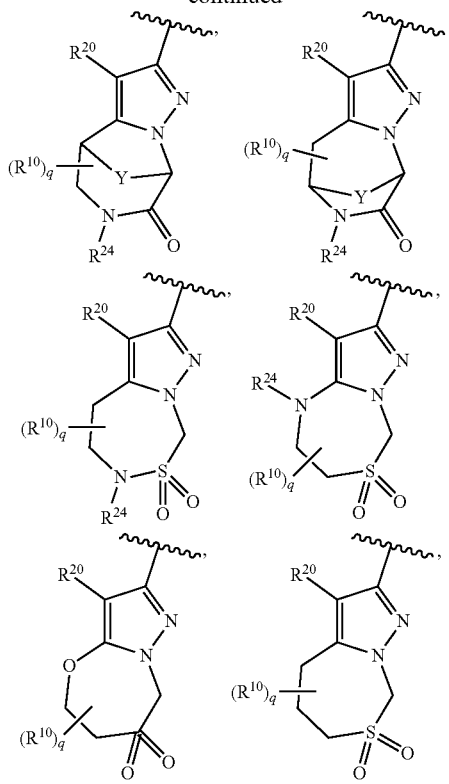

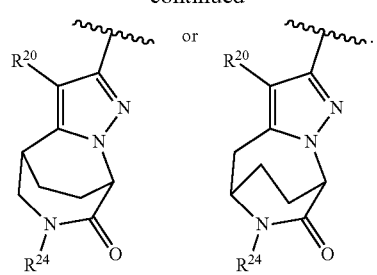

In one such variation, $R^{24}$ is independently hydrogen or $C_{1-6}$ alkyl; and $R^{20}$ is hydrogen. In one such variation, $R^{24}$ is hydrogen.

In some embodiments, $R^2$ in the Formula (I) or the moiety of formula (a) in the Formula (IA) is:

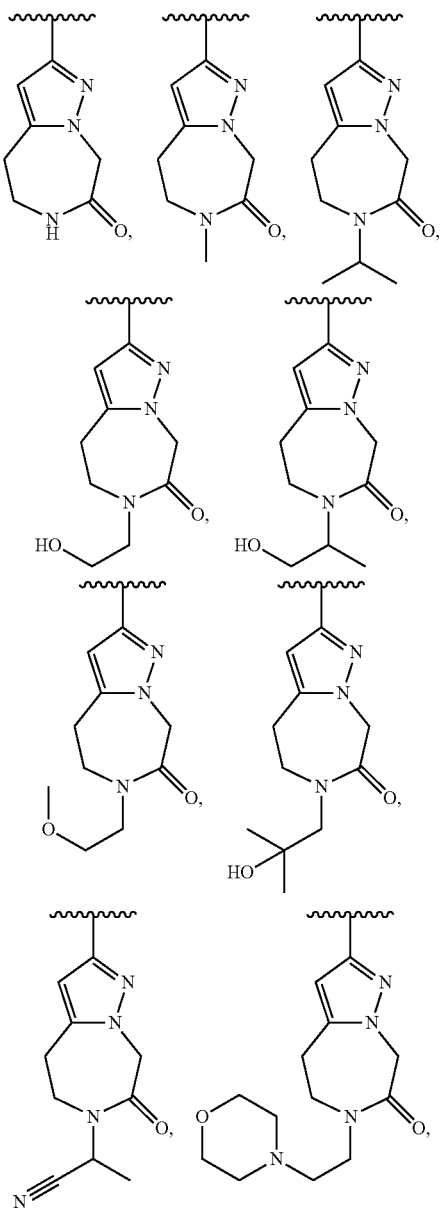

wherein q is 0, 1, 2, 3, 4, 5 or 6; $R^{24}$ is independently hydrogen or $R^{10}$; Y is $C_{1-4}$ alkylene wherein optionally one or more of the carbon atoms of the $C_{1-4}$ alkylene are replaced by a heteroatom selected from oxygen, sulfur and nitrogen, and the $C_{1-4}$ alkylene is optionally substituted with $R^{10}$; and $R^{10}$ and $R^{20}$ are as detailed herein. In some embodiments, two of the $R^{10}$ substituents optionally taken together form a spiro, fused or bridged cycloalkyl (e.g., $C_{3-6}$ cycloalkyl) optionally substituted with 1, 2, 3 or 4 substituents independently selected from $R^{11}$ or a sprio, fused or bridged heterocyclyl (e.g., 3- to 6-membered heterocyclyl) optionally substituted with 1, 2, 3 or 4 substituents independently selected from $R^{11}$. In one variation, $R^{24}$ is independently hydrogen or $C_{1-6}$ alkyl; and $R^{20}$ is hydrogen. In one variation, $R^{24}$ is hydrogen.

In one variation, Y is $C_{1-4}$ alkylene optionally substituted with $R^{10}$. In one variation, $R^2$ in the Formula (I) or the moiety of formula (a) in the Formula (IA) is:

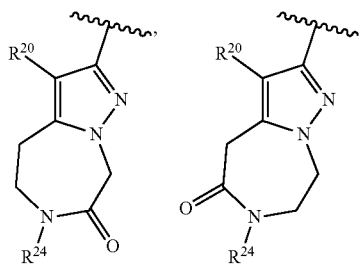

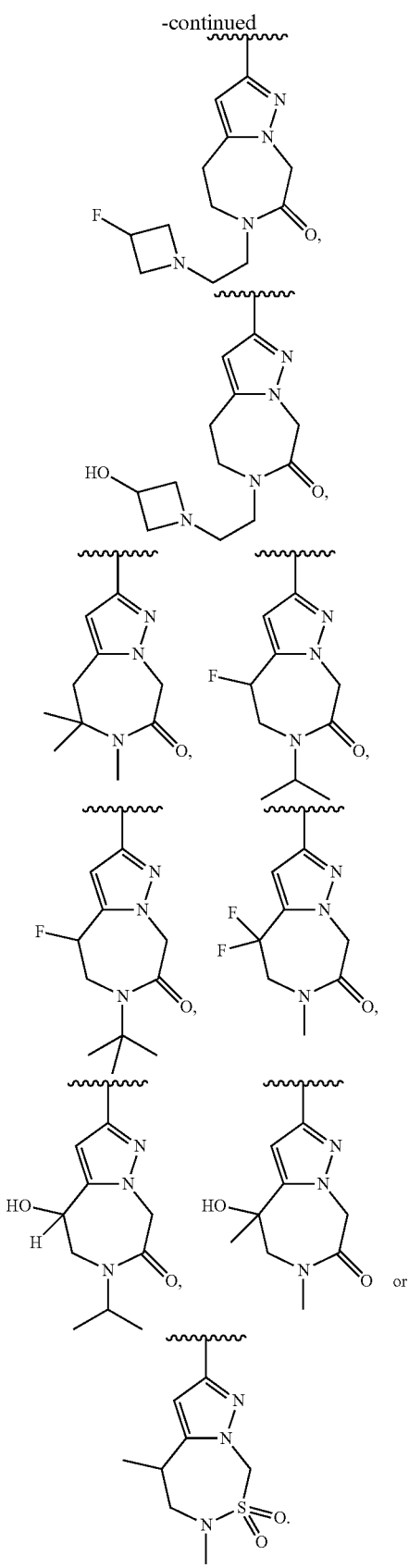

In some of these embodiments, R² in the Formula (I) or the moiety of formula (a) in the Formula (IA) is:

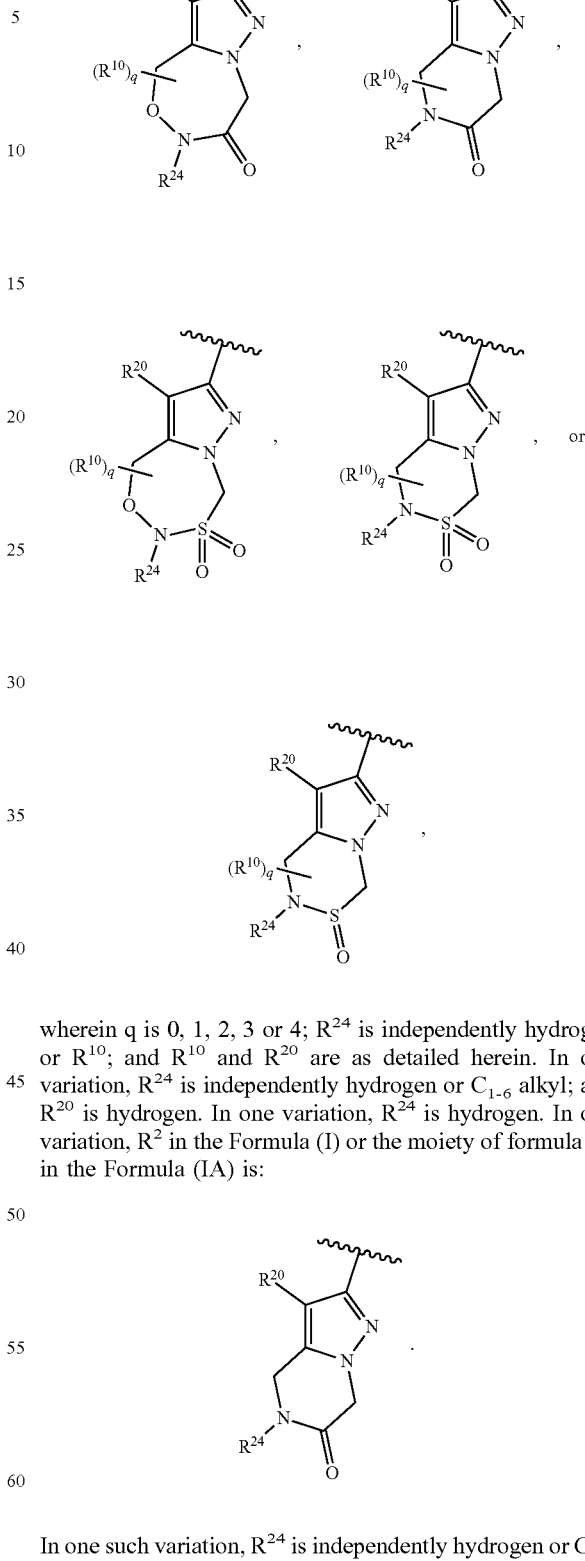

wherein q is 0, 1, 2, 3 or 4; $R^{24}$ is independently hydrogen or $R^{10}$; and $R^{10}$ and $R^{20}$ are as detailed herein. In one variation, $R^{24}$ is independently hydrogen or $C_{1-6}$ alkyl; and $R^{20}$ is hydrogen. In one variation, $R^{24}$ is hydrogen. In one variation, $R^2$ in the Formula (I) or the moiety of formula (a) in the Formula (IA) is:

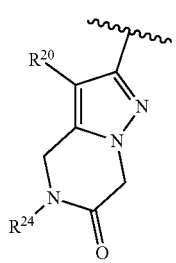

In one such variation, $R^{24}$ is independently hydrogen or $C_{1-6}$ alkyl; and $R^{20}$ is hydrogen. In one such variation, $R^{24}$ is hydrogen.

In some embodiments $R^2$ in the Formula (I) or the moiety of formula (a) in the Formula (IA) is:

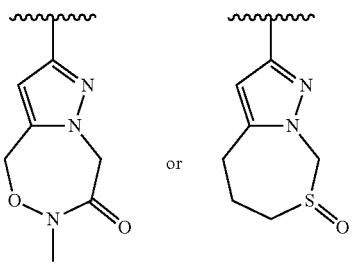 or ,

In some of these embodiments, $R^2$ in the Formula (I) or the moiety of formula (a) in the Formula (IA) is:

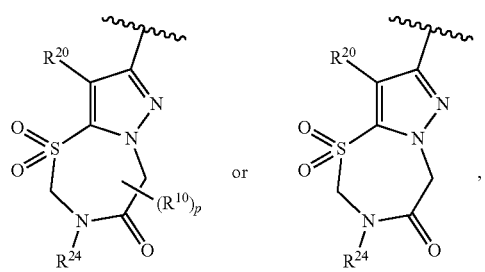

wherein p is 0, 1, 2, 3 or 4; $R^{24}$ is independently hydrogen or $R^{10}$; and $R^{10}$ and $R^{20}$ are as detailed herein. In one variation, $R^{24}$ is independently hydrogen or $C_{1-6}$ alkyl; and $R^{20}$ is hydrogen.

In some of these embodiments, $R^2$ in the Formula (I) or the moiety of formula (a) in the Formula (IA) is:

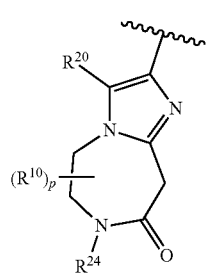

wherein p is 0, 1, 2, 3 or 4; $R^{24}$ is independently hydrogen or $R^{10}$; and $R^{10}$ and $R^{20}$ are as detailed herein. In one variation, $R^{24}$ is independently hydrogen or $C_{1-6}$ alkyl; and $R^{20}$ is hydrogen.

In some embodiments, $R^2$ in the Formula (I) or the moiety of formula (a) in the Formula (IA) is

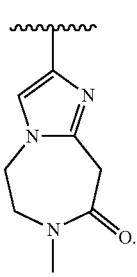 [SMILES: *c1cn2c(n1)CC(=O)N(C)CC2]

In some of these embodiments, $R^2$ in the Formula (I) or the moiety of formula (a) in the Formula (IA) is:

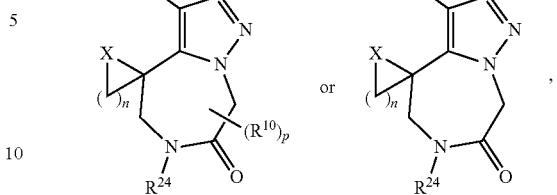

wherein X is $CH_2$, N, O or S; n is 1, 2, 3 or 4; p is 0, 1, 2, 3 or 4; $R^{24}$ is hydrogen or $R^{10}$; and $R^{10}$ and $R^{20}$ are as detailed herein. In one variation, $R^{24}$ is independently hydrogen or $C_{1-6}$ alkyl; and $R^{20}$ is hydrogen.

In some of these embodiments, $R^2$ in the Formula (I) or the moiety of formula (a) in the Formula (IA) is:

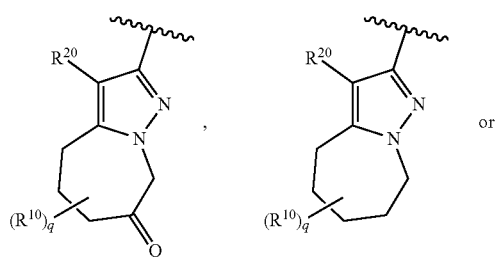

wherein q is 0, 1, 2, 3, 4, 5 or 6; and $R^{10}$ and $R^{20}$ are as detailed herein. In one variation, $R^{20}$ is hydrogen.

In some embodiments, $R^2$ in the Formula (I) or the moiety of formula (a) in the Formula (IA) is

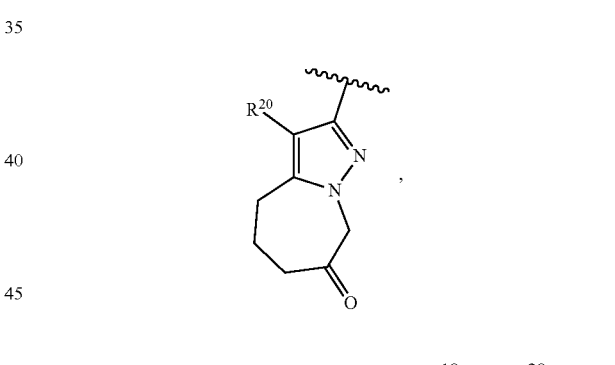

In some of these embodiments, $R^2$ in the Formula (I) or the moiety of formula (a) in the Formula (IA) is:

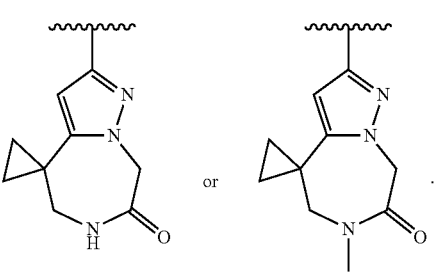

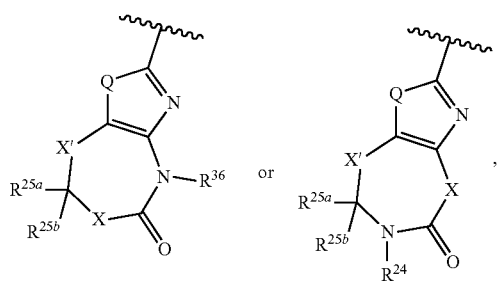

wherein Q is $NR^{21}$, O or S;
X is $CR^{26a}R^{26b}$, $NR^{24}$, O or S,
X' is $CR^{27a}R^{27b}$, $NR^{24}$, O, S or $S(O)_2$,
$R^{24}$, $R^{25a}$, $R^{25b}$, $R^{26a}$ and $R^{26b}$ are independently hydrogen or $R^{10}$.
$R^{27a}$ and $R^{27b}$ are independently hydrogen or $R^{10}$, or $R^{27a}$ and $R^{27b}$ are taken together with the carbon atom to which they are attached to form a $C_{3-8}$ cycloalkyl or 3- to 8-membered heterocyclyl; and
$R^{10}$ and $R^{21}$ are as detailed herein.

In one variation, $R^2$ in the Formula (I) or the moiety of formula (a) in the Formula (IA) is:

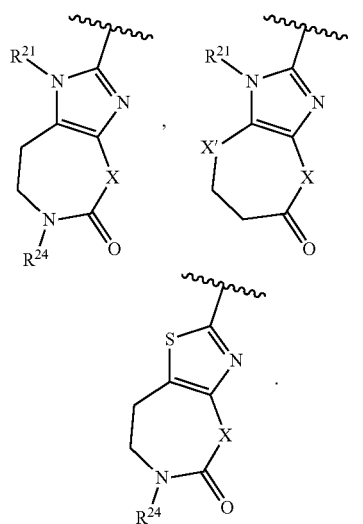

In one such variation, $R^{24}$, where present, is independently hydrogen or $C_{1-6}$ alkyl; and $R^{21}$ where present, is hydrogen.

In some of these embodiments, $R^2$ in the Formula (I) or the moiety of formula (a) in the Formula (IA) is:

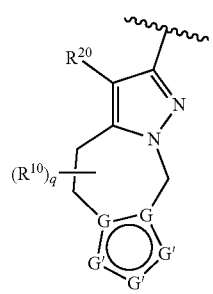

wherein q is 0, 1, 2, 3, 4, 5 or 6;
G is independently C or N;
G' is independently N, $NR^{28}$, $CR^{29}$, S or O;
$R^{28}$ and $R^{29}$ are independently hydrogen or $R^{11}$; or two vicinal groups $R^{28}$ and $R^{29}$ are taken together to form a 5- to 6-membered heterocyclyl; and
$R^{10}$, $R^{11}$ and $R^{20}$ are as detailed herein.

In one variation, $R^2$ in the Formula (I) or the moiety of formula (a) in the Formula (IA) is:

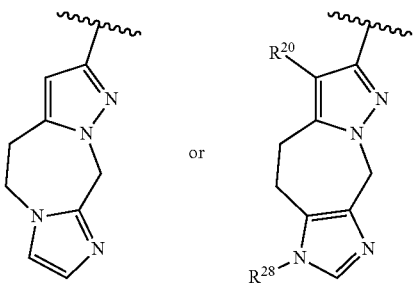

In one variation, $R^2$ in the Formula (I) or the moiety of formula (a) in the Formula (IA) is:

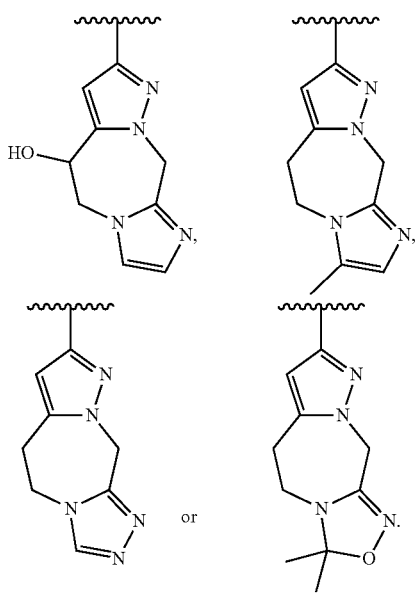

In one such variation, $R^{28}$ is independently hydrogen or $C_{1-6}$ alkyl; and $R^{20}$ is hydrogen.

In some embodiments, the compound is of the Formula (I), or a salt (e.g., a pharmaceutically acceptable salt) thereof, wherein $R^2$ is a polycyclic heteroaryl having the formula (b):

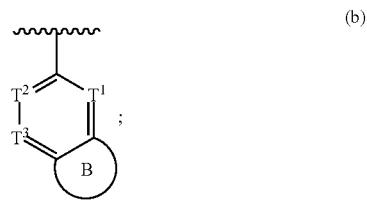

(b)

or the compound is of the Formula (IB):

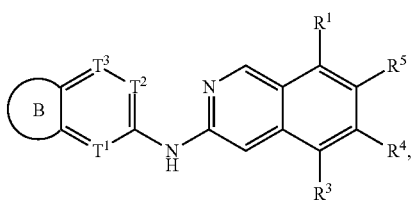

(IB)

or a salt (e.g., a pharmaceutically acceptable salt) thereof, wherein $T^1$, $T^2$, $T^3$, and ring B are as described herein.

In some embodiments, $T^1$, $T^2$ and $T^3$ are independently N or $CR^{23}$; ring B is a 5- to 8-membered heterocycle having at least 3 ring-forming carbon atoms and 1, 2 or 3 ring-forming heteroatoms independently selected from the group consisting of N, P, O and S, wherein the 5- to 8-membered heterocycle is optionally substituted with 1, 2, 3, 4 or 5 substituents independently selected from $R^{10}$, and two geminal substituents of the 5- to 8-membered heterocycle, where present, optionally taken together with the atom to which they are attached form a spiro $C_{3-6}$ cycloalkyl optionally substituted with 1, 2, 3 or 4 substituents independently selected from $R^{10}$ or a sprio 3- to 6-membered heterocyclyl optionally substituted with 1, 2, 3 or 4 substituents independently selected from $R^{10}$, or two vicinal substituents of the 5- to 8-membered heterocycle, where present, optionally taken together with the atoms to which they are attached form a fused 5- or 6-membered heteroaryl optionally substituted with 1, 2, 3 or 4 substituents independently selected from $R^{10}$ or a fused 5- or 6-membered heterocyclyl optionally substituted with 1, 2, 3 or 4 substituents independently selected from $R^{10}$; and $R^{23}$ is hydrogen or $R^{10}$. In one variation, at least one of $T^1$, $T^2$ and $T^3$ is N. In one variation, $R^{23}$ is hydrogen, halogen, hydroxyl, —O($C_{1-6}$ alkyl), cyano, $C_{1-6}$ alkyl or $C_{1-6}$ haloalkyl.

In some embodiments, at least one of $T^1$, $T^2$ and $T^3$ is N. In some embodiments, one of $T^1$, $T^2$ and $T^3$ is N; and the remaining two of $T^1$, $T^2$ and $T^3$ are independently $CR^{23}$. In some embodiments, $T^1$ is N, and $T^2$ and $T^3$ are independently $CR^{23}$. In some embodiments, $T^2$ is N, and $T^1$ and $T^3$ are independently $CR^{23}$. In some embodiments, $T^3$ is N, and $T^1$ and $T^2$ are independently $CR^{23}$. In some embodiments, one of $T^1$, $T^2$ and $T^3$ is $CR^{23}$; and the remaining two of $T^1$, $T^2$ and $T^3$ are N. In some embodiments, $T^1$ and $T^2$ are N; and $T^3$ is $CR^{23}$. In some embodiments, $T^1$ and $T^3$ are N; and $T^2$ is $CR^{23}$. In one variation, $R^{23}$ is hydrogen, halogen, hydroxyl, —O($C_{1-6}$ alkyl), cyano, $C_{1-6}$ alkyl (e.g., methyl), or $C_{1-6}$ haloalkyl (e.g., —$CF_3$). In one variation, $R^{23}$ is hydrogen or methyl. In one variation, $R^{23}$ is hydroxyl. In one variation, $R^{23}$ is hydrogen.

In some of these embodiments, $R^2$ in the Formula (I) or the moiety of formula (b) in the Formula (IB) is:

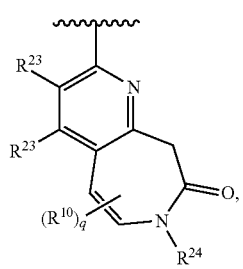

wherein q is 0, 1, 2, 3 or 4; and $R^{10}$, $R^{23}$ and $R^{24}$ are as detailed herein. In one variation, each $R^{23}$ is hydrogen and $R^{24}$ is hydrogen or $C_{1-6}$ alkyl (e.g., methyl). In one variation, $R^2$ in the Formula (I) or the moiety of formula (b) in the Formula (IB) is:

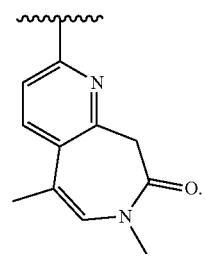 [SMILES: *c1ccc2c(n1)CC(=O)N(C)C=C2C]

In some embodiments, the compound is of the Formula (I) or (IC):

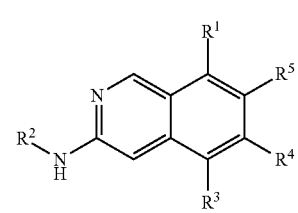

(IC)

or a salt (e.g., a pharmaceutically acceptable salt) thereof, wherein $R^2$ is a monocyclic 5- or 6-membered heteroaryl optionally substituted with 1, 2, 3 or 4 substituents independently selected from $R^{10}$.

In some of these embodiments, $R^2$ is a 5-membered heteroaryl optionally substituted with 1, 2, 3 or 4 substituents independently selected from $R^{10}$. In some of these embodiments, $R^2$ is a 6-membered heteroaryl optionally substituted with 1, 2, 3 or 4 substituents independently selected from $R^{10}$.

In some of these embodiments, $R^2$ is

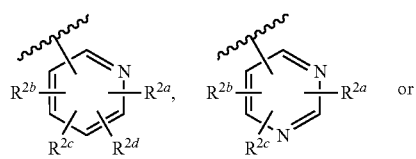

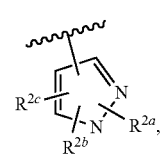

wherein the wavy line represents the attachment point to the parent structure, and $R^{2a}$, $R^{2b}$, $R^{2c}$ and $R^{2d}$ are each independently hydrogen or $R^{10}$. In one variation, $R^2$ is

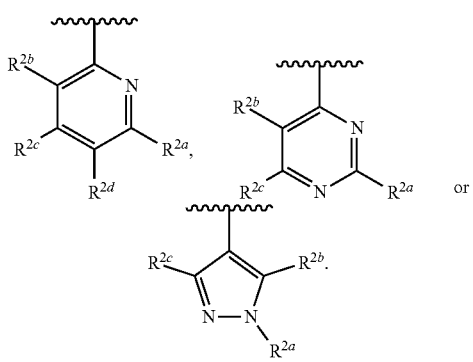

In some embodiments, $R^{2a}$, $R^{2b}$, $R^{2c}$ and $R^{2d}$ (where present) are each independently hydrogen; $C_{1-6}$ alkyl optionally substituted with 1, 2, 3 or 4 substituents independently selected from $R^{11}$; $C_{3-8}$ cycloalkyl optionally substituted with 1, 2, 3 or 4 substituents independently selected from $R^{11}$; or 3- to 14-membered heterocyclyl optionally substituted with 1, 2, 3 or 4 substituents independently selected from $R^1$. In some embodiments, $R^{2a}$, $R^{2b}$, $R^{2c}$ and $R^{2d}$ (where present) are each independently hydrogen or $C_{1-6}$ alkyl optionally substituted with 1, 2, 3 or 4 substituents independently selected from halogen and cyano [e.g., methyl, ethyl, difluoromethyl, or 1-cyanoethyl]. In some embodiments, $R^{2a}$, $R^{2b}$, $R^{2c}$ and $R^{2d}$ (where present) are each independently hydrogen or $C_{1-6}$ alkyl optionally substituted with 3- to 14-membered heterocyclyl with is optionally substituted with $C_{1-6}$ alkyl [e.g., (1-methylpyrrolidin-3-yl)methyl]. In some embodiments, $R^{2a}$, $R^{2b}$, $R^{2c}$ and $R^{2d}$ (where present) are each independently hydrogen or 3- to 14-membered heterocyclyl [e.g., tetrahydrofuran-3-yl]optionally substituted with 1, 2, 3 or 4 substituents independently selected from R.

In some embodiments, $R^2$ is or F

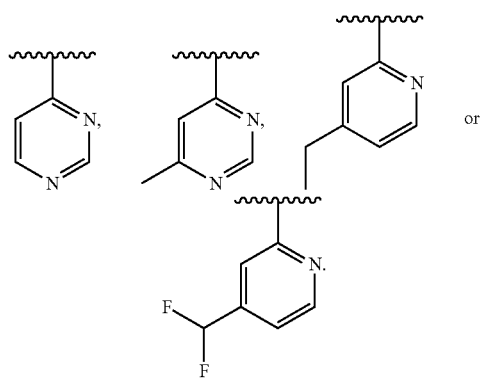

In some embodiments, $R^2$ is or

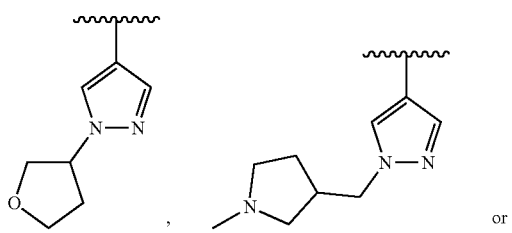

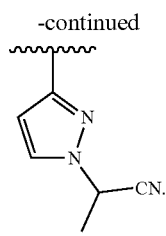

In some embodiments of the compounds of the Formula (IC), $R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, cyano, —C(O)R$^6$, —OC(O)R$^6$, —OC(O)NR$^{8a}$R$^{8b}$, —SR$^7$, —S(O)R$^9$, —S(O)$_2$R$^9$, —S(O)$_2$NR$^{8a}$R$^{8b}$, —NR$^{8a}$R$^{8b}$, —N(R$^8$)C(O)R$^6$, —N(R$^8$)C(O)OR$^7$, —N(R$^8$)C(O)NR$^{8a}$R$^{8b}$, —N(R$^8$)S(O)$_2$R$^9$, or —N(R$^8$)S(O)$_2$NR$^{8a}$R$^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$. In one variation, $R^4$ is $C_{3-8}$ cycloalkyl, $C_{6-14}$ aryl, 5- to 14-membered heteroaryl or 3- to 14-membered heterocyclyl; wherein the $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

It is intended and understood that each and every variation of $R^1$, $R^3$, $R^4$ and $R^5$, or a combination thereof, described for the Formula (I), (IA), (IB) or (IC) may be combined with each and every variation of $R^2$ described for the Formula (I), or the Formula (IA), (IB) or (IC) where applicable, the same as if each and every combination is specifically and individually described. For example, in some embodiments, $R^1$ is hydrogen, fluoro, chloro, or $C_{1-6}$ alkyl (e.g., methyl); $R^3$ is hydrogen or fluoro; $R^5$ is hydrogen, fluoro, or cyano; $R^4$ is $C_{6-10}$ aryl, 5- to 10-membered heteroaryl or 5- to 6-membered heterocyclyl; wherein the $C_{6-10}$ aryl, 5- to 10-membered heteroaryl and 5- to 6-membered heterocyclyl of $R^4$ are each optionally substituted with 1, 2, 3, 4 or 5 substituents independently selected from $R^{10}$; and $R^2$ is of the formula (a) wherein Q is CR$^{20}$; T is N; $Z^1$ is N; $Z^2$ is C; and ring A is as detailed herein. In one variation, $R^1$ is hydrogen, fluoro, or methyl; $R^3$ is hydrogen; $R^5$ is hydrogen; $R^4$ is

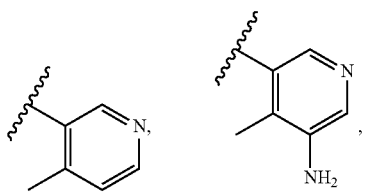

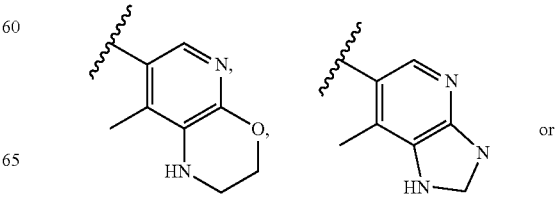

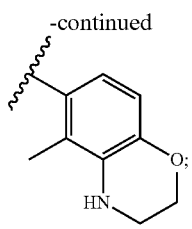

and R² is of the formula (a) wherein Q is CH; T is N; Z¹ is N and Z² is C.

In some embodiments of the compound of the Formula (I), or variations thereof such as Formula (IA), (IB) and (IC) where applicable, or a salt (e.g., a pharmaceutically acceptable salt) thereof, each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$. In one variation, $R^6$ is $C_{1-6}$ alkyl, $C_{3-8}$ cycloalkyl, or 3- to 12-membered heterocyclyl; wherein the $C_{1-6}$ alkyl, $C_{3-8}$ cycloalkyl, and 3- to 12-membered heterocyclyl of $R^6$ are each optionally substituted with 1, 2, 3, 4 or 5 substituents independently selected from $R^{10}$. In one variation, $R^6$ is 3- to 12-membered heterocyclyl optionally substituted with 1, 2, 3, 4 or 5 substituents independently selected from $R^{10}$ [e.g., 4-methylpiperazin-1-yl].

In some embodiments of the compound of the Formula (I), or variations thereof such as Formula (IA), (IB) and (IC) where applicable, or a salt (e.g., a pharmaceutically acceptable salt) thereof, each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$. In one variation, $R^7$ is hydrogen, $C_{1-6}$ alkyl optionally substituted with $R^{10}$. In one variation, $R^7$ is 3- to 12-membered heterocyclyl [e.g., piperidin-4-yl].

In some embodiments of the compound of the Formula (I), or variations thereof such as Formula (IA), (IB) and (IC) where applicable, or a salt (e.g., a pharmaceutically acceptable salt) thereof, each $R^8$ is independently hydrogen or $C_{1-6}$ alkyl; and each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$; or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$. In one variation, $R^8$ is hydrogen or $C_{1-6}$ alkyl (e.g., methyl). In one variation, each $R^{8a}$ and $R^{8b}$ is independently hydrogen or $C_{1-6}$ alkyl. In one variation, $R^{8a}$ and $R^{8b}$ are taken together with the nitrogen atom to which they are attached to form a 5- to 7-membered heterocyclyl optionally substituted with $R^{10}$.

In some embodiments of the compound of the Formula (I), or variations thereof such as Formula (IA), (IB) and (IC) where applicable, or a salt (e.g., a pharmaceutically acceptable salt) thereof, each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$. In one variation, $R^9$ is $C_{1-6}$ alkyl optionally substituted with $R^{10}$; or $C_{6-10}$ aryl optionally substituted with $R^{10}$.

In some embodiments of the compound of the Formula (I), or variations thereof such as Formula (IA), (IB) and (IC) where applicable, or a salt (e.g., a pharmaceutically acceptable salt) thereof, each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —OC(O)R$^a$, —OC(O)NR$^c$R$^d$, —SR$^b$, —S(O)R$^e$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^1$.

In one variation, $R^{10}$ is independently oxo; $C_{1-6}$ alkyl optionally substituted with 1, 2, 3 or 4 substituents independently selected from $R^{11}$; 5- to 10-membered heteroaryl optionally substituted with 1, 2, 3 or 4 substituents independently selected from $R^{11}$; halogen, —OR$^b$, —S(O)(=NH)R$^e$, —NR$^c$R$^d$, —N(R$^f$)C(O)R$^a$, or —N(R$^f$)S(O)$_2$NR$^c$R$^d$.

In one variation, $R^{10}$ is independently oxo, halogen, cyano, $C_{1-6}$ alkyl optionally substituted with 1, 2, 3 or 4 substituents independently selected from $R^{11}$, or —OR$^b$.

In one variation, $R^{10}$ is independently —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$.

In one variation, $R^{10}$ is independently oxo, —OR$^b$, —OC(O)R$^a$, —OC(O)NR$^c$R$^d$, —SR$^b$, —S(O)R$^e$, —S(O)$_2$R$^e$, —S(O)(=NH)R$^e$, or —S(O)$_2$NR$^c$R$^d$.

In one variation, each $R^{10}$ is independently $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^1$.

In one variation, each $R^{10}$ is independently $C_{1-6}$ alkyl, $C_{2-6}$ alkenyl, $C_{2-6}$ alkynyl, each optionally substituted with 1, 2, 3 or 4 substituents independently selected from $R^1$.

In one variation, $R^{10}$ is $C_{1-6}$ alkyl optionally substituted with 1, 2, 3 or 4 substituents independently selected from $R^{11}$. In one variation, $R^{10}$ is 3- to 12-membered heterocyclyl optionally substituted with 1, 2, 3 or 4 substituents independently selected from $R^1$.

In one variation, $R^{10}$ is halogen, cyano, —NR$^c$R$^d$, —C(O)NR$^c$R$^d$, —OR$^b$, —S(O)$_2$R$^e$, $C_{1-6}$ haloalkyl, —($C_{1-6}$ alkylene)-OH, or —($C_{1-6}$ alkylene)-OH.

In one variation, $R^{10}$ is hydroxyl, cyano, halogen, —CHF$_2$, —CF$_3$, —NH$_2$, —NH($C_{1-6}$ alkyl), —N($C_{1-6}$ alkyl)$_2$, —O($C_{1-6}$ alkyl), —SO$_2$($C_{1-6}$ alkyl), —S(O)$_2$NR$^c$R$^d$, —C(O)NR$^c$R$^d$, or —N(R$^f$)C(O)R$^a$.

In some embodiments, each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$. In one variation, $R^a$ is independently hydrogen or $C_{1-6}$ alkyl.

In some embodiments, each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$. In one variation, $R^b$ is independently hydrogen or $C_{1-6}$ alkyl.

In some embodiments, each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$; or $R^c$ and $R^d$ are taken together with the nitrogen atom to which they are attached to form a 4- to 12-membered heterocyclyl optionally substituted with 1, 2, 3 or 4 substituents independently selected from $R^{11}$. In one variation, each $R^c$ and $R^d$ is independently hydrogen or $C_{1-6}$ alkyl.

In some embodiments, each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$. In one variation, $R^e$ is independently $C_{1-6}$ alkyl.

In some embodiments, each $R^f$ is independently hydrogen or $C_{1-6}$ alkyl. In one variation, $R^f$ is hydrogen.

In some embodiments, each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e}1$, —S(O)$_2$N$R^{c1}R^{d1}$, —N$R^{c1}R^{d1}$, —N($R^f$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, or —N($R^{f1}$)S(O)$_2$N$R^{c1}R^{d1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$.

In one variation, each $R^{11}$ is independently oxo, $C_{1-6}$ alkyl, $C_{3-6}$ cycloalkyl, 3- to 8-membered heterocyclyl, halogen, cyano, or —O$R^{b1}$; wherein the $C_{1-6}$ alkyl, $C_{3-6}$ cycloalkyl, and 3- to 14-membered heterocyclyl of $R^{11}$ are each optionally substituted with 1, 2, 3 or 4 substituents independently selected from $R^2$.

In one variation, $R^{11}$ is $C_{1-6}$ alkyl optionally substituted with 1, 2, 3 or 4 substituents independently selected from $R^{12}$. In one variation, $R^{11}$ is 3- to 8-membered heterocyclyl optionally substituted with 1, 2, 3 or 4 substituents independently selected from $R^{12}$.

In one variation, $R^{11}$ is halogen, cyano, —N$R^{c1}R^{d1}$, —C(O)N$R^{c1}R^{d1}$, —O$R^{b1}$, —S(O)$_2R^{e1}$, $C_{1-6}$ haloalkyl, —(C$_{1-6}$ alkylene)-OH, or —(C$_{1-6}$ alkylene)-OH.

In one variation, $R^{11}$ is hydroxl, cyano, halogen, —CHF$_2$, —CF$_3$, —NH$_2$, —NH(C$_{1-6}$ alkyl), —N(C$_{1-6}$ alkyl)$_2$, —O(C$_{1-6}$ alkyl), —SO$_2$(C$_{1-6}$ alkyl), —S(O)$_2$N$R^{c1}R^{d1}$, —C(O)N$R^{c1}R^{d1}$, or —N($R^{f1}$)C(O)$R^{a1}$.

In one variation, $R^{11}$ is halogen, cyano, —O(C$_{1-6}$ alkyl), —O(C$_{1-6}$ alkylene)-NH$_2$, or —(C$_{1-6}$ alkylene)-OH.

In some embodiments, each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^2$.

In some embodiments, each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$. In one variation, $R^{b1}$ is independently hydrogen or $C_{1-6}$ alkyl.

In some embodiments, each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$; or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$. In one variation, each $R^{c1}$ and $R^{d1}$ is independently hydrogen or $C_{1-6}$ alkyl.

In some embodiments, each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$. In one variation, $R^{e1}$ is independently $C_{1-6}$ alkyl.

In some embodiments, each $R^{f1}$ is independently hydrogen or $C_{1-6}$ alkyl. In one variation, $R^{f1}$ is hydrogen.

In some embodiments, each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, or —N($R^{f2}$)S(O)$_2$N$R^{c2}R^{d2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$.

In one variation, each $R^{12}$ is independently oxo, halogen, cyano, —O$R^{b2}$, or $C_{1-6}$ alkyl optionally substituted with 1, 2, 3 or 4 substituents independently selected from $R^{13}$. In one variation, each $R^{12}$ is independently oxo, halogen, cyano, or hydroxyl.

In one variation, $R^{12}$ is $C_{1-6}$ alkyl optionally substituted with 1, 2, 3 or 4 substituents independently selected from $R^{13}$.

In one variation, $R^{12}$ is oxo, hydroxyl, $C_{1-6}$ alkyl, or —O(C$_{1-6}$ alkyl).

In some embodiments, each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^a2$ are each optionally substituted with 1, 2, 3 or 4 substituents independently selected from $R^{13}$. In one variation, $R^{a2}$ is independently hydrogen or $C_{1-6}$ alkyl.

In some embodiments, each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$. In one variation, $R^{b2}$ is hydrogen.

In some embodiments, each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$; or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$. In one variation, each $R^{c2}$ and $R^2$ is independently hydrogen or $C_{1-6}$ alkyl.

In some embodiments, each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$. In one variation, $R^{e2}$ is independently $C_{1-6}$ alkyl.

In some embodiments, each $R^{f2}$ is independently hydrogen or $C_{1-6}$ alkyl. In one variation, $R^2$ is hydrogen.

In some embodiments, each $R^{13}$ is independently oxo, halogen, hydroxyl, —O($C_{1-6}$ alkyl), cyano, $C_{1-6}$ alkyl or $C_{1-6}$ haloalkyl.

In one variation, each $R^{13}$ is independently halogen, hydroxyl, —O($C_{1-6}$ alkyl), cyano, or $C_{1-6}$ alkyl.

In one variation, $R^{13}$ is oxo, hydroxyl, $C_{1-6}$ alkyl, or —O($C_{1-6}$ alkyl).

Representative compounds are listed in Table 1. It is understood that individual enatiomers and diastereomers are included in the table below by Compound No. and Compound Name, and their corresponding structures can be readily determined therefrom. In some instances, the enantiomers or diastereomers are identified by their respective perperties, for example, retention times on a chiral HPLC or its biological activities, and the absolute stereo configurations of the chiral centers are arbitrarily assigned.

TABLE 1

| Cpd. No. | Structure | Name |
|---|---|---|
| 101 | 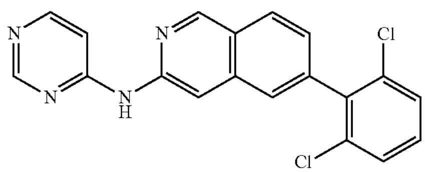 [SMILES: Clc1cccc(Cl)c1-c1ccc2cnc(Nc3ccncn3)cc2c1] | 6-(2,6-dichlorophenyl)-N-(pyrimidin-4-yl)isoquinolin-3-amine |
| 102 | 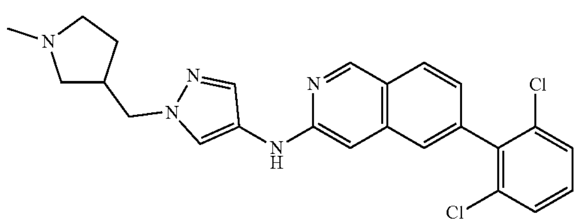 [SMILES: CN1CCC(Cn2cc(Nc3cc4cc(-c5c(Cl)cccc5Cl)ccc4cn3)cn2)C1] | 6-(2,6-dichlorophenyl)-N-(1-((1-methylpyrrolidin-3-yl)methyl)-1H-pyrazol-4-yl)isoquinolin-3-amine |
| 103 | 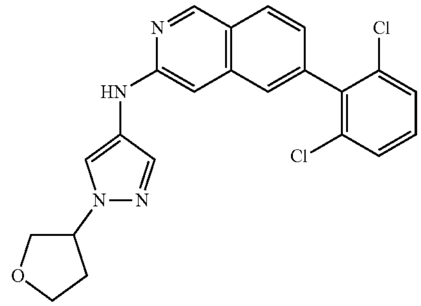 [SMILES: Clc1cccc(Cl)c1-c1ccc2cnc(Nc3cnn(C4CCOC4)c3)cc2c1] | 6-(2,6-dichlorophenyl)-N-(1-(tetrahydrofuran-3-yl)-1H-pyrazol-4-yl)isoquinolin-3-amine |
| 104 | 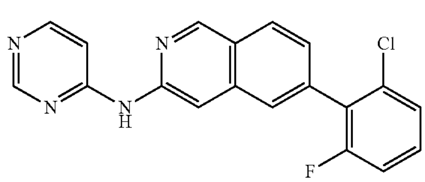 [SMILES: Fc1cccc(Cl)c1-c1ccc2cnc(Nc3ccncn3)cc2c1] | 6-(2-chloro-6-fluorophenyl)-N-(pyrimidin-4-yl)isoquinolin-3-amine |

TABLE 1-continued

| Cpd. No. | Structure | Name |
|---|---|---|
| 105 | 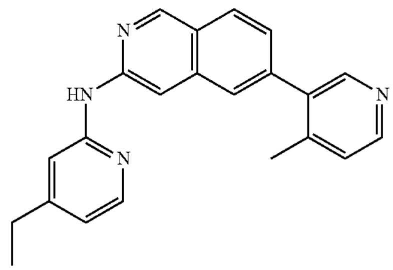 [SMILES: CCc1ccnc(Nc2cc3cc(-c4cnccc4C)ccc3cn2)c1] | N-(4-ethylpyridin-2-yl)-6-(4-methylpyridin-3-yl)isoquinolin-3-amine |
| 106 | 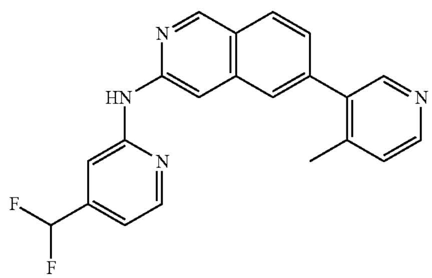 [SMILES: Cc1ccncc1-c1ccc2cnc(Nc3cc(C(F)F)ccn3)cc2c1] | N-(4-(difluoromethyl)pyridin-2-yl)-6-(4-methylpyridin-3-yl)isoquinolin-3-amine |
| 107 | 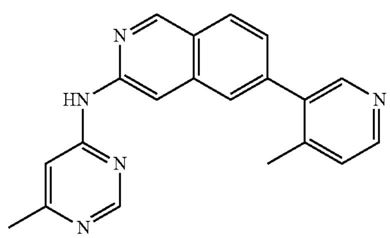 [SMILES: Cc1cc(Nc2cc3cc(-c4cnccc4C)ccc3cn2)ncn1] | 6-(4-methylpyridin-3-yl)-N-(6-methylpyrimidin-4-yl)isoquinolin-3-amine |
| 108 | 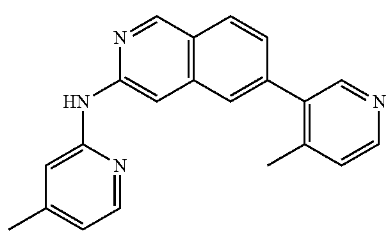 [SMILES: Cc1ccnc(Nc2cc3cc(-c4cnccc4C)ccc3cn2)c1] | N-(4-methylpyridin-2-yl)-6-(4-methylpyridin-3-yl)isoquinolin-3-amine |
| 109 | 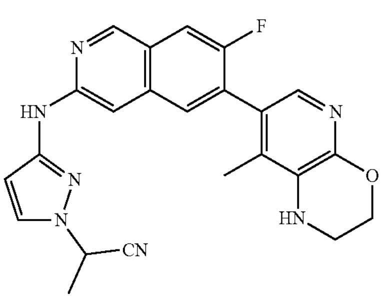 [SMILES: Cc1c(-c2cc3cc(Nc4ccn(C(C)C#N)n4)ncc3cc2F)cnc2c1NCCO2] | 2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile |
| 109a 109b | | (R)-2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile (S)-2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile |

TABLE 1-continued

| Cpd. No. | Structure | Name |
|---|---|---|
| 110 | 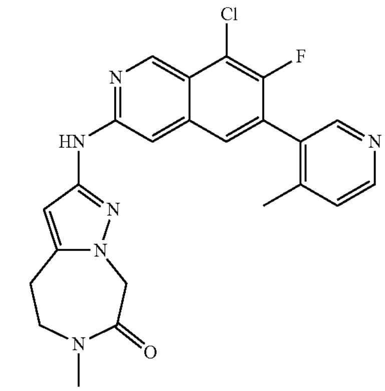 [SMILES: Cc1ccncc1-c1cc2cc(Nc3cc4n(n3)CC(=O)N(C)CC4)ncc2c(Cl)c1F] | 2-[[8-Chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one |
| 111 | 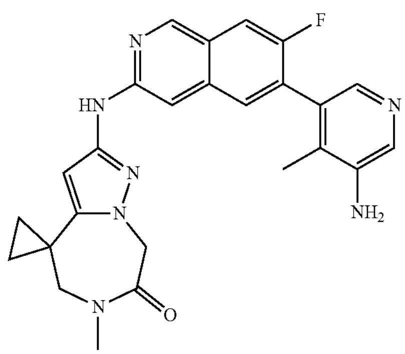 [SMILES: Cc1c(N)cncc1-c1cc2cc(Nc3cc4n(n3)CC(=O)N(C)CC43CC3)ncc2cc1F] | 2-[[6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one |
| 112 | 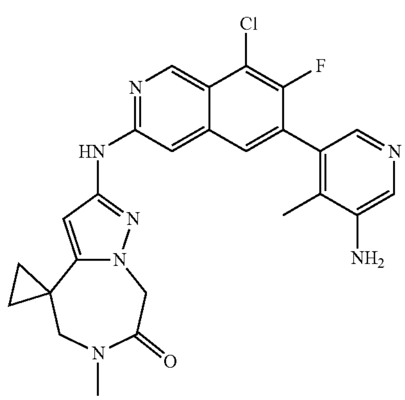 [SMILES: Cc1c(N)cncc1-c1cc2cc(Nc3cc4n(n3)CC(=O)N(C)CC43CC3)ncc2c(Cl)c1F] | 2-[[6-(5-amino-4-methyl-3-pyridyl)-8-chloro-7-fluoro-3-isoquinolyl]amino]-6-methyl-spiro[5,8-dihydropyrazolo[1,5-d][1,4]diazepine-4,1'-cyclopropane]-7-one |
| 113 | 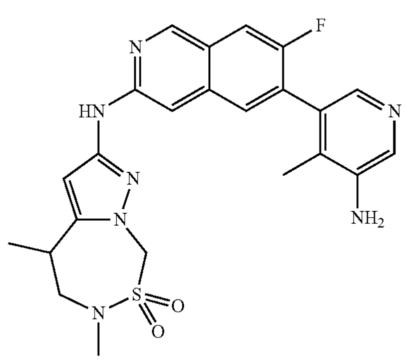 [SMILES: Cc1c(N)cncc1-c1cc2cc(Nc3cc4n(n3)CS(=O)(=O)N(C)CC4C)ncc2cc1F] | 2-((6-(5-amino-4-methylpyridin-3-yl)-7-fluoroisoquinolin-3-yl)amino)-4,6-dimethyl-5,6-dihydro-4H,8H-pyrazolo[5,1-e][1,2,6]thiadiazepine 7,7-dioxide |

TABLE 1-continued

| Cpd. No. | Structure | Name |
|---|---|---|
| 114 | 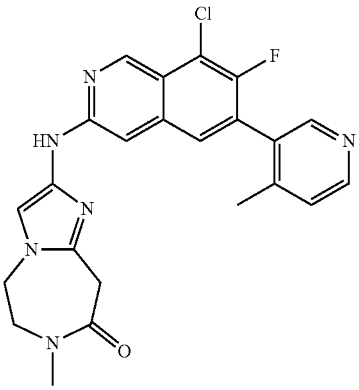 [SMILES: Cc1ccncc1-c1cc2cc(Nc3cn4c(n3)CC(=O)N(C)CC4)ncc2c(Cl)c1F] | 2-((8-chloro-7-fluoro-6-(4-methylpyridin-3-yl)isoquinolin-3-yl)amino)-7-methyl-6,7-dihydro-5H-imidazo[1,2-d][1,4]diazepin-8(9H)-one |
| 115 | 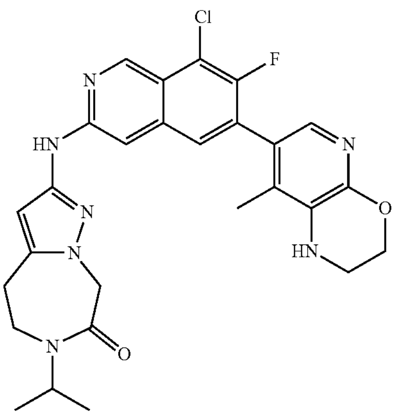 | 2-((8-chloro-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one |
| 116 | 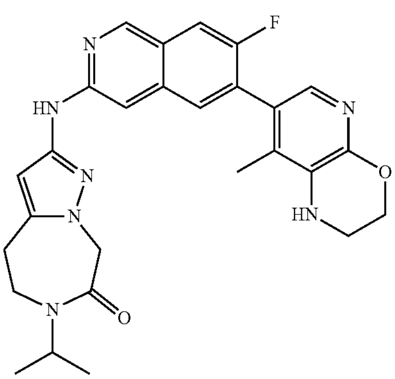 [SMILES: Cc1c(-c2cc3cc(Nc4cc5n(n4)CC(=O)N(C(C)C)CC5)ncc3cc2F)cnc2c1NCCO2] | 2-((7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one |
| 117 | 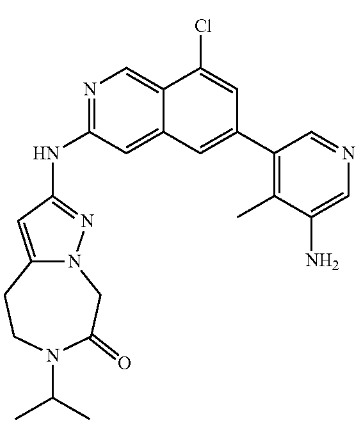 [SMILES: Cc1c(N)cncc1-c1cc(Cl)c2cnc(Nc3cc4n(n3)CC(=O)N(C(C)C)CC4)cc2c1] | 2-((6-(5-amino-4-methylpyridin-3-yl)-8-chloroisoquinolin-3-yl)amino)-6-isopropyl-5,6-dihydro-4H-pyrazolo[1,5-d][1,4]diazepin-7(8H)-one |

TABLE 1-continued

| Cpd. No. | Structure | Name |
|---|---|---|
| 118 | 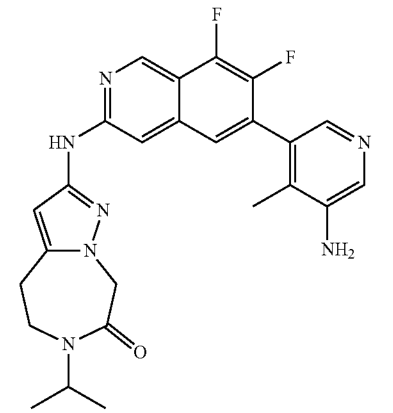 [SMILES: Cc1c(N)cncc1-c1cc2cc(Nc3cc4n(n3)CC(=O)N(C(C)C)CC4)ncc2c(F)c1F] | 2-((6-(5-amino-4-methylpyridin-3-yl)-7,8-difluoroisoquinolin-3-yl)amino)-6-isopropyl-5,6-dihydro-4H-pyrazolo[1,5-d][1,4]diazepin-7(8H)-one |
| 119 | 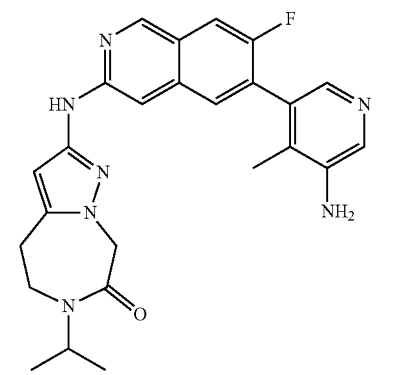 [SMILES: Cc1c(N)cncc1-c1cc2cc(Nc3cc4n(n3)CC(=O)N(C(C)C)CC4)ncc2cc1F] | 2-((6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one |
| 120 | 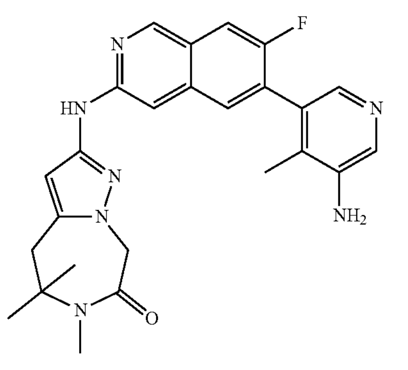 | 2-((6-(5-amino-4-methylpyridin-3-yl)-7-fluoroisoquinolin-3-yl)amino)-5,5,6-trimethyl-5,6-dihydro-4H-pyrazolo[1,5-d][1,4]diazepin-7(8H)-one |
| 121 | 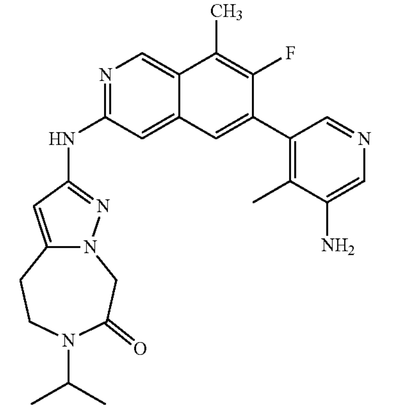 [SMILES: Cc1c(N)cncc1-c1cc2cc(Nc3cc4n(n3)CC(=O)N(C(C)C)CC4)ncc2c(C)c1F] | 2-((6-(5-amino-4-methylpyridin-3-yl)-7-fluoro-8-methylisoquinolin-3-yl)amino)-6-isopropyl-5,6-dihydro-4H-pyrazolo[1,5-d][1,4]diazepin-7(8H)-one |

TABLE 1-continued

| Cpd. No. | Structure | Name |
|---|---|---|
| 122 | 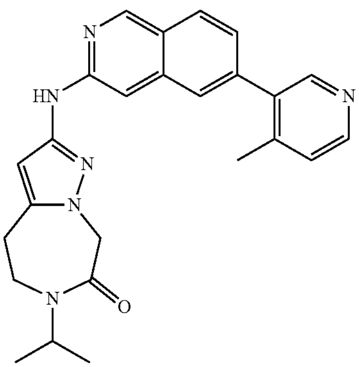 [SMILES: Cc1ccncc1-c1ccc2cnc(Nc3cc4n(n3)CC(=O)N(C(C)C)CC4)cc2c1] | 6-isopropyl-2-[6-(4-methyl-3-pyridyl)-3-isoquinolyl]amino]-5,8-dihydro-4H-pyrazolo[1,5-d][1,4]diazepin-7-one |
| 123 | 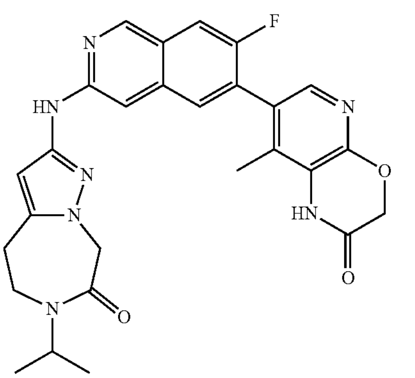 [SMILES: Cc1c(-c2cc3cc(Nc4cc5n(n4)CC(=O)N(C(C)C)CC5)ncc3cc2F)cnc2c1NC(=O)CO2] | 7-[7-fluoro-3-[(6-isopropyl-7-oxo-5,8-dihydro-4H-pyrazolo[1,5-d][1,4]diazepin-2-yl)amino]-6-isoquinolyl]-8-methyl-1H-pyrido[2,3-b][1,4]oxazin-2-one |
| 124 | 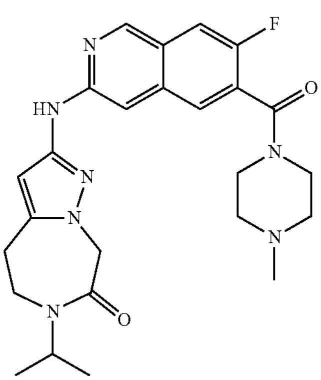 [SMILES: CC(C)N1CCc2cc(Nc3cc4cc(C(=O)N5CCN(C)CC5)c(F)cc4cn3)nn2CC1=O] | 2-((7-fluoro-6-(4-methylpiperazine-1-carbonyl)isoquinolin-3-yl)amino)-6-isopropyl-5,6-dihydro-4H-pyrazolo[1,5-d][1,4]diazepin-7(8H)-one |
| 125 | 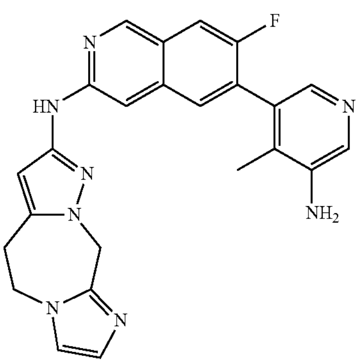 [SMILES: Cc1c(N)cncc1-c1cc2cc(Nc3cc4n(n3)Cc3nccn3CC4)ncc2cc1F] | N-(6-(5-amino-4-methylpyridin-3-yl)-7-fluoroisoquinolin-3-yl)-5,6-dihydro-11H-imidazo[1,2-a]pyrazolo[1,5-d][1,4]diazepin-8-amine |

TABLE 1-continued

| Cpd. No. | Structure | Name |
|---|---|---|
| 126 | 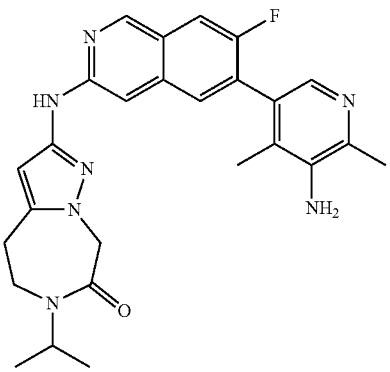 [SMILES: Cc1ncc(-c2cc3cc(Nc4cc5n(n4)CC(=O)N(C(C)C)CC5)ncc3cc2F)c(C)c1N] | 2-((6-(5-amino-4,6-dimethylpyridin-3-yl)-7-fluoroisoquinolin-3-yl)amino)-6-isopropyl-5,6-dihydro-4H-pyrazolo[1,5-d][1,4]diazepin-7(8H)-one |
| 127 | 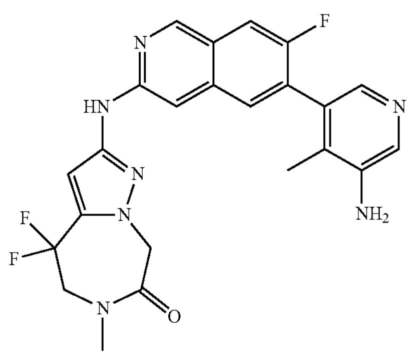 [SMILES: Cc1c(N)cncc1-c1cc2cc(Nc3cc4n(n3)CC(=O)N(C)CC4(F)F)ncc2cc1F] | 2-[[6-(5-amino-4-methyl-3-pyridyl)-7-fluoro-3-isoquinolyl]amino]-4,4-difluoro-6-methyl-5,8-dihydropyrazolo[1,5-d][1,4]diazepin-7-one |
| 128 | 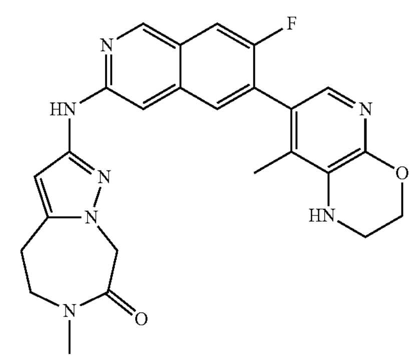 [SMILES: Cc1c(-c2cc3cc(Nc4cc5n(n4)CC(=O)N(C)CC5)ncc3cc2F)cnc2c1NCCO2] | tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate |
| 129 | 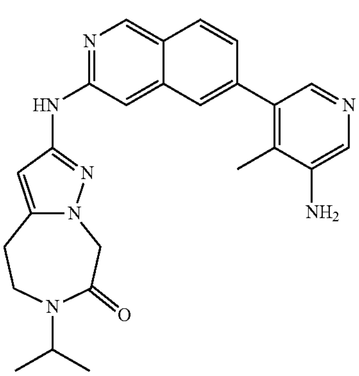 [SMILES: Cc1c(N)cncc1-c1ccc2cnc(Nc3cc4n(n3)CC(=O)N(C(C)C)CC4)cc2c1] | 2-[[6-(5-amino-4-methyl-3-pyridyl)-3-isoquinolyl]amino]-6-isopropyl-5,8-dihydro-4H-pyrazolo[1,5-d][1,4]diazepin-7-one |

TABLE 1-continued

| Cpd. No. | Structure | Name |
|---|---|---|
| 130 | 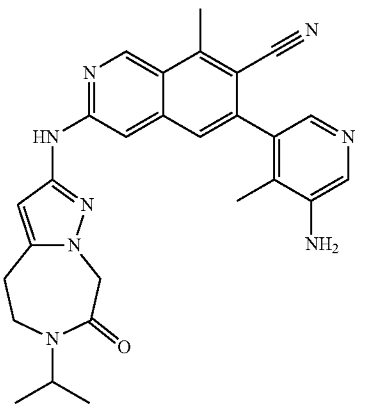 [SMILES: Cc1c(N)cncc1-c1cc2cc(Nc3cc4n(n3)CC(=O)N(C(C)C)CC4)ncc2c(C)c1C#N] | 6-(5-amino-4-methyl-3-pyridyl)-3-[(6-isopropyl-7-oxo-5,8-dihydro-4H-pyrazolo[1,5-d][1,4]diazepin-2-yl)amino]-8-methyl-isoquinoline-7-carbonitrile |
| 131 | 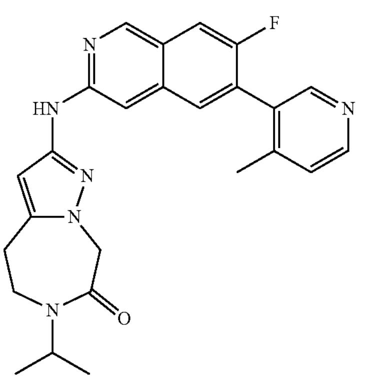 [SMILES: Cc1ccncc1-c1cc2cc(Nc3cc4n(n3)CC(=O)N(C(C)C)CC4)ncc2cc1F] | 2-[[7-fluoro-6-(4-methyl-3-pyridyl)-3-isoquinolyl]amino]-6-isopropyl-5,8-dihydro-4H-pyrazolo[1,5-d][1,4]diazepin-7-one |
| 132 | 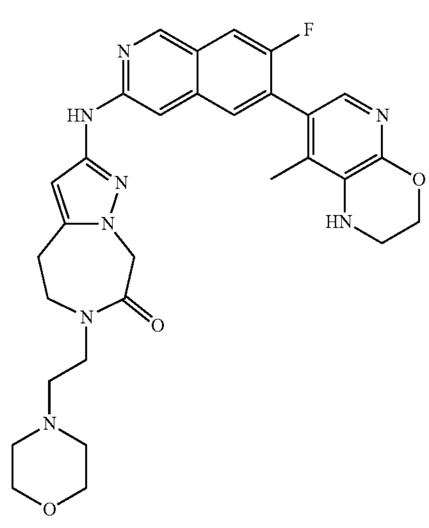 [SMILES: Cc1c(-c2cc3cc(Nc4cc5n(n4)CC(=O)N(CCN4CCOCC4)CC5)ncc3cc2F)cnc2c1NCCO2] | 2-[[7-fluoro-6-(8-methyl-2,3-dihydro-1H-pyrido[2,3-b][1,4]oxazin-7-yl)-3-isoquinolyl]amino]-6-(2-morpholinoethyl)-5,8-dihydro-4H-pyrazolo[1,5-d][1,4]diazepin-7-one |

TABLE 1-continued

| Cpd. No. | Structure | Name |
|---|---|---|
| 133 | 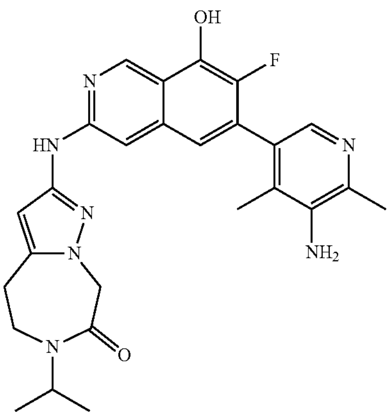 [SMILES: Cc1ncc(-c2cc3cc(Nc4cc5n(n4)CC(=O)N(C(C)C)CC5)ncc3c(O)c2F)c(C)c1N] | 2-((6-(5-amino-4,6-dimethylpyridin-3-yl)-7-fluoro-8-hydroxyisoquinolin-3-yl)amino)-6-isopropyl-5,6-dihydro-4H-pyrazolo[1,5-d][1,4]diazepin-7(8H)-one |
| 134 | 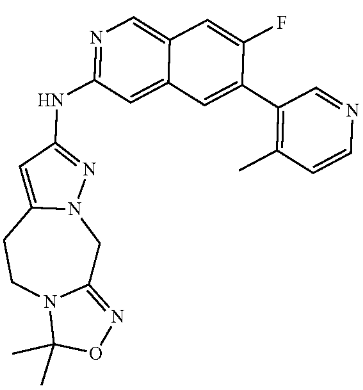 [SMILES: Cc1ccncc1-c1cc2cc(Nc3cc4n(n3)CC3=NOC(C)(C)N3CC4)ncc2cc1F] | N-(7-fluoro-6-(4-methylpyridin-3-yl)isoquinolin-3-yl)-3,3-dimethyl-5,6-dihydro-3H,11H-[1,2,4]oxadiazolo[4,3-a]pyrazolo[1,5-d][1,4]diazepin-8-amine |
| 135 | 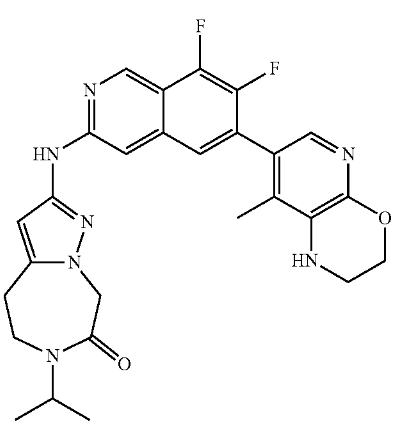 [SMILES: Cc1c(-c2cc3cc(Nc4cc5n(n4)CC(=O)N(C(C)C)CC5)ncc3c(F)c2F)cnc2c1NCCO2] | 2-((7,8-difluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one |

TABLE 1-continued

| Cpd. No. | Structure | Name |
|---|---|---|
| 136 | 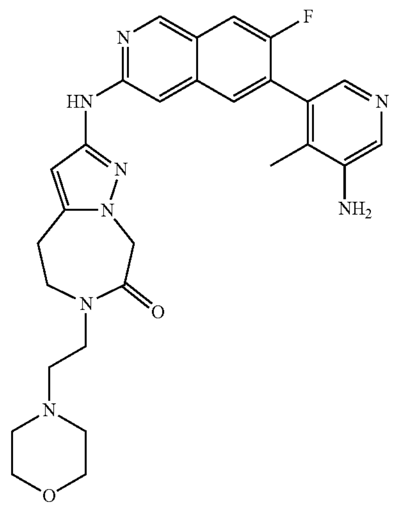 [SMILES: Cc1c(N)cncc1-c1cc2cc(Nc3cc4n(n3)CC(=O)N(CCN3CCOCC3)CC4)ncc2cc1F] | 2-((6-(5-amino-4-methylpyridin-3-yl)-7-fluoroisoquinolin-3-yl)amino)-6-(2-morpholinoethyl)-5,6-dihydro-4H-pyrazolo[1,5-d][1,4]diazepin-7(8H)-one |
| 137 | 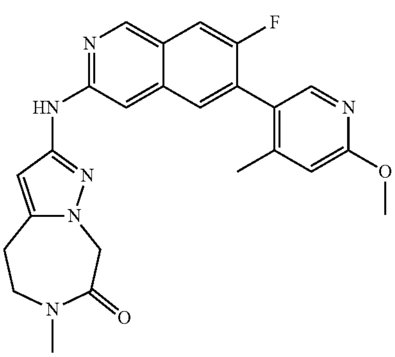 [SMILES: COc1cc(C)c(-c2cc3cc(Nc4cc5n(n4)CC(=O)N(C)CC5)ncc3cc2F)cn1] | 2-((7-fluoro-6-(6-methoxy-4-methylpyridin-3-yl)isoquinolin-3-yl)amino)-6-methyl-5,6-dihydro-4H-pyrazolo[1,5-d][1,4]diazepin-7(8H)-one |
| 138 | 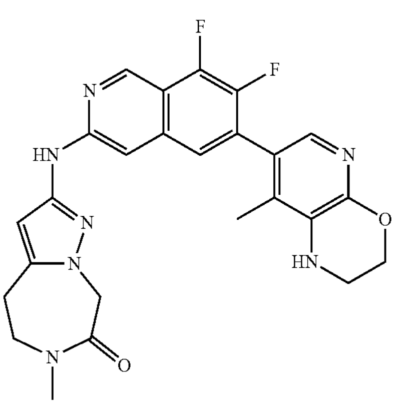 [SMILES: Cc1c(-c2cc3cc(Nc4cc5n(n4)CC(=O)N(C)CC5)ncc3c(F)c2F)cnc2c1NCCO2] | 2-((7,8-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 139 | 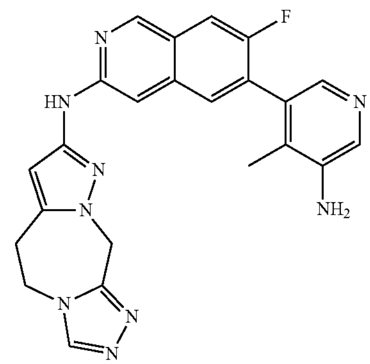 [SMILES: Cc1c(N)cncc1-c1cc2cc(Nc3cc4n(n3)Cc3nncn3CC4)ncc2cc1F] | N-(6-(5-amino-4-methylpyridin-3-yl)-7-fluoroisoquinolin-3-yl)-5,6-dihydro-11H-pyrazolo[1,5-d][1,2,4]triazolo[4,3-a][1,4]diazepin-8-amine |
| 140 | 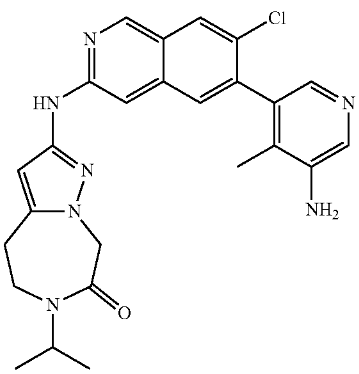 | 2-((6-(5-amino-4-methylpyridin-3-yl)-7-chloroisoquinolin-3-yl)amino)-6-isopropyl-5,6-dihydro-4H-pyrazolo[1,5-d][1,4]diazepin-7(8H)-one |
| 141 | 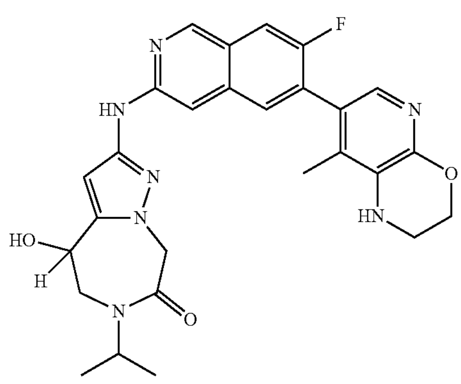 [SMILES: Cc1c(-c2cc3cc(Nc4cc5n(n4)CC(=O)N(C(C)C)CC5O)ncc3cc2F)cnc2c1NCCO2] | 2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diazepin-7(8H)-one |
| 141a | | (R)-2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diazepin-7(8H)-one |
| 141b | | (S)-2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diazepin-7(8H)-one |

TABLE 1-continued

| Cpd. No. | Structure | Name |
|---|---|---|
| 142 | 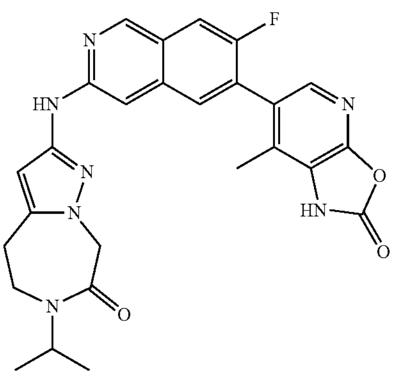 [SMILES: Cc1c(-c2cc3cc(Nc4cc5n(n4)CC(=O)N(C(C)C)CC5)ncc3cc2F)cnc2oc(=O)[nH]c12] | 6-(7-fluoro-3-((6-isopropyl-7-oxo-5,6,7,8-tetrahydro-4H-pyrazolo[1,5-d][1,4]diazepin-2-yl)amino)isoquinolin-6-yl)-7-methyloxazolo[5,4-b]pyridin-2(1H)-one |
| 143 | 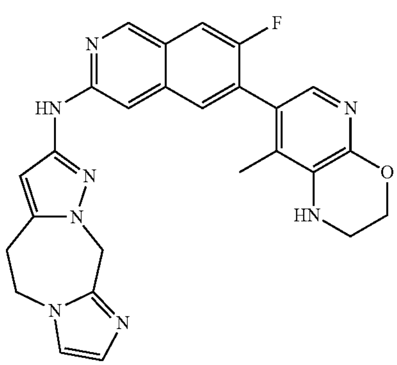 [SMILES: Cc1c(-c2cc3cc(Nc4cc5n(n4)Cc4nccn4CC5)ncc3cc2F)cnc2c1NCCO2] | N-(7-fluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine |
| 144 | 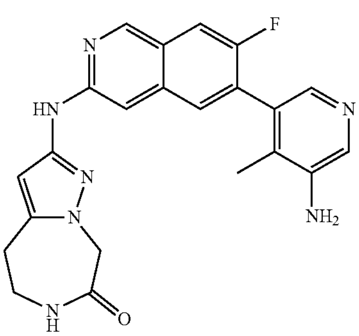 [SMILES: Cc1c(N)cncc1-c1cc2cc(Nc3cc4n(n3)CC(=O)NCC4)ncc2cc1F] | 2-((6-(5-amino-4-methylpyridin-3-yl)-7-fluoroisoquinolin-3-yl)amino)-5,6-dihydro-4H-pyrazolo[1,5-d][1,4]diazepin-7(8H)-one |
| 145 | 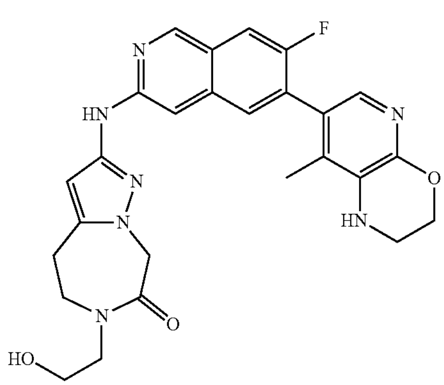 [SMILES: Cc1c(-c2cc3cc(Nc4cc5n(n4)CC(=O)N(CCO)CC5)ncc3cc2F)cnc2c1NCCO2] | 2-((7-fluoro-6-(8-methyl-2,3-dihydro-1H-pyrido[2,3-b][1,4]oxazin-7-yl)isoquinolin-3-yl)amino)-6-(2-hydroxyethyl)-5,6-dihydro-4H-pyrazolo[1,5-d][1,4]diazepin-7(8H)-one |

TABLE 1-continued

| Cpd. No. | Structure | Name |
|---|---|---|
| 146 | 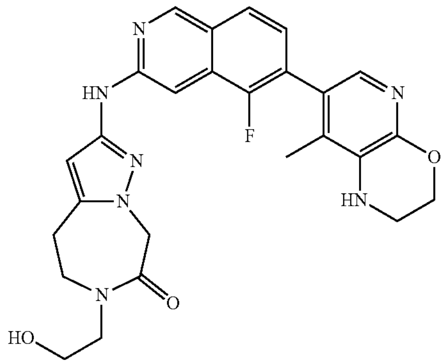 [SMILES: Cc1c(-c2ccc3cnc(Nc4cc5n(n4)CC(=O)N(CCO)CC5)cc3c2F)cnc2c1NCCO2] | 2-((5-fluoro-6-(8-methyl-2,3-dihydro-1H-pyrido[2,3-b][1,4]oxazin-7-yl)isoquinolin-3-yl)amino)-6-(2-hydroxyethyl)-5,6-dihydro-4H-pyrazolo[1,5-d][1,4]diazepin-7(8H)-one |
| 147 | 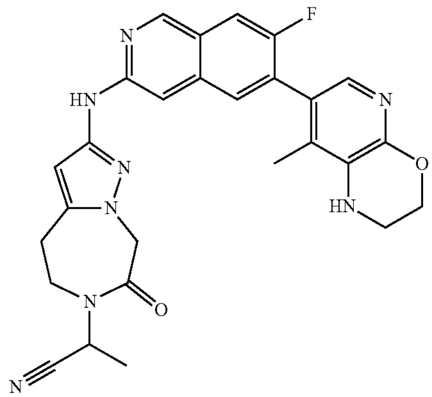 | 2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile |
| 147a 147b | | (S)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile (R)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile |
| 148 | 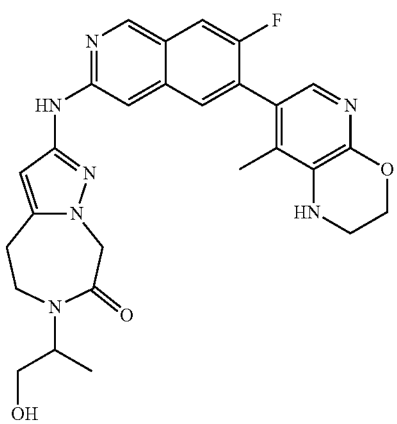 [SMILES: Cc1c(-c2cc3cc(Nc4cc5n(n4)CC(=O)N(C(C)CO)CC5)ncc3cc2F)cnc2c1NCCO2] | 2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one |
| 148a 148b | | (S)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one (R)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6- |

TABLE 1-continued

| Cpd. No. | Structure | Name |
|---|---|---|
| | | dihydro-4H-pyrazolo[1,5-d][1,4]diazepin-7(8H)-one |
| 149 | 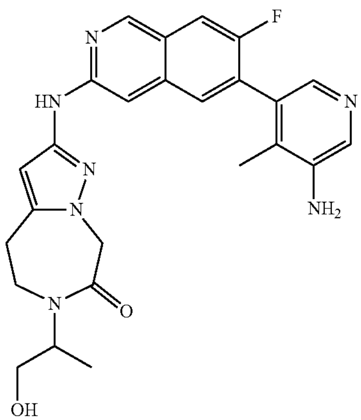 [SMILES: Cc1c(N)cncc1-c1cc2cc(Nc3cc4n(n3)CC(=O)N(C(C)CO)CC4)ncc2cc1F] | 2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one |
| 149a 149b | | (S)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one (R)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one |
| 150 | 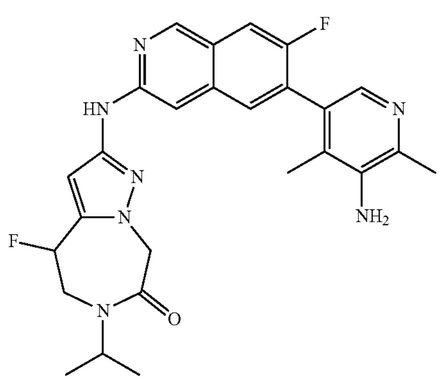 [SMILES: Cc1ncc(-c2cc3cc(Nc4cc5n(n4)CC(=O)N(C(C)C)CC5F)ncc3cc2F)c(C)c1N] | 2-((6-(5-amino-4,6-dimethylpyridin-3-yl)-7-fluoroisoquinolin-3-yl)amino)-4-fluoro-6-isopropyl-5,6-dihydro-4H-pyrazolo[1,5-d][1,4]diazepin-7(8H)-one |
| 151 | 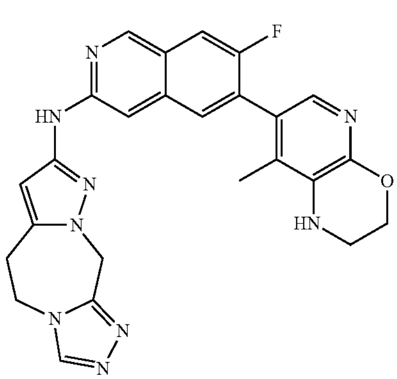 [SMILES: Cc1c(-c2cc3cc(Nc4cc5n(n4)Cc4nncn4CC5)ncc3cc2F)cnc2c1NCCO2] | N-(7-fluoro-6-(8-methyl-2,3-dihydro-1H-pyrido[2,3-b][1,4]oxazin-7-yl)isoquinolin-3-yl)-5,6-dihydro-11H-pyrazolo[1,5-d][1,2,4]triazolo[4,3-a][1,4]diazepin-8-amine |

TABLE 1-continued

| Cpd. No. | Structure | Name |
|---|---|---|
| 152 | 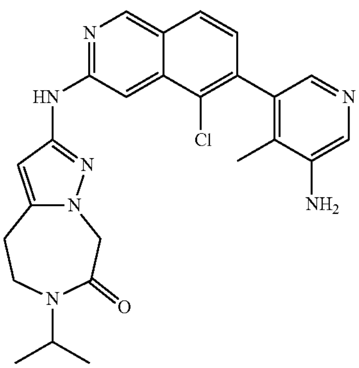 [SMILES: Cc1c(N)cncc1-c1ccc2cnc(Nc3cc4n(n3)CC(=O)N(C(C)C)CC4)cc2c1Cl] | 2-((6-(5-amino-4-methylpyridin-3-yl)-5-chloroisoquinolin-3-yl)amino)-6-isopropyl-5,6-dihydro-4H-pyrazolo[1,5-d][1,4]diazepin-7(8H)-one |
| 153 | 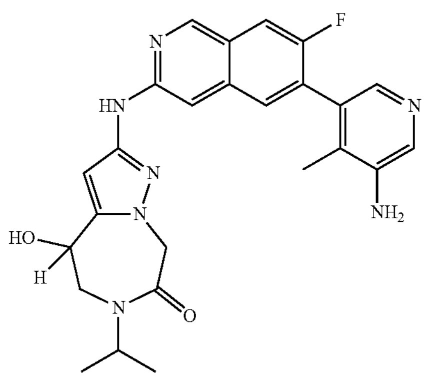 [SMILES: Cc1c(N)cncc1-c1cc2cc(Nc3cc4n(n3)CC(=O)N(C(C)C)CC4O)ncc2cc1F] | 2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one |
| 153a 153b | | (R)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one (S)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one |
| 154 | 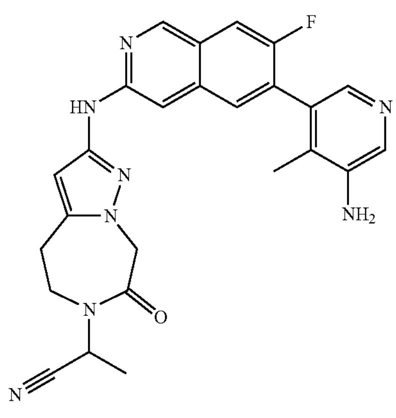 [SMILES: Cc1c(N)cncc1-c1cc2cc(Nc3cc4n(n3)CC(=O)N(C(C)C#N)CC4)ncc2cc1F] | 2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile |
| 154a 154b | | (S)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile (R)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile |

TABLE 1-continued

| Cpd. No. | Structure | Name |
| --- | --- | --- |
| 155 | 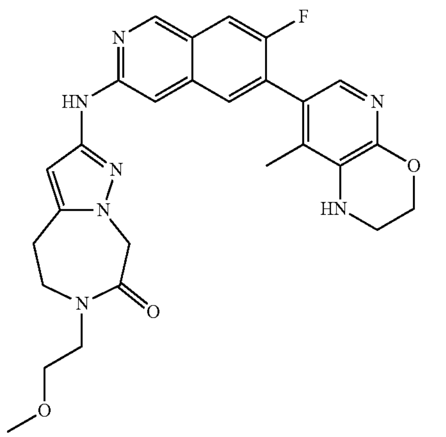 [SMILES: COCCN1CCc2cc(Nc3cc4cc(-c5cnc6c(c5C)NCCO6)c(F)cc4cn3)nn2CC1=O] | 2-((7-fluoro-6-(8-methyl-2,3-dihydro-1H-pyrido[2,3-b][1,4]oxazin-7-yl)isoquinolin-3-yl)amino)-6-(2-methoxyethyl)-5,6-dihydro-4H-pyrazolo[1,5-d][1,4]diazepin-7(8H)-one |
| 156 | 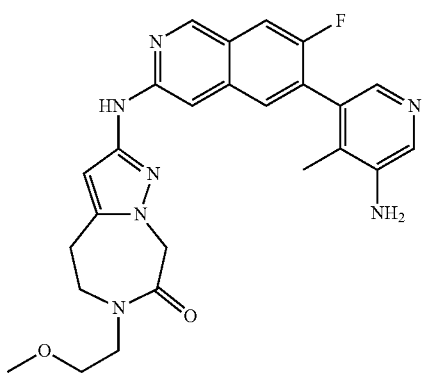 [SMILES: COCCN1CCc2cc(Nc3cc4cc(-c5cncc(N)c5C)c(F)cc4cn3)nn2CC1=O] | 2-((6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one |
| 157 | 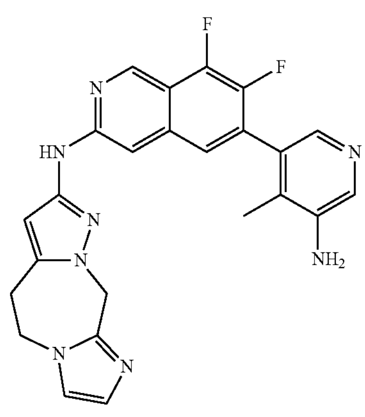 [SMILES: Cc1c(N)cncc1-c1cc2cc(Nc3cc4n(n3)Cc3nccn3CC4)ncc2c(F)c1F] | N-(6-(5-amino-4-methylpyridin-3-yl)-7,8-difluoroisoquinolin-3-yl)-5,6-dihydro-11H-imidazo[1,2-a]pyrazolo[1,5-d][1,4]diazepin-8-amine |

TABLE 1-continued

| Cpd. No. | Structure | Name |
|---|---|---|
| 158 | 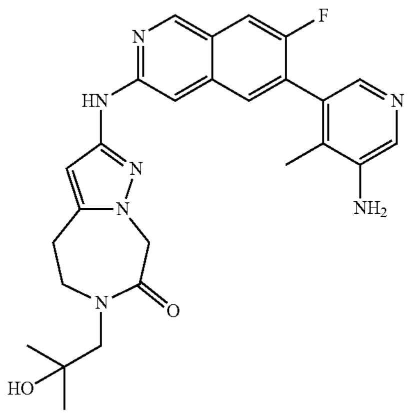 [SMILES: Cc1c(N)cncc1-c1cc2cc(Nc3cc4n(n3)CC(=O)N(CC(C)(C)O)CC4)ncc2cc1F] | 2-((6-(5-amino-4-methylpyridin-3-yl)-7-fluoroisoquinolin-3-yl)amino)-6-(2-hydroxy-2-methylpropyl)-5,6-dihydro-4H-pyrazolo[1,5-d][1,4]diazepin-7(8H)-one |
| 159 | 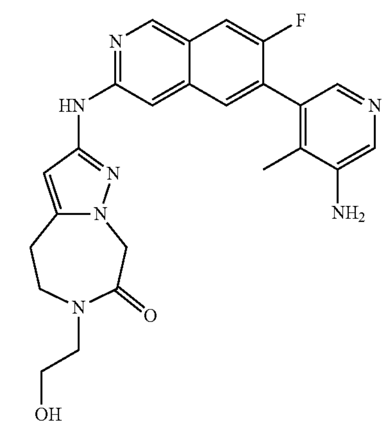 [SMILES: Cc1c(N)cncc1-c1cc2cc(Nc3cc4n(n3)CC(=O)N(CCO)CC4)ncc2cc1F] | 2-((6-(5-amino-4-methylpyridin-3-yl)-7-fluoroisoquinolin-3-yl)amino)-6-(2-hydroxyethyl)-5,6-dihydro-4H-pyrazolo[1,5-d][1,4]diazepin-7(8H)-one |
| 160 | 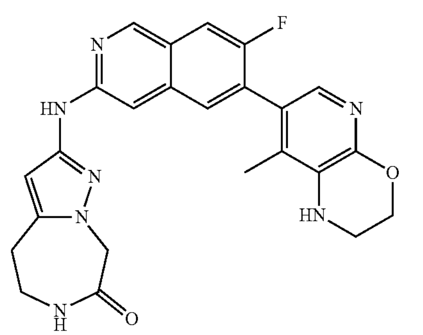 [SMILES: Cc1c(-c2cc3cc(Nc4cc5n(n4)CC(=O)NCC5)ncc3cc2F)cnc2c1NCCO2] | 2-((7-fluoro-6-(8-methyl-2,3-dihydro-1H-pyrido[2,3-b][1,4]oxazin-7-yl)isoquinolin-3-yl)amino)-5,6-dihydro-4H-pyrazolo[1,5-d][1,4]diazepin-7(8H)-one |
| 161 | 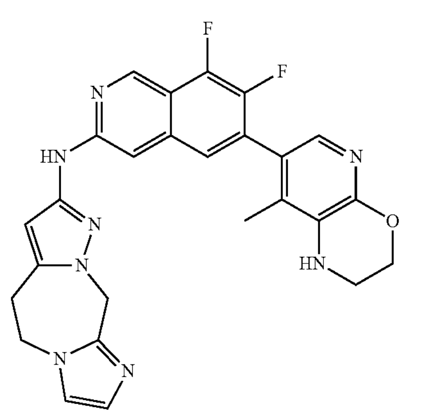 [SMILES: Cc1c(-c2cc3cc(Nc4cc5n(n4)Cc4nccn4CC5)ncc3c(F)c2F)cnc2c1NCCO2] | N-(7,8-difluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine |

TABLE 1-continued

| Cpd. No. | Structure | Name |
|---|---|---|
| 162 | 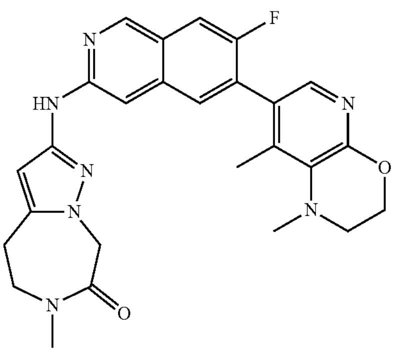 [SMILES: Cc1c(-c2cc3cc(Nc4cc5n(n4)CC(=O)N(C)CC5)ncc3cc2F)cnc2c1N(C)CCO2] | 2-((6-(1,8-dimethyl-2,3-dihydro-1H-pyrido[2,3-b][1,4]oxazin-7-yl)-7-fluoroisoquinolin-3-yl)amino)-6-methyl-5,6-dihydro-4H-pyrazolo[1,5-d][1,4]diazepin-7(8H)-one |
| 163 | 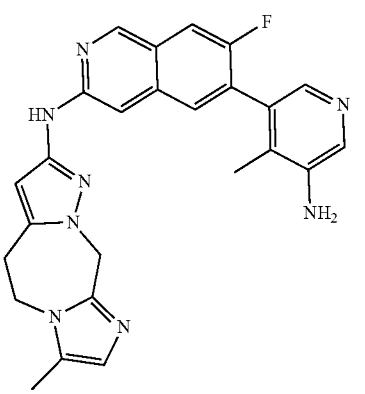 [SMILES: Cc1c(N)cncc1-c1cc2cc(Nc3cc4n(n3)Cc3ncc(C)n3CC4)ncc2cc1F] | N-(6-(5-amino-4-methylpyridin-3-yl)-7-fluoroisoquinolin-3-yl)-3-methyl-5,6-dihydro-11H-imidazo[1,2-a]pyrazolo[1,5-d][1,4]diazepin-8-amine |
| 164 | 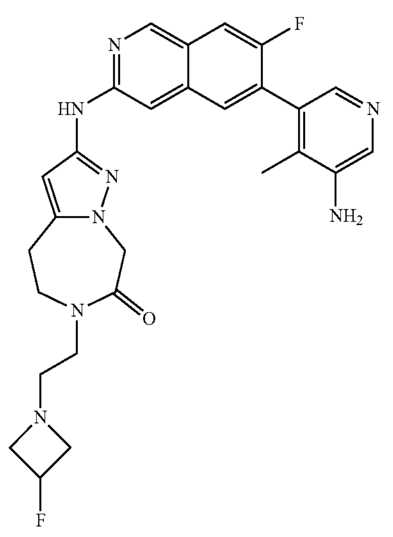 [SMILES: Cc1c(N)cncc1-c1cc2cc(Nc3cc4n(n3)CC(=O)N(CCN3CC(F)C3)CC4)ncc2cc1F] | 2-((6-(5-amino-4-methylpyridin-3-yl)-7-fluoroisoquinolin-3-yl)amino)-6-(2-(3-fluoroazetidin-1-yl)ethyl)-5,6-dihydro-4H-pyrazolo[1,5-d][1,4]diazepin-7(8H)-one |

TABLE 1-continued

| Cpd. No. | Structure | Name |
|---|---|---|
| 165 | 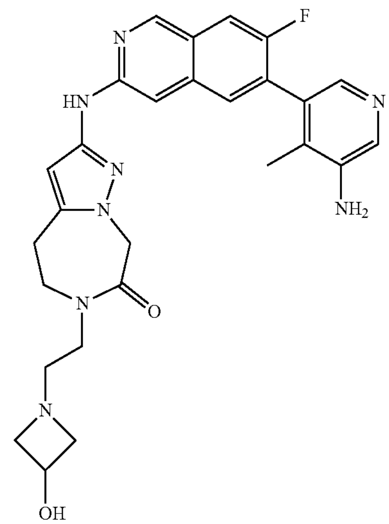 [SMILES: Cc1c(N)cncc1-c1cc2cc(Nc3cc4n(n3)CC(=O)N(CCN3CC(O)C3)CC4)ncc2cc1F] | 2-((6-(5-amino-4-methylpyridin-3-yl)-7-fluoroisoquinolin-3-yl)amino)-6-(2-(3-hydroxyazetidin-1-yl)ethyl)-5,6-dihydro-4H-pyrazolo[1,5-d][1,4]diazepin-7(8H)-one |
| 166 | 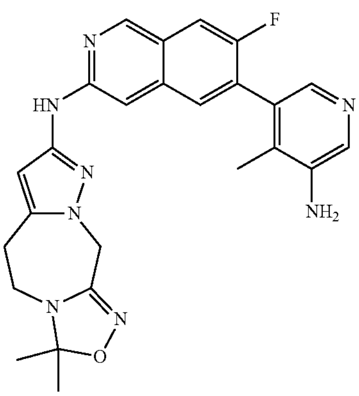 [SMILES: Cc1c(N)cncc1-c1cc2cc(Nc3cc4n(n3)CC3=NOC(C)(C)N3CC4)ncc2cc1F] | N-(6-(5-amino-4-methylpyridin-3-yl)-7-fluoroisoquinolin-3-yl)-3,3-dimethyl-5,6-dihydro-3H,11H-[1,2,4]oxadiazolo[4,3-a]pyrazolo[1,5-d][1,4]diazepin-8-amine |
| 167 | 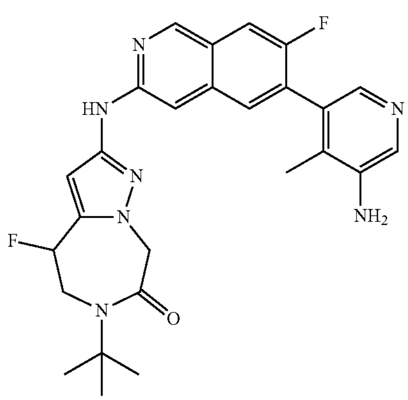 [SMILES: Cc1c(N)cncc1-c1cc2cc(Nc3cc4n(n3)CC(=O)N(C(C)(C)C)CC4F)ncc2cc1F] | 2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one |
| 167a 167b | | (R)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one<br>(S)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one |

| Cpd. No. | Structure | Name |
|---|---|---|
| 168 | 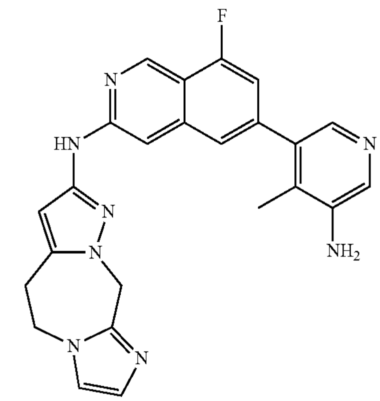 [SMILES: Cc1c(N)cncc1-c1cc(F)c2cnc(Nc3cc4n(n3)Cc3nccn3CC4)cc2c1] | N-(6-(5-amino-4-methylpyridin-3-yl)-8-fluoroisoquinolin-3-yl)-5,6-dihydro-11H-imidazo[1,2-a]pyrazolo[1,5-d][1,4]diazepin-8-amine |
| 169 | 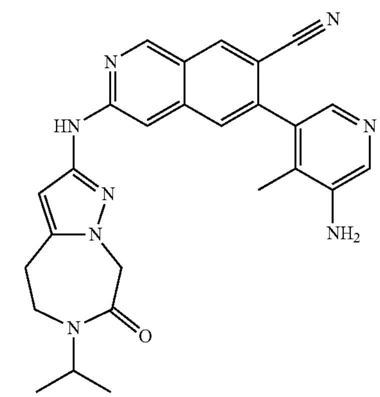 [SMILES: Cc1c(N)cncc1-c1cc2cc(Nc3cc4n(n3)CC(=O)N(C(C)C)CC4)ncc2cc1C#N] | 6-(5-amino-4-methylpyridin-3-yl)-3-((6-isopropyl-7-oxo-5,6,7,8-tetrahydro-4H-pyrazolo[1,5-d][1,4]diazepin-2-yl)amino)isoquinoline-7-carbonitrile |
| 170 | 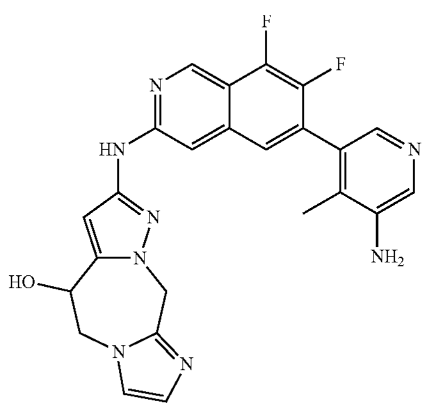 [SMILES: Cc1c(N)cncc1-c1cc2cc(Nc3cc4n(n3)Cc3nccn3CC4O)ncc2c(F)c1F] | 8-((6-(5-amino-4-methylpyridin-3-yl)-7,8-difluoroisoquinolin-3-yl)amino)-5,6-dihydro-11H-imidazo[1,2-a]pyrazolo[1,5-d][1,4]diazepin-6-ol |
| 171 | 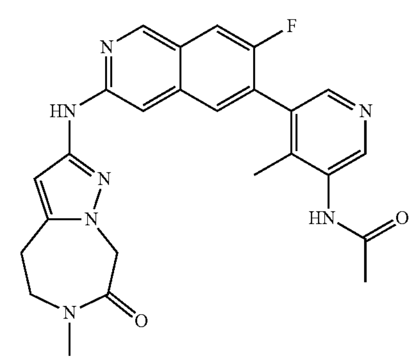 [SMILES: CC(=O)Nc1cncc(-c2cc3cc(Nc4cc5n(n4)CC(=O)N(C)CC5)ncc3cc2F)c1C] | N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)acetamide |

TABLE 1-continued

| Cpd. No. | Structure | Name |
|---|---|---|
| 172 | 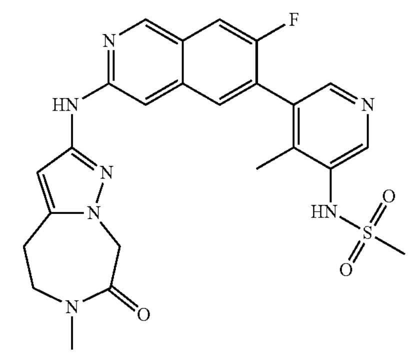 [SMILES: Cc1c(NS(C)(=O)=O)cncc1-c1cc2cc(Nc3cc4n(n3)CC(=O)N(C)CC4)ncc2cc1F] | N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)methanesulfonamide |
| 173 | 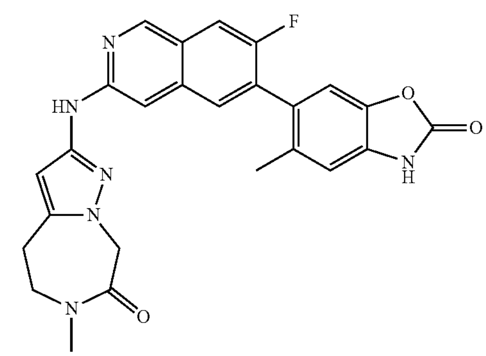 [SMILES: Cc1cc2[nH]c(=O)oc2cc1-c1cc2cc(Nc3cc4n(n3)CC(=O)N(C)CC4)ncc2cc1F] | 6-(7-fluoro-3-((6-methyl-7-oxo-5,6,7,8-tetrahydro-4H-pyrazolo[1,5-d][1,4]diazepin-2-yl)amino)isoquinolin-6-yl)-5-methylbenzo[d]oxazol-2(3H)-one |
| 174 | 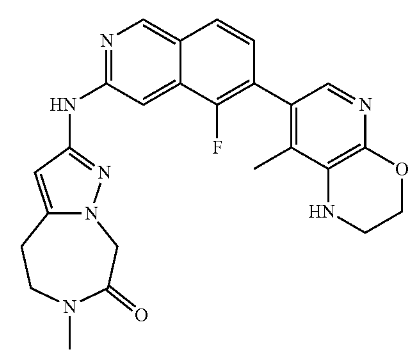 [SMILES: Cc1c(-c2ccc3cnc(Nc4cc5n(n4)CC(=O)N(C)CC5)cc3c2F)cnc2c1NCCO2] | 2-((5-fluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one |
| 175 | 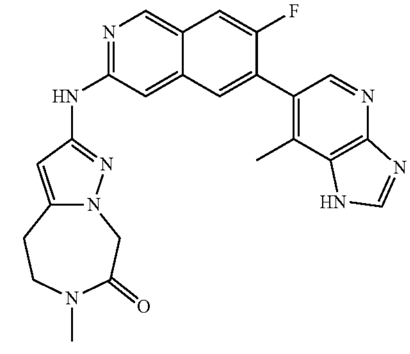 [SMILES: Cc1c(-c2cc3cc(Nc4cc5n(n4)CC(=O)N(C)CC5)ncc3cc2F)cnc2nc[nH]c12] | 2-((7-fluoro-6-(7-methyl-1H-imidazo[4,5-b]pyridin-6-yl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 176 | 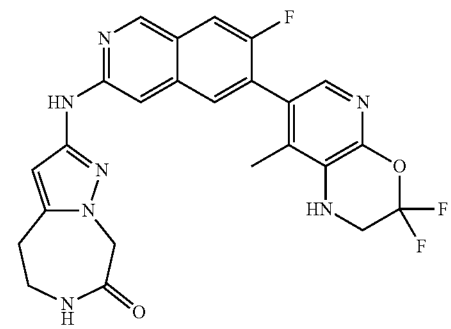 [SMILES: Cc1c(-c2cc3cc(Nc4cc5n(n4)CC(=O)NCC5)ncc3cc2F)cnc2c1NCC(F)(F)O2] | 2-((6-(3,3-difluoro-8-methyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one |
| 177 | 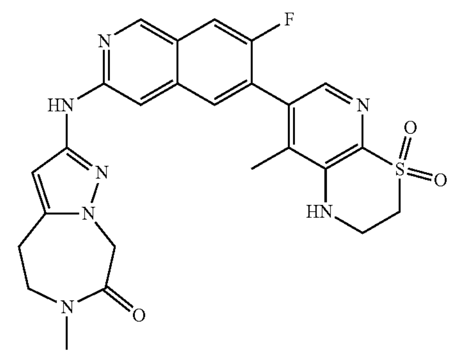 [SMILES: Cc1c(-c2cc3cc(Nc4cc5n(n4)CC(=O)N(C)CC5)ncc3cc2F)cnc2c1NCCS2(=O)=O] | 2-((7-fluoro-6-(8-methyl-4,4-dioxido-2,3-dihydro-1H-pyrido[2,3-b][1,4]thiazin-7-yl)isoquinolin-3-yl)amino)-6-methyl-5,6-dihydro-4H-pyrazolo[1,5-d][1,4]diazepin-7(8H)-one |
| 178 | 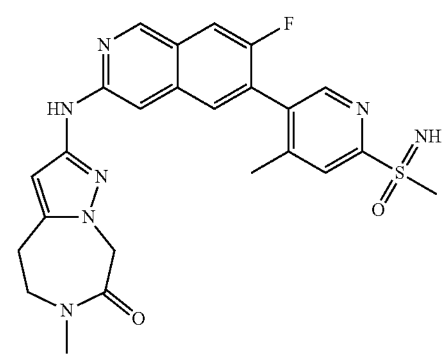 [SMILES: Cc1cc(S(C)(=N)=O)ncc1-c1cc2cc(Nc3cc4n(n3)CC(=O)N(C)CC4)ncc2cc1F] | 2-((7-fluoro-6-(4-methyl-6-(S-methylsulfonimidoyl)pyridin-3-yl)isoquinolin-3-yl)amino)-6-methyl-5,6-dihydro-4H-pyrazolo[1,5-d][1,4]diazepin-7(8H)-one |
| 179 | 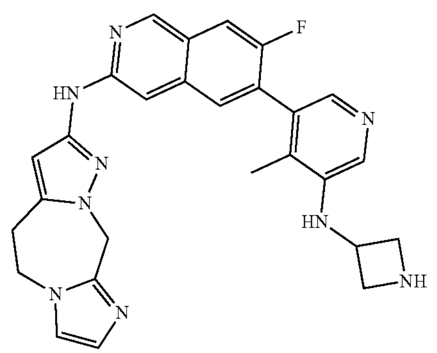 [SMILES: Cc1c(NC2CNC2)cncc1-c1cc2cc(Nc3cc4n(n3)Cc3nccn3CC4)ncc2cc1F] | N-(6-(5-(azetidin-3-ylamino)-4-methylpyridin-3-yl)-7-fluoroisoquinolin-3-yl)-5,6-dihydro-11H-imidazo[1,2-a]pyrazolo[1,5-d][1,4]diazepin-8-amine |

TABLE 1-continued

| Cpd. No. | Structure | Name |
|---|---|---|
| 180 | 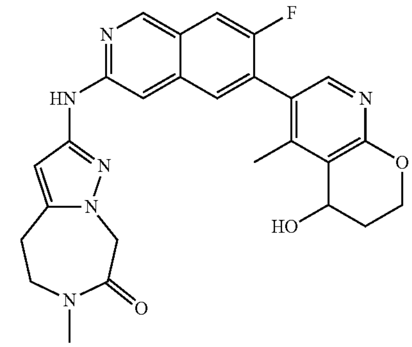 [SMILES: Cc1c(-c2cc3cc(Nc4cc5n(n4)CC(=O)N(C)CC5)ncc3cc2F)cnc2c1C(O)CCO2] | 2-((7-fluoro-6-(4-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 180a 180b | | (S)-2-((7-fluoro-6-(4-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (R)-2-((7-fluoro-6-(4-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 181 | 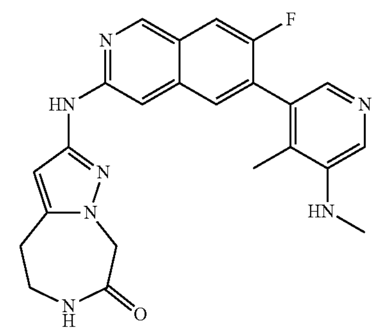 [SMILES: CNc1cncc(-c2cc3cc(Nc4cc5n(n4)CC(=O)NCC5)ncc3cc2F)c1C] | 2-((7-fluoro-6-(4-methyl-5-(methylamino)pyridin-3-yl)isoquinolin-3-yl)amino)-5,6-dihydro-4H-pyrazolo[1,5-d][1,4]diazepin-7(8H)-one |
| 182 | 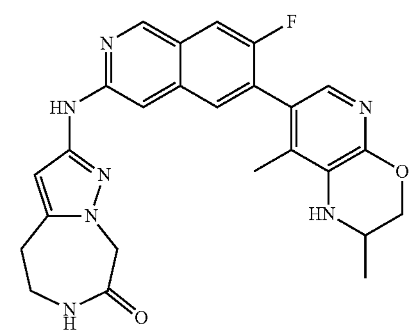 [SMILES: Cc1c(-c2cc3cc(Nc4cc5n(n4)CC(=O)NCC5)ncc3cc2F)cnc2c1NC(C)CO2] | 2-((6-(2,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one |
| 183 | 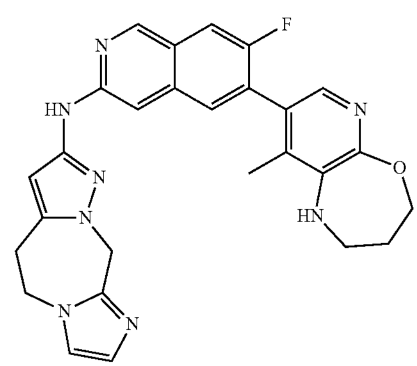 [SMILES: Cc1c(-c2cc3cc(Nc4cc5n(n4)Cc4nccn4CC5)ncc3cc2F)cnc2c1NCCCO2] | N-(7-fluoro-6-(9-methyl-1,2,3,4-tetrahydropyrido[2,3-b][1,4]oxazepin-8-yl)isoquinolin-3-yl)-5,6-dihydro-11H-imidazo[1,2-a]pyrazolo[1,5-d][1,4]diazepin-8-amine |

TABLE 1-continued

| Cpd. No. | Structure | Name |
|---|---|---|
| 184 | 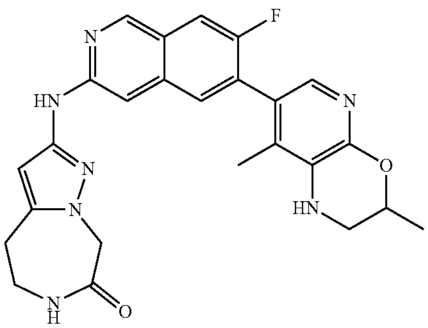 [SMILES: Cc1c(-c2cc3cc(Nc4cc5n(n4)CC(=O)NCC5)ncc3cc2F)cnc2c1NCC(C)O2] | 2-((6-(3,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one |
| 185 | 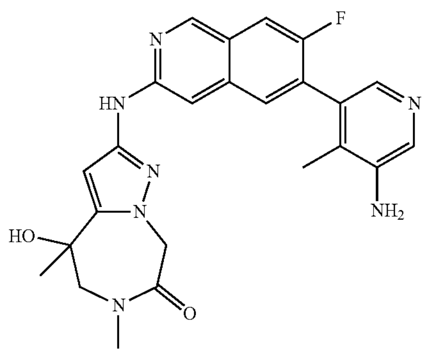 [SMILES: Cc1c(N)cncc1-c1cc2cc(Nc3cc4n(n3)CC(=O)N(C)CC4(C)O)ncc2cc1F] | 2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one |
| 185a 185b | | (R)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one<br>(S)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one |
| 186 | 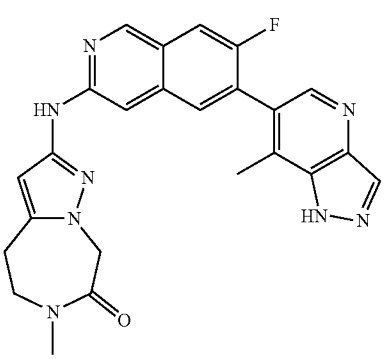 [SMILES: Cc1c(-c2cc3cc(Nc4cc5n(n4)CC(=O)N(C)CC5)ncc3cc2F)cnc2cn[nH]c12] | 2-((7-fluoro-6-(7-methyl-1H-pyrazolo[4,3-b]pyridin-6-yl)isoquinolin-3-yl)amino)-6-methyl-5,6-dihydro-4H-pyrazolo[1,5-d][1,4]diazepin-7(8H)-one |
| 187 | 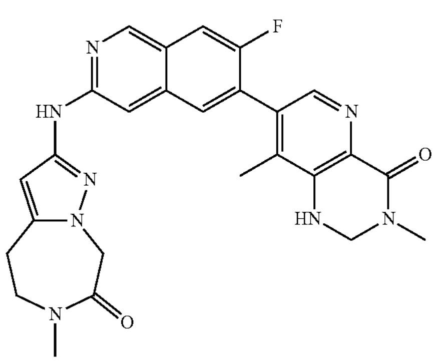 [SMILES: Cc1c(-c2cc3cc(Nc4cc5n(n4)CC(=O)N(C)CC5)ncc3cc2F)cnc2c1NCN(C)C2=O] | 7-(7-fluoro-3-((6-methyl-7-oxo-5,6,7,8-tetrahydro-4H-pyrazolo[1,5-d][1,4]diazepin-2-yl)amino)isoquinolin-6-yl)-3,8-dimethyl-2,3-dihydropyrido[3,2-d]pyrimidin-4(1H)-one |

TABLE 1-continued

| Cpd. No. | Structure | Name |
|---|---|---|
| 188 | 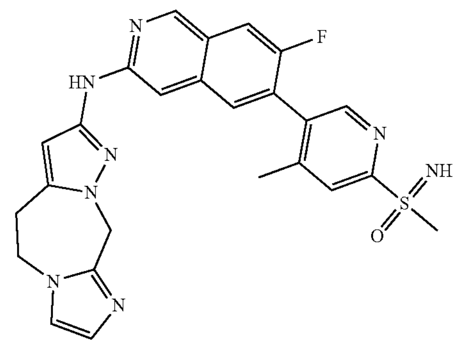 [SMILES: Cc1cc(S(C)(=N)=O)ncc1-c1cc2cc(Nc3cc4n(n3)Cc3nccn3CC4)ncc2cc1F] | (5-(3-((5,6-dihydro-11H-imidazo[1,2-a]pyrazolo[1,5-d][1,4]diazepin-8-yl)amino)-7-fluoroisoquinolin-6-yl)-4-methylpyridin-2-yl)(imino)(methyl)-l6-sulfanone |
| 189 | 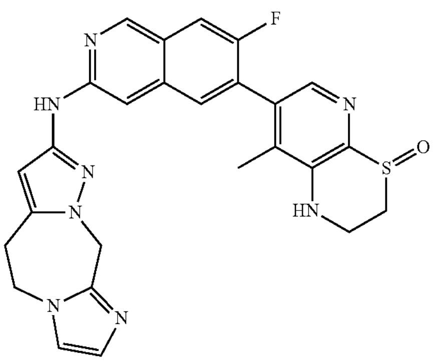 [SMILES: Cc1c(-c2cc3cc(Nc4cc5n(n4)Cc4nccn4CC5)ncc3cc2F)cnc2c1NCCS2=O] | 7-(3-((5,6-dihydro-11H-imidazo[1,2-a]pyrazolo[1,5-d][1,4]diazepin-8-yl)amino)-7-fluoroisoquinolin-6-yl)-8-methyl-2,3-dihydro-1H-pyrido[2,3-b][1,4]thiazine 4-oxide |
| 190 | 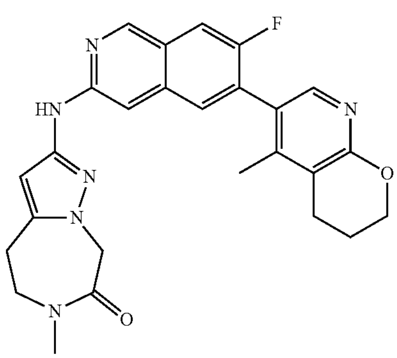 | 2-((7-fluoro-6-(5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 191 | 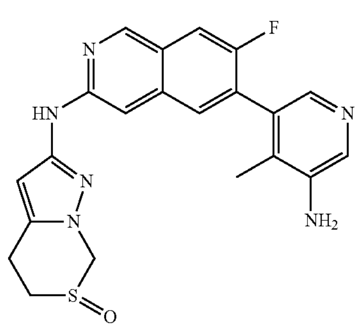 [SMILES: Cc1c(N)cncc1-c1cc2cc(Nc3cc4n(n3)CS(=O)CC4)ncc2cc1F] | (+/-)-2-((6-(5-amino-4-methylpyridin-3-yl)-7-fluoroisoquinolin-3-yl)amino)-4,5-dihydro-7H-pyrazolo[1,5-c][1,3]thiazine 6-oxide |

TABLE 1-continued

| Cpd. No. | Structure | Name |
|---|---|---|
| 192 | 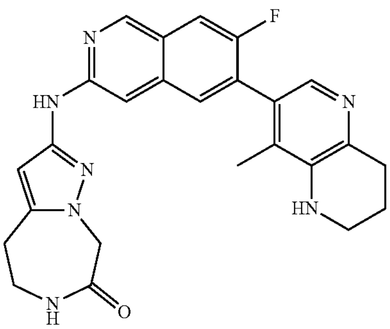 [SMILES: Cc1c(-c2cc3cc(Nc4cc5n(n4)CC(=O)NCC5)ncc3cc2F)cnc2c1NCCC2] | 2-((7-fluoro-6-(4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 193 | 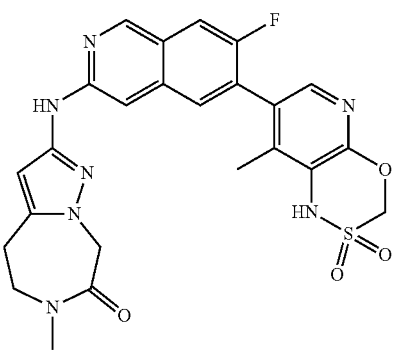 [SMILES: Cc1c(-c2cc3cc(Nc4cc5n(n4)CC(=O)N(C)CC5)ncc3cc2F)cnc2c1NS(=O)(=O)CO2] | 2-((7-fluoro-6-(8-methyl-2,2-dioxido-1H,3H-pyrido[3,2-e][1,3,4]oxathiazin-7-yl)isoquinolin-3-yl)amino)-6-methyl-5,6-dihydro-4H-pyrazolo[1,5-d][1,4]diazepin-7(8H)-one |
| 194 | 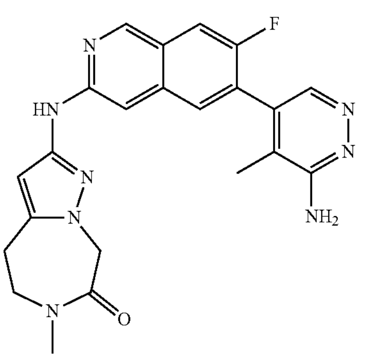 [SMILES: Cc1c(-c2cc3cc(Nc4cc5n(n4)CC(=O)N(C)CC5)ncc3cc2F)cnnc1N] | 2-((6-(6-amino-5-methylpyridazin-4-yl)-7-fluoroisoquinolin-3-yl)amino)-6-methyl-5,6-dihydro-4H-pyrazolo[1,5-d][1,4]diazepin-7(8H)-one |
| 195 | 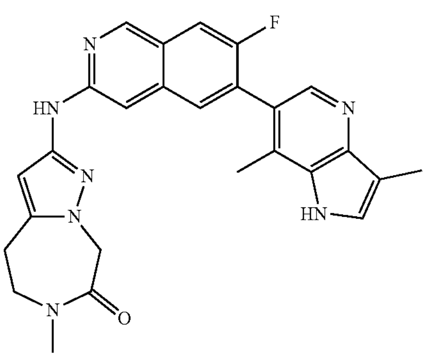 [SMILES: Cc1c[nH]c2c(C)c(-c3cc4cc(Nc5cc6n(n5)CC(=O)N(C)CC6)ncc4cc3F)cnc12] | 2-((6-(3,7-dimethyl-1H-pyrrolo[3,2-b]pyridin-6-yl)-7-fluoroisoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 196 | 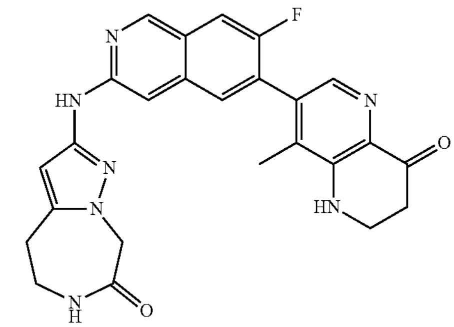 [SMILES: Cc1c(-c2cc3cc(Nc4cc5n(n4)CC(=O)NCC5)ncc3cc2F)cnc2c1NCCC2=O] | 2-((7-fluoro-6-(4-methyl-8-oxo-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 197 | 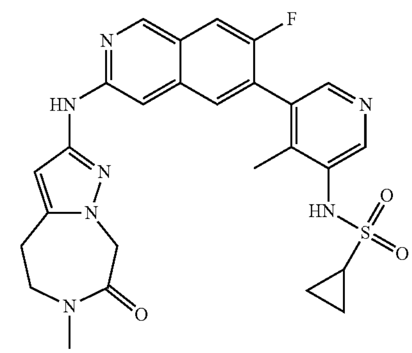 [SMILES: Cc1c(NS(=O)(=O)C2CC2)cncc1-c1cc2cc(Nc3cc4n(n3)CC(=O)N(C)CC4)ncc2cc1F] | N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)cyclopropanesulfonamide |
| 198 | 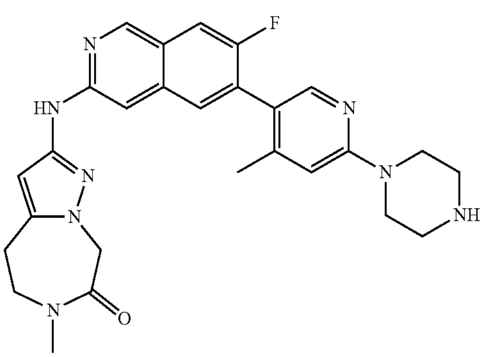 [SMILES: Cc1cc(N2CCNCC2)ncc1-c1cc2cc(Nc3cc4n(n3)CC(=O)N(C)CC4)ncc2cc1F] | 2-((7-fluoro-6-(4-methyl-6-(piperazin-1-yl)pyridin-3-yl)isoquinolin-3-yl)amino)-6-methyl-5,6-dihydro-4H-pyrazolo[1,5-d][1,4]diazepin-7(8H)-one |
| 199 | 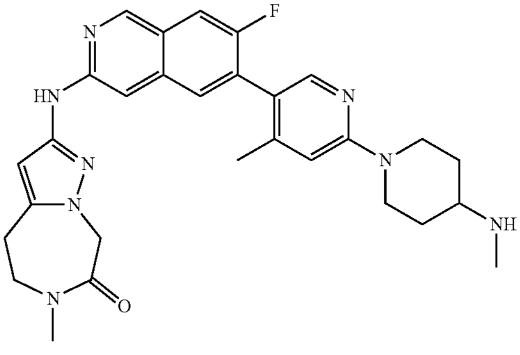 [SMILES: CNC1CCN(c2cc(C)c(-c3cc4cc(Nc5cc6n(n5)CC(=O)N(C)CC6)ncc4cc3F)cn2)CC1] | 2-((7-fluoro-6-(4-methyl-6-(4-(methylamino)piperidin-1-yl)pyridin-3-yl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 200 | 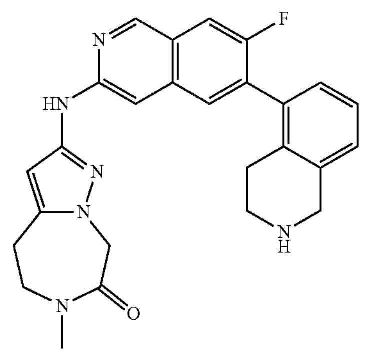 [SMILES: CN1CCc2cc(Nc3cc4cc(-c5cccc6c5CCNC6)c(F)cc4cn3)nn2CC1=O] | 2-((7'-fluoro-1,2,3,4-tetrahydro-[5,6'-biisoquinolin]-3'-yl)amino)-6-methyl-5,6-dihydro-4H-pyrazolo[1,5-d][1,4]diazepin-7(8H)-one |
| 201 | 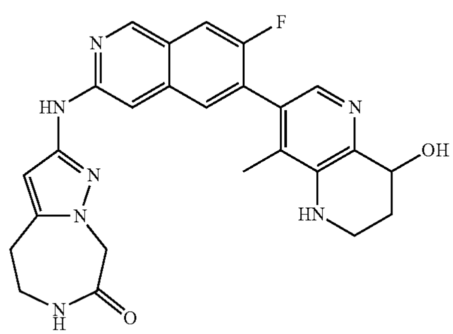 [SMILES: Cc1c(-c2cc3cc(Nc4cc5n(n4)CC(=O)NCC5)ncc3cc2F)cnc2c1NCCC2O] | 2-((7-fluoro-6-(8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 201a 201b | | 2-((7-fluoro-6-((8R)-8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one 2-((7-fluoro-6-((8S)-8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 202 | 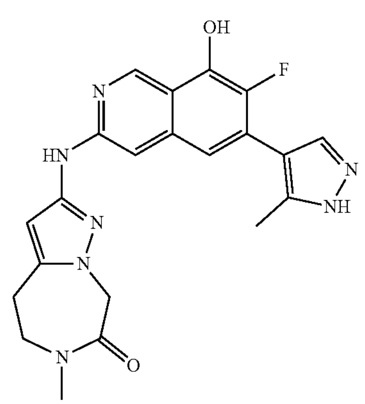 [SMILES: Cc1[nH]ncc1-c1cc2cc(Nc3cc4n(n3)CC(=O)N(C)CC4)ncc2c(O)c1F] | 2-((7-fluoro-8-hydroxy-6-(5-methyl-1H-pyrazol-4-yl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 203 | 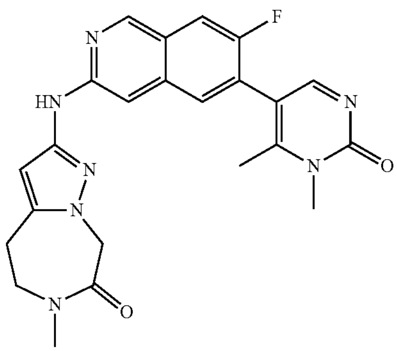 [SMILES: Cc1c(-c2cc3cc(Nc4cc5n(n4)CC(=O)N(C)CC5)ncc3cc2F)cnc(=O)n1C] | 2-((6-(1,6-dimethyl-2-oxo-1,2-dihydropyrimidin-5-yl)-7-fluoroisoquinolin-3-yl)amino)-6-methyl-5,6-dihydro-4H-pyrazolo[1,5-d][1,4]diazepin-7(8H)-one |
| 204 | 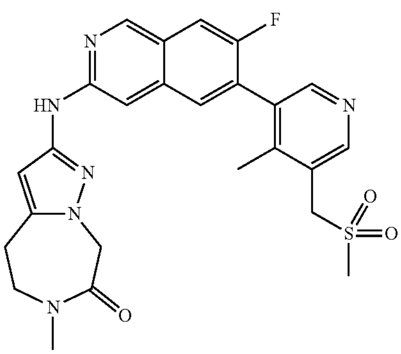 [SMILES: Cc1c(CS(C)(=O)=O)cncc1-c1cc2cc(Nc3cc4n(n3)CC(=O)N(C)CC4)ncc2cc1F] | 2-((7-fluoro-6-(4-methyl-5-((methylsulfonyl)methyl)pyridin-3-yl)isoquinolin-3-yl)amino)-6-methyl-5,6-dihydro-4H-pyrazolo[1,5-d][1,4]diazepin-7(8H)-one |
| 205 | 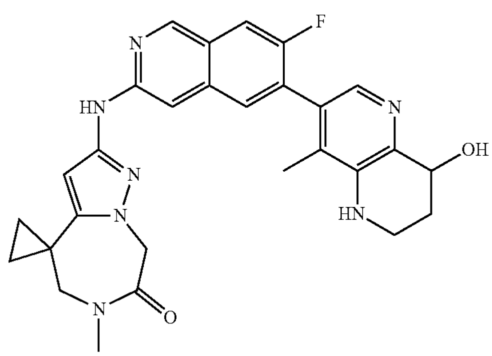 [SMILES: Cc1c(-c2cc3cc(Nc4cc5n(n4)CC(=O)N(C)CC54CC4)ncc3cc2F)cnc2c1NCCC2O] | 2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 205a 205b | | (R)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (S)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |

TABLE 1-continued

| Cpd. No. | Structure | Name |
|---|---|---|
| 206 | 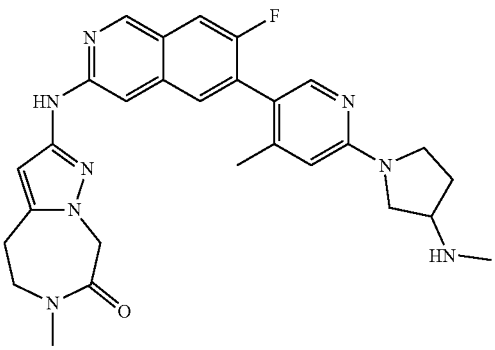 | 2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one |
| 206a 206b | | (R)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d] [1,4]diazepin-7(8H)-one<br>(S)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d] [1,4]diazepin-7(8H)-one |
| 207 | 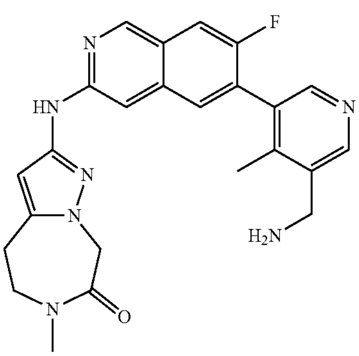 [SMILES: Cc1c(CN)cncc1-c1cc2cc(Nc3cc4n(n3)CC(=O)N(C)CC4)ncc2cc1F] | 2-((6-(3-(aminomethyl)-2-methylphenyl)-7-fluoroisoquinolin-3-yl)amino)-6-methyl-5,6-dihydro-4H-pyrazolo[1,5-d][1,4]diazepin-7(8H)-one |
| 208 | 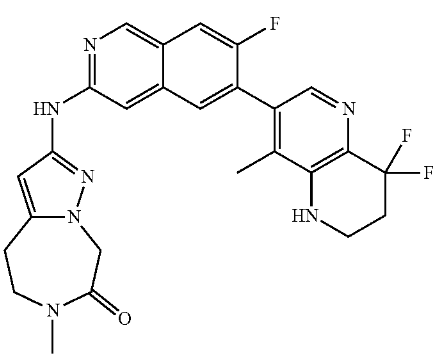 [SMILES: Cc1c(-c2cc3cc(Nc4cc5n(n4)CC(=O)N(C)CC5)ncc3cc2F)cnc2c1NCCC2(F)F] | 2-((6-(8,8-difluoro-4-methyl-5,6,7,8-tetrahydro-1,5-naphthyridin-3-yl)-7-fluoroisoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 209 | 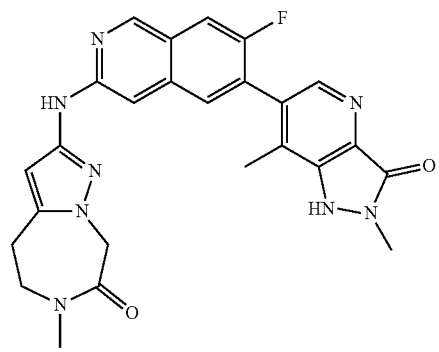 [SMILES: Cc1c(-c2cc3cc(Nc4cc5n(n4)CC(=O)N(C)CC5)ncc3cc2F)cnc2c(=O)n(C)[nH]c12] | 2-((6-(2,7-dimethyl-3-oxo-2,3-dihydro-1H-pyrazolo[4,3-b]pyridin-6-yl)-7-fluoroisoquinolin-3-yl)amino)-6-methyl-5,6-dihydro-4H-pyrazolo[1,5-d][1,4]diazepin-7(8H)-one |
| 210 | 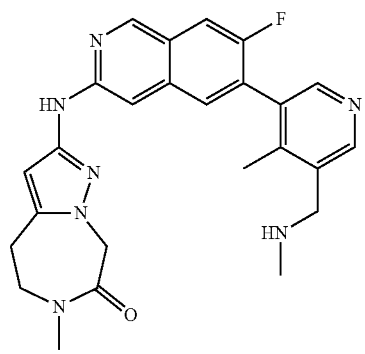 [SMILES: CNCc1cncc(-c2cc3cc(Nc4cc5n(n4)CC(=O)N(C)CC5)ncc3cc2F)c1C] | 2-((7-fluoro-6-(4-methyl-5-((methylamino)methyl)pyridin-3-yl)isoquinolin-3-yl)amino)-6-methyl-5,6-dihydro-4H-pyrazolo[1,5-d][1,4]diazepin-7(8H)-one |
| 211 | 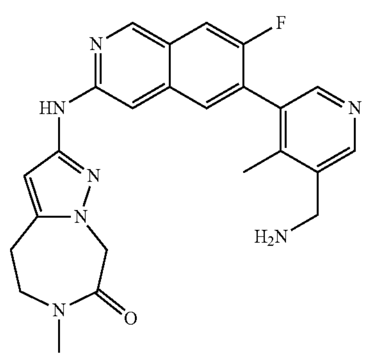 [SMILES: Cc1c(CN)cncc1-c1cc2cc(Nc3cc4n(n3)CC(=O)N(C)CC4)ncc2cc1F] | 2-((6-(5-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one |
| 212 | 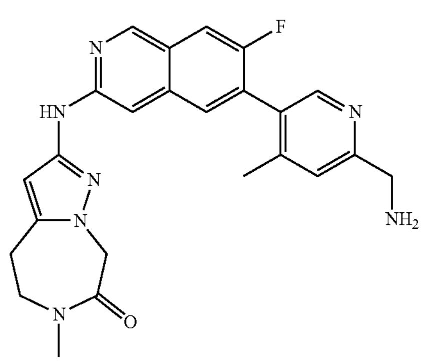 | 2-((6-(6-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 213 | 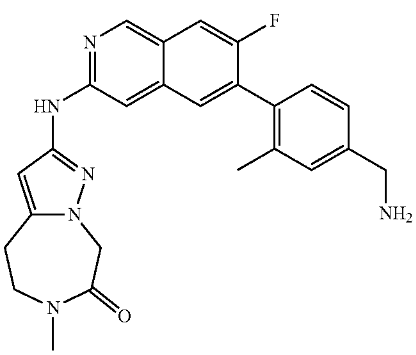 [SMILES: Cc1cc(CN)ccc1-c1cc2cc(Nc3cc4n(n3)CC(=O)N(C)CC4)ncc2cc1F] | 2-((6-(4-(aminomethyl)-2-methylphenyl)-7-fluoroisoquinolin-3-yl)amino)-6-methyl-5,6-dihydro-4H-pyrazolo[1,5-d][1,4]diazepin-7(8H)-one |
| 214 | 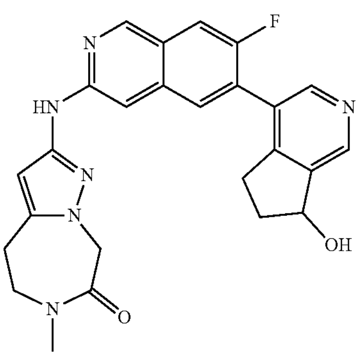 [SMILES: CN1CCc2cc(Nc3cc4cc(-c5cncc6c5CCC6O)c(F)cc4cn3)nn2CC1=O] | (+/-)-2-((7-fluoro-6-(7-hydroxy-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one |
| 215 | 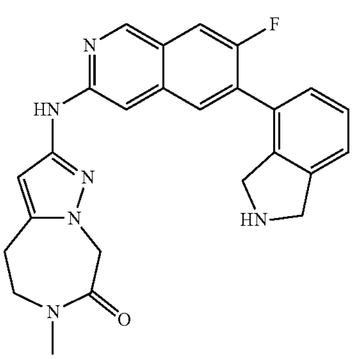 [SMILES: CN1CCc2cc(Nc3cc4cc(-c5cccc6c5CNC6)c(F)cc4cn3)nn2CC1=O] | 2-((7-fluoro-6-(isoindolin-4-yl)isoquinolin-3-yl)amino)-6-methyl-5,6-dihydro-4H-pyrazolo[1,5-d][1,4]diazepin-7(8H)-one |
| 216 | 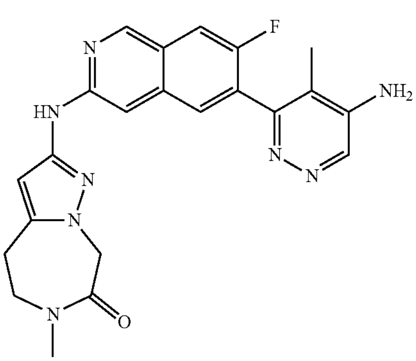 [SMILES: Cc1c(N)cnnc1-c1cc2cc(Nc3cc4n(n3)CC(=O)N(C)CC4)ncc2cc1F] | 2-((6-(5-amino-4-methylpyridazin-3-yl)-7-fluoroisoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 217 | 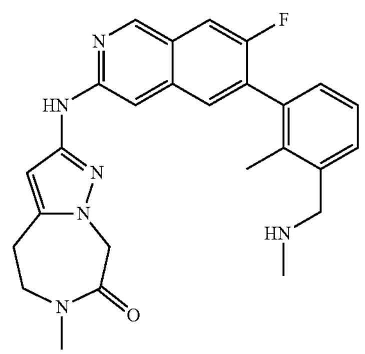 | 2-((7-fluoro-6-(2-methyl-3-((methylamino)methyl)phenyl)isoquinolin-3-yl)amino)-6-methyl-5,6-dihydro-4H-pyrazolo[1,5-d][1,4]diazepin-7(8H)-one |
| 218 | 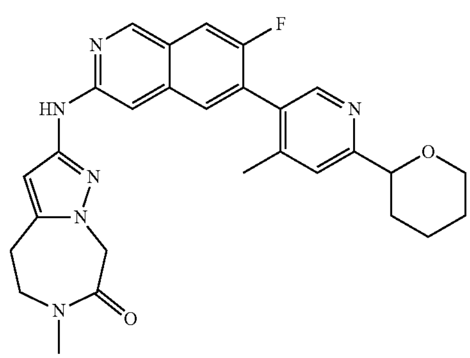 [SMILES: Cc1cc(C2CCCCO2)ncc1-c1cc2cc(Nc3cc4n(n3)CC(=O)N(C)CC4)ncc2cc1F] | (+/-)-2-((7-fluoro-6-(4-methyl-6-(tetrahydro-2H-pyran-2-yl)pyridin-3-yl)isoquinolin-3-yl)amino)-6-methyl-5,6-dihydro-4H-pyrazolo[1,5-d][1,4]diazepin-7(8H)-one |
| 219 | 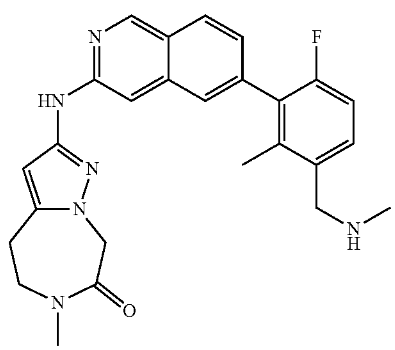 [SMILES: CNCc1ccc(F)c(-c2ccc3cnc(Nc4cc5n(n4)CC(=O)N(C)CC5)cc3c2)c1C] | 2-((6-(6-fluoro-2-methyl-3-((methylamino)methyl)phenyl)isoquinolin-3-yl)amino)-6-methyl-5,6-dihydro-4H-pyrazolo[1,5-d][1,4]diazepin-7(8H)-one |
| 220 | 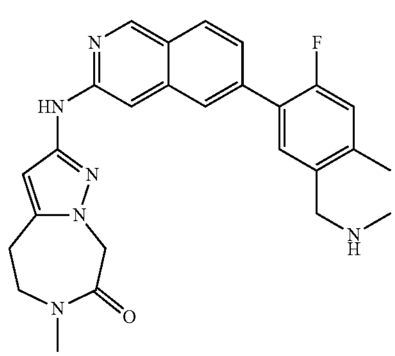 [SMILES: CNCc1cc(-c2ccc3cnc(Nc4cc5n(n4)CC(=O)N(C)CC5)cc3c2)c(F)cc1C] | 2-((6-(2-fluoro-4-methyl-5-((methylamino)methyl)phenyl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 221 | 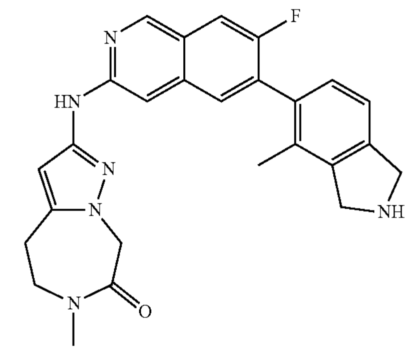 [SMILES: Cc1c(-c2cc3cc(Nc4cc5n(n4)CC(=O)N(C)CC5)ncc3cc2F)ccc2c1CNC2] | 2-((7-fluoro-6-(4-methylisoindolin-5-yl)isoquinolin-3-yl)amino)-6-methyl-5,6-dihydro-4H-pyrazolo[1,5-d][1,4]diazepin-7(8H)-one |
| 222 | 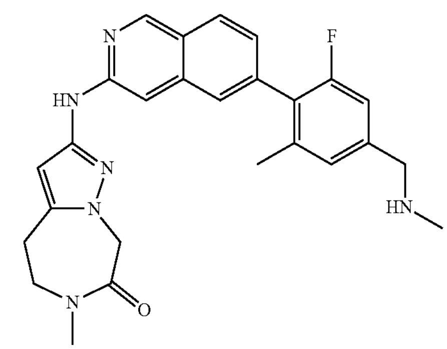 [SMILES: CNCc1cc(C)c(-c2ccc3cnc(Nc4cc5n(n4)CC(=O)N(C)CC5)cc3c2)c(F)c1] | 2-((6-(2-fluoro-6-methyl-4-((methylamino)methyl)phenyl)isoquinolin-3-yl)amino)-6-methyl-5,6-dihydro-4H-pyrazolo[1,5-d][1,4]diazepin-7(8H)-one |
| 223 | 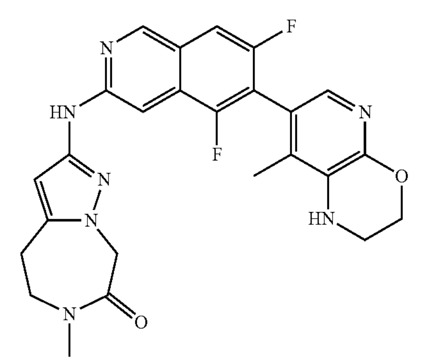 [SMILES: Cc1c(-c2c(F)cc3cnc(Nc4cc5n(n4)CC(=O)N(C)CC5)cc3c2F)cnc2c1NCCO2] | 2-((5,7-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one |
| 224 | 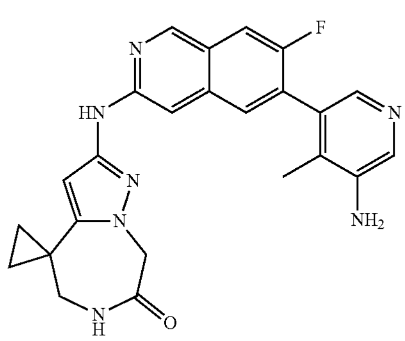 [SMILES: Cc1c(N)cncc1-c1cc2cc(Nc3cc4n(n3)CC(=O)NCC43CC3)ncc2cc1F] | 2'-((6-(5-amino-4-methylpyridin-3-yl)-7-fluoroisoquinolin-3-yl)amino)-5',6'-dihydrospiro[cyclopropane-1,4'-pyrazolo[1,5-d][1,4]diazepin]-7'(8'H)-one |

TABLE 1-continued

| Cpd. No. | Structure | Name |
|---|---|---|
| 225 | 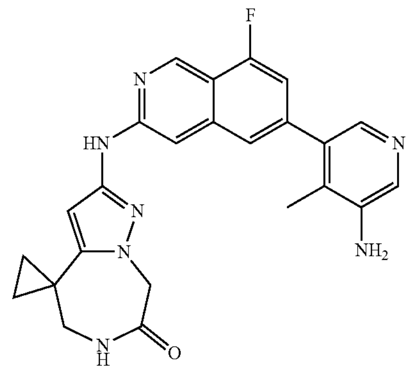 [SMILES: Cc1c(N)cncc1-c1cc(F)c2cnc(Nc3cc4n(n3)CC(=O)NCC43CC3)cc2c1] | 2'-((6-(5-amino-4-methylpyridin-3-yl)-8-fluoroisoquinolin-3-yl)amino)-5',6'-dihydrospiro[cyclopropane-1,4'-pyrazolo[1,5-d][1,4]diazepin]-7'(8'H)-one |
| 226 | 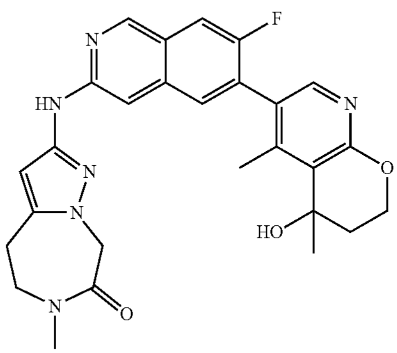 [SMILES: Cc1c(-c2cc3cc(Nc4cc5n(n4)CC(=O)N(C)CC5)ncc3cc2F)cnc2c1C(C)(O)CCO2] | 2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 226a 226b | | (S)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one<br>(R)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 227 | 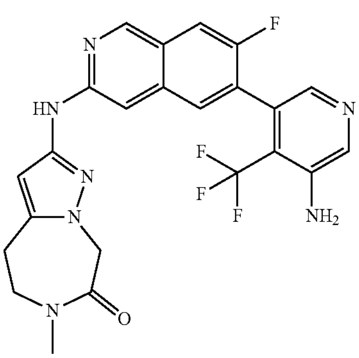 [SMILES: CN1CCc2cc(Nc3cc4cc(-c5cncc(N)c5C(F)(F)F)c(F)cc4cn3)nn2CC1=O] | 2-((6-(5-amino-4-(trifluoromethyl)pyridin-3-yl)-7-fluoroisoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 228 | 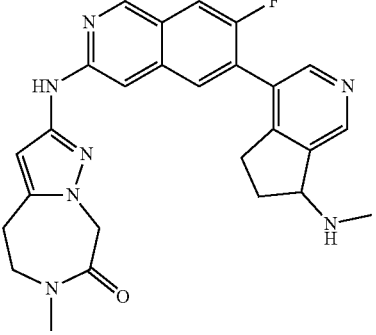 | 2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one |
| 228a 228b | | (R)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d] [1,4]diazepin-7(8H)-one<br>(S)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d] [1,4]diazepin-7(8H)-one |
| 229 | 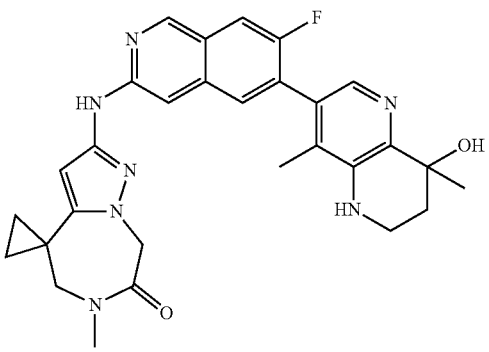 [SMILES: Cc1c(-c2cc3cc(Nc4cc5n(n4)CC(=O)N(C)CC54CC4)ncc3cc2F)cnc2c1NCCC2(C)O] | 2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 229a 229b | | (S)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one<br>(R)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 230 | 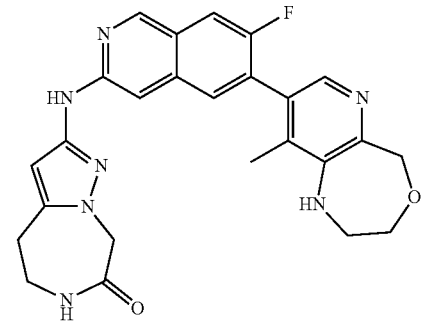 [SMILES: Cc1c(-c2cc3cc(Nc4cc5n(n4)CC(=O)NCC5)ncc3cc2F)cnc2c1NCCOC2] | 2-((7-fluoro-6-(9-methyl-1,2,3,5-tetrahydropyrido[3,2-e][1,4]oxazepin-8-yl)isoquinolin-3-yl)amino)-5,6-dihydro-4H-pyrazolo[1,5-d][1,4]diazepin-7(8H)-one |

TABLE 1-continued

| Cpd. No. | Structure | Name |
|---|---|---|
| 231 | 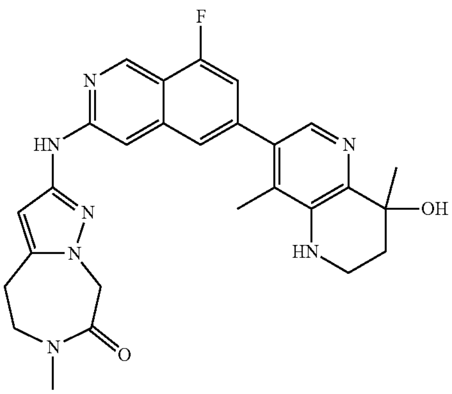 | 2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 231a 231b | | (R)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (S)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 232 | 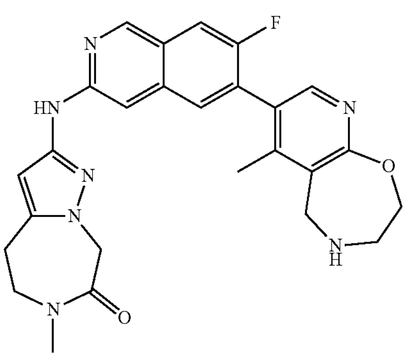 [SMILES: Cc1c(-c2cc3cc(Nc4cc5n(n4)CC(=O)N(C)CC5)ncc3cc2F)cnc2c1CNCCO2] | 2-((7-fluoro-6-(6-methyl-2,3,4,5-tetrahydropyrido[3,2-f][1,4]oxazepin-7-yl)isoquinolin-3-yl)amino)-6-methyl-5,6-dihydro-4H-pyrazolo[1,5-d][1,4]diazepin-7(8H)-one |
| 233 | 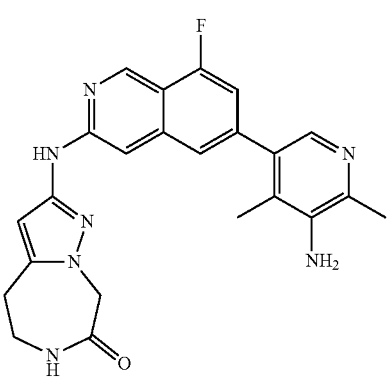 [SMILES: Cc1ncc(-c2cc(F)c3cnc(Nc4cc5n(n4)CC(=O)NCC5)cc3c2)c(C)c1N] | 2-((6-(5-amino-4,6-dimethylpyridin-3-yl)-8-fluoroisoquinolin-3-yl)amino)-5,6-dihydro-4H-pyrazolo[1,5-d][1,4]diazepin-7(8H)-one |

TABLE 1-continued

| Cpd. No. | Structure | Name |
|---|---|---|
| 234 | 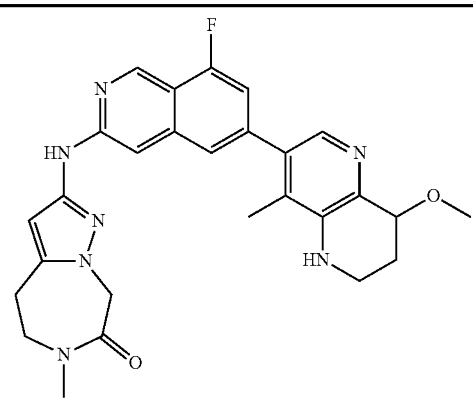 | 2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 234a 234b | | (S)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (R)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 235 | 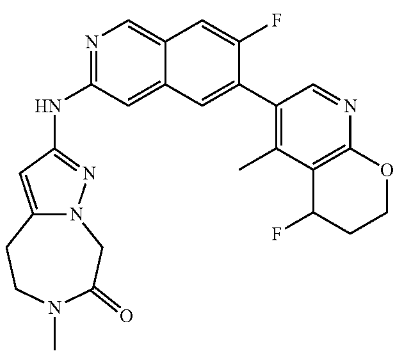 | 2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 235a 235b | | (S)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (R)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d] [1,4]diazepin-7(8H)-one |
| 236 | 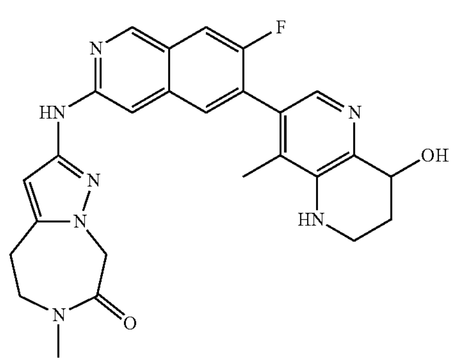 [SMILES: Cc1c(-c2cc3cc(Nc4cc5n(n4)CC(=O)N(C)CC5)ncc3cc2F)cnc2c1NCCC2O] | 2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |

TABLE 1-continued

| Cpd. No. | Structure | Name |
|---|---|---|
| 236a 236b | | (S)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (R)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 237 | 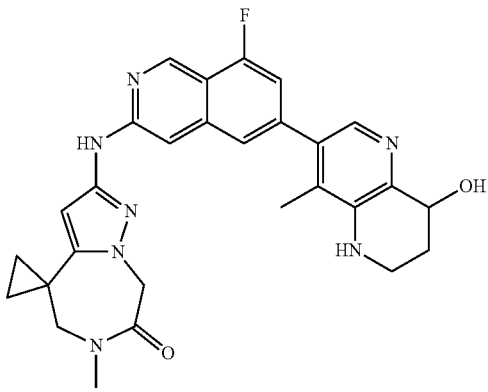 | 2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 237a 237b | | (S)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (R)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 238 | 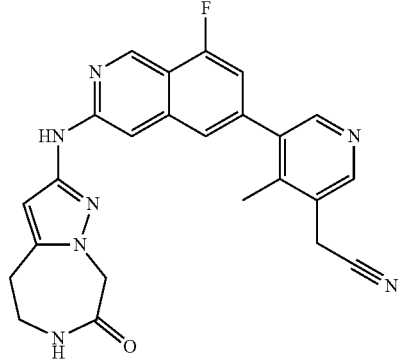 [SMILES: Cc1c(CC#N)cncc1-c1cc(F)c2cnc(Nc3cc4n(n3)CC(=O)NCC4)cc2c1] | 2-(5-(8-fluoro-3-((7-oxo-5,6,7,8-tetrahydro-4H-pyrazolo[1,5-d][1,4]diazepin-2-yl)amino)isoquinolin-6-yl)-4-methylpyridin-3-yl)acetonitrile |
| 239 | 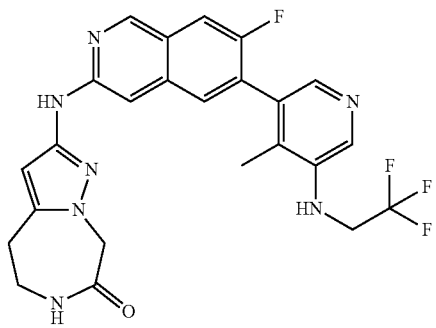 [SMILES: Cc1c(NCC(F)(F)F)cncc1-c1cc2cc(Nc3cc4n(n3)CC(=O)NCC4)ncc2cc1F] | 2-((7-fluoro-6-(4-methyl-5-((2,2,2-trifluoroethyl)amino)pyridin-3-yl)isoquinolin-3-yl)amino)-5,6-dihydro-4H-pyrazolo[1,5-d][1,4]diazepin-7(8H)-one |

TABLE 1-continued

| Cpd. No. | Structure | Name |
|---|---|---|
| 240 | 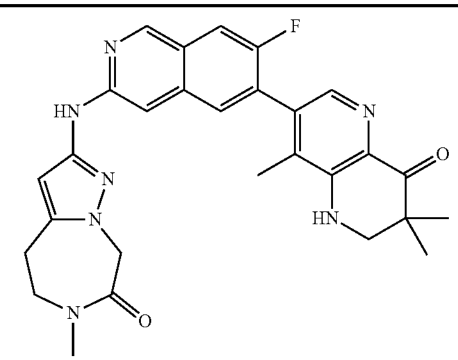 | 2-((7-fluoro-6-(4,7,7-trimethyl-8-oxo-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 241 | 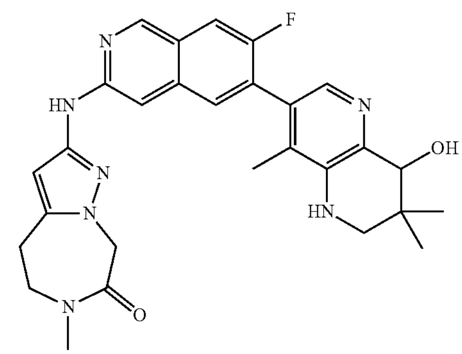 [SMILES: Cc1c(-c2cc3cc(Nc4cc5n(n4)CC(=O)N(C)CC5)ncc3cc2F)cnc2c1NCC(C)(C)C2O] | 2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 241a 241b | | (R)-2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (S)-2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 242 | | 2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide |
| 242a 242b | | (S)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide (R)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide |
| 243 | | 7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol |
| 243a 243b | | (S)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol (R)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol |

TABLE 1-continued

| Cpd. No. | Structure | Name |
|---|---|---|
| 244 | | 2-((7-fluoro-6-(8-methyl-2,3-dihydro-1H-pyrido[2,3-b][1,4]oxazin-7-yl)isoquinolin-3-yl)amino)-6-methyl-4H,6H-pyrazolo[1,5-e][1,2,5]oxadiazepin-7(8H)-one |

In some embodiments, provided is a compound selected from Compound Nos. 101-244 in Table 1, or a salt (e.g., a pharmaceutically acceptable salt) thereof. In some embodiments, provided is a compound selected from Compound Nos. 101-239 in Table 1, or a salt (e.g., a pharmaceutically acceptable salt) thereof. In some embodiments, provided is a compound selected from Compound Nos. 101-201, 203-204 and 206-239 in Table 1, or a salt (e.g., a pharmaceutically acceptable salt) thereof. In some embodiments, provided is a compound selected from Compound Nos. 101-109 in Table 1, or a salt (e.g., a pharmaceutically acceptable salt) thereof. In some embodiments, provided is a compound selected from Compound Nos. 110-239 in Table 1, or a salt (e.g., a pharmaceutically acceptable salt) thereof. In some embodiments, provided is a compound selected from Compound Nos. 110-201, 203-204 and 206-239 in Table 1, or a salt (e.g., a pharmaceutically acceptable salt) thereof. In some embodiments, provided is a compound selected from Compound Nos. 110-244 in Table 1, or a salt (e.g., a pharmaceutically acceptable salt) thereof. In some embodiments, provided is a compound selected from Compound Nos. 202, 205 and 240-244 in Table 1, or a salt (e.g., a pharmaceutically acceptable salt) thereof.

Compounds of Formula (I) described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas (I) may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

The subject matter disclosed herein includes prodrugs, metabolites, derivatives, and pharmaceutically acceptable salts of compounds of Formula (I). Metabolites of the compounds of Formula (I) include compounds produced by a process comprising contacting a compound of Formula (I) with a mammal for a period of time sufficient to yield a metabolic product thereof.

If the compound of Formula (I) is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula (I) is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula (I) can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

General Synthetic Method

Compounds of Formula (I) can be prepared by procedures in the Examples and generally by Schemes 1 and 2, where R groups are as described in Formula (I), or precursors thereof.

Scheme 1

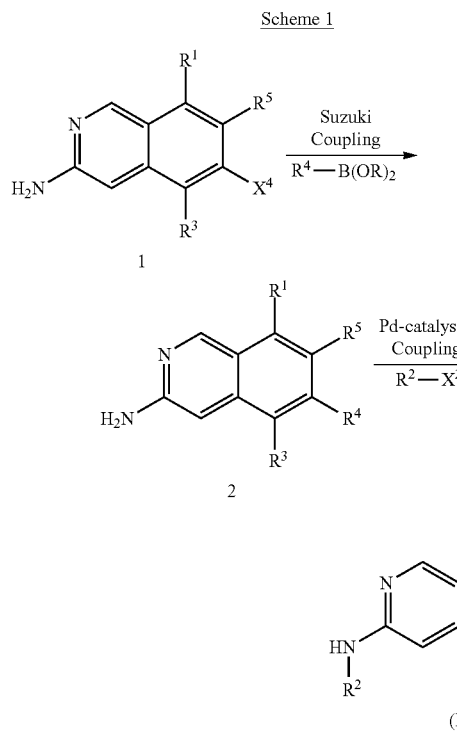

Scheme 1 shows a general synthetic scheme for preparing a compound of Formula (I), wherein $R^1$, $R^2$, $R^3$, $R^4$ and $R^5$ are as detailed herein, from a compound of Formula 2, which in term can be prepared from a compound of Formula 1, wherein $X^4$ is a halogen (e.g., Cl, Br or I). Installation of $R^4$ can be achieved via a Suzuki coupling a compound of Formula 1 with the corresponding boronic acid or boronate pinacol ester of the formula $R^4$—B(OR)$_2$, where R is H, optionally substituted $C_{1-6}$ alkyl, or the two OR groups taken together with the boron atom to which they are attached form a ring (e.g., pinacol boronate), using a palladium-based catalyst (e.g., Pd(dppf)Cl$_2$ or (Ph$_3$P)$_4$Pd) in the presence of a base (e.g. sodium carbonate or potassium acetate) in a solvent (e.g. 1,4-dioxane and water or acetonitrile and water). $R^2$ is then installed via a Pd-catalyzed coupling of a compound of Formula 2 with corresponding aryl or heteroaryl halide of the formula $R^2$—$X^2$ (where $X^2$ is Cl, Br or I) in the presence of a catalyst (e.g., tBuBrettPhos Pd G$_3$ or XantPhos/Pd$_2$(dba)$_3$), a base (e.g. cesium carbonate) and a solvent (e.g. 1,4-dioxane).

Provided is a method for making a compound of Formula (I):

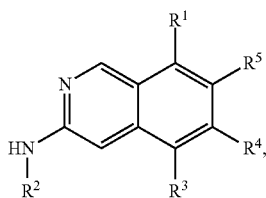

or a salt thereof, wherein $R^1$, $R^2$, $R^3$, $R^4$ and $R^5$ are as detailed herein, comprising reacting a compound of Formula 2:

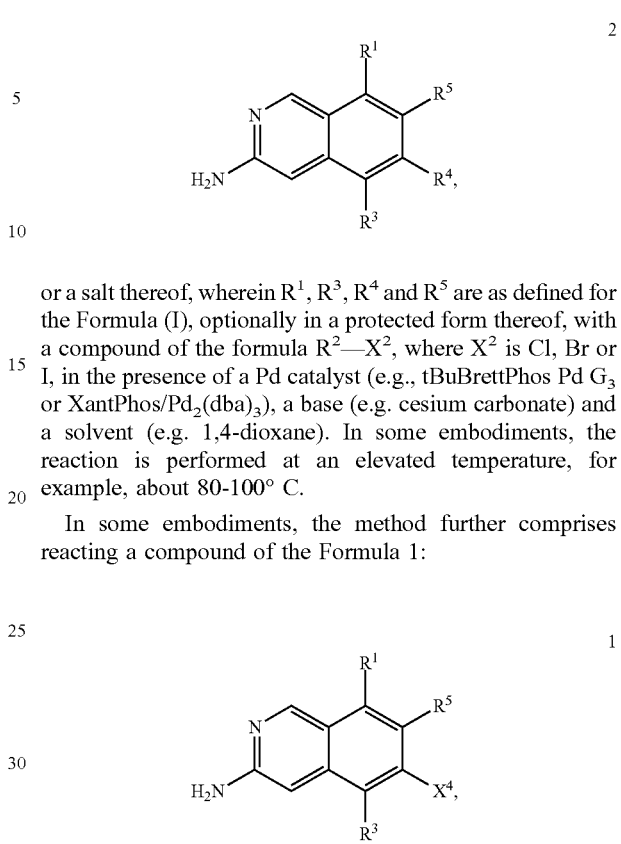

or a salt thereof, wherein $R^1$, $R^3$, $R^4$ and $R^5$ are as defined for the Formula (I), optionally in a protected form thereof, with a compound of the formula $R^2$—$X^2$, where $X^2$ is Cl, Br or I, in the presence of a Pd catalyst (e.g., tBuBrettPhos Pd G$_3$ or XantPhos/Pd$_2$(dba)$_3$), a base (e.g. cesium carbonate) and a solvent (e.g. 1,4-dioxane). In some embodiments, the reaction is performed at an elevated temperature, for example, about 80-100° C.

In some embodiments, the method further comprises reacting a compound of the Formula 1:

or a salt thereof, wherein $R^1$, $R^3$ and $R^5$ are as defined for the Formula (I) or Formula 2, optionally in a protected form thereof, with a compound of the formula $R^4$—B(OR)$_2$, wherein R is H, optionally substituted $C_{1-6}$ alkyl, or the two OR groups taken together with the boron atom to which they are attached form a ring (e.g., pinacol boronate), in the presence of a catalyst for Suzuki coupling (e.g., Pd(dppf)Cl$_2$ or (Ph$_3$P)$_4$Pd), a base (e.g. sodium carbonate or potassium acetate), and a solvent (e.g. 1,4-dioxane and water or acetonitrile and water), to form a compound of Formula 2. In some embodiments, the Suzuki coupling reaction is performed at an elevated temperature, for example, about 100-120° C.

Scheme 2

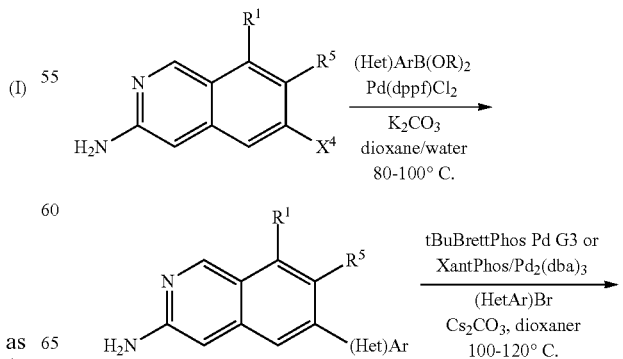

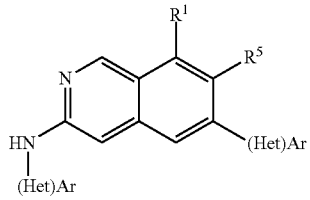

Scheme 2 shows an example of the general synthetic method as in Scheme 1, where in the compound of Formula (I), $R^2$ is an optionally substituted heteroaryl, $R^3$ is hydrogen, and $R^4$ is an optionally substituted heteroaryl; in the step of the Suzuki coupling reaction forming the compound of Formula 2, the catalyst for Suzuki coupling is Pd(dppf)Cl$_2$, the base is potassium carbonate, and the solvent is 1,4-dioxane and water; and in the step of the palladium-catalyzed coupling reaction forming the compound of Formula (I), the Pd catalyst is tBuBrettPhos Pd G$_3$ or XantPhos/Pd$_2$(dba)$_3$), the base is cesium carbonate, and the solvent is 1,4-dioxane.

Pharmaceutical Compositions and Formulations

The presently disclosed compounds can be formulated into pharmaceutical compositions along with a pharmaceutically acceptable carrier or excipient.

Compounds of Formula (I), or variations thereof such as Formula (IA), (IB) and (IC), can be formulated in accordance with standard pharmaceutical practice as a pharmaceutical composition. According to this aspect, there is provided a pharmaceutical composition comprising a compound of Formula (I), or variations thereof such as Formula (IA), (IB) and (IC), in association with a pharmaceutically acceptable excipient, diluent or carrier.

A typical formulation is prepared by mixing a compound of Formula (I), or variations thereof such as Formula (IA), (IB) and (IC), and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula (I), or variations thereof such as Formula (IA), (IB) and (IC), is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula (I), or variations thereof such as Formula (IA), (IB) and (IC), or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula (I), or variations thereof such as Formula (IA), (IB) and (IC), or stabilized form of the Compound of Formula (I), or variations thereof such as Formula (IA), (IB) and (IC), (e.g., complex with a cyclodextrin derivative or other known complexation agent) is dissolved in a suitable solvent in the presence of one or more of the excipients described above. The compound of Formula (I) is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable excipients or carriers, i.e., excipients or carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula (I) can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula (I) can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. In some embodiments, the amount is below the amount that is toxic to the host or renders the host more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980).

Sustained-release preparations of Formula (I) compounds may be prepared. Suitable examples of sustained-release preparations include semipermeable matrices of solid hydrophobic polymers containing a compound of Formula (I) or Ia, which matrices are in the form of shaped articles, e.g., films, or microcapsules. Examples of sustained-release matrices include polyesters, hydrogels (for example, poly (2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, PA). Such methods include the step of bringing into association the active ingredient with the excipient or carrier which constitutes one or more accessory ingredients. In general the formulations are prepared by uniformly and intimately bringing into association the active ingredient with liquid excipients or carriers or finely divided solid excipients or carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I) or Ia.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxyc- etanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I), or variations thereof such as Formula (IA), (IB) and (IC), may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the excipient or carrier material to produce a single dosage form will vary depending upon the host treated and the particular mode of administration. For example, a time-release formulation intended for oral administration to humans may contain approximately 1 to 1000 mg of active material compounded with an appropriate and convenient amount of excipient or carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable excipient or carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid excipient or carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of disorders as described below.

Formulations suitable for vaginal administration may be presented as pessaries, tampons, creams, gels, pastes, foams or spray formulations containing in addition to the active ingredient such excipients or carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid excipient or carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary excipient or carrier therefore. Veterinary excipients or carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods of Use

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threnonine kinases. HPK1 functions as a MAP4K by phosphorylating and activating MAP3K proteins, including MEKK1, MLK3 and TAK1, leading to the activation of the MAPK Jnk.

In an embodiment, the subject matter disclosed herein is directed to a method of inhibiting HPK1, the method comprising contacting HPK1 with an effective amount of a compound of Formula (I), or variations thereof such as Formula (IA), (IB) and (IC), or a pharmaceutical composition described herein.

In an embodiment, the subject matter disclosed herein is directed to a method for enhancing an immune response in a subject in need thereof, wherein the method comprises administering to said subject an effective amount of a compound of Formula (I), or variations thereof such as Formula (IA), (IB) and (IC), or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+CD8 T cells, an elevated frequency of γ-IFN+CD4 T cells, or enhanced levels of IL-2 or granzyme B production by T cells, relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the T cell is an antigen-specific CD4 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells. In some aspects, compounds of Formula (I), or variations thereof such as Formula (IA), (IB) and (IC), or a pharmaceutical composition thereof provides general priming of the immune response (i.e., vaccines) to tumors or viruses for boosting/generating anti-viral/tumor immunity.

In the methods described herein, a compound of Formula (I), or variations thereof such as Formula (IA), (IB) and (IC), or a pharmaceutical composition thereof is administered to a subject that has cancer as described elsewhere herein.

In an embodiment, the subject matter disclosed herein is directed to a method for treating a HPK1-dependent disorder, the method comprising administering to a subject in need thereof an effective amount of a compound of Formula (I), or variations thereof such as Formula (IA), (IB) and (IC), or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a chemotherapeutic agent to said subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or said composition.

HPK1 polynucleotides and polypeptides are known in the art (Hu et al. (1996) Genes Dev. 10: 2251-2264, which is herein incorporated by reference in its entirety). Certain HPK1 polynucleotides and polypeptides comprise the human HPK11 polynucleotide are accessible and the sequences are known, for example, nucleotides 141-2642 of GenBank Accession No. NM_007181.5 and the encoded human HPK11 polypeptide (Accession No. NP_009112.1); and nucleotides 141-2606 of GenBank Accession No. NM_001042600.2 and the encoded human HPK1 polypeptide (Accession No. NP_001036065.1).

HPK1 polypeptides comprise a variety of conserved structural motifs. HPK11 polypeptides comprise an amino-terminal Ste20-like kinase domain, which includes the ATP-binding site. The kinase domain is followed by four proline-rich (PR) motifs that serve as binding sites for SH3-containing proteins, such as CrkL, Grb2, HIP-55, Gads, Nck, and Crk. HPK1 becomes phosphorylated and activated in response to TCR or BCR stimulation. TCR- and BCR-induced phosphorylation of a tyrosine residue located between PR1 and PR2, mediates binding to SLP-76 in T cells or BLNK in B cells via a SLP-76 or BLNK SH2 domain, and is required for activation of the kinase. A citron homology domain found in the C-terminus of HPK1 may act as a regulatory domain and may be involved in macromolecular interactions.

The presently disclosed compounds bind directly to HPK11 and inhibit its kinase activity. In some embodiments, the presently disclosed compounds reduce, inhibit, or otherwise diminish the HPK11-mediated phosphorylation of SLP76 and/or Gads.

The presently disclosed compounds may or may not be a specific HPK11 antagonist. A specific HPK11 antagonist reduces the biological activity of HPK11 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK11 antagonist for HPK11 is about 90%, 80%, 70%, 60%, 50%, 40%, 30%, 20%, 10%, 0.1%, 0.01%, 0.001%, or less of the $IC_{50}$ of the HPK11 antagonist for another serine/threonine kinase or other type of kinase (e.g., tyrosine kinase).

The presently disclosed compounds can be used in a method for inhibiting HPK1. Such methods comprise contacting HPK11 with an effective amount of a presently disclosed compound. By "contact" is intended bringing the compound within close enough proximity to an isolated HPK11 enzyme or a cell expressing HPK11 (e.g., T cell, B cell, dendritic cell) such that the compound is able to bind to and inhibit the activity of HPK1. The compound can be contacted with HPK11 in vitro or in vivo via administration of the compound to a subject.

Any method known in the art to measure the kinase activity of HPK11 may be used to determine if HPK11 has been inhibited, including in vitro kinase assays, immunoblots with antibodies specific for phosphorylated targets of HPK1, such as SLP76 and Gads, or the measurement of a downstream biological effect of HPK11 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK11-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula (I), or variations thereof such as Formula (IA), (IB) and (IC), or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN+CD8 T cells. In some embodiments, the CD8 T cell is an antigen-specific T-cell.

In some embodiments, the CD4 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD4 T cell priming is characterized by elevated CD44 expression and/or enhanced cytolytic activity in CD4 T cells. In some embodiments, the CD4 T cell activation is characterized by an elevated frequency of γ-IFN+CD4 T cells. In some embodiments, the CD4 T cell is an antigen-specific T-cell.

In some embodiments, the antigen presenting cells in the subject have enhanced maturation and activation relative to prior to the administration of the compound of Formula (I), or variations thereof such as Formula (IA), (IB) and (IC), or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula (I), or variations thereof such as Formula (IA), (IB) and (IC), or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growthours.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular Ca$^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula (I), or variations thereof such as Formula (IA), (IB) and (IC), or a pharmaceutically acceptable salt, prodrug, metabolite, or derivative thereof to a subject results in an enhancement of T cell function. In some embodiments, administration of HPK1 inhibitors described herein may enhance/renew/reactivate immune response or activate de nove immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells or CD4 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula (I), or variations thereof such as Formula (IA), (IB) and (IC), or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response. Viruses may also be immunogenic and enhancing/activating immunogenicity may aid in clearance of viral particles by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating cancer in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In one aspect, provided is a method for treating viral infection in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In one aspect, provided is a method for enhancing or boosting response to a vaccine (such as a cancer vaccine or a personalized cancer vaccine (PCV)) or a CAR-T cell therapy in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof.

The presently disclosed compounds may be administered in any suitable manner known in the art. In some embodiments, the compound of Formula (I), or variations thereof such as Formula (IA), (IB) and (IC), or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula (I), or variations thereof such as Formula (IA), (IB) and (IC), or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, about 0.01 µg/kg, about 0.05 µg/kg, about 0.1 µg/kg, about 0.5 µg/kg, about 1 µg/kg, about 10 µg/kg, about 25 µg/kg, about 50 µg/kg, about 100 µg/kg, about 250 µg/kg, about 500 µg/kg, about 1 mg/kg, about 5 mg/kg, about 10 mg/kg, about 25 mg/kg, about 50 mg/kg, about 100 mg/kg, and about 200 mg/kg.

In some embodiments, provided is a method for treating a cancer in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PD-L1/PD-1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4.—See more at: http://www.onclive.com/web-exclusives/the-role-of-anti-pd-l1-immunotherapy-in-cancer/2 #sthash.cGfYa1T1.dpuf. Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses.

Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others. In some embodiments, the HPK1 antagonist is administered in conjunction with a PD-1 antagonist such as an anti-PD-1 antibody, a PD-L1 antagonist such as an anti-PD-L1 antibody, and/or a PD-L2 antagonist such as an anti-PD-L2 antibody. Examples of anti-PD-L1 antibodies include but are not limited to avelumab, atezolizumab (also known as MPDL3280A), pembrolizumab (also known as MK-3475), LY3300054 (Eli Lilly), STI-A1014 (Sorrento), KN035 (Suzhou Alphamab) and BMS-936559 (Bristol Myers Squibb). Examples of anti-PD-1 antibodies include but are not limited to nivolumab, pidlizumab, PDR001 (Novartis), REGN2810 (Regeneron), BGB-108 (BeiGene), BGB-A317 (BeiGene), JS-001 (Shanghai Junshi), STI-A1110 (Sorrento), INCSHR-1210 (Incyte), PF-06801591 (Pfizer), TSR-042 (also known as ANBO11; Tesaro/AnaptysBio), AM0001 (ARMO Biosciences), and ENUM 244C8 (Enumeral Biomedical Holdings).

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In other examples, the HPK1 antagonist can be combined with a chemotherapeutic agent or biologic that targets a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, TLR, PD-L1 axis, CTLA-4, TIM-3, BTLA, VISTA, LAG-3, B7H4, CD96, CD226, prostaglandin, VEGF, endothelin B, IDO, arginase, MICA/MICB, TIM-3, IL-10, IL-4, IL-13, TIGIT or TGFβ. In other examples, the HPK1 antagonist can be combined with an immunotherapy comprising a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonis. In other examples, the HPK1 antagonist can be combined with an immunotherapy comprising a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, or TLR agonist.

In another example, the HPK1 antagonist can be combined with a PCV. In another example, the HPK1 antagonist can be combined with an adoptive T cell therapy.

Provided is a method of inhibiting HPK1, said method comprising contacting HPK1 in a subject with an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

A method for enhancing an immune response in a subject in need thereof, wherein the method comprises administering to said subject an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

In some embodiments, said subject has cancer.

Also provided is a method for treating a HPK1i-dependent disorder, said method comprising administering to a subject in need thereof an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

In some embodiments, said HPK1i-dependent disorder is a cancer.

In some embodiments, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

In some embodiments, said method further comprises administering a chemotherapeutic agent to said subject.

In some embodiments, the invention also provides compounds of Formula (I), or variations thereof such as Formula (IA), (IB) and (IC), described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula (I), or variations thereof such as Formula (IA), (IB) and (IC), described herein or pharmaceutical compositions described herein for use in a method for inhibiting HPK1 as described herein.

In some embodiments, the invention also provides compounds of Formula (I), or variations thereof such as Formula (IA), (IB) and (IC), described herein or pharmaceutical compositions described herein for use in a method for enhancing an immune response in a subject in need thereof as described herein.

In some embodiments, the invention also provides compounds of Formula (I), or variations thereof such as Formula (IA), (IB) and (IC), described herein or pharmaceutical compositions described herein for use in a method for treating a HPK1-dependent disorder as described herein.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1.

In some embodiments, the invention also provides the use of a compound of Formula (I), or variations thereof such as Formula (IA), (IB) and (IC), described herein or a pharmaceutical composition described herein for the manufacture of a medicament for enhancing an immune response in a subject in need thereof.

In some embodiments, the invention also provides the use of a compound of Formula (I), or variations thereof such as Formula (IA), (IB) and (IC), described herein or a pharmaceutical composition described herein for the manufacture of a medicament treating a HPK1-dependent disorder.

In some embodiments, the invention also provides the use of compounds of Formula (I), or variations thereof such as Formula (IA), (IB) and (IC), described herein or pharmaceutical compositions described herein in a method for inhibiting HPK1 as described herein, in a method for enhancing an immune response in a subject in need thereof as described herein and/or in a method for treating a HPK11-dependent disorder as described herein.

In some embodiments, the invention also provides the use of compounds of Formula (I), or variations thereof such as Formula (IA), (IB) and (IC), described herein or pharmaceutical compositions described herein in a method for inhibiting HPK1 as described herein.

In some embodiments, the invention also provides the use of compounds of Formula (I), or variations thereof such as Formula (IA), (IB) and (IC), described herein or pharmaceutical compositions described herein in a method for enhancing an immune response in a subject in need thereof as described herein.

In some embodiments, the invention also provides the use of compounds of Formula (I), or variations thereof such as Formula (IA), (IB) and (IC), described herein or pharmaceutical compositions described herein in a method for treating a HPK1T-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

In any of the described methods, in one aspect the subject is a human, such as a human in need of the method. The subject may be a human who has been diagnosed with or is suspected of having an HPK1-dependent disorder such as cancer. The individual may be a human who does not have detectable disease but who has one or more risk factors for developing a cancer.

Further provided are kits for carrying out the methods detailed herein, which comprises one or more compounds described herein or a pharmaceutical composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of an HPK1-dependent disorder such as cancer. In some embodiments, the kit contains instructions for use in the treatment of a cancer.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for an HPK1-dependent disorder (e.g., cancer) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to a subject.

The following examples are offered by way of illustration and not by way of limitation.

EXAMPLES

LC/MS Methods

Method K: Experiments were performed on a Shimadzu 20AD HPLC with Shimadzu LCMS2020 mass spectrometer using ESI as ionization source, a Shim-Pack XR-ODS C18 2.2 um, 3.0×50 column, and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method L: Experiments were performed on a Shimadzu 30AD HPLC with Shimadzu LCMS2020 mass spectrometer using ESI as ionization source, an Ascentis Express C18 2.7 um, 2.1×50 mm column, and a 1.0 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method M: Experiments were performed on a Shimadzu 20AD XR HPLC with Shimadzu LCMS2020 mass spectrometer using ESI as ionization source, a Poroshell HPH-C18 2.7 um, 3.0×50 mm column, and a 1.2 ml/minute flow rate. The solvent system was a gradient starting with 95% water with 5 Mm Ammonium bicarbonate (solvent A) and 5% acetonitrile (solvent B), ramping up to 95% solvent B over 2.0 minutes. The final solvent system was held constant for a further 0.7 minutes.

Method N: Experiments performed on an Agilent 1290 UHPLC coupled with Agilent MSD (6140) mass spectrometer using ESI as ionization source. The LC separation used a Phenomenex XB-C18, 1.7 mm, 50×2.1 mm column with a 0.4 ml/minute flow rate. Solvent A was water with 0.1% FA and solvent B was acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Method O: Experiment was performed on a Waters Acquity UPLC with Waters LCT Premier XE mass spectrometer using ESI ionization. The LC separation was using an Acquity UPLC BEH C18, 1.7 mm, 2.1×50 mm column and a 0.6 ml/min flow rate. MPA (mobile phase A) was water with 0.05% TFA and MPB (mobile phase B) was acetonitrile with 0.05% TFA. The gradient consisted with 2-98% MPB over 5 min and hold 98% B for 0.5 min following equilibration for 0.5 min. LC column temperature is 40° C. UV data was collected at 220 nm and 254 nm and mass spec full scan was applied to all experiments.

Method P: Experiments were performed on a Shimadzu 20AD HPLC with Shimadzu LCMS2020 mass spectrometer using ESI as ionization source, a Shim-Pack GIST 2.0 um, 3.0 mm×50 mm column, and a 1.0 ml/minute flow rate. The solvent system was a gradient starting with 90% water with 5 mM NH$_4$HCO$_3$ (solvent A) and 10% acetonitrile (solvent B), ramping up to 100% solvent B over 2.0 minutes. The final solvent system was held constant for a further 0.7 minutes.

SYNTHETIC EXAMPLES

Example 1

6-bromo-7-fluoro-isoquinolin-3-amine

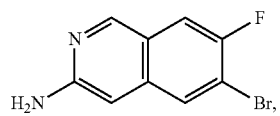

Step 1: (4-bromo-3-fluorophenyl)methanamine

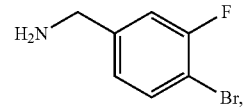

A solution of 4-bromo-3-fluoro-benzonitrile (5.0 g, 25 mmol) in BH₃·THF (80 mL, 1 mol/L, 80 mmol) was stirred at 60° C. for 3 hrs. The reaction was quenched with MeOH (20 mL) and HCl (20 mL, 12 M). The resulting solution was extracted with EtOAc (3×200 mL), dried over anhydrous MgSO₄, and concentrated under vacuum to afford (4-bromo-3-fluorophenyl)methanamine (4.5 g, crude), which was directly used in the next step without purification. LCMS (ESI) [M+H]⁺=204.

Step 2: methyl 2,2-diethoxyacetimidate

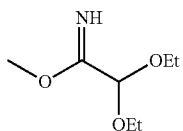

A solution of 2,2-diethoxyacetonitrile (4.0 g, 30.97 mmol) and sodium methoxide (1.2 mL, 5.4 mol/L, 6.19 mmol) in methyl alcohol (40 mL) was stirred at 25° C. for 3 hrs, then concentrated to dryness. The residue was taken up in dichloromethane (200 mL) and washed with water (3×80 mL) and brine, dried over anhydrous MgSO₄, filtered and concentrated under vacuum to give methyl 2,2-diethoxyacetimidate (5 g, crude), which was directly used in the next step without purification. LCMS (ESI) [M+H]⁺=162.

Step 3: N-(4-bromo-3-fluorobenzyl)-2,2-diethoxy-acetimidamide

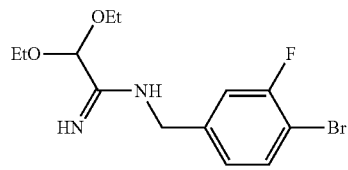 [SMILES: CCOC(OCC)C(=N)NCc1ccc(Br)c(F)c1]

A solution of (4-bromo-3-fluoro-phenyl)methanamine (4.5 g, crude), methyl 2,2-diethoxyethanimidate (5 g, crude) in methyl alcohol (40 mL) was stirred at 25° C. for 3 hrs. The reaction was concentrated to dryness and the residue was taken up in dichloromethane. The organic layer was washed with brine, dried (Na₂SO₄) and concentrated to afford N-(4-bromo-3-fluorobenzyl)-2,2-diethoxyacetimidamide (5.0 g, crude), which was directly used in the next step without purification. LCMS (ESI) [M+H]⁺=333.

Step 4: 6-bromo-7-fluoro-isoquinolin-3-amine

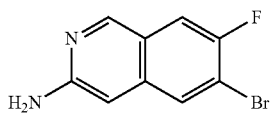 [SMILES: Nc1cc2cc(Br)c(F)cc2cn1]

A solution of N-[(4-bromo-3-fluoro-phenyl)methyl]-2,2-diethoxy-acetamidine (5.0 g, crude) in H₂SO₄ (30 mL) was stirred at 60° C. for 12 hrs. The reaction mixture was cooled to 0° C. and NaOH was added to adjust the pH=9. The mixture was extracted with DCM (3×150 mL). The combined organic layers were washed with brine, dried (Na₂SO₄), filtered and concentrated to dryness. The residue was purified on a silica gel column eluting with EA/PE (3/7) to afford a mixture of 6-bromo-7-fluoro-isoquinolin-3-amine and 6-bromo-5-fluoroisoquinolin-3-amine (800 mg, 6:6a=5:1, 3.32 mmol) as a yellow solid. LCMS (ESI) [M+H]⁺=241.

Example 2 tert-butyl 8-methyl-7-(4,4,5,5-tetramethyl-1,3,2-dioxaborolan-2-yl)-2,3-dihydropyrido[2,3-b][1,4]oxazine-1-carboxylate

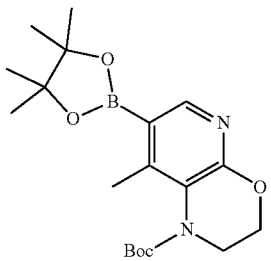 [SMILES: Cc1c(B2OC(C)(C)C(C)(C)O2)cnc2c1N(C(=O)OC(C)(C)C)CCO2]

Step 1: tert-butyl 7-bromo-8-methyl-2,3-dihydropyrido[2,3-b][1,4]oxazine-1-carboxylate

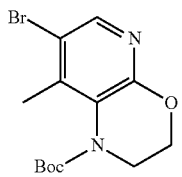

To a solution of 7-bromo-8-methyl-2,3-dihydro-1H-pyrido[2,3-b][1,4]oxazine (1 g, 4.37 mmol) in tetrahydrofuran (2 mL) was added dropwise LiHMDS (8.73 mL, 8.73 mmol, 1 mol/L) at 0° C. The resulting solution was stirred under nitrogen for 0.5 h at 0° C. Then di-tert-butyl dicarbonate (2.85 g, 13.07 mmol) was added and the reaction was stirred at room temperature for 2 h. The reaction was quenched by methanol (50 mL). The solvent was concentrated under vacuum. The residue was purified by silica gel flash chromatography (ethyl acetate/petroleum ether, 1/4) to afford tert-butyl 7-bromo-8-methyl-2,3-dihydropyrido[2,3-b][1,4]oxazine-1-carboxylate (800 mg, 2.43 mmol) as a yellow oil. LCMS (ESI) [M+H]⁺=329.2.

Step 2: tert-butyl 8-methyl-7-(4,4,5,5-tetramethyl-1,3,2-dioxaborolan-2-yl)-2,3-dihydropyrido[2,3-b][1,4]oxazine-1-carboxylate

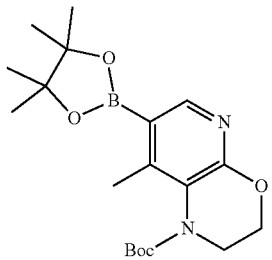 [SMILES: Cc1c(B2OC(C)(C)C(C)(C)O2)cnc2c1N(C(=O)OC(C)(C)C)CCO2]

A mixture of tert-butyl 7-bromo-8-methyl-2,3-dihydropyrido[2,3-b][1,4]oxazine-1-carboxylate (6.2 g, 18.83 mmol), bis(pinacolato)diboron (23.93 g, 94.22 mmol), [1,1'-bis(diphenylphosphino)ferrocene]dichloropalladium(II) (2.76 g, 3.77 mmol) and potassium acetate (5.55 g, 56.62 mmol) in 1,4-dioxane (2 mL) was stirred under nitrogen for 2.5 h at 90° C. The solvent was concentrated under vacuum. The residue was purified by flash chromatography on silica gel eluting with ethyl acetate/petroleum ether (30%) to afford tert-butyl 8-methyl-7-(4,4,5,5-tetramethyl-1,3,2-dioxaborolan-2-yl)-2,3-dihydropyrido[2,3-b][1,4]oxazine-1-carboxylate (5 g, 13.29 mmol) as a yellow oil. LCMS (ESI) [M+H]$^+$=376.3.

Example 3

2-bromo-5,5,6-trimethyl-4,8-dihydropyrazolo[1,5-d][1,4]diazepin-7-one

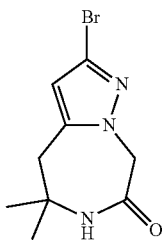

Step 1: 2-(3,5-dibromopyrazol-1-yl)acetonitrile

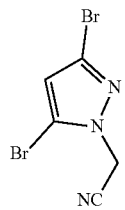

A mixture of 3,5-dibromo-1H-pyrazole (1.0 g, 4.43 mmol) and potassium carbonate (1.22 g, 8.85 mmol) in N,N-dimethylformamide (20 mL) was stirred at 25° C. for 10 min. Bromoacetonitrile (796.59 mg, 6.64 mmol) was added and the reaction was stirred at 25° C. for 2 h. After filtration, the filtrate was diluted with ethyl acetate (30 mL). The reaction was washed with water. The organic phase was dried with anhydrous sodium sulfate. After filtration, the filtrate was concentrated under vacuum. The residue was purified by flash chromatography on silica gel eluting with petroleum ether/dichloromethanol (1/1) to afford 2-(3,5-dibromopyrazol-1-yl)acetonitrile (950 mg, 3.59 mmol) as a white solid. LCMS (ESI) [M+H]$^+$=264.

Step 2: 2-[3-bromo-5-(2-methylprop-1-enyl)pyrazol-1-yl]acetonitrile

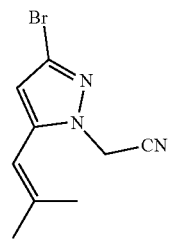

A mixture of 2-(3,5-dibromopyrazol-1-yl)acetonitrile (1.0 g, 3.77 mmol), 4,4,5,5-tetramethyl-2-(2-methylprop-1-en-1-yl)-1,3,2-dioxaborolane (687.29 mg, 3.77 mmol), Pd(dppf)Cl$_2$ (552.64 mg, 0.75 mmol), and potassium carbonate (1.56 g, 11.32 mmol) in 1,4-dioxane (20 mL) and water (2 mL) was stirred under nitrogen for 1 h at 100° C. After filtration, the filtrate was concentrated under vacuum. The residue was purified by silica gel flash chromatography eluting with ethyl acetate/petroleum ether (1/3) to afford 2-[3-bromo-5-(2-methylprop-1-enyl)pyrazol-1-yl]acetonitrile (700 mg, 2.92 mmol) as a white solid. LCMS (ESI) [M+H]$^+$=240.

Step 3: 2-bromo-5,5-dimethyl-6,8-dihydro-4H-pyrazolo[1,5-d][1,4]diazepin-7-one

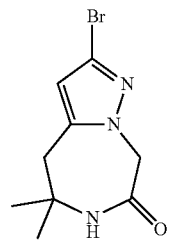

A mixture of 2-[3-bromo-5-(2-methylprop-1-enyl)pyrazol-1-yl]acetonitrile (700 mg, 2.92 mmol) in methylsulfonic acid (15 mL) was stirred at 65° C. for 3 d. The reaction was quenched with ice water. The reaction mixture was adjusted to pH 9-10 with an aqueous sodium hydroxide solution. The resulting solution was extracted with dichloromethane and dried with anhydrous sodium sulfate. After filtration, the filtrate was concentrated under vacuum. The residue was purified by reverse phase chromatography (acetonitrile 0-40/0.1% NH$_4$HCO$_3$ in water) to afford 2-bromo-5,5-dimethyl-6,8-dihydro-4H-pyrazolo[1,5-d][1,4]diazepin-7-one (300 mg, 1.16 mmol) as a white solid. LCMS (ESI) [M+H]$^+$=258.

Step 4: 2-bromo-5,5,6-trimethyl-4,8-dihydropyrazolo[1,5-d][1,4]diazepin-7-one

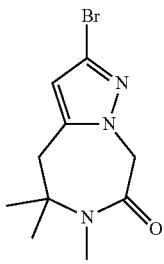

A mixture of 2-bromo-5,5-dimethyl-6,8-dihydro-4H-pyrazolo[1,5-d][1,4]diazepin-7-one (100 mg, 0.39 mmol) and potassium tert-butoxide (52.07 mg, 0.46 mmol) in tetrahydrofuran (10 mL) was stirred at 25° C. for 10 min. Iodomethane (82.52 mg, 0.58 mmol) was added. The reaction was stirred at 25° C. for 1 h. The reaction was concentrated under vacuum and purified by flash chromatography on silica gel eluting with dichloromethane/methanol (95/5) to afford 2-bromo-5,5,6-trimethyl-4,8-dihydropyrazolo[1,5-d][1,4]diazepin-7-one (80 mg, 0.29 mmol) as a white solid. LCMS (ESI) [M+H]$^+$=272.

Example 4

2-bromo-4-methylene-5,6-dihydro-4H-pyrazolo[1,5-d][1,4]diazepin-7(8H)-one

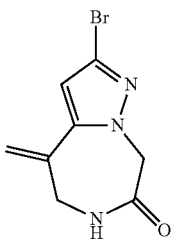

Step 1: 3,5-dibromo-1H-pyrazole

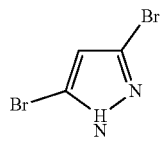

To a 3 L 3-necked round-bottom flask was added compound 1 (200 g, 656 mmol, 1.0 eq) in dimethyl tetrahydrofuran (1000 mL) under N$_2$ and then the solution was cooled to –78° C. n-BuLi (2.5 M, 525 mL, 2.0 eq) was added dropwise to the above solution for 1 hour at –78° C. and the mixture was stirred at –78° C. for 3 hours. TLC (Petroleum ether/Ethyl acetate=3/1, R$_f$=0.51) showed the reaction was completed and one main new spot formed. The reaction mixture was poured into water (1000 mL) at 0° C. and the pH value of the solution was acidified to 4-5 with 2N HCl. The resulting solution was extracted with ethyl acetate (1000 mL, 800 mL, 400 mL). The combined organic phase was washed with brine (800 mL), dried with anhydrous Na$_2$SO$_4$ and concentrated under vacuum to give the title compound (284 g, 1.26 mol, 95.8% yield) as a yellow solid. The crude product was directly used to the next step without further purification.

Step 2: tert-butyl 2-(3,5-dibromo-1H-pyrazol-1-yl)acetate

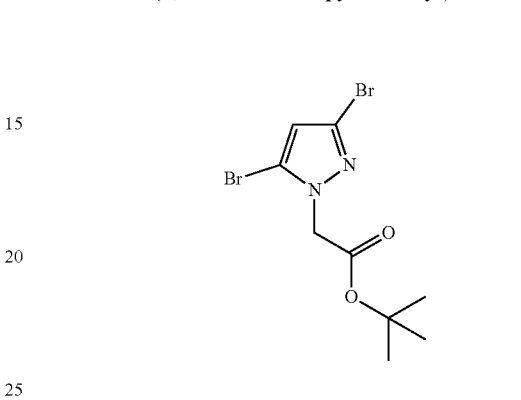

To the solution of 3,5-dibromo-1H-pyrazole (137 g, 607 mmol, 1.0 eq) in MeCN (959 mL) was added tert-butyl 2-chloroacetate (137 g, 910 mmol, 131 mL, 1.5 eq), K$_2$CO$_3$ (137 g, 989 mmol, 1.63 eq) and TBAI (11.0 g, 29.7 mmol, 0.049 eq). The resulting solution was stirred at 25° C. for 12 hours. TLC (Petroleum ether/Ethyl acetate=5/1, R$_f$=0.74) showed the reaction was complete and one main new spot formed. The reaction mixture was filtered and the filter cake was washed with EtOAc (500 mL x3, 300 mL, 200 mL). The combined filtrate was concentrated to give a residue which was dissolved in EtOAc (2.0 L) then washed with water (1.0 L), then brine (1.0 L). The organic phase was dried with anhydrous Na$_2$SO$_4$, filtered and concentrated in vacuum to give the title compound (744 g, crude) as a brown oil. $^1$H NMR: (400 MHz, CDCl$_3$): δ 6.35 (s, 1H), 4.80 (s, 2H), 1.46 (s, 9H).

Step 3: 2-(3,5-dibromo-1H-pyrazol-1-yl)acetic acid

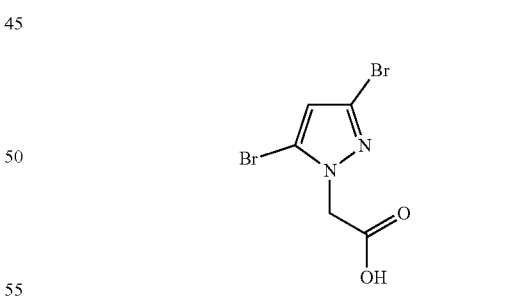

To the solution of compound tert-butyl 2-(3,5-dibromo-1H-pyrazol-1-yl)acetate (248 g, 729 mmol, 1.0 eq) in DCM (140 mL) was added TFA (2.08 kg, 18.2 mol, 1.35 L, 25 eq) and the resulting solution was heated to 80° C. and stirred for 2 hours. The reaction was set up on this scale in triplicate. TLC (Petroleum ether/Ethyl acetate=5/1, R$_f$=0.03) showed the reaction was complete and one main new spot formed. The combined reaction mixtures were concentrated under reduced pressure to give a crude product. The crude product was diluted with petroleum ether/ethyl acetate (4/1, 1.0 L) and the resulting suspension was stirred at 25° C. for 1 hour, then filtered. The filter cake was collected and dried in vacuum to give the title compound (471 g, 1.66 mol, 75.8% yield) as an off white solid. ¹H NMR: (400 MHz, DMSO) δ 13.3 (br s, 1H), 6.70 (s, 1H), 4.96 (s, 2H).

Step 4: N-allyl-2-(3,5-dibromo-1H-pyrazol-1-yl)acetamide

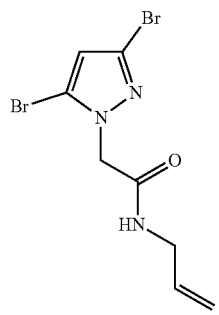

To the solution of 2-(3,5-dibromo-1H-pyrazol-1-yl)acetic acid (157 g, 553 mmol, 1.0 eq) in DMF (1.10 L) was added DIPEA (357 g, 2.77 mol, 482 mL, 5.0 eq) and EDCI (138 g, 719 mmol, 1.3 eq) at 0° C., the resulting solution was stirred at 0° C. for 30 min. HOBt (97.1 g, 719 mmol, 1.3 eq) was added and the mixture was stirred at 0° C. for another 30 min. Prop-2-en-1-amine (47.4 g, 830 mmol, 62.2 mL, 1.5 eq) was added at 0° C. and the mixture was warmed to 25° C. and stirred for 16 hours. The reaction was set up on this scale in triplicate. TLC (Petroleum ether/Ethyl acetate=1/1, R$_f$=0.60) showed the reaction was completed and one main new spot formed. The three batches of reactions were combined and the reaction mixture was poured into ice water (12.0 L), then extracted with ethyl acetate (2.00 L, 2.00 L, 1.00 L). The combined organic phases were washed with brine (2.0 L), and then concentrated in vacuum to give a crude product. The crude product was purified by column chromatography on silica gel (Petroleum ether/Ethyl acetate=3/1) to afford the title compound (340 g, 1.05 mol, 63.5% yield) as a white solid. ¹H NMR: (400 MHz, CDCl3) δ 6.41 (s, 1H), 5.89 (br s, 1H), 5.79 (m, 1H), 5.08-5.17 (m, 2H), 4.85 (s, 2H), 3.86-3.93 (m, 2H).

Step 5: N-allyl-2-(3,5-dibromo-1H-pyrazol-1-yl)-N-(4-methoxybenzyl)acetamide

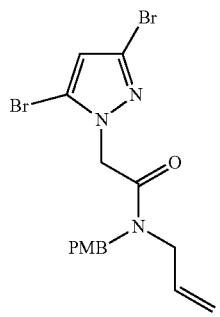

To a solution of N-allyl-2-(3,5-dibromo-1H-pyrazol-1-yl) acetamide (103 g, 319 mmol, 1.0 eq) in THF (721 mL) was added KOH (32.2 g, 574 mmol, 1.8 eq), 18-Crown-6 (3.37 g, 12.8 mmol, 0.04 eq) and 1-(chloromethyl)-4-methoxybenzene (64.9 g, 415 mmol, 56.5 mL, 1.3 eq), then the mixture was stirred at 25° C. for 64 h. TLC (Petroleum ether/Ethyl acetate=2/1, R$_f$=0.50) showed one main new spot formed. The reaction was repeated two more times. The three batches reactions were combined and the reaction mixture was added water (1.00 L), and the pH value was adjusted to 7-8 with 1M HCl, then extracted with EtOAc (1.00 L, 800 mL×3). The combined organic phase was washed with brine (800 mL), dried with anhydrous Na$_2$SO$_4$, filtered and concentrated in vacuum to give a crude product. The crude product was purified by column chromatography on silica gel (Petroleum ether/Ethyl acetate=2/1) to afford the title compound (320 g, 722 mmol, 75.5% yield) as a yellow oil.

Step 6: 2-bromo-6-(4-methoxybenzyl)-4-methylene-5,6-dihydro-4H-pyrazolo[1,5-d][1,4]diazepin-7(8H)-one

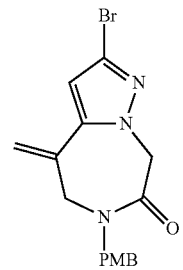

To a solution of N-allyl-2-(3,5-dibromo-1H-pyrazol-1-yl)-N-(4-methoxybenzyl)acetamide (50.0 g, 113 mmol, 1.0 eq) in DMF (1.0 L) was added K$_2$CO$_3$ (31.2 g, 226 mmol, 2.0 eq), Pd(PPh$_3$)$_4$(17.0 g, 14.7 mmol, 0.13 eq) under Ar, then the mixture was stirred at 120° C. for 16 hours. The reaction was repeated six more times. The seven batches of reactions were combined and the reaction mixture was concentrated in vacuum to remove the solvent to give a residue. To the residue was added water (2.0 L) and ethyl acetate (2.0 L). The organic layer was collected, then the aqueous layer was extracted twice more with ethyl acetate (1.0 L, 1.0 L). The combined organic layers were washed with brine (1.0 L) and concentrated to give a crude product. The crude product was purified by column chromatography on silica gel (Petroleum ether/Ethyl acetate=2/1) to afford the title compound compound (74.1 g, 204 mmol, 25.9% yield, 98.7% purity) as a white solid. ¹H NMR: (400 MHz, CDCl$_3$) δ 7.21 (d, J=8.8 Hz, 2H), 6.86-6.92 (m, 2H), 6.52 (s, 1H), 5.50 (s, 1H), 5.20 (s, 2H), 5.02 (s, 1H), 4.58 (s, 2H), 4.13 (s, 2H), 3.83 (s, 3H).

Step 7: 2-bromo-4-methylene-5,6-dihydro-4H-pyrazolo[1,5-d][1,4]diazepin-7(8H)-one

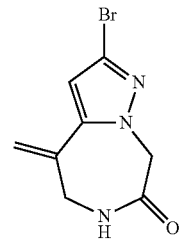

A solution of 2-bromo-6-(4-methoxybenzyl)-4-methylene-5,6-dihydro-4H-pyrazolo[1,5-d][1,4]diazepin-7(8H)-one (3.90 g, 10.8 mmol, 1.0 eq), TFA (38.4 g, 336 mmol, 24.9 mL, 31.3 eq) and trifluoromethanesulfonic acid (16.2 g, 108 mmol, 9.5 mL, 10 eq) in DCM (28 mL) was stirred at 25° C. for 12 hours. The reaction mixture was concentrated to give a residue. To the residue was added water (100 mL), then the pH value was adjusted to 6-7 with saturated aqueous NaHCO$_3$ solution, extracted with EtOAc (100 mL×3, 60 mL×3). The combined organic phase was dried with anhydrous Na$_2$SO$_4$, filtered and concentrated in vacuum to give a crude product. The crude product was purified by column chromatography on silica gel (Petroleum ether/Ethyl acetate=1/1) to afford the title compound (1.90 g, 7.85 mmol, 72.9% yield) as a gray solid. $^1$H NMR: (400 MHz, CDCl$_3$) δ 6.88 (s, 1H), 6.54 (s, 1H), 5.55 (s, 1H), 5.21 (s, 1H), 5.08 (s, 2H), 4.15 (d, J=6.0 Hz, 2H).

Example 5

2-Bromo-6-methyl-4-methylidene-4H,5H,6H,7H,8H-pyrazolo[1,5-d][1,4]diazepin-7-one

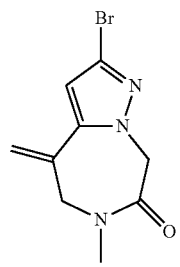

Step 1: 2-(3,5-Dibromo-1H-pyrazol-1-yl)-N-methyl-N-(prop-2-en-1-yl)acetamide

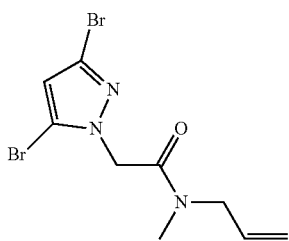

A solution of 2-(3,5-dibromo-1H-pyrazol-1-yl)acetic acid (15 g, 52.84 mmol), methyl(prop-2-en-1-yl)amine (5.7 g, 80.15 mmol), N,N-diisopropylethylamine (27 g, 208.9 mmol) and HATU (30 g, 78.9 mmol) in N,N-dimethylformamide (500 mL) was stirred for 16 hours at room temperature. The resulting mixture was diluted with ethyl acetate and then washed with sodium chloride solution. The organic phase was dried with anhydrous sodium sulfate, filtered, and then concentrated under vacuum. The residue was purified by flash chromatography on silica gel eluting with ethyl acetate/petroleum ether (2/3) to afford 2-(3,5-dibromo-1H-pyrazol-1-yl)-N-methyl-N-(prop-2-en-1-yl)acetamide (16.3 g, 92%) as a yellow oil. LCMS (ESI) [M+H]$^+$= 338.0.

Step 2: 2-Bromo-6-methyl-4-methylidene-4H,5H,6H,7H,8H-pyrazolo[1,5-d][1,4]diazepin-7-one

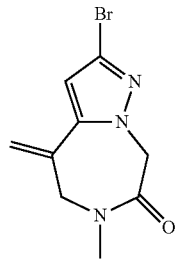

A mixture of 2-(3,5-dibromo-1H-pyrazol-1-yl)-N-methyl-N-(prop-2-en-1-yl)acetamide (5 g, 14.84 mmol), palladium acetate (166 mg, 0.74 mmol), triphenylphosphine (388 mg, 1.48 mmol), TBAB (4.8 g, 14.890 mmol) and potassium acetate (4.2 g, 42.80 mmol) in N,N-dimethylformamide (100 mL) was stirred for 10 h at 80° C. The mixture was cooled to room temperature, then filtered and concentrated under vacuum. The residue was purified on a silica gel column eluting with ethyl acetate/petroleum ether (2/1) to afford 2-bromo-6-methyl-4-methylidene-4H,5H,6H,7H,8H-pyrazolo[1,5-d][1,4]diazepin-7-one (3.2 g, 84%) as a brown oil. LCMS (ESI) [M+H]$^+$=258.1.

Example 6

2-Bromo-6-isopropyl-4-methylidene-5,6-dihydro-4H-pyrazolo[1,5-d][1,4]diazepin-7(8H)-one

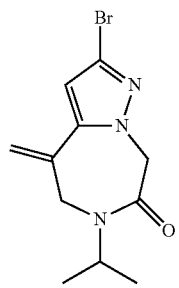 [SMILES: C=C1CN(C(C)C)C(=O)Cn2nc(Br)cc21]

To a mixture of N-allyl-2-(3,5-dibromopyrazol-1-yl)-N-isopropyl-acetamide (6.3 g, 17.26 mmol), palladium diacetate (386.5 mg, 1.73 mmol), triphenylphosphine (904.29 mg, 3.45 mmol) and tetrabutylammonium bromide (5.56 g, 17.26 mmol) in N,N-dimethylformamide (150 mL) was added potassium acetate (4.87 g, 51.77 mmol) at 25° C. The resulting mixture was stirred for 12 hours at 90° C. The reaction mixture was diluted with ethyl acetate and then washed with water. The organic layer was dried over anhydrous sodium sulfate, filtered and concentrated under vacuum. The residue was purified by flash chromatography on silica gel eluting with ethyl acetate/petroleum ether (2/3) to afford 2-bromo-6-isopropyl-4-methylene-5,8-dihydropyrazolo[1,5-d][1,4]diazepin-7-one (2.34 g, 8.23 mmol, 47.7% yield) as a yellow solid. LCMS (ESI) [M+H]$^+$=284.

Example 7

2'-bromo-6'-methyl-5',6'-dihydrospiro[cyclopropane-1,4'-pyrazolo[1,5-d][1,4]diazepin]-7'(8'H)-one

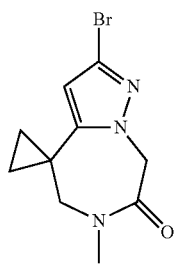

A mixture of trimethylsulfoxonium iodide (1.29 g, 5.86 mmol) and potassium tert-butoxide (656 mg, 5.85 mmol) in dimethyl sulfoxide (30 mL) was stirred for 30 min at room temperature. Then a solution of 2-bromo-6-methyl-4-methylidene-4H,5H,6H,7H,8H-pyrazolo[1,5-d][1,4]diazepin-7-one (500 mg, 1.95 mmol) in dimethyl sulfoxide (3 mL) was added and the mixture was stirred for 12 h at 50° C. The reaction mixture cooled to room temperature, then diluted with ethyl acetate and washed with water. The organic layer was dried over anhydrous sodium sulfate, filtered and concentrated under vacuum. The residue was purified by silica gel column with dichloromethane/methanol (10/1) to afford 2'-bromo-6'-methyl-5',6'-dihydrospiro[cyclopropane-1,4'-pyrazolo[1,5-d][1,4]diazepin]-7'(8'H)-one (120 mg, 23%) as a white solid. LCMS (ESI) [M+H]$^+$=270.

Example 8

2-bromo-6-methyl-5,6-dihydro-4H-pyrazolo[1,5-d][1,4]diazepin-7(8H)-one

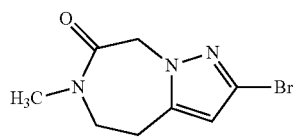

Step 1: Methyl 2-(3-bromo-5-methyl-pyrazol-1-yl)acetate

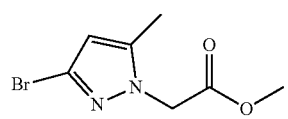

A solution of 3-bromo-5-methyl-1H-pyrazole (100 g, 621.12 mmol), methyl 2-chloroacetate (101.11 g, 931.68 mmol) and K$_2$CO$_3$ (154.29 g, 1118 mmol) in N,N-dimethylformamide (1 L) was added TBAI (11.46 g, 31.06 mmol). The resulting solution was stirred for 12 h at 20° C. The reaction mixture was diluted with EA (5000 mL). The solution was washed with water (300 mL×3), then the organic layer was dried over anhydrous sodium sulfate and concentrated under vacuum. The residue was purified by flash chromatography on silica gel eluting with PE/DCM (60/40) to afford methyl 2-(3-bromo-5-methyl-pyrazol-1-yl)acetate (120 g, 82.9% yield) as a white solid.

Step 2: Methyl 2-[3-bromo-5-(bromomethyl)pyrazol-1-yl]acetate

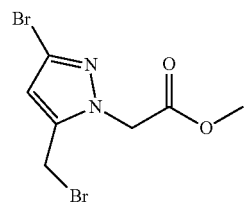

A solution of methyl 2-(3-bromo-5-methyl-pyrazol-1-yl)acetate (50.0 g, 214.54 mmol) and AIBN (3.52 g, 21.45 mmol) in carbon tetrachloride (1500 mL) was stirred at RT for 5 mins. 1-Bromo-2,5-pyrrolidinedione (40.09 g, 225.26 mmol) was added. The mixture was stirred at 80° C. for 1 hour. The reaction mixture was concentrated under vacuum. The residue was purified by flash chromatography on silica gel eluting with PE/EA (92/8) to afford methyl 2-[3-bromo-5-(bromomethyl)pyrazol-1-yl]acetate (35.5 g, 53% yield) as a white solid.

Step 3: Methyl 2-(3-bromo-5-(cyanomethyl)-1H-pyrazol-1-yl)acetate

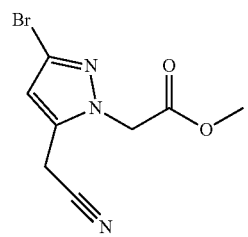

A solution of methyl 2-[3-bromo-5-(bromomethyl)pyrazol-1-yl]acetate (35.4 g, 113.48 mmol) and sodium cyanide (8.87 g, 181.02 mmol) in dimethyl sulfoxide (550 mL) was stirred at RT for 1 hour. The reaction solution was diluted with EA (2.5 L). The solution was washed with water (200 mL×5), then the organic layer was dried over anhydrous sodium sulfate, filtered and concentrated under vacuum. The residue was purified by flash chromatography on silica gel eluting with DCM/MeOH (99/1) to afford methyl 2-(3-bromo-5-(cyanomethyl)-1H-pyrazol-1-yl)acetate (17.6 g, 60% yield) as a white solid.

Step 4: Methyl 2-(5-(2-aminoethyl)-3-bromo-1H-pyrazol-1-yl)acetate

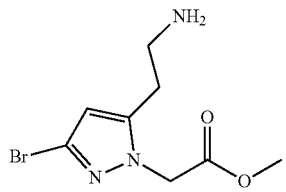

To a solution of methyl 2-[3-bromo-5-(cyanomethyl)pyrazol-1-yl]acetate (3.0 g, 11.62 mmol) in methanol (600 mL) was added PtO$_2$ (600 mg, 2.64 mmol). The mixture was stirred under 10 atm of hydrogen gas at 25° C. for 15 hours, then filtered and used directly in the next step without purification.

Step 5: 2-bromo-4,5,6,8-tetrahydropyrazolo[1,5-d][1,4]diazepin-7-one

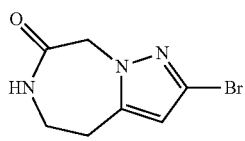

To a crude methanol solution (600 mL) of methyl 2-[5-(2-aminoethyl)-3-bromo-pyrazol-1-yl]acetate was added triethylamine (70 mL). The mixture was stirred at 25° C. for 15 hours. The resulting solution was concentrated under vacuum. The residue was purified by flash chromatography on silica gel eluting with DCM/MeOH (98/2) to afford 2-bromo-4,5,6,8-tetrahydropyrazolo[1,5-d][1,4]diazepin-7-one (1.12 g, 41.9% yield in two steps) as a white solid.

Step 6: 2-bromo-6-methyl-5,6-dihydro-4H-pyrazolo[1,5-d][1,4]diazepin-7(8H)-one

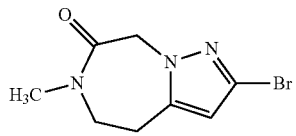

To a mixture of 2-bromo-5,6,7,8-tetrahydro-4H-pyrazolo[1,5-d][1,4]diazepine (469.53 mg, 2.17 mmol) and potassium tert-butoxide (365.74 mg, 3.26 mmol) in tetrahydrofuran (20 mL) was added iodomethane (616.86 mg, 4.35 mmol) at 20° C. The resulting solution was stirred at 20° C. for 1 h. The mixture was concentrated under vacuum. The residue was purified by flash chromatography on silica gel eluting with dichloromethane/methanol (20/1) to afford 2-bromo-6-methyl-4,5,7,8-tetrahydropyrazolo[1,5-d][1,4]diazepine (400 mg, 1.74 mmol, 80% yield). LCMS (ESI) [M+H]$^+$=244

Example 9

2-bromo-6-isopropyl-5,6-dihydro-4H-pyrazolo[1,5-d][1,4]diazepin-7(8H)-one

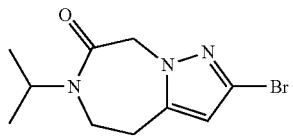

A solution of 2-bromo-4,5,6,8-tetrahydropyrazolo[1,5-d][1,4]diazepin-7-one (3.0 g, 13.04 mmol) and NaH (1.56 g, 39.12 mmol) in N,N-dimethylformamide (75 mL) was stirred at 0° C. for 10 min. Then 2-iodopropane (11.08 g, 65.2 mmol) was added. The mixture was stirred at 25° C. for 1 hour. The reaction was quenched with water. The mixture was concentrated under vacuum. The resulting residue was purified by reverse phase chromatography (acetonitrile 0-40/0.1% NH$_4$HCO$_3$ in water) to afford 2-bromo-6-isopropyl-5,8-dihydro-4H-pyrazolo[1,5-d][1,4]diazepin-7-one (2.1 g, 7.7166 mmol, 59.2% yield) as a white solid. LCMS (ESI) [M+H]$^+$=272.

Example 10

8-bromo-5,6-dihydro-11H-imidazo[1,2-a]pyrazolo[1,5-d][1,4]diazepine

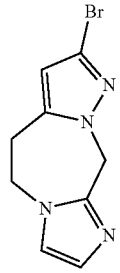 [SMILES: Brc1cc2n(n1)Cc1nccn1CC2]

Step 1: 2-bromo-4,5,6,8-tetrahydropyrazolo[1,5-d][1,4]diazepine-7-thione

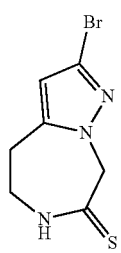

A mixture of 2-bromo-4,5,6,8-tetrahydropyrazolo[1,5-d][1,4]diazepin-7-one (314 mg, 1.36 mmol) and Lawesson reagent (551.4 mg, 1.36 mmol) in 1,4-dioxane (10 mL) was stirred at 90° C. for 1 h. The reaction was concentrated under vacuum. The residue was purified by flash chromatography on silica gel eluting with dichloromethane/methanol (96/4) to afford 2-bromo-4,5,6,8-tetrahydropyrazolo[1,5-d][1,4]diazepine-7-thione (265 mg, 78.9%) as a white solid. LCMS (ESI) [M+H]⁺=246.0.

Step 2: 2-bromo-N-(2,2-diethoxyethyl)-5,8-dihydro-4H-pyrazolo[1,5-d][1,4]diazepin-7-amine

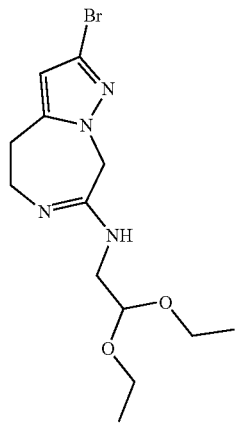 [SMILES: CCOC(CNC1=NCCc2cc(Br)nn2C1)OCC]

A mixture of 2-bromo-5,6-dihydro-4H-pyrazolo[1,5-d][1,4]diazepine-7(8H)-thione (265.0 mg, 1.07 mmol), 2,2-diethoxyethan-1-amine(1.42 g, 10.7 mmol) and silver carbonate (590 mg, 2.14 mmol) in tetrahydrofuran (10 mL) was stirred at 80° C. for 1 h. The reaction mixture was concentrated under vacuum. The residue was purified by reverse-phase HPLC eluting with water (0.05% TFA)/CH₃CN (85/15) to afford 2-bromo-N-(2,2-diethoxyethyl)-5,8-dihydro-4H-pyrazolo[1,5-d][1,4]diazepin-7-amine (295 mg, 80%) as a brown oil. LCMS (ESI) [M+H]⁺=345.0.

Step 3: 8-bromo-5,6-dihydro-11H-imidazo[1,2-a]pyrazolo[1,5-d][1,4]diazepine

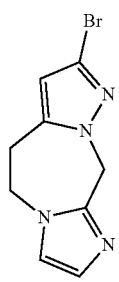

A solution of 2-bromo-N-(2,2-diethoxyethyl)-5,8-dihydro-4H-pyrazolo[1,5-d][1,4]diazepin-7-amine (228 mg, 0.66 mmol) and concentrated hydrochloric acid (0.17 mL, 0.66 mmol) in acetic acid (5 mL) was stirred at 80° C. for 1 h. The reaction was concentrated under vacuum. The residue was purified by reverse-phase HPLC eluting with water (0.05% TFA)/ACN (85/15) to afford 8-bromo-5,6-dihydro-11H-imidazo[1,2-a]pyrazolo[1,5-d][1,4]diazepine (150 mg, 89.7%) as a brown oil. LCMS (ESI) [M+H]⁺=253.0.

Example 11

7-bromo-8-chloro-6-iodoisoquinolin-3-amine

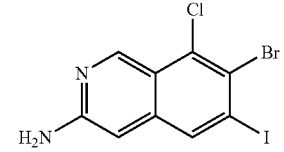

Step 1: 4-amino-3-bromo-2-chlorobenzonitrile

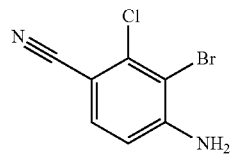 [SMILES: N#Cc1ccc(N)c(Br)c1Cl]

To a solution of 4-amino-2-chlorobenzonitrile (1.5 g, 9.83 mmol) in acetonitrile (30 mL) was added 1,3-dibromo-5,5-dimethyl-2,4-imidazolidinedione (1.5 g, 5.25 mmol). The solution was stirred at 25° C. for 2 hours. The reaction was quenched by addition with a saturated solution of NaHSO₃ (30 mL) and extracted with ethyl acetate (50 mL×2). The organic layer was concentrated, then purified by flash chromatography (10% ethyl acetate in petroleum ether) to give a mixture of 4-amino-3-bromo-2-chlorobenzonitrile and 4-amino-5-bromo-2-chlorobenzonitrile (850 mg, 5/2 ratio of regio-isomers, 26% yield) as a yellow solid which was used directly in the next step. ¹H NMR (400 MHz, CDCl₃) δ 7.67 (s, 1H), 7.38 (d, J=8.4 Hz, 2.6H), 6.80 (s, 1H), 6.65 (d, J=8.4 Hz, 2.6H), 4.81 (bs, 5H), 4.71 (bs, 2H).

Step 2: 3-bromo-2-chloro-4-iodobenzonitrile

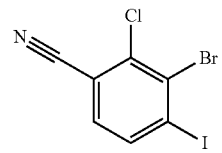 [SMILES: N#Cc1ccc(I)c(Br)c1Cl]

To a suspension of CuI (51.63 g, 271.74 mmol) in acetonitrile (300 mL) was added tert-butyl nitrite (33.59 g, 326.09 mmol). The mixture was stirred at 65° C. for 10 minutes. A mixture of 4-amino-3-bromo-2-chlorobenzonitrile and 4-amino-5-bromo-2-chlorobenzonitrile (3/4 ratio, 25 g, 108.7 mmol) was added, then the reaction mixture was stirred at 65° C. for 12 hours. Upon cooling to room temperature, the mixture was quenched with saturated Na₂S₂O₄ solution (30 mL) and extracted with ethyl acetate (3×50 mL). The combined organic layers were washed with brine (10 mL), dried over by Na₂SO₄ and filtered. The filtrate was concentrated and purified by flash column chromatography (5% ethyl acetate in petroleum ether) to give 3-bromo-2-chloro-4-iodobenzonitrile (5 g, 310% yield) as a yellow solid. ¹H NMR (400 MHz, CDCl₃) 7.91 (d, J=8.0 Hz, 1H), 7.30 (d, J=8.0 Hz, 1H).

Step 3:
(3-bromo-2-chloro-4-iodophenyl)methanamine

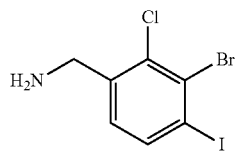

To a solution of 3-bromo-2-chloro-4-iodobenzonitrile (3 g, 8.76 mmol) in THF (30 mL) was added borane-THF (30 mL, 1 M in THF, 30 mmol). The mixture was stirred at 65° C. for 3 h under $N_2$. Upon cooling to room temperature, the mixture was quenched by addition of methanol (10 mL) and HCl (12 N, 10 mL). The reaction was concentrated to dryness, then the residue was taken up in ethyl acetate (100 mL) and extracted with water (50 mL×2). The organic layer was discarded and the aqueous layer was adjusted to pH 9 through the addition of a saturated aqueous solution of $NaHCO_3$. The mixture was extracted with ethyl acetate (50 mL×3), then the combined organic layers were washed with water (10 mL×2) and brine (10 mL), dried ($Na_2SO_4$), filtered and concentrated to give (3-bromo-2-chloro-4-iodophenyl) methanamine (3 g, 99% yield) as a yellow oil, which was used directly in the next step. LCMS (ESI) [M+H]$^+$=345.9.

Step 4: N-(3-bromo-2-chloro-4-iodobenzyl)-2,2-diethoxyacetimidamide

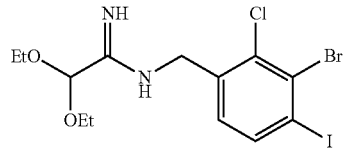 [SMILES: CCOC(OCC)C(=N)NCc1ccc(I)c(Br)c1Cl]

To a solution of (3-bromo-2-chloro-4-iodophenyl)methanamine (2.5 g, 7.22 mmol) in methanol (20 mL) was added methyl 2,2-diethoxyacetimidate (3.75 g, 23.26 mmol). The solution was stirred at 25° C. for 12 hours, then concentrated to dryness. The residue was dissolved in dichloromethane (20 mL), washed with water and brine, dried over $MgSO_4$, filtered and concentrated to give N-(3-bromo-2-chloro-4-iodobenzyl)-2,2-diethoxyacetimidamide (3 g, 87% yield) as a yellow solid, which was used directly in the next step. LCMS (ESI) [M+H]$^+$=474.9.

Step 5:
7-bromo-8-chloro-6-iodoisoquinolin-3-amine

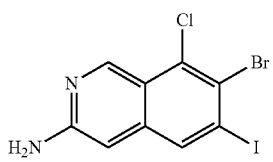 [SMILES: Nc1cc2cc(I)c(Br)c(Cl)c2cn1]

A mixture of sulfuric acid (10 mL) and N-(3-bromo-2-chloro-4-iodobenzyl)-2,2-diethoxyacetimidamide (3 g, 6.31 mmol) was stirred at 60° C. for 12 hours. The reaction mixture was cooled to 0° C. and then NaOH solution was added to adjust the pH to 9. The resulting solution was extracted with dichloromethane (100 mL×3). The combined organic layers were washed with brine, dried over $Na_2SO_4$, filtered and concentrated to give 7-bromo-8-chloro-6-iodo-isoquinolin-3-amine (2.4 g, 99% yield) as a yellow solid. LCMS (ESI) [M+H]$^+$=382.8. $^1$H NMR (400 MHz, DMSO-d$_6$): δ 8.99 (s, 1H), 8.32 (s, 1H), 6.56 (s, 1H), 6.49 (s, 2H).

Example 12

6-bromo-8-chloro-isoquinolin-3-amine

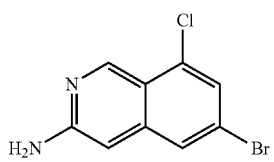

Step 1: methyl 2,2-diethoxyethanimidate

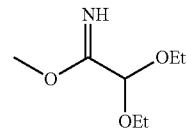

To a stirred solution of diethoxyacetonitrile (7.0 g, 54.2 mmol) in dry methanol (50 mL) was added a solution of sodium methoxide in methanol (4.2 mL, 20%, 8.4 mmol). After the addition, the reaction mixture was stirred at room temperature for 48 hours. The reaction was concentrated to dryness and the residue was taken up in chloroform and the organic layer washed with water, dried and concentrated to give methyl 2,2-diethoxyethanimidate (8.37 g, 95% yield) as a colorless oil, which was used in the next step without further purification. $^1$H NMR (400 MHz, DMSO-d$_6$) δ 7.95 (s, 1H), 4.82 (s, 1H), 3.65 (s, 3H), 3.51 (q, J=7.2 Hz, 4H), 1.14 (t, J=7.2 Hz, 6H).

Step 2: 4-bromo-2-chloro-phenyl)methanamine

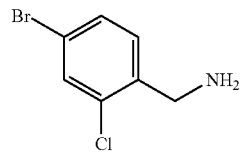

To a 50 mL round bottom flask was added $BH_3$-THF (1.0 M in THF, 32.5 mL, 32.5 mmol) and 4-bromo-2-chlorobenzonitrile (1.76 g, 8.13 mmol) in THF (10 mL). The mixture was heated to reflux for 2 hours. The reaction mixture was quenched by the addition of aqueous 3 M HCl. The pH was adjusted to 8 by adding an aqueous solution of NaOH (5 wt %) and extracted with dichloromethane. The organic layer was dried, filtered and concentrated to afford (4-bromo-2- chloro-phenyl)methanamine (1.62 g, 90% yield), which was used in the next step without further purification. LCMS (ESI) [M+H]⁺=220.0.

Step 3: N-[(4-bromo-2-chloro-phenyl)methyl]-2,2-diethoxy-acetamidine

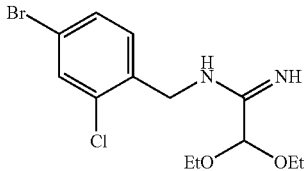 [SMILES: CCOC(OCC)C(=N)NCc1ccc(Br)cc1Cl]

Methyl 2,2-diethoxyethanimidate (2.7 g, 16.8 mmol) was added drop-wise to a stirred solution of (4-bromo-2-chloro-phenyl)methanamine (2.47 g, 11.2 mmol) in methanol (100 mL). The mixture was stirred for 2 hours at room temperature. The reaction was concentrated to dryness and the residue was taken up in dichloromethane. The organic layer washed with brine, dried ($Na_2SO_4$) and concentrated to afford crude N-[(4-bromo-2-chloro-phenyl)methyl]-2,2-diethoxy-acetamidine (3.76 g, 89% yield) as a white solid, which was used in the next step without further purification. LCMS (ESI) [M+H]⁺=349.0

Step 4: 6-bromo-8-chloro-isoquinolin-3-amine

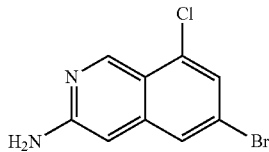 [SMILES: Nc1cc2cc(Br)cc(Cl)c2cn1]

To the crude N-[(4-bromo-2-chloro-phenyl)methyl]-2,2-diethoxy-acetamidine (1.9 g, 5.05 mmol) was added conc. $H_2SO_4$ (14.9 g, 152 mmol) at 0° C. under $N_2$. The reaction mixture was stirred at room temperature for 16 hours, then cooled to 0° C. and adjusted to pH 7.0 with aqueous 1 M NaOH. The mixture was then extracted with dichloromethane (3×) and the combined organic layers were washed with brine, dried ($Na_2SO_4$), and concentrated to dryness. The crude mixture was purified by flash column chromatography (ethyl acetate:petroleum ether=1:3) to give 6-bromo-8-chloro-isoquinolin-3-amine (410 mg, 33% yield) as a yellow solid. LCMS (ESI) [M+H]⁺=256.9

Example 13

8-chloro-7-fluoro-6-iodoisoquinolin-3-amine

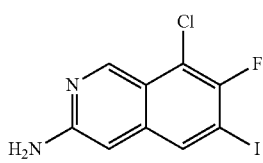 [SMILES: Nc1cc2cc(I)c(F)c(Cl)c2cn1]

Step 1: 4-amino-2-chloro-3-fluorobenzonitrile

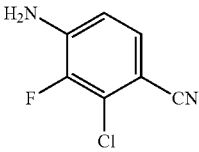 [SMILES: N#Cc1ccc(N)c(F)c1Cl]

To a sealed tube were added copper (I) cyanide (1.2 g, 13.37 mmol), 4-bromo-3-chloro-2-fluoroaniline (1 g, 4.46 mmol) and 1-methyl-2-pyrrolidinone (8 mL). The mixture was heated at 170° C. for 1 hour in a microwave reactor. The reaction mixture was quenched by addition of a saturated solution of $NH_4Cl$ (20 mL) and filtered. The filtrate was extracted with ethyl acetate (3×100 mL). The combined organic layers were washed with brine (3×10 mL), dried with $Na_2SO_4$, filtered through a pad of silica gel, and concentrated to dryness to give 4-amino-2-chloro-3-fluorobenzonitrile (700 mg, 92% yield) as a yellow solid. LCMS (ESI) [M+H]⁺=171.1.

Step 2: 2-chloro-3-fluoro-4-iodobenzonitrile

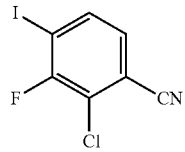 [SMILES: N#Cc1ccc(I)c(F)c1Cl]

To a suspension of CuI (3341 mg, 17.59 mmol) in acetonitrile (50 mL) was added tert-butyl nitrite (1811 mg, 17.59 mmol) at 65° C. under $N_2$. The mixture was stirred at 65° C. for 10 minutes, then 4-amino-2-chloro-3-fluorobenzonitrile (2 g, 11.73 mmol) was added. The mixture was stirred at 65° C. for 12 hours. Upon cooling to room temperature, the mixture was quenched with saturated aqueous $Na_2S_2O_4$ (30 mL) and aqueous $NH_4C_1$ (30 mL) and extracted with ethyl acetate (3×300 mL). The combined organic layers were washed with brine (2×10 mL), dried over $Na_2SO_4$ and filtered. The filtrate was concentrated to give crude product, which was purified by flash chromatography (petroleum ether/ethyl acetate=5/1) to give 2-chloro-3-fluoro-4-iodobenzonitrile (1 g, 30% yield) as a yellow solid. ¹H NMR (400 MHz, $CDCl_3$) δ 7.80 (dd, J=5.6, 8.2 Hz, 1H), 7.22 (dd, J=1.4, 8.2 Hz, 1H).

Step 3: (2-chloro-3-fluoro-4-iodophenyl)methanamine

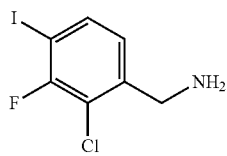 [SMILES: NCc1ccc(I)c(F)c1Cl]

2-Chloro-3-fluoro-4-iodobenzonitrile (1 g, 3.55 mmol) was added to a solution of borane-THF (35.53 mL, 1 M in THF, 35.53 mmol) in THF (30 mL) at 0° C. The mixture was then warmed to room temperature and stirred overnight. The reaction solution was quenched by the dropwise addition of a solution of HCl (6 M, 2 mL) then neutralized with an aqueous solution of NaHCO₃ to pH=8 and extracted with dichloromethane (2×200 mL). The combined organic layer was washed with water (2×10 mL) and brine (1×10 mL), dried (Na₂SO₄), filtered and concentrated to give (2-chloro-3-fluoro-4-iodophenyl)methanamine (400 mg, crude), which was used directly in the next step without further purification. LCMS (ESI) [M+H]⁺=285.9.

Step 4: N-(2-chloro-3-fluoro-4-iodobenzyl)-2,2-diethoxyacetimidamide

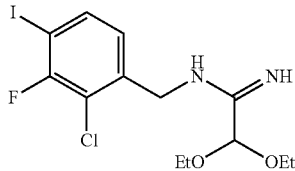 [SMILES: CCOC(OCC)C(=N)NCc1ccc(I)c(F)c1Cl]

To a solution of methyl 2,2-diethoxyacetimidate (0.3 g, 1.88 mmol) in methanol (5 mL) was added (2-chloro-3-fluoro-4-iodophenyl)methanamine (250 mg, 0.88 mmol). The reaction mixture was stirred at 25° C. for 12 hours, and then concentrated to dryness. The residue was taken up in dichloromethane (20 mL), washed with water (2×10 mL) then brine, dried (MgSO₄), filtered and concentrated to give N-(2-chloro-3-fluoro-4-iodobenzyl)-2,2-diethoxyacetimidamide (360 mg, crude) as a yellow solid which was used directly in the next step without further purification. LCMS (ESI) [M+H]⁺=415.0.

Step 5: 8-chloro-7-fluoro-6-iodoisoquinolin-3-amine

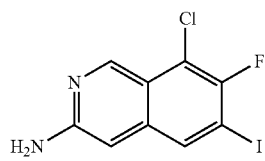 [SMILES: Nc1cc2cc(I)c(F)c(Cl)c2cn1]

A solution of N-(2-chloro-3-fluoro-4-iodobenzyl)-2,2-diethoxyacetimidamide (0.36 g, 0.87 mmol) and conc. H₂SO₄ (10 mL, 26.05 mmol) was stirred at 60° C. for 12 hours. The mixture was cooled to 0° C. adjusted to pH=9 with NaOH (10 wt %), then extracted with dichloromethane (5×100 mL). The combined organic layers were washed with brine, dried (Na₂SO₄), filtered and concentrated to give 8-chloro-7-fluoro-6-iodoisoquinolin-3-amine (0.25 g, crude) as a yellow solid, which was used directly without further purification. LCMS (ESI) [M+H]⁺=322.9. ¹H NMR (400 MHz, CD₃OD) δ 9.00 (s, 1H), 8.08 (d, J=5.6 Hz, 1H), 6.70 (s, 1H).

Example 101

2-[[8-Chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one (Compound 110)

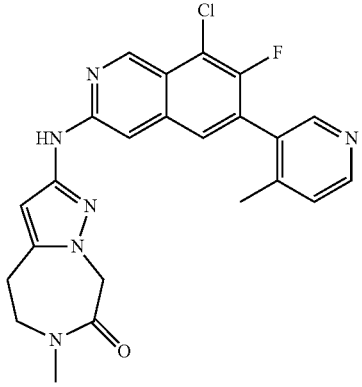 [SMILES: Cc1ccncc1-c1cc2cc(Nc3cc4n(n3)CC(=O)N(C)CC4)ncc2c(Cl)c1F]

To a solution of 8-chloro-7-fluoro-6-(4-methylpyridin-3-yl)isoquinolin-3-amine (100 mg, 0.35 mmol) in 1,4-dioxane (10 mL) was added 2-bromo-6-methyl-4H,5H,6H,7H,8H-pyrazolo[1,5-d][1,4]diazepin-7-one (110 mg, 0.45 mmol), tris(dibenzylideneacetone)dipalladium(0) (72 mg, 0.07 mmol), 9,9-dimethyl-4,5-bis(diphenylphosphino)xanthene (80 mg, 0.14 mmol) and cesium carbonate (290 mg, 0.89 mmol). The resulting mixture was stirred for 2 h at 110° C. and cooled to room temperature. After filtration, the filtrate was concentrated under vacuum. The residue was purified by Prep-HPLC (XBridge Prep C18 OBD, 19*15 mm, 5 μm; 10 mmol NH₄HCO₃ in water: CH₃CN=50%-77% in 8 min) to afford 2-[[8-chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one (45 mg, 29%) as a yellow solid. LCMS (ESI) [M+H]⁺=451.2; ¹H NMR (400 MHz, DMSO-d₆) δ 9.57 (s, 1H), 9.22 (s, 1H), 8.57 (d, J=5.2 Hz, 1H), 8.51 (s, 1H), 8.03 (s, 1H), 7.86 (d, J=7.2 Hz, 1H), 7.45 (d, J=5.2 Hz, 1H), 6.02 (s, 1H), 5.01 (s, 2H), 3.85-3.82 (m, 2H), 3.07-3.04 (m, 2H), 2.96 (s, 3H), 2.23 (s, 3H).

Example 102

2-[[6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one (Compound 111)

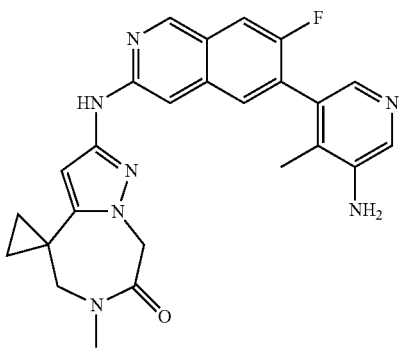 [SMILES: Cc1c(N)cncc1-c1cc2cc(Nc3cc4n(n3)CC(=O)N(C)CC43CC3)ncc2cc1F]

Step 1: tert-butyl N-tert-butoxycarbonyl-N-[5-[7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate

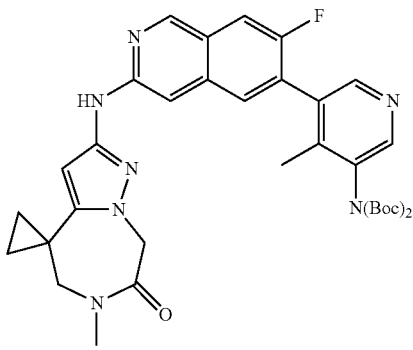

A solution of tert-butyl N-[5-(3-amino-8-chloro-7-fluoro-6-isoquinolyl)-4-methyl-3-pyridyl]-N-tert-butoxycarbonyl-carbamate (200 mg, 0.40 mmol), 2-bromo-6-methyl-spiro[5,8-dihydropyrazolo[1,5-d][1,4]diazepine-4,1'-cyclopropane]-7-one (129 mg, 0.48 mmol), t-BuBrettphos Pd G3 (137 mg, 0.16 mmol), t-Bubrettphos (97 mg, 0.2 mmol), and cesium carbonate (391 mg, 1.2 mmol) in 1,4-dioxane was stirred at 130° C. for 1 hour. The solvent was concentrated under vacuum. The residue was purified by silica gel flash chromatography eluting with dichloromethane/methanol (96/4) to afford tert-butyl N-tert-butoxycarbonyl-N-[5-[7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate (60 mg, 0.091 mmol) as a yellow solid. LCMS (ESI) [M+H]$^+$= 658.3.

Step 2: 2-[[6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one

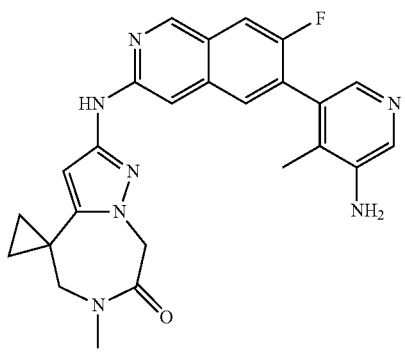 [SMILES: Cc1c(N)cncc1-c1cc2cc(Nc3cc4n(n3)CC(=O)N(C)CC43CC3)ncc2cc1F]

A solution of tert-butyl N-tert-butoxycarbonyl-N-[5-[7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate (50 mg, 0.08 mmol) and 2,2,2-trifluoroacetic acid (1.0 mL) in dichloromethane (1 mL) was stirred at room temperature for 1 h. The solvent was concentrated under vacuum. The residue was redissolved in methanol and then the pH value was adjusted to pH=8 with ammonia in methanol (7 M). After filtration, the filtrate was concentrated under vacuum. The residue was purified by Prep-HPLC (Xbridge C18, 19*15 mm, 5 μm; 10 mmol NH$_4$HCO$_3$ in water:CH$_3$CN=28-43% in 7 min) to afford 2-[[6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one (13.8 mg, 0.03 mmol) as a yellow solid. LCMS (ESI) [M+H]$^+$=458.2; $^1$H NMR (300 MHz, DMSO-d$_6$) δ 9.19 (s, 1H), 8.99 (s, 1H), 8.02 (s, 1H), 7.88 (s, 1H), 7.82 (d, J=9.9 Hz, 1H), 7.72 (d, J=9.9 Hz, 1H), 7.70 (s, 1H), 5.62 (s, 1H), 5.28 (s, 2H), 5.08 (s, 2H), 3.73 (s, 2H), 2.99 (s, 3H), 1.92 (s, 3H), 1.24-1.17 (m, 2H), 0.97-093 (m, 2H).

Example 103

2-[[6-(5-amino-4-methyl-3-pyridyl)-8-chloro-7-fluoro-3-isoquinolyl]amino]-6-methyl-spiro[5,8-dihydropyrazolo[1,5-d][1,4]diazepine-4,1'-cyclopropane]-7-one (Compound 112)

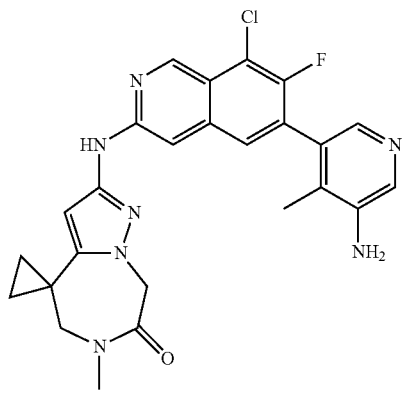 [SMILES: Cc1c(N)cncc1-c1cc2cc(Nc3cc4n(n3)CC(=O)N(C)CC43CC3)ncc2c(Cl)c1F]

Step 1: tert-butyl N-tert-butoxycarbonyl-N-[5-[8-chloro-7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate

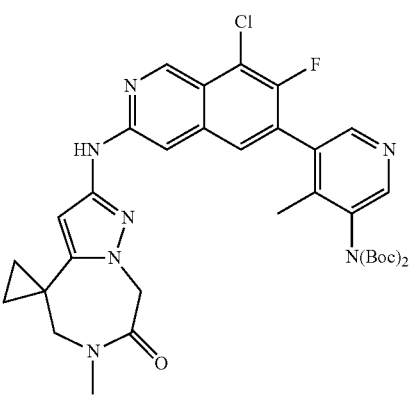

A solution of tert-butyl N-[5-(3-amino-8-chloro-7-fluoro-6-isoquinolyl)-4-methyl-3-pyridyl]-N-tert-butoxycarbonylcarbamate (90 mg, 0.18 mmol), 2-bromo-6-methyl-spiro[5,8-dihydropyrazolo[1,5-d][1,4]diazepine-4,1'-cyclopropane]-7-one (50 mg, 0.19 mmol), t-BuBrettphos Pd G3 (63 mg, 0.07 mmol), t-Bubrettphos (45.0 mg, 0.09 mmol), cesium carbonate (181.0 mg, 0.56 mmol) in 1,4-dioxane (6 mL) was stirred at 130° C. for 1 h. The resulting mixture was concentrated under vacuum. The residue was purified by flash chromatography on silica gel eluting with methanol/dichloromethane (4/96) to afford tert-butyl N-tert-butoxycarbonyl-N-[5-[8-chloro-7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate (58 mg, 45% yield) as a yellow solid. LCMS (ESI) [M+H]$^+$=694.3.

Step 2: 2-[[6-(5-amino-4-methyl-3-pyridyl)-8-chloro-7-fluoro-3-isoquinolyl]amino]-6-methyl-spiro[5,8-dihydropyrazolo[1,5-d][1,4]diazepine-4,1'-cyclopropane]-7-one

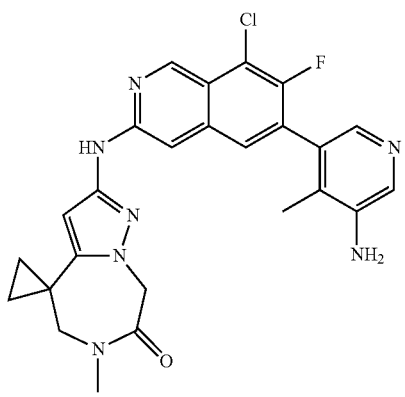 [SMILES: Cc1c(N)cncc1-c1cc2cc(Nc3cc4n(n3)CC(=O)N(C)CC43CC3)ncc2c(Cl)c1F]

A solution of tert-butyl N-tert-butoxycarbonyl-N-[5-[8-chloro-7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl]carbamate (105.0 mg, 0.15 mmol) and 2,2,2-trifluoroacetic acid (1.0 mL) in dichloromethane (1 mL) was stirred at 25° C. for 1 h. The residue was redissolved in methanol and then adjusted to pH=8 with ammonia in methanol (7 M). After filtration, the filtrate was concentrated under vacuum. The crude product was purified by Prep-HPLC (Xbridge C18 19×150; CH$_3$CN/10 mmol/L NH$_4$HCO$_3$ in H$_2$O=30%-48%; 7 mins, 25 ml/min) to afford 2-[[6-(5-amino-4-methyl-3-pyridyl)-8-chloro-7-fluoro-3-isoquinolyl]amino]-6-methyl-spiro[5,8-dihydropyrazolo[1,5-d][1,4]diazepine-4,1'-cyclopropane]-7-one (1.5 mg, 1.9%).

LCMS (ESI) [M+H]$^+$=492.2; $^1$H NMR (300 MHz, DMSO-d$_6$) δ 9.45 (s, 1H), 9.19 (s, 1H), 8.04 (s, 1H), 7.94 (s, 1H), 7.77 (d, J=6.0 Hz, 1H), 7.72 (s, 1H), 5.65 (s, 1H), 5.33 (s, 2H), 5.09 (s, 2H), 3.74 (s, 2H), 2.99 (s, 3H), 1.92 (s, 3H), 1.19-1.17 (m, 2H), 0.98-0.96 (m, 2H).

Example 104

2-((6-(5-amino-4-methylpyridin-3-yl)-7-fluoroisoquinolin-3-yl)amino)-4,6-dimethyl-5,6-dihydro-4H,8H-pyrazolo[5,1-e][1,2,6]thiadiazepine 7,7-dioxide (Compound 113)

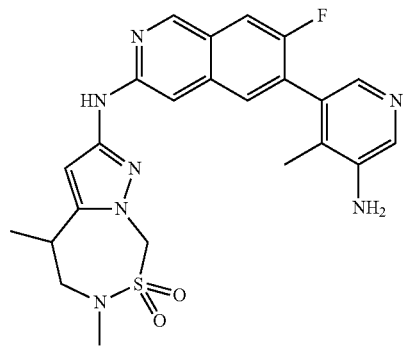 [SMILES: Cc1c(N)cncc1-c1cc2cc(Nc3cc4n(n3)CS(=O)(=O)N(C)CC4C)ncc2cc1F]

Step 1: 1-bromo-N-methyl-methanesulfonamide

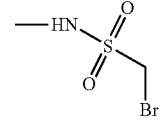

A solution of methylamine (1.94 mL, 3.88 mmol) and bromomethanesulfonyl chloride (500.0 mg, 2.58 mmol) in tetrahydrofuran (10 mL) was stirred at 25° C. for 2 h. The reaction solution was diluted with dichloromethane (40 mL) and then washed with water (10 mL). The organic layer was dried with anhydrous sodium sulfate. After filtration, the filtrate was concentrated under vacuum to afford 1-bromo-N-methyl-methanesulfonamide (400 mg, 2.13 mmol) as a white solid. LCMS (ESI, m/z) [M+H]$^+$=188.

Step 2: 1-(3,5-dibromopyrazol-1-yl)-N-methyl-methane sulfonamide

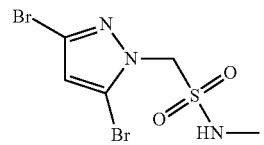

A solution of 1-bromo-N-methyl-methanesulfonamide (200 mg, 1.06 mmol), 3,5-dibromo-TH-pyrazole (240.24 mg, 1.06 mmol) and potassium carbonate (220.17 mg, 1.6 mmol) in acetonitrile (10 mL) was stirred at 80° C. for 12 h. After filtration, the filtrate was concentrated under vacuum to afford 1-(3,5-dibromopyrazol-1-yl)-N-methyl-methanesulfonamide (300 mg, 0.90 mmol) as a colorless oil. LCMS (ESI) [M+H]$^+$=332.

Step 3: N-allyl-1-(3,5-dibromopyrazol-1-yl)-N-methyl-methanesulfonamide

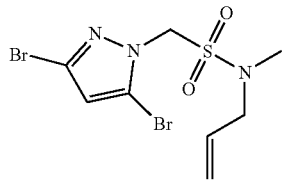 [SMILES: C=CCN(C)S(=O)(=O)Cn1nc(Br)cc1Br]

A solution of 1-(3,5-dibromopyrazol-1-yl)-N-methyl-methanesulfonamide (200 mg, 0.60 mmol), allyl bromide (145.32 mg, 1.2 mmol) and potassium carbonate (165.77 mg, 1.2 mmol) in acetonitrile (10 mL) was stirred at 25° C. for 12 h. The solvent was concentrated under vacuum. The residue was purified by reverse phase chromatography (acetonitrile 0-50/0.1% NH$_3$ in water) to afford N-allyl-1-(3,5-dibromopyrazol-1-yl)-N-methyl-methanesulfonamide (200 mg, 0.54 mmol) as a colorless oil. LCMS (ESI) [M+H]$^+$= 372.

Step 4: 2-bromo-6-methyl-4-methylene-5,8-dihydropyrazolo[5,1-e][1,2,6]thiadiazepine 7,7-dioxide

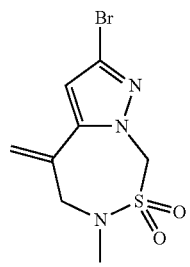

A solution of [N-allyl-1-(3,5-dibromopyrazol-1-yl)-N-methyl-methanesulfonamide (200 mg, 0.54 mmol), tetrabuylammonium bromide (172.63 mg, 0.54 mmol), palladium diacetate (12.01 mg, 0.05 mmol), triphenylphosphine (28.09 mg, 0.11 mmol) and potassium acetate (157.62 mg, 1.61 mmol) in N,N-dimethylformamide (2 mL) was stirred for 12 h at 90° C. under nitrogen. The reaction mixture was diluted with water. The resulting solution was extracted with ethyl acetate and dried with anhydrous sodium sulfate. After filtration, the filtrate was concentrated under vacuum.. The residue was purified by flash chromatography on silica gel eluting with EA/PE (1/4) to afford 2-bromo-6-methyl-4-methylene-5,8-dihydropyrazolo[5,1-e][1,2,6]thiadiazepine 7,7-dioxide (90 mg, 0.31 mmol) as a colorless oil. LCMS (ESI, m/z): [M+H]$^+$=292.

Step 5: tert-butyl N-tert-butoxycarbonyl-N-[5-[7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate

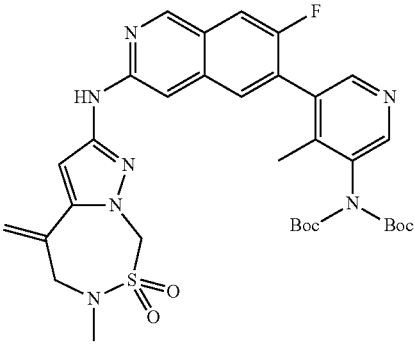 [SMILES: C=C1CN(C)S(=O)(=O)Cn2nc(Nc3cc4cc(-c5cncc(N(C(=O)OC(C)(C)C)C(=O)OC(C)(C)C)c5C)c(F)cc4cn3)cc21]

A mixture of 2-bromo-6-methyl-4-methylene-5,8-dihydropyrazolo[5,1-e][1,2,6]thiadiazepine 7,7-dioxide (200 mg, 0.68 mmol), tert-butyl N-[5-(3-amino-8-chloro-7-fluoro-6-isoquinolyl)-4-methyl-3-pyridyl]-N-tert-butoxycarbonyl-carbamate (309.89 mg, 0.62 mmol), t-BuBrettphos (165.67 mg, 0.34 mmol), t-BuBrettphos G3 (233.85 mg, 0.27 mmol) and cesium carbonate (557.93 mg, 1.71 mmol) in 1,4-dioxane (15 mL) was stirred under nitrogen for 1 h at 120° C. After filtration, the filtrate was concentrated under vacuum. The residue was purified by flash chromatography on silica gel eluting with ethyl acetate/petroleum ether (4/1) to afford tert-butyl N-tert-butoxycarbonyl-N-[5-[7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (60 mg, 0.088 mmol) as a brown solid. LCMS (ESI) [M+H]$^+$=680.

Step 6: tert-butyl N-tert-butoxycarbonyl-N-[5-[3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate

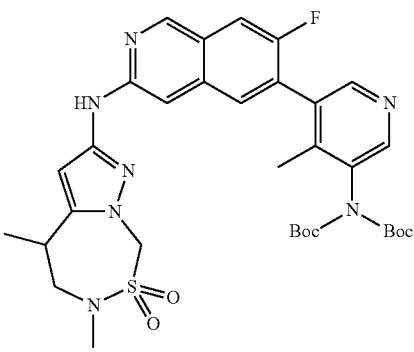 [SMILES: Cc1c(-c2cc3cc(Nc4cc5n(n4)CS(=O)(=O)N(C)CC5C)ncc3cc2F)cncc1N(C(=O)OC(C)(C)C)C(=O)OC(C)(C)C]

A solution of tert-butyl N-tert-butoxycarbonyl-N-[5-[7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (60.0 mg, 0.09 mmol) and Raney nickel (10.0 mg) in methyl alcohol (10 mL) was stirred at 25° C. under a hydrogen atmosphere for 5 h. After filtration, the filtrate was concentrated under vacuum to afford tert-butyl N-tert-butoxycarbonyl-N-[5-[3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate (50 mg, 0.073 mmol) as a yellow solid. LCMS (ESI) [M+H]$^+$=682.

Step 7: N-[6-(5-amino-4-methyl-3-pyridyl)-7-fluoro-3-isoquinolyl]-4,6-dimethyl-7,7-dioxo-5,8-dihydro-4H-pyrazolo[5,1-e][1,2,6]thiadiazepin-2-amine

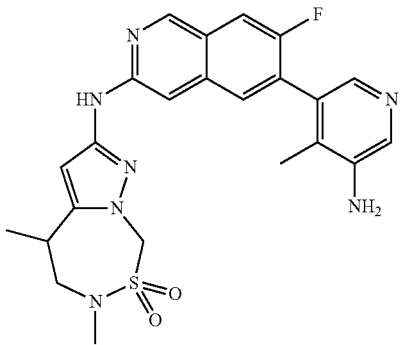 [SMILES: Cc1c(N)cncc1-c1cc2cc(Nc3cc4n(n3)CS(=O)(=O)N(C)CC4C)ncc2cc1F]

A solution of tert-butyl N-tert-butoxycarbonyl-N-[5-[3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate (60 mg, 0.09 mmol) and 2,2,2-trifluoroacetic acid (1 mL, 1.76 mmol) in dichloromethane (2 mL) was stirred at 25° C. for 2 h. The residue was redissolved in methanol and then adjusted to pH=8 with ammonia in methanol (7 M). The resulting residue was purified by reverse phase chromatography (acetonitrile 0-40%/0.1% NH$_3$ in water) to afford N-[6-(5-amino-4-methyl-3-pyridyl)-7-fluoro-3-isoquinolyl]-4,6-dimethyl-7,7-dioxo-5,8-dihydro-4H-pyrazolo[5,1-e][1,2,6]thiadiazepin-2-amine (12.2 mg, 0.025 mmol) as a yellow solid. LCMS (ESI) [M+H]$^+$=482; $^1$H NMR (400 MHz, DMSO-d$_6$) δ 9.42 (s, 1H) 9.03 (s, 1H) 8.03 (s, 2H) 7.84-7.82 (m, 1H) 7.70 (s, 2H) 6.19-6.02 (m, 2H) 5.50-5.28 (m, 3H), 3.58-3.56 (m, 2H) 3.28-3.21 (m, 1H) 3.05 (s, 3H), 1.92 (s, 3H) 1.26 (s, 3H).

Example 105

2-((8-chloro-7-fluoro-6-(4-methylpyridin-3-yl)isoquinolin-3-yl)amino)-7-methyl-6,7-dihydro-5H-imidazo[1,2-d][1,4]diazepin-8(9H)-one (Compound 114)

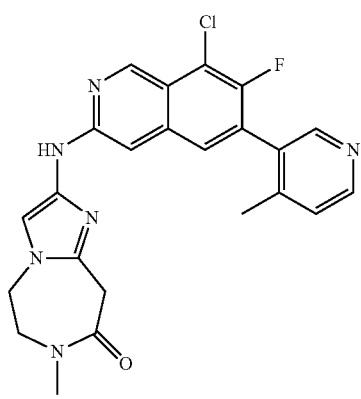 [SMILES: Cc1ccncc1-c1cc2cc(Nc3cn4c(n3)CC(=O)N(C)CC4)ncc2c(Cl)c1F]

Step 1: 2-[tert-butoxycarbonyl(methyl)amino]ethyl methanesulfonate

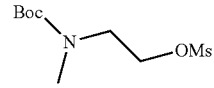

A solution of tert-butyl (2-hydroxyethyl)(methyl)carbamate (6.0 g, 34.24 mmol) and triethylamine (6.92 g, 68.48 mmol) in dichloromethane (100 mL) was added dropwise methanesulfonyl chloride (4.68 g, 41.09 mmol) at 0° C. under nitrogen. The reaction was stirred for 1 h at 0° C. The resulting solution was washed with water (3×20 mL). The organic phase was dried with anhydrous sodium sulfate. After filtration, the filtrate was concentrated under vacuum to afford 2-[tert-butoxycarbonyl(methyl)amino]ethyl methanesulfonate (8 g, 31.58 mmol, 92.2% yield) as a colorless oil. LCMS (ESI) [M+H]$^+$=254.

Step 2: tert-butyl N-[2-(4-bromo-2-methyl-imidazol-1-yl)ethyl]-N-methyl-carbamate

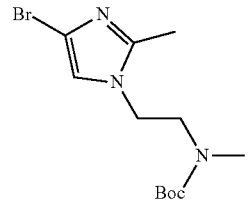 [SMILES: Cc1nc(Br)cn1CCN(C)C(=O)OC(C)(C)C]

A solution of 5-bromo-2-methyl-1H-imidazole (5.0 g, 31.06 mmol) in N,N-dimethylformamide (100 mL) was added sodium hydride (1.12 g, 46.58 mmol, 60%) in portions at 0° C. under nitrogen. The reaction was stirred for 30 min at 0° C. before 2-[tert-butoxycarbonyl(methyl)amino] ethyl methanesulfonate (8.0 g, 31.58 mmol) was added. The reaction was stirred for 12 h at room temperature. The reaction was quenched with water (1 mL) and further diluted with water (100 mL). The resulting solution was extracted with ethyl acetate (3×100 mL). The organic layers were combined and dried with anhydrous sodium sulfate. After filtration, the filtrate was concentrated under vacuum. The residue was purified by reverse phase chromatography (C18, acetonitrile 0-40/0.1% NH$_3$H$_2$O in water) to afford tert-butyl N-[2-(4-bromo-2-methyl-imidazol-1-yl)ethyl]-N-methyl-carbamate (6 g, 18.86 mmol) as a colorless oil. LCMS (ESI) [M+H]$^+$=318.

Step 3: methyl 2-[4-bromo-1-[2-[tert-butoxycarbonyl(methyl)amino]ethyl]imidazol-2-yl]acetate

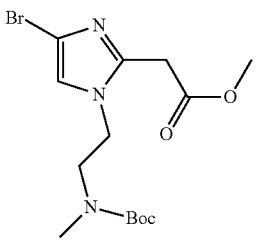 [SMILES: COC(=O)Cc1nc(Br)cn1CCN(C)C(=O)OC(C)(C)C]

To a solution of tert-butyl N-[2-(4-bromo-2-methyl-imidazol-1-yl)ethyl]-N-methyl-carbamate (2.0 g, 6.29 mmol) and dimethyl carbonate (2.83 g, 31.43 mmol) in tetrahydrofuran (100 mL) was added dropwise LDA (7.54 mL, 18.86 mmol, 2.5 mol/L) at −70° C. under nitrogen. The resulting solution was stirred for 2 h at −70° C. to −30° C. and then quenched with water (1 mL). The resulting solution was concentrated under vacuum and purified by reverse phase chromatography (C18, acetonitrile 0-40/0.1% NH$_3$ in water) to afford methyl 2-[4-bromo-1-[2-[tert-butoxycarbonyl(methyl)amino]ethyl]imidazol-2-yl]acetate (400 mg, 1.06 mmol) as a colorless solid. LCMS (ESI) [M+H]$^+$=376.

Step 4: methyl 2-[4-bromo-1l-[2-(methylamino)ethyl]imidazol-2-yl]acetate

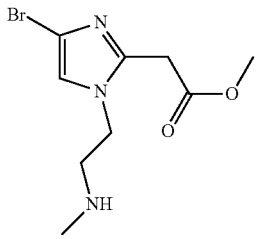

A solution of methyl 2-[4-bromo-1-[2-[tert-butoxycarbonyl(methyl)amino]ethyl]imidazol-2-yl]acetate (400 mg, 1.06 mmol) and 2,2,2-trifluoroacetic acid (1 mL, 1.06 mmol) in dichloromethane (3 mL) was stirred at 25° C. for 2 h. The reaction was concentrated under vacuum to afford methyl 2-[4-bromo-1-[2-(methylamino)ethyl]imidazol-2-yl]acetate (250 mg, crude) as a colorless solid. LCMS (ESI) [M+H]$^+$= 276.

Step 5: 2-bromo-7-methyl-6,9-dihydro-5H-imidazo[1,2-d][1,4]diazepin-8-one

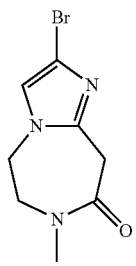

A solution of methyl 2-[4-bromo-1-[2-(methylamino)ethyl]imidazol-2-yl]acetate (250 mg, crude) and triethylamine (914.42 mg, 9.05 mmol) in methyl alcohol (10 mL) was stirred at 25° C. for 12 h. The reaction was concentrated under vacuum and purified by reverse phase chromatography (acetonitrile 0-40/0.1% NH$_3$ in water) to afford 2-bromo-7-methyl-6,9-dihydro-5H-imidazo[1,2-d][1,4]diazepin-8-one (160 mg, 0.66 mmol) as a colorless oil. LCMS (ESI) [M+H]$^+$=244.

Step 6: 2-[[8-chloro-7-fluoro-6-(4-methyl-3-pyridyl)-3-isoquinolyl]amino]-7-methyl-6,9-dihydro-5H-imidazo[1,2-d][1,4]diazepin-8-one

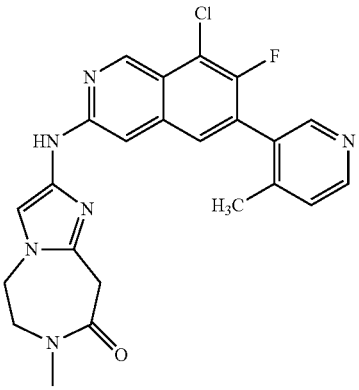 [SMILES: Cc1ccncc1-c1cc2cc(Nc3cn4c(n3)CC(=O)N(C)CC4)ncc2c(Cl)c1F]

A mixture of 2-bromo-7-methyl-6,9-dihydro-5H-imidazo[1,2-d][1,4]diazepin-8-one (50 mg, 0.20 mmol), 8-chloro-7-fluoro-6-(4-methyl-3-pyridyl)isoquinolin-3-amine (47.15 mg, 0.16 mmol), t-BuBrettPhos G3 (69.97 mg, 0.08 mmol), t-BuBrettPhos (49.67 mg, 0.10 mmol) and cesium carbonate (200 mg, 0.61 mmol) in 1,4-dioxane (6 mL) was stirred at 120° C. for 3 h under nitrogen. After filtration, the filtrate was concentrated under vacuum. The residue was purified by reverse phase chromatography (acetonitrile, 0-40/0.1% NH$_4$HCO$_3$ in water) to afford 2-[[8-chloro-7-fluoro-6-(4-methyl-3-pyridyl)-3-isoquinolyl]amino]-7-methyl-6,9-dihydro-5H-imidazo[1,2-d][1,4]diazepin-8-one (5.7 mg, 0.013 mmol) as a yellow solid. LCMS (ESI) [M+H]$^+$=451; $^1$H NMR (400 MHz, DMSO-d) δ 9.35 (s, 1H), 9.22 (s, 1H), 8.55 (d, J=5.2 Hz, 1H), 8.49 (s, 1H) 7.72 (s, 1H) 7.45 (s, 1H), 7.32 (s, 1H), 7.15 (s, 1H), 4.15-4.09 (m, 2H), 4.05-3.98 (m, 2H), 3.90 (s, 2H), 2.96 (s, 3H), 2.22 (s, 3H).

Example 106

2-((8-chloro-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one (Compound 115)

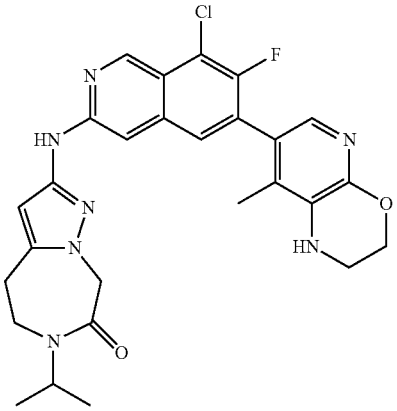 [SMILES: Cc1c(-c2cc3cc(Nc4cc5n(n4)CC(=O)N(C(C)C)CC5)ncc3c(Cl)c2F)cnc2c1NCCO2]

Step 1: tert-butyl 7-(3-amino-8-chloro-7-fluoro-6-isoquinolyl)-8-methyl-2,3-dihydropyrido[2,3-b][1,4]oxazine-1-carboxylate

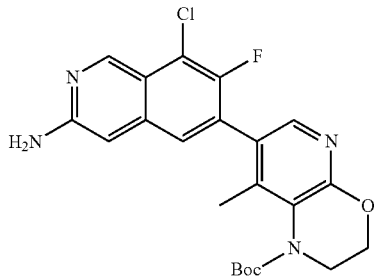 [SMILES: Cc1c(-c2cc3cc(N)ncc3c(Cl)c2F)cnc2c1N(C(=O)OC(C)(C)C)CCO2]

A mixture of 8-chloro-7-fluoro-6-iodo-isoquinolin-3-amine (1.14 g, 3.54 mmol), [1,1'-bis(diphenylphosphino)ferrocene]dichloropalladium(II) (518.19 mg, 0.71 mmol), potassium carbonate (1.47 g, 10.62 mmol) and tert-butyl 8-methyl-7-(4,4,5,5-tetramethyl-1,3,2-dioxaborolan-2-yl)-2,3-dihydropyrido[2,3-b][1,4]oxazine-1-carboxylate (2.0 g, 5.32 mmol) in 1,4-dioxane (20 mL) and water (4 mL) was stirred for 1 h at 90° C. After filtration, the filtrate was concentrated under vacuum. The residue was purified by flash chromatography on silica gel eluting with PE/EA(3/1) to afford tert-butyl 7-(3-amino-8-chloro-7-fluoro-6-isoquinolyl)-8-methyl-2,3-dihydropyrido[2,3-b][1,4]oxazine-1-carboxylate (1.5 g, 3.37 mmol) as a yellow solid. LCMS (ESI) [M+H]$^+$=445.

Step 2: tert-butyl7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

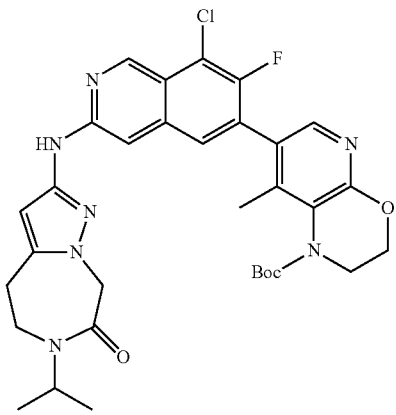 [SMILES: Cc1c(-c2cc3cc(Nc4cc5n(n4)CC(=O)N(C(C)C)CC5)ncc3c(Cl)c2F)cnc2c1N(C(=O)OC(C)(C)C)CCO2]

A mixture of tert-butyl 7-(3-amino-8-chloro-7-fluoro-6-isoquinolyl)-8-methyl-2,3-dihydropyrido[2,3-b][1,4]oxazine-1-carboxylate (50 mg, 0.11 mmol), 2-bromo-6-isopropyl-5,8-dihydro-4H-pyrazolo[1,5-d][1,4]diazepin-7-one (36.7 mg, 0.13 mmol), t-BuBrettphos Pd G3 (19.17 mg, 0.02 mmol), t-BuBrettphos (25.98 mg, 0.04 mmol) and cesium carbonate (109.85 mg, 0.34 mmol) in 1,4-dioxane (10 mL) was stirred at 120° C. for 1 h. The reaction was set up on quadruplicate, then the combined batches were filtered and concentrated under vacuum. The residue was purified by flash chromatography on silica gel eluting with dichloromethanol/methanol (20/1) to afford tert-butyl7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (150 mg, 0.024 mmol) as a yellow solid. LCMS (ESI) [M+H]$^+$=517.24.

Step 3: 2-((8-chloro-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one

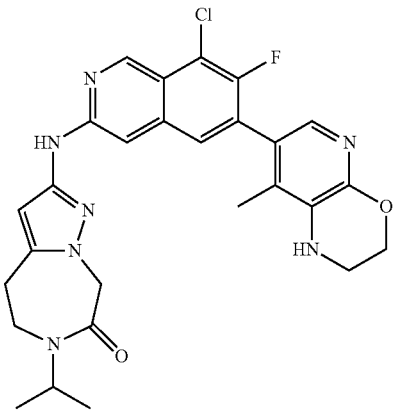 [SMILES: Cc1c(-c2cc3cc(Nc4cc5n(n4)CC(=O)N(C(C)C)CC5)ncc3c(Cl)c2F)cnc2c1NCCO2]

A solution of tert-butyl7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (150 mg, 0.024 mmol) and 2,2,2-trifluoroacetic acid (2 mL) in dichloromethane (4 mL) was stirred at 25° C. for 1 h. The reaction mixture was concentrated under vacuum. The residue was redissolved in methanol and the pH value was then adjusted to pH=8 with ammonia in methanol (7 M). After filtration the filtrate was concentrated under vacuum. The residue was purified by flash chromatography on silica gel eluting with dichloromethanol/methanol (20/1) to afford 2-((8-chloro-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one (30 mg, 0.056 mmol) as a yellow solid.

Example 107

2-((7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one (Compound 116)

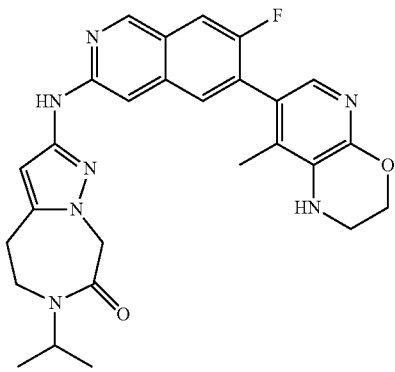 [SMILES: Cc1c(-c2cc3cc(Nc4cc5n(n4)CC(=O)N(C(C)C)CC5)ncc3cc2F)cnc2c1NCCO2]

Step 1: tert-butyl 7-bromo-8-methyl-2,3-dihydropyrido[2,3-b][1,4]oxazine-1-carboxylate

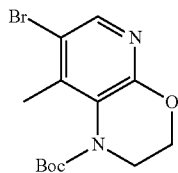 [SMILES: Cc1c(Br)cnc2c1N(C(=O)OC(C)(C)C)CCO2]

To a solution of 7-bromo-8-methyl-2,3-dihydro-1H-pyrido[2,3-b][1,4]oxazine (1 g, 4.37 mmol) in tetrahydrofuran (2 mL) was added dropwise LiHMDS (8.73 mL, 8.73 mmol, 1 mol/L) at 0° C. The resulting solution was stirred under nitrogen for 0.5 h at 0° C. Then di-tert-butyl dicarbonate (2.85 g, 13.07 mmol) was added and the reaction was stirred at room temperature for 2 h. The reaction was quenched with methanol (50 mL). The reaction mixture was concentrated under vacuum. The residue was purified by silica gel flash chromatography (ethyl acetate/petroleum ether, 1/4) to afford tert-butyl 7-bromo-8-methyl-2,3-dihydropyrido[2,3-b][1,4]oxazine-1-carboxylate (800 mg, 2.43 mmol) as a yellow oil. LCMS (ESI) $[M+H]^+=329.2$.

Step 2: tert-butyl 8-methyl-7-(4,4,5,5-tetramethyl-1,3,2-dioxaborolan-2-yl)-2,3-dihydropyrido[2,3-b][1,4]oxazine-1-carboxylate

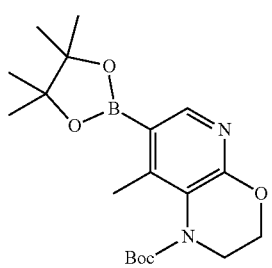 [SMILES: Cc1c(B2OC(C)(C)C(C)(C)O2)cnc2c1N(C(=O)OC(C)(C)C)CCO2]

A mixture of tert-butyl 7-bromo-8-methyl-2,3-dihydropyrido[2,3-b][1,4]oxazine-1-carboxylate (6.2 g, 18.83 mmol), bispinacolatodiboron (23.93 g, 94.22 mmol), [1,1'-bis(diphenylphosphino)ferrocene]dichloropalladium(II) (2.76 g, 3.77 mmol) and potassium acetate (5.55 g, 56.62 mmol) in 1,4-dioxane (2 mL) was stirred under nitrogen for 2.5 h at 90° C. The reaction mixture was concentrated under vacuum. The residue was purified by flash chromatography on silica gel eluting with ethyl acetate/petroleum ether (30%) to afford tert-butyl 8-methyl-7-(4,4,5,5-tetramethyl-1,3,2-dioxaborolan-2-yl)-2,3-dihydropyrido[2,3-b][1,4]oxazine-1-carboxylate (5 g, 13.29 mmol) as a yellow oil. LCMS (ESI) $[M+H]^+=376.3$.

Step 3: tert-butyl 7-(3-amino-7-fluoro-6-isoquinolyl)-8-methyl-2,3-dihydropyrido 2,3-b[1,4]oxazine-1-carboxylate

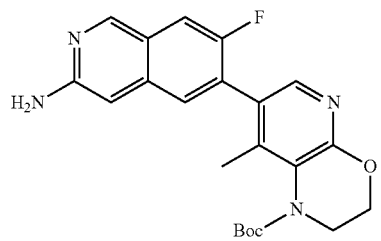 [SMILES: Cc1c(-c2cc3cc(N)ncc3cc2F)cnc2c1N(C(=O)OC(C)(C)C)CCO2]

A mixture of tert-butyl 8-methyl-7-(4,4,5,5-tetramethyl-1,3,2-dioxaborolan-2-yl)-2,3-dihydropyrido[2,3-b][1,4]oxazine-1-carboxylate (160 mg, 0.43 mmol), 6-bromo-7-fluoro-isoquinolin-3-amine (80 mg, 0.33 mmol), [1,1'-bis(diphenylphosphino)ferrocene]dichloropalladium(II) (41.14 mg, 0.06 mmol) and sodium carbonate (91.43 mg, 0.86 mmol) in 1,4-dioxane (1 mL)/water (0.2 mL) was stirred under nitrogen for 12 h at 100° C. The reaction mixture was concentrated under vacuum. The residue was purified by flash chromatography on silica gel eluting with EA/PE (30%) to afford tert-butyl 7-(3-amino-7-fluoro-6-isoquinolyl)-8-methyl-2,3-dihydropyrido[2,3-b][1,4]oxazine-1-carboxylate (100 mg, 0.24 mmol) as a yellow oil. LCMS (ESI) $[M+H]^+=411.2$.

Step 4: tert-butyl 7-[7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

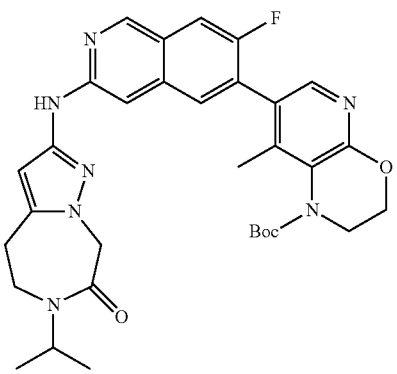 [SMILES: Cc1c(-c2cc3cc(Nc4cc5n(n4)CC(=O)N(C(C)C)CC5)ncc3cc2F)cnc2c1N(C(=O)OC(C)(C)C)CCO2]

A mixture of tert-butyl 7-(3-amino-7-fluoro-6-isoquinolyl)-8-methyl-2,3-dihydropyrido[2,3-b][1,4]oxazine-1-carboxylate (200 mg, 0.49 mmol), 2-bromo-6-isopropyl-5,8-dihydro-4H-pyrazolo[1,5-d][1,4]diazepin-7-one (200 mg, 0.73 mmol), tris(dibenzylideneacetone)dipalladium(0) (100 mg, 0.10 mmol), 9,9-dimethyl-4,5-bis(diphenylphosphino)xanthene (120 mg, 0.21 mmol), and cesium carbonate (500 mg, 1.53 mmol) in 1,4-dioxane (10 mL) was stirred for 3 h at 100° C. The reaction mixture was concentrated under vacuum. The residue was purified by flash chromatography on silica gel eluting with dichloromethane/methanol (20/1) to afford tert-butyl 7-[7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (300 mg, 0.50 mmol) as a brown oil. LCMS (ESI) [M+H]⁺=601.7.

Step 5: 2-[[7-fluoro-6-(8-methyl-2,3-dihydro-TH-pyrido[2,3-b][1,4]oxazin-7-yl)-3-isoquinolyl]amino]-6-isopropyl-5,8-dihydro-4H-pyrazolo[1,5-d][1,4]diazepin-7-one

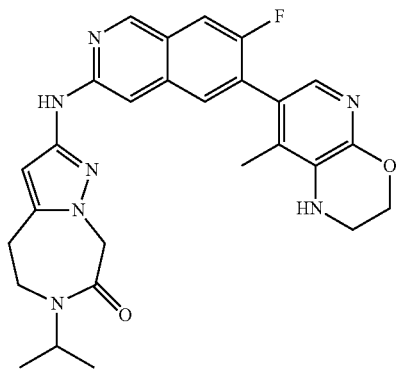 [SMILES: Cc1c(-c2cc3cc(Nc4cc5n(n4)CC(=O)N(C(C)C)CC5)ncc3cc2F)cnc2c1NCCO2]

A mixture of tert-butyl 7-[7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (300 mg, 0.50 mmol) in dichloromethane (5 mL) and 2,2,2-trifluoroacetic acid (5 mL) was stirred at 25° C. for 3 h. The reaction mixture was concentrated under vacuum. The residue was redissolved in methanol and then the pH value was adjusted to pH=8 with ammonia in methanol (7 M). The residue was purified by Prep-HPLC (Atlantis HILIC OBD, 19*150 mm*5 um; water (0.1% FA):CH₃CN=22%-30% in 10 min) to afford 2-[[7-fluoro-6-(8-methyl-2,3-dihydro-1H-pyrido[2,3-b][1,4]oxazin-7-yl)-3-isoquinolyl]amino]-6-isopropyl-5,8-dihydro-4H-pyrazolo[1,5-d][1,4]diazepin-7-one (22.5 mg, 0.045 mmol) as a yellow solid. LCMS (ESI) [M+H]⁺=501; ¹H NMR (300 MHz, DMSO-d₆) δ 9.24 (s, 1H), 8.93 (s, 1H), 7.90 (s, 1H), 7.79 (d, J=10.2 Hz, 1H), 7.68 (d, J=10.2 Hz, 1H), 7.38 (s, 1H), 5.98 (s, 1H), 5.70 (s, 1H), 4.98 (s, 2H), 4.61-4.57 (m, 1H), 4.31-4.29 (m, 2H), 3.79-3.77 (m, 2H), 3.34-3.32 (m, 2H), 3.30-2.98 (m, 2H), 1.93 (d, J=1.9 Hz, 3H), 1.13 (d, J=6.9 Hz, 6H).

Example 108

2-((6-(5-amino-4-methylpyridin-3-yl)-8-chloroisoquinolin-3-yl)amino)-6-isopropyl-5,6-dihydro-4H-pyrazolo[1,5-d][1,4]diazepin-7(8H)-one (Compound 117)

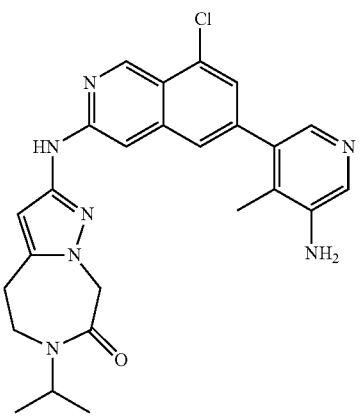 [SMILES: Cc1c(N)cncc1-c1cc(Cl)c2cnc(Nc3cc4n(n3)CC(=O)N(C(C)C)CC4)cc2c1]

Step 1: tert-butyl N-[5-(3-amino-8-chloro-6-isoquinolyl)-4-methyl-3-pyridyl]-N-tert-butoxycarbonyl-carbamate

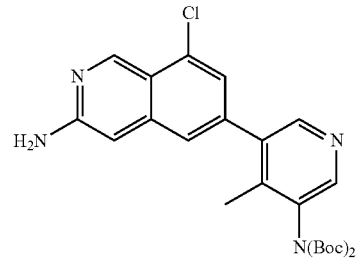

A solution of tert-butyl N-tert-butoxycarbonyl-N-[4-methyl-5-(4,4,5,5-tetramethyl-1,3,2-dioxaborolan-2-yl)-3-pyridyl]carbamate (927.66 mg, 2.14 mmol), 6-bromo-8-chloro-isoquinolin-3-amine (500 mg, 1.94 mmol), [1,1'-bis(diphenylphosphino)ferrocene]dichloropalladium(II) (141.94 mg, 0.19 mmol), potassium carbonate (803.85 mg, 5.83 mmol) in 1,4-dioxane(10 mL) and water (1 mL) was stirred at 90° C. for 8 h. The reaction mixture was concentrated under vacuum. The residue was purified by flash chromatography on silica gel eluting with dichloromethane/methanol (15/1) to afford tert-butyl N-[5-(3-amino-8-chloro-6-isoquinolyl)-4-methyl-3-pyridyl]-N-tert-butoxycarbonyl-carbamate (500 mg, 1.03 mmol) as a yellow solid. LCMS (ESI) [M+H]⁺=485.

Step 2: tert-butyl N-tert-butoxycarbonyl-N-[5-[8-chloro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

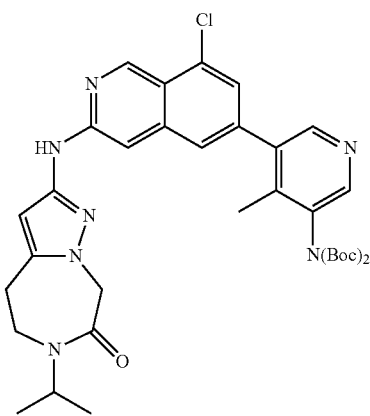

A solution of tert-butyl N-[5-(3-amino-8-chloro-6-isoquinolyl)-4-methyl-3-pyridyl]-N-tert-butoxycarbonyl-carbamate (120 mg, 0.25 mmol), 2-bromo-6-isopropyl-5,8-dihydro-4H-pyrazolo[1,5-d][1,4]diazepin-7-one (101 mg, 0.37 mmol), tBuBrettphospd G3 (84.52 mg, 0.10 mmol), tBu-Brettphos (60 mg, 0.12 mmol) and cesium carbonate (241.99 mg, 0.74 mmol) in 1,4-dioxane (6 mL) was stirred at 130° C. for 1.5 hours. The reaction mixture was concentrated under vacuum. The residue was purified by flash chromatography on silica gel eluting with dichloromethane/methanol (10/1) to afford tert-butyl N-tert-butoxycarbonyl-N-[5-[8-chloro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (82 mg, 0.12 mmol) as a yellow solid. LCMS (ESI) [M+H]⁺=676.

Step 3: 2-[[6-(5-amino-4-methyl-3-pyridyl)-8-chloro-3-isoquinolyl]amino]-6-isopropyl-5,8-dihydro-4H-pyrazolo[1,5-d][1,4]diazepin-7-one

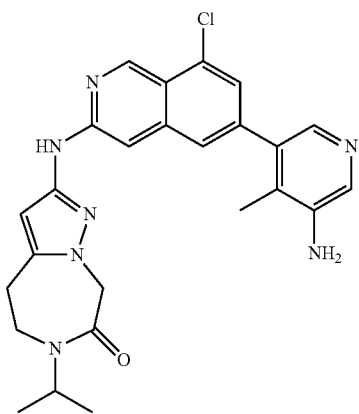 [SMILES: Cc1c(N)cncc1-c1cc(Cl)c2cnc(Nc3cc4n(n3)CC(=O)N(C(C)C)CC4)cc2c1]

A solution of tert-butyl N-tert-butoxycarbonyl-N-[5-[8-chloro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (120 mg, 0.18 mmol) and 2,2,2-trifluoroacetic acid (1.0 mL, 0.18 mmol) in dichloromethane (5 mL) was stirred at 20° C. for 1 hours. The reaction mixture was concentrated under vacuum. The residue was redissolved in methanol and then adjusted the pH value to pH=8 with ammonia in methanol (7 M). After filtration the filtrate was concentrated under vacuum. The residue was purified by Prep-HPLC (Atlantis HILIC OBD, 19*150 mm, 5 μm; 10 mmol NH₄HCO₃ in water: CH₃CN=18%-43% in 9 min) to afford 2-[[6-(5-amino-4-methyl-3-pyridyl)-8-chloro-3-isoquinolyl]amino]-6-isopropyl-5,8-dihydro-4H-pyrazolo[1,5-d][1,4]diazepin-7-one (80 mg, 0.17 mmol) as a yellow solid. LCMS (ESI) [M+H]⁺=476; $^1$H NMR (300 MHz, DMSO-d$_6$) δ 9.24 (s, 1H), 9.00 (s, 1H), 7.98-7.93 (m, 2H), 7.85 (s, 1H), 7.71 (s, 1H), 7.61 (s, 1H), 7.24-7.21 (m, 1H), 6.01 (s, 1H), 5.23 (s, 2H), 4.99 (s, 2H), 4.64-4.55 (m, 1H), 3.80-3.76 (m, 2H), 3.01-2.97 (m, 2H), 2.02 (s, 3H), 1.13 (d, J=6.9 Hz, 6H).

Example 109

2-((6-(5-amino-4-methylpyridin-3-yl)-7,8-difluoroisoquinolin-3-yl)amino)-6-isopropyl-5,6-dihydro-4H-pyrazolo[1,5-d][1,4]diazepin-7(8H)-one (Compound 118)

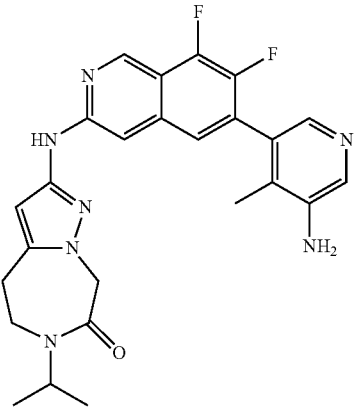 [SMILES: Cc1c(N)cncc1-c1cc2cc(Nc3cc4n(n3)CC(=O)N(C(C)C)CC4)ncc2c(F)c1F]

Step 1: 2,3-difluoro-4-iodobenzonitrile

A mixture of tert-butyl nitrite (6.48 mL, 54.5 mmol) and copper (I) iodide (0.69 mL, 20.44 mmol) in acetonitrile (50 mL) was stirred for 10 min at 65° C. under nitrogen. 4-Amino-2, 3-difluoro-benzonitrile (2.1 g, 13.63 mmol) was then added and the mixture was stirred for 6 h at 65° C. The reaction solution was cooled to room temperature and then quenched through addition of an aqueous solution of sodium thiosulfate (1 M, 30 mL). The resulting solution was extracted with ethyl acetate (3×100 mL) and dried with anhydrous sodium sulfate. After filtration, the filtrate was concentrated under vacuum. The residue was purified by flash chromatography on silica gel eluting with petroleum ether/ethyl acetate (5/1) to afford 2, 3-difluoro-4-iodo-benzonitrile (2.2 g, 8.30 mmol) as a yellow solid. GCMS M+: 265.

Step 2: (2,3-difluoro-4-iodophenyl)methanamine

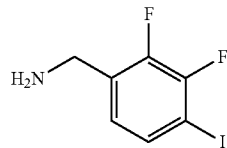 [SMILES: NCc1ccc(I)c(F)c1F]

To a solution of 2,3-difluoro-4-iodo-benzonitrile (2.2 g, 8.30 mmol) in tetrahydrofuran (30 mL) was added borane-tetrahydrofuran complex (83 ml, 83 mmol, 1 M in THF) under nitrogen at 0° C. The reaction was stirred at room temperature for 12 h and quenched by adding a solution of hydrogen chloride (20 ml, 6 M in water). The resulting solution was extracted with dichloromethane (3×100 ml) and dried with anhydrous sodium sulfate. After filtration, the filtrate was concentrated under vacuum to afford (2,3-difluoro-4-iodophenyl)methanamine (0.84 g, crude), which was used directly in the next step without further purification. LCMS (ESI) [M+H]+=270.

Step 3: methyl 2,2-diethoxyacetimidate

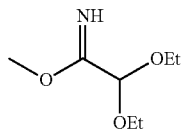

To a solution of diethoxyacetonitrile (5 g, 38.75 mmol) in methyl alcohol (40 mL) was added sodium ethoxide (0.42 g, 7.75 mmol). The reaction was stirred for 3 h at room temperature. The resulting solution was concentrated under vacuum, then the residue was diluted with dichloromethane (100 mL) and washed with water (20 mL). The organic phase was dried with anhydrous sodium sulfate. After filtration, the filtrate was concentrated under vacuum to afford methyl 2,2-diethoxyethanimidate (4.8 g, crude) as a yellow oil. The crude product was directly used in the next step without purification. LCMS (ESI) [M+H]+=162.

Step 4: N-(2,3-difluoro-4-iodobenzyl)-2,2-diethoxy-acetimidamide

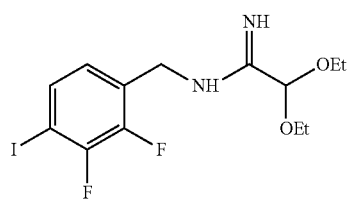 [SMILES: CCOC(OCC)C(=N)NCc1ccc(I)c(F)c1F]

To a solution of (2,3-difluoro-4-iodo-phenyl)methanamine (0.84 g, crude) in methyl alcohol (14 mL) was added methyl 2,2-diethoxyethanimidate (2.01 g, 12.49 mmol). The mixture was stirred at room temperature for 12 h. The resulting solution was diluted with dichloromethane (100 mL) and then washed with brine (50 mL). The organic layer was dried with anhydrous sodium sulfate. After filtration, the filtrate was concentrated under vacuum to afford N-[(2,3-difluoro-4-iodo-phenyl)methyl]-2,2-diethoxy-acetamidine (910 mg, crude) as a yellow solid. The crude product was used directly in the next step without further purification. LCMS (ESI) [M+H]+=399.

Step 5: 7,8-difluoro-6-iodoisoquinolin-3-amine

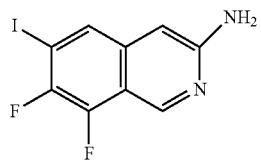 [SMILES: Nc1cc2cc(I)c(F)c(F)c2cn1]

A mixture of N-[(2, 3-difluoro-4-iodo-phenyl)methyl]-2, 2-diethoxy-acetamidine (910.0 mg, crude) in concentrated sulfuric acid (10 mL) was stirred at 60° C. for 2 h. The reaction mixture was cooled to room temperature and then poured onto ice (10 mL). The resulting solution was adjusted to pH 8 with sodium hydroxide solution (5 wt %). The resulting solution was extracted with dichloromethane (3×100 mL) and dried with anhydrous sodium sulfate. After filtration, the filtrate was concentrated under vacuum. The residue was purified by flash chromatography on silica gel eluting with petroleum ether/ethyl acetate (1/1) to afford 7,8-difluoro-6-iodoisoquinolin-3-amine (500 mg, 1.63 mmol) as a yellow solid. LCMS (ESI) [M+H]+=307.

Step 6: tert-butyl N-[5-(3-amino-7,8-difluoro-6-isoquinolyl)-4-methyl-3-pyridyl]-N-tert-butoxycarbonyl-carbamate

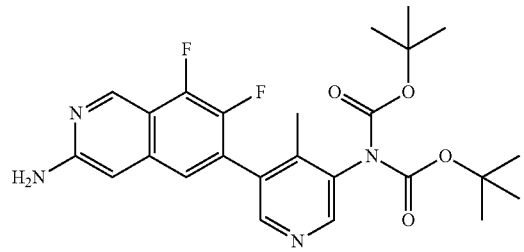 [SMILES: Cc1c(-c2cc3cc(N)ncc3c(F)c2F)cncc1N(C(=O)OC(C)(C)C)C(=O)OC(C)(C)C]

To a mixture of 7,8-difluoro-6-iodo-isoquinolin-3-amine (300.0 mg, 0.98 mmol) and tert-butyl N-tert-butoxycarbonyl-N-[4-methyl-5-(4,4,5,5-tetramethyl-1,3,2-dioxaborolan-2-yl)-3-pyridyl]carbamate (638.62 mg, 1.47 mmol) in 1,4-dioxane (10 mL) and water (1 mL) was added [1,1'-bis(diphenylphosphino)ferrocene]dichloropalladium(II) (110.26 mg, 0.20 mmol) and potassium carbonate (405 mg, 2.94 mmol). The mixture was stirred at 80° C. for 3 h. The resulting mixture was cooled to room temperature and then concentrated under vacuum. The residue was purified by flash chromatography on silica gel eluting with petroleum/ether (1/1) to afford tert-butyl N-[5-(3-amino-7,8-difluoro-6-isoquinolyl)-4-methyl-3-pyridyl]-N-tert-butoxycarbonyl-carbamate (230 mg, 0.46 mmol) as a yellow solid. LCMS (ESI) [M+H]+=487.5.

Step 7: tert-butyl N-tert-butoxycarbonyl-N-[5-[7,8-difluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

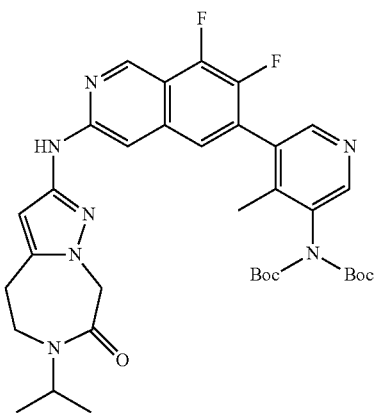 [SMILES: Cc1c(-c2cc3cc(Nc4cc5n(n4)CC(=O)N(C(C)C)CC5)ncc3c(F)c2F)cncc1N(C(=O)OC(C)(C)C)C(=O)OC(C)(C)C]

To a solution of tert-butyl N-[5-(3-amino-7,8-difluoro-6-isoquinolyl)-4-methyl-3-pyridyl]-N-(tert-butoxymethyl)carbamate (225.0 mg, 0.46 mmol) in 1,4-dioxane (10 mL) was added 2-bromo-6-isopropyl-5,8-dihydro-4H-pyrazolo[1,5-d][1,4]diazepin-7-one (187.99 mg, 0.69 mmol), tris(dibenzylideneacetone)dipalladium (84.34 mg, 0.09 mmol), 4,5-bis(diphenylphosphino)-9,9-dimethylxanthene(106 mg, 0.184 mmol) and cesium carbonate (452.93 mg, 1.38 mmol) under nitrogen. The reaction was stirred at 100° C. for 4 h. The resulting mixture was cooled to room temperature and then concentrated under vacuum. The residue was purified by flash chromatography on silica gel eluting with dichloromethane/methanol (20/1) to afford tert-butyl N-tert-butoxycarbonyl-N-[5-[7,8-difluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (171 mg, 0.25 mmol) as a yellow solid. LCMS (ESI, m/z) [M+H]=678.7.

Step 8: 2-[[6-(5-amino-4-methyl-3-pyridyl)-7,8-difluoro-3-isoquinolyl]amino]-6-isopropyl-5,8-dihydro-4H-pyrazolo[15-d]1,4]diazepin-7-one

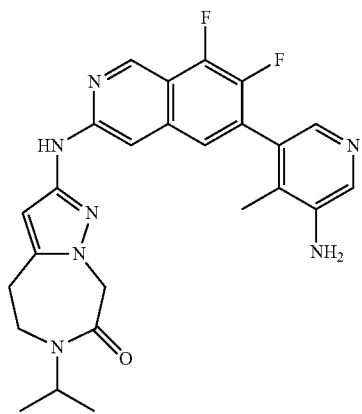 [SMILES: Cc1c(N)cncc1-c1cc2cc(Nc3cc4n(n3)CC(=O)N(C(C)C)CC4)ncc2c(F)c1F]

To a solution of tert-butyl N-tert-butoxycarbonyl-N-[5-[7,8-difluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (171.25 mg, 0.21 mmol) in dichloromethane (10 mL) was added 2,2,2-trifluoroacetic acid (2 mL). The mixture was stirred for 1 h at room temperature. The residue was redissolved in methanol and then adjusted to pH=8 with ammonia in methanol (7 M). The resulting solution was concentrated under vacuum. The residue was purified by Prep-HPLC (XBridge Shield RP18 OBD, 5 um, 19*150 mm; 10 mmol/L NH$_4$HCO$_3$ in water/CH$_3$CN=20-40% in 7 min, 25 ml/min) to afford 2-[[6-(5-amino-4-methyl-3-pyridyl)-7,8-difluoro-3-isoquinolyl]amino]-6-isopropyl-5,8-dihydro-4H-pyrazolo[1,5-d][1,4]diazepin-7-one (24.9 mg, 0.052 mmol) as a yellow solid. LCMS (ESI) [M+H]$^+$=478.5; $^1$H NMR (300 MHz, DMSO-d$_6$) δ 9.49 (s, 1H), 9.18 (s, 1H), 8.04 (s, 1H), 7.97 (s, 1H), 7.72 (s, 1H), 7.57 (d, J=6.9 Hz, 1H), 6.00 (s, 1H), 5.33 (s, 2H), 5.00 (s, 2H), 4.65-4.54 (m, 1H), 3.79-3.77 (m, 2H), 3.01-2.99 (m, 2H), 1.95 (s, 3H), 1.13 (d, J=6.9 Hz, 6H).

Example 110

2-((6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one (Compound 119)

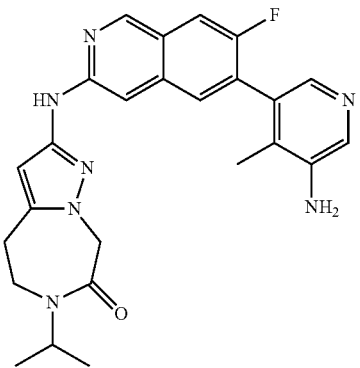 [SMILES: Cc1c(N)cncc1-c1cc2cc(Nc3cc4n(n3)CC(=O)N(C(C)C)CC4)ncc2cc1F]

Step 1: tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

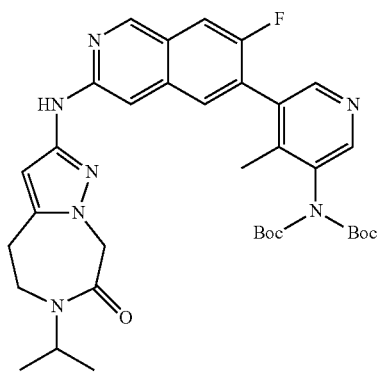 [SMILES: Cc1c(-c2cc3cc(Nc4cc5n(n4)CC(=O)N(C(C)C)CC5)ncc3cc2F)cncc1N(C(=O)OC(C)(C)C)C(=O)OC(C)(C)C]

A solution of tert-butyl N-[5-(3-amino-7-fluoro-6-isoquinolyl)-4-methyl-3-pyridyl]-N-tert-butoxycarbonyl-carbamate (200 mg, 0.43 mmol) in 1,4-dioxane (1 mL) was added 2-bromo-6-isopropyl-5,8-dihydro-4H-pyrazolo[1,5-d][1,4]diazepin-7-one (140 mg, 0.51 mmol), tBuBretphospG3 (146 mg, 0.17 mmol), tBuBretphos (100 mg, 0.21 mmol) and Cs$_2$CO$_3$ (420 mg, 1.29 mmol) under nitrogen. The reaction was stirred for 1 h at 120° C. and then cooled to room temperature. The resulting mixture was concentrated under vacuum. The residue was purified by flash chromatography on silica gel eluting with methanol/dichloromethane (1/10) to afford tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (200 mg, 0.30 mmol)] as a brown oil. LCMS (ESI) [M+H]$^+$=659.8.

Step 2: 2-((6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one

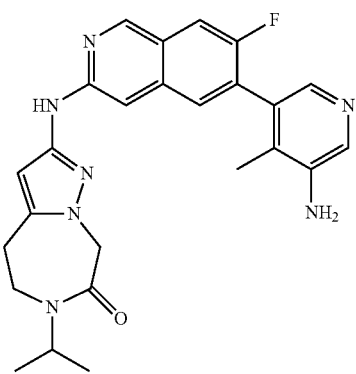

A solution of tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (200 mg, 0.30 mmol) and 2,2,2-trifluoroacetic acid (1 mL, 0.30 mmol) in dichloromethane (5 mL) was stirred at 25° C. for 2 hours. The residue was redissolved in methanol and then adjusted to pH=8 with ammonia in methanol (7 M). The residue was purified by Prep-HPLC (Atlantis HILIC OBD Column19*150 mm*5 um; Water (10 mmol/L NH$_4$HCO$_3$):CH$_3$CN=10%-60% in 7 min) to afford [2-[[6-(5-amino-4-methyl-3-pyridyl)-7-fluoro-3-isoquinolyl]amino]-6-isopropyl-5,8-dihydro-4H-pyrazolo[1,5-d][1,4]diazepin-7-one (45.7 mg, 0.10 mmol) as a color solid. LCMS (ESI) [M+H]$^+$=459; $^1$H NMR (300 MHz, DMSO-d$_6$) δ 9.25 (s, 1H), 8.99 (s, 1H), 8.01 (s, 1H), 7.92 (s, 1H), 7.82 (d, J=10.2 Hz, 1H), 7.71-7.69 (m, 2H), 5.98 (s, 1H), 5.27 (s, 2H), 4.98 (s, 2H), 4.61-4.57 (m, 1H), 3.78-3.76 (m, 2H), 3.00-2.97 (m, 2H), 1.92 (s, 3H), 1.13 (d, J=6.9 Hz, 6H).

Example 111

2-((6-(5-amino-4-methylpyridin-3-yl)-7-fluoroisoquinolin-3-yl)amino)-5,5,6-trimethyl-5,6-dihydro-4H-pyrazolo[1,5-d][1,4]diazepin-7(8H)-one (Compound 120)

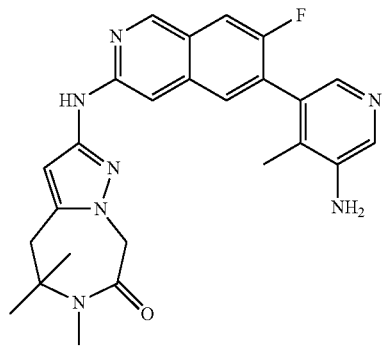

Step 1: 2-(3,5-dibromopyrazol-1-yl)acetonitrile

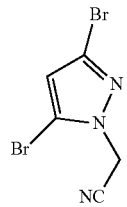

A mixture of 3,5-dibromo-1H-pyrazole (1.0 g, 4.43 mmol) and potassium carbonate (1.22 g, 8.85 mmol) in N,N-dimethylformamide (20 mL) was stirred at 25° C. for 10 min. Bromoacetonitrile (796.59 mg, 6.64 mmol) was added and the reaction was stirred at 25° C. for 2 h. After filtration, the filtrate was diluted with ethyl acetate (30 mL), then washed with water. The organic phase was dried with anhydrous sodium sulfate. After filtration, the filtrate was concentrated under vacuum. The residue was purified by flash chromatography on silica gel eluting with petroleum ether/dichloromethanol (1/1) to afford 2-(3,5-dibromopyrazol-1-yl)acetonitrile (950 mg, 3.59 mmol) as a white solid. LCMS (ESI) [M+H]$^+$=264.

Step 2: 2-[3-bromo-5-(2-methylprop-1-enyl)pyrazol-1-yl]acetonitrile

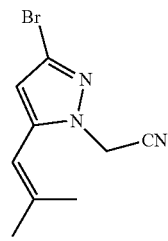

A mixture of 2-(3,5-dibromopyrazol-1-yl)acetonitrile (1.0 g, 3.77 mmol), 4,4,5,5-tetramethyl-2-(2-methylprop-1-en-1-yl)-1,3,2-dioxaborolane (687.29 mg, 3.77 mmol), Pd(dppf)Cl₂ (552.64 mg, 0.75 mmol), and potassium carbonate (1.56 g, 11.32 mmol) in 1,4-dioxane (20 mL) and water (2 mL) was stirred under nitrogen for 1 h at 100° C. After filtration, the filtrate was concentrated under vacuum. The residue was purified by silica gel flash chromatography eluting with ethyl acetate/petroleum ether (1/3) to afford 2-[3-bromo-5-(2-methylprop-1-enyl)pyrazol-1-yl]acetonitrile (700 mg, 2.92 mmol) as a white solid. LCMS (ESI) [M+H]⁺=240.

Step 3: 2-bromo-5,5-dimethyl-6,8-dihydro-4H-pyrazolo[1,5-d][1,4]diazepin-7-one

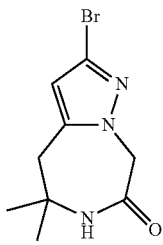

A mixture of 2-[3-bromo-5-(2-methylprop-1-enyl)pyrazol-1-yl]acetonitrile (700 mg, 2.92 mmol) in methylsulfonic acid (15 mL) was stirred at 65° C. for 3 d. The reaction was quenched with ice water. The reaction mixture was adjusted to pH 9-10 with an aqueous sodium hydroxide solution. The resulting solution was extracted with dichloromethane and dried with anhydrous sodium sulfate. After filtration, the filtrate was concentrated under vacuum. The residue was purified by reverse phase chromatography (acetonitrile 0-40/0.1% NH₄HCO₃ in water) to afford 2-bromo-5,5-dimethyl-6,8-dihydro-4H-pyrazolo[1,5-d][1,4]diazepin-7-one (300 mg, 1.16 mmol) as a white solid. LCMS (ESI) [M+H]⁺=258.

Step 4: 2-bromo-5,5,6-trimethyl-4,8-dihydropyrazolo[1,5-d][1,4]diazepin-7-one

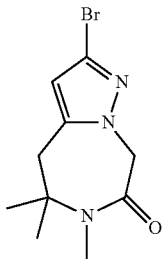

A mixture of 2-bromo-5,5-dimethyl-6,8-dihydro-4H-pyrazolo[1,5-d][1,4]diazepin-7-one (100 mg, 0.39 mmol) and potassium tert-butoxide (52.07 mg, 0.46 mmol) in tetrahydrofuran (10 mL) was stirred at 25° C. for 10 min. Iodomethane (82.52 mg, 0.58 mmol) was added. The reaction was stirred at 25° C. for 1 h. The reaction was concentrated under vacuum and purified by flash chromatography on silica gel eluting with dichloromethane/methanol (95/5) to afford 2-bromo-5,5,6-trimethyl-4,8-dihydropyrazolo[1,5-d][1,4]diazepin-7-one (80 mg, 0.29 mmol) as a white solid. LCMS (ESI) [M+H]⁺=272.

Step 5: tert-butyl N-tert-butoxycarbonyl-N-[5-[7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate

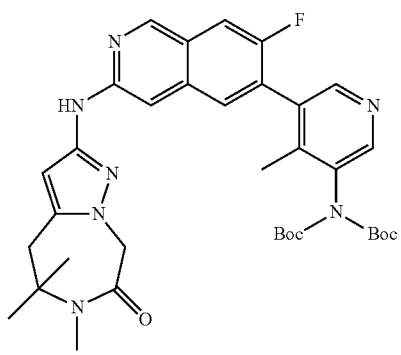

A mixture of 2-bromo-5,5,6-trimethyl-4,8-dihydropyrazolo[1,5-d][1,4]diazepin-7-one (70 mg, 0.26 mmol), tert-butyl N-[5-(3-amino-7-fluoro-6-isoquinolyl)-4-methyl-3-pyridyl]-N-tert-butoxycarbonyl-carbamate (120.51 mg, 0.26 mmol), t-BuBrettPhos-Pd-G3 (87.87 mg, 0.10 mmol), t-BuBrettPhos (62.38 mg, 0.13 mmol), and cesium carbonate (251.56 mg, 0.77 mmol) in 1,4-dioxane (10 mL) was stirred under nitrogen for 2 h at 120° C. After filtration, the filtrate was concentrated under vacuum. The residue was purified by flash chromatography on silica gel eluting with ethyl acetate/petroleum ether (95/5) to afford tert-butyl N-tert-butoxycarbonyl-N-[5-[7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate (30 mg, 0.046 mmol) as a brown solid. LCMS (ESI) [M+H]⁺=660.

Step 6: 2-[[6-(5-amino-4-methyl-3-pyridyl)-7-fluoro-3-isoquinolyl]amino]-5,5,6-trimethyl-4,8-dihydropyrazolo[1,5-d][1,4]diazepin-7-one formate

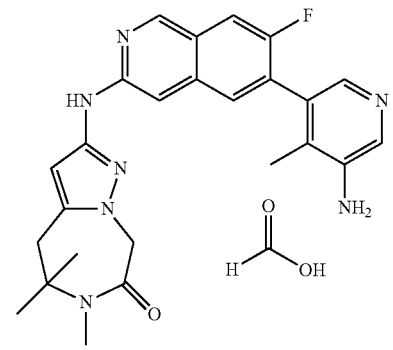

A solution of tert-butyl N-tert-butoxycarbonyl-N-[5-[7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate (30 mg, 0.05 mmol) and 2,2,2-trifluoroacetic acid (1 mL, 0.05 mmol) in dichloromethane (3 mL) was stirred at 25° C. for 2 h. The reaction was concentrated under vacuum. The residue was redissolved in methanol and the pH value was then adjusted to pH=8 with ammonia in methanol (7 M). After filtration the filtrate was concentrated under vacuum. The residue was purified by reverse-phase HPLC (acetonitrile 0-40/0.1% formic acid in water) to afford 2-[[6-(5-amino-4-methyl-3-pyridyl)-7-fluoro-3-isoquinolyl]amino]-5,5,6-trimethyl-4,8-dihydropyrazolo[1,5-d][1,4]diazepin-7-one formic acid salt (7.4 mg, 0.015 mmol) as a yellow solid. LCMS (ESI) [M+H]$^+$=460; $^1$H NMR (400 MHz, CD$_3$OD) δ 8.94 (s, 1H), 8.04 (s, 1H), 7.82-7.78 (m, 2H), 7.69-7.67 (m, 2H), 6.15 (s, 1H), 5.21 (s, 2H), 3.24 (s, 2H), 2.98 (s, 3H), 2.07 (s, 3H), 1.40 (s, 6H).

Example 112

2-((6-(5-amino-4-methylpyridin-3-yl)-7-fluoro-8-methylisoquinolin-3-yl)amino)-6-isopropyl-5,6-dihydro-4H-pyrazolo[1,5-d][1,4]diazepin-7(8H)-one (Compound 121)

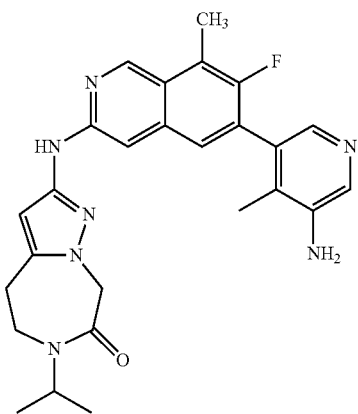 [SMILES: Cc1c(N)cncc1-c1cc2cc(Nc3cc4n(n3)CC(=O)N(C(C)C)CC4)ncc2c(C)c1F]

Step 1: tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

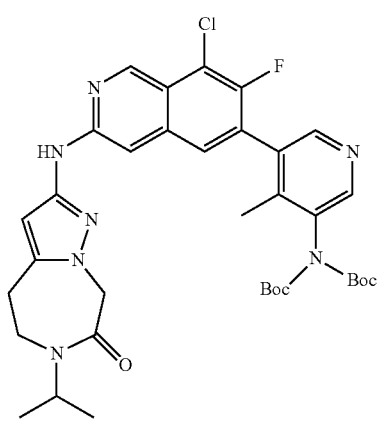 [SMILES: Cc1c(-c2cc3cc(Nc4cc5n(n4)CC(=O)N(C(C)C)CC5)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (100 mg, 0.20 mmol), 2-bromo-6-isopropyl-5,8-dihydro-4H-pyrazolo[1,5-d][1,4]diazepin-7-one (50 mg, 0.18 mmol), tris(dibenzylideneacetone)dipalladium (75 mg, 0.07 mmol), 9,9-dimethyl-4,5-bis(diphenylphosphino)xanthene (85 mg, 0.15 mmol), and cesium carbonate (360 mg, 1.1 mmol) in 1,4-dioxane (10 mL) was stirred under nitrogen for 3 h at 100° C. The reaction was concentrated under vacuum. The residue was purified by flash chromatography on silica gel eluting with dichloromethane/methanol (95/5) to afford tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (61 mg, 0.088 mmol) as a brown oil. LCMS (ESI) [M+H]$^+$=694.2.

Step 2: tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-8-methyl-6-isoquinolyl]-4-methyl-3-pyridyl]carbamate

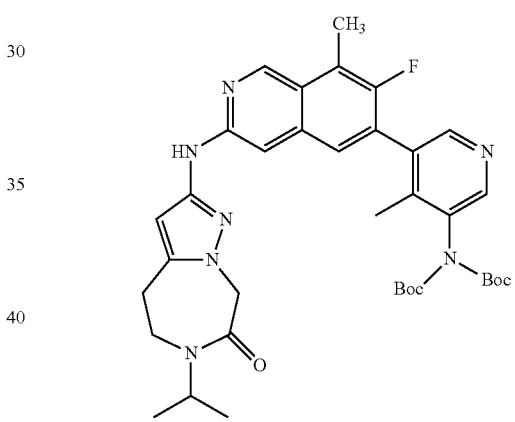

A mixture of trimethylboroxine (61 mg, 0.07 mmol), tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (60 mg, 0.12 mmol), tetrakis(triphenylphosphine)palladium (14 mg, 0.012 mmol), and potassium carbonate (50 mg, 0.36 mmol) in 1,4-dioxane (10 mL) and water (2.5 mL) was stirred under nitrogen for 12 h at 100° C. The reaction was concentrated under vacuum. The residue was purified by flash chromatography on silica gel eluting with dichloromethane/methanol (95/5) to afford tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-8-methyl-6-isoquinolyl]-4-methyl-3-pyridyl]carbamate (60 mg, 0.089 mmol) as a brown oil. LCMS (ESI) [M+H]$^+$= 673.8.

Step 3: 2-[[6-(5-amino-4-methyl-3-pyridyl)-7-fluoro-8-methyl-3-isoquinolyl]amino]-6-isopropyl-5,8-dihydro-4H-pyrazolo[1,5-d][1,4]diazepin-7-one

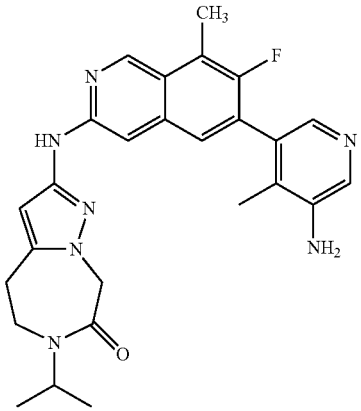 [SMILES: Cc1c(N)cncc1-c1cc2cc(Nc3cc4n(n3)CC(=O)N(C(C)C)CC4)ncc2c(C)c1F]

A solution of tert-butyl N-tert-butoxycarbonyl-N-[5-[7-fluoro-3-[(6-isopropyl-7-oxo-5,8-dihydro-4H-pyrazolo[1,5-d][1,4]diazepin-2-yl)amino]-8-methyl-6-isoquinolyl]-4-methyl-3-pyridyl]carbamate (80 mg, 0.12 mmol) and 2,2,2-trifluoroacetic acid (2 mL, 0.12 mmol) in dichloromethane (5 mL) was stirred at 25° C. for 3 h. The reaction mixture was adjusted to pH=7 with ammonia in methanol (7 M). The reaction was concentrated under vacuum. The residue was purified by reverse phase HPLC to afford [2-[[6-(5-amino-4-methyl-3-pyridyl)-7-fluoro-8-methyl-3-isoquinolyl]amino]-6-isopropyl-5,8-dihydro-4H-pyrazolo[1,5-d][1,4]diazepin-7-one (11.7 mg, 0.023 mmol) as a yellow solid. LCMS (ESI) [M+H]$^+$=473; $^1$H NMR (300 MHz, DMSO-d$_6$) δ 9.23 (s, 1H), 9.12 (s, 1H), 8.00 (s, 1H), 7.88 (s, 1H), 7.67 (s, 1H), 7.51 (d, J=7.1 Hz, 1H), 5.98 (s, 1H), 5.25 (s, 2H), 4.96 (s, 2H), 4.62-4.54 (m, 1H), 3.78-3.76 (m, 2H), 3.00-2.97 (m, 2H), 2.59 (s, 3H), 1.89 (s, 3H), 1.10 (d, J=6.8 Hz, 6H).

Example 113

6-isopropyl-2-[[6-(4-methyl-3-pyridyl)-3-isoquinolyl]amino]-5,8-dihydro-4H-pyrazolo[1,5-d][1,4]diazepin-7-one (Compound 122)

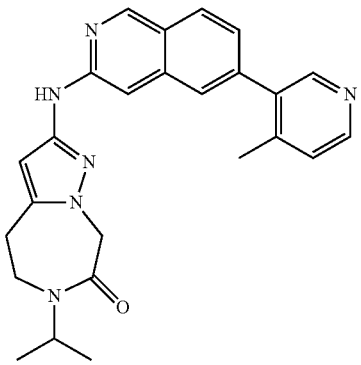 [SMILES: Cc1ccncc1-c1ccc2cnc(Nc3cc4n(n3)CC(=O)N(C(C)C)CC4)cc2c1]

Step 1: 2-((8-chloro-6-(4-methylpyridin-3-yl)isoquinolin-3-yl)amino)-6-isopropyl-5,6-dihydro-4H-pyrazolo[1,5-d][1,4]diazepin-7(8H)-one

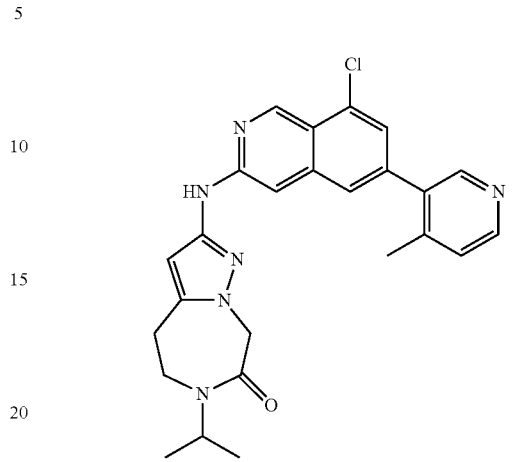

A mixture of 8-chloro-6-(4-methylpyridin-3-yl)isoquinolin-3-amine (120 mg, 0.44 mmol), 2-bromo-6-isopropyl-5,8-dihydro-4H-pyrazolo[1,5-d][1,4]diazepin-7-one (101 mg, 0.37 mmol), tBuBrettphospd G3 (84.52 mg, 0.10 mmol), tBuBrettphos (60 mg, 0.12 mmol), and cesium carbonate (241.99 mg, 0.74 mmol) in 1,4-dioxane (6 mL) was stirred at 120° C. for 1.5 h. The reaction was concentrated under vacuum and purified by flash chromatography on silica gel eluting with ethyl acetate/petroleum ether (1/1) to 2-((8-chloro-6-(4-methylpyridin-3-yl)isoquinolin-3-yl)amino)-6-isopropyl-5,6-dihydro-4H-pyrazolo[1,5-d][1,4]diazepin-7(8H)-one (82 mg, 0.18 mmol) as a yellow solid. LCMS (ESI) [M+H]$^+$=461.

Step 2: 6-isopropyl-2-[[6-(4-methyl-3-pyridyl)-3-isoquinolyl]amino]-5,8-dihydro-4H-pyrazolo[1,5-d][1,4]diazepin-7-one

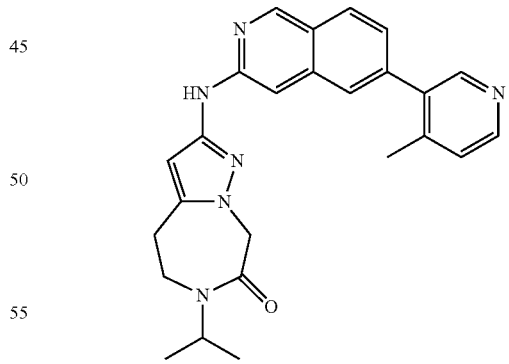

A mixture of 2-[[8-chloro-6-(4-methyl-3-pyridyl)-3-isoquinolyl]amino]-6-isopropyl-5,8-dihydro-4H-pyrazolo[1,5-d][1,4]diazepin-7-one (40 mg, 0.09 mmol), sodium borohydride (16.49 mg, 0.43 mmol), [1,1'-bis(diphenylphosphino)ferrocene]dichloropalladium(II) (12.67 mg, 0.02 mmol), and TMEDA (80.53 mg, 0.69 mmol) in tetrahydrofuran (6 mL) was stirred at 25° C. for 1.5 h. The reaction was concentrated under vacuum. The residue was purified by flash chromatography on silica gel eluting with dichloromethane/methanol (15/1) to afford 6-isopropyl-2-[[6-(4-methyl-3-pyridyl)-3-isoquinolyl]amino]-5,8-dihydro-4H-pyrazolo[1,5-d][1,4]diazepin-7-one (10.8 mg, 0.025 mmol) as a yellow solid. LCMS (ESI) [M+H]$^+$=427; $^1$H NMR (300 MHz, DMSO-d$_6$) δ 9.28 (s, 1H), 9.03 (s, 1H), 8.48 (t, J=2.5 Hz, 2H), 8.00 (d, J=8.4 Hz, 1H), 7.90 (s, 1H), 7.72 (s, 1H), 7.39-7.30 (m, 2H), 6.01 (s, 1H), 4.99 (s, 2H), 4.65-4.56 (m, 1H), 3.79 (t, J=5.2 Hz, 2H), 2.99 (t, J=5.2 Hz, 2H), 2.33 (s, 3H), 1.12 (d, J=6.6 Hz, 6H).

Example 114

7-[7-fluoro-3-[(6-isopropyl-7-oxo-5,8-dihydro-4H-pyrazolo[1,5-d][1,4]diazepin-2-yl)amino]-6-isoquinolyl]-8-methyl-1H-pyrido[2,3-b][1,4]oxazin-2-one (Compound 123)

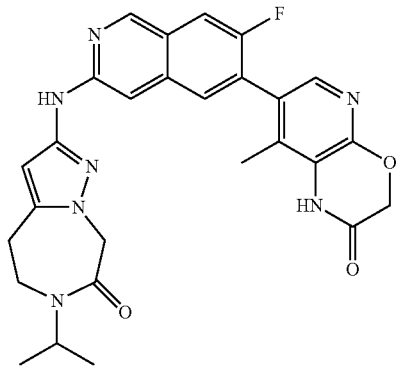 [SMILES: Cc1c(-c2cc3cc(Nc4cc5n(n4)CC(=O)N(C(C)C)CC5)ncc3cc2F)cnc2c1NC(=O)CO2]

Step 1: 7(3-amino-7-fluoro-6-isoquinolyl)-8-methyl-1H-pyrido[2,3-b][1,4]oxazin-2-one

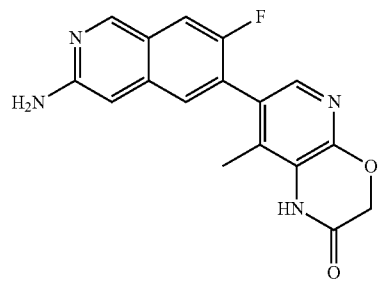 [SMILES: Cc1c(-c2cc3cc(N)ncc3cc2F)cnc2c1NC(=O)CO2]

A mixture of 7-fluoro-6-iodoisoquinolin-3-amine (149 mg, 0.52 mmol), Pd(dppf)Cl$_2$ (76 mg, 0.10 mmol), potassium carbonate (215.6 mg, 1.56 mmol) and 8-methyl-7-(4,4,5,5-tetramethyl-1,3,2-dioxaborolan-2-yl)-1H-pyrido[2,3-b][1,4]oxazin-2-one (151 mg, 0.52 mmol) in 1,4-dioxane (10 mL) was stirred under nitrogen at 80° C. for 2 h. The reaction was concentrated under vacuum and purified by silica gel eluting with ethyl acetate/petroleum ether (1:1) to afford 7-(3-amino-7-fluoro-6-isoquinolyl)-8-methyl-1H-pyrido[2,3-b][1,4]oxazin-2-one (120 mg, 0.37 mmol) as a yellow solid. LCMS (ESI) [M+H]$^+$=325.1.

Step 2: 7-[7-fluoro-3-[(6-isopropyl-7-oxo-5,8-dihydro-4H-pyrazolo[1,5-d][1,4]diazepin-2-yl)amino]-6-isoquinolyl]-8-methyl-1H-pyrido [2,3-b][1,4]oxazin-2-one

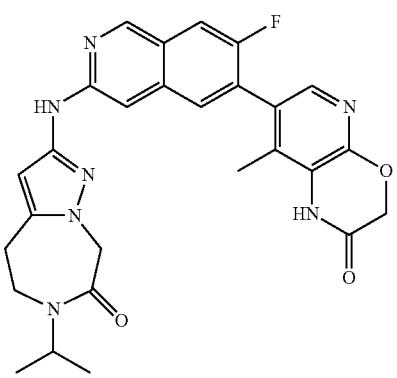 [SMILES: Cc1c(-c2cc3cc(Nc4cc5n(n4)CC(=O)N(C(C)C)CC5)ncc3cc2F)cnc2c1NC(=O)CO2]

A mixture of 2-bromo-6-isopropyl-5,8-dihydro-4H-pyrazolo[1,5-d][1,4]diazepin-7-one (80.56 mg, 0.30 mmol), 7-(3-amino-7-fluoro-6-isoquinolyl)-8-methyl-1H-pyrido[2,3-b][1,4]oxazin-2-one (80 mg, 0.25 mmol), t-BuBrettphosPd G3 (84.27 mg, 0.10 mmol), t-BuBrettphos (59.57 mg, 0.12 mmol), and cesium carbonate (241.25 mg, 0.74 mmol) in 1,4-dioxane (8 mL, extra dry) was stirred at 130° C. for 1.5 h. After filtration, the filtrate was concentrated under vacuum and purified by reverse phase chromatography (acetonitrile 0-40/0.1% NH$_4$HCO$_3$ in water) to afford 7-[7-fluoro-3-[(6-isopropyl-7-oxo-5,8-dihydro-4H-pyrazolo[1,5-d][1,4]diazepin-2-yl)amino]-6-isoquinolyl]-8-methyl-1H-pyrido[2,3-b][1,4]oxazin-2-one (19.4 mg, 0.038 mmol) as a yellow solid. LCMS (ESI) [M+H]$^+$=516; $^1$H NMR (300 MHz, DMSO-d$_6$) δ 10.58 (s, 1H), 9.28 (s, 1H), 9.01 (s, 1H), 7.93 (s, 1H), 7.88-7.70 (m, 3H), 5.99 (s, 1H), 4.99 (s, 2H), 4.82 (s, 2H), 4.60 (q, J=6.7 Hz, 1H), 3.81-3.77 (m, 2H), 3.01-2.97 (m, 2H), 2.11 (s, 3H), 1.12 (d, J=6.8 Hz, 6H).

Example 115

2-((7-fluoro-6-(4-methylpiperazine-1-carbonyl)isoquinolin-3-yl)amino)-6-isopropyl-5,6-dihydro-4H-pyrazolo[1,5-d][1,4]diazepin-7(8H)-one (Compound 124)

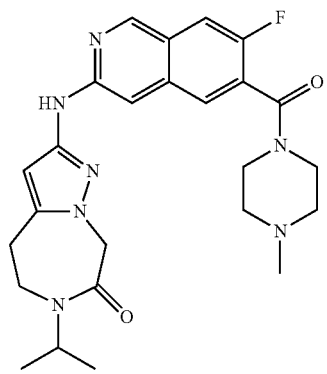 [SMILES: CC(C)N1CCc2cc(Nc3cc4cc(C(=O)N5CCN(C)CC5)c(F)cc4cn3)nn2CC1=O]

Step 1: 3-amino-8-chloro-7-fluoroisoquinoline-6-carboxylic acid

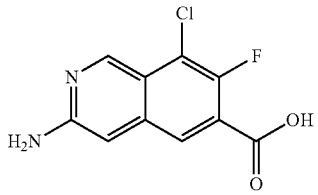 [SMILES: Nc1cc2cc(C(=O)O)c(F)c(Cl)c2cn1]

A mixture of methyl 3-amino-8-chloro-7-fluoro-isoquinoline-6-carboxylate (240 mg, 0.94 mmol) and LiOH (120 mg, 5.01 mmol) in tetrahydrofuran (10 mL) and water (1 mL) was stirred for 16 h at room temperature. The resulting mixture was concentrated under vacuum. The residue was re-dissolved in water (5 mL). The resulting solution was adjusted to pH 2 with 1M HCl. After filtration, the solids were collected and washed by water (2 mL) to afford 3-amino-8-chloro-7-fluoro-isoquinoline-6-carboxylic acid (130 mg, 0.54 mmol) as a yellow solid. LCMS (ESI) [M+H]$^+$=241.0.

Step 2: (3-amino-8-chloro-7-fluoroisoquinolin-6-yl)(4-methylpiperazin-1-yl)methanone

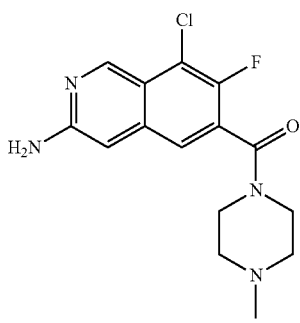 [SMILES: CN1CCN(C(=O)c2cc3cc(N)ncc3c(Cl)c2F)CC1]

To a mixture of 3-amino-8-chloro-7-fluoro-isoquinoline-6-carboxylic acid (130.0 mg, 0.54 mmol) in N,N-dimethylformamide (10 mL) was added 1-methylpiperazine (108.2 mg, 1.08 mmol), ethyldiisopropylamine (139.4 mg, 1.08 mmol), and HATU (246.5 mg, 0.65 mmol). The solution was stirred at 20° C. for 12 h. The resulting solution was concentrated under vacuum. The resulting mixture was purified by reverse phase chromatography on C18 column eluting with water (contained 0.05% TFA)/ACN (0-40% in 10 min) to afford (3-amino-7-fluoro-6-isoquinolyl)-(4-methylpiperazin-1-yl) methanone (150 mg, 0.52 mmol) as a yellow solid. LCMS (ESI) [M+H]$^+$=323.0.

Step 3: 2-((8-chloro-7-fluoro-6-(4-methylpiperazine-1-carbonyl)isoquinolin-3-yl)amino)-6-isopropyl-5,6-dihydro-4H-pyrazolo[1,5-d][1,4]diazepin-7(8H)-one A mixture of (3-amino-8-chloro-7-fluoro-6-isoquinolyl)-(4-methylpiperazin-1-yl) methanone (150 mg, 0.46 mmol), 2-bromo-6-isopropyl-5,8-dihydro-4H-pyrazolo[1,5-d][1,4]diazepin-7-one (270 mg, 0.99 mmol), tBubrettPhos Pb G3 (210 mg, 0.25 mmol), tBubrettPhos (240 mg, 0.42 mmol), and Cs$_2$CO$_3$ (450 mg, 1.38 mmol) in 1,4-dioxane (15 mL) was stirred under nitrogen at 120° C. for 1.5 h. The suspension was filtered through a pad of celite. The filtrate was concentrated under vacuum. The residue was purified by flash chromatography on silica gel eluting with dichloromethane/methanol (10/1) to afford (3-amino-8-chloro-7-fluoro-6-isoquinolyl)-(4-methylpiperazin-1-yl) methanone (150 mg, 0.46 mmol) as a yellow solid. LCMS (ESI) [M+H]$^+$=514.0.

Step 4: 2-((7-fluoro-6-(4-methylpiperazine-1-carbonyl)isoquinolin-3-yl)amino)-6-isopropyl-5,6-dihydro-4H-pyrazolo[1,5-d][1,4]diazepin-7(8H)-one A mixture of 2-[[8-chloro-7-fluoro-6-(4-methylpiperazine-1-carbonyl)-3-isoquinolyl]amino]-6-isopropyl-5,8-dihydro-4H-pyrazolo[1,5-d][1,4]diazepin-7-one (85.0 mg, 0.17 mmol), [1,1'-bis(diphenylphosphino)ferrocene]dichloropalladium(II) (34 mg, 0.05 mmol), TMEDA (255 mg, 1.58 mmol), and sodium borohydride (26.15 mg, 0.69 mmol) in tetrahydrofuran (8 mL) was stirred under nitrogen for 1.5 h at room temperature. The resulting solution was diluted with acetonitrile and water (0.05 mL). After filtration, the filtrate was concentrated under vacuum. The residue was purified by silica gel flash chromatography eluting with dichloromethane/methanol (10/1) to afford crude product (60 mg). The crude product was purified by reverse phase chromatography eluting with water (contained 0.05% NH$_4$HCO$_3$) and acetonitrile (0-50% in 10 min) to afford 2-[[7-fluoro-6-(4-methylpiperazine-1-carbonyl)-3-isoquinolyl]amino]-6-isopropyl-5,8-dihydro-4H-pyrazolo[1,5-d][1,4]diazepin-7-one (10.5 mg, 0.022 mmol, 13.2% yield) as a yellow solid. LCMS (ESI) [M+H]$^+$=480.0; $^1$H NMR (300 MHz, DMSO-d$_6$) δ 9.31 (s, 1H), 8.98 (s, 1H), 7.93 (s, 1H), 7.81 (t, J=7.2 Hz, 2H), 5.97 (s, 1H), 5.00 (s, 2H), 4.65-4.56 (m, 1H), 3.83-3.76 (m, 2H), 3.73-3.66 (m, 2H), 3.29-3.23 (m, 2H), 3.04-2.97 (m, 2H), 2.44-2.36 (m, 2H), 2.30-2.23 (m, 2H), 2.22 (s, 3H), 1.14 (d, J=6.9 Hz, 6H).

Example 116

N-(6-(5-amino-4-methylpyridin-3-yl)-7-fluoroisoquinolin-3-yl)-5,6-dihydro-11H-imidazo[1,2-a]pyrazolo[1,5-d][1,4]diazepin-8-amine (Compound 125)

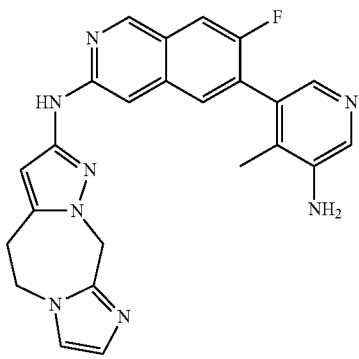 [SMILES: Cc1c(N)cncc1-c1cc2cc(Nc3cc4n(n3)Cc3nccn3CC4)ncc2cc1F]

Step 1: 2-bromo-4,5,6,8-tetrahydropyrazolo[1,5-d][1,4]diazepine-7-thione

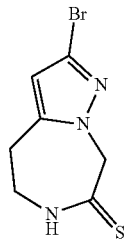 [SMILES: S=C1Cn2nc(Br)cc2CCN1]

A mixture of 2-bromo-4,5,6,8-tetrahydropyrazolo[1,5-d][1,4]diazepin-7-one (314 mg, 1.36 mmol) and Lawesson reagent (551.4 mg, 1.36 mmol) in 1,4-dioxane (10 mL) was stirred at 90° C. for 1 h. The reaction was concentrated under vacuum. The residue was purified by flash chromatography on silica gel eluting with dichloromethane/methanol (96/4) to afford 2-bromo-4,5,6,8-tetrahydropyrazolo[1,5-d][1,4]diazepine-7-thione (265 mg, 78.9%) as a white solid. LCMS (ESI) [M+H]$^+$=246.0.

Step 2: 2-bromo-N-(2,2-diethoxyethyl)-5,8-dihydro-4H-pyrazolo[1,5-d][1,4]diazepin-7-amine

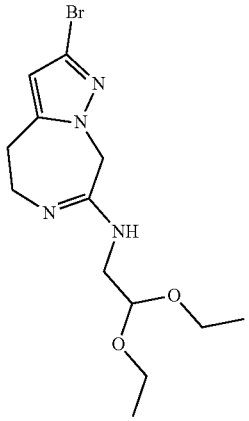 [SMILES: CCOC(CNC1=NCCc2cc(Br)nn2C1)OCC]

A mixture of 2-bromo-5,6-dihydro-4H-pyrazolo[1,5-d][1,4]diazepine-7(8H)-thione (265.0 mg, 1.07 mmol), 2,2-diethoxyethan-1-amine(1.42 g, 10.7 mmol) and silver carbonate (590 mg, 2.14 mmol) in tetrahydrofuran (10 mL) was stirred at 80° C. for 1 h. The reaction mixture was concentrated under vacuum. The residue was purified by reverse-phase column eluting with water (0.05% TFA)/CH$_3$CN (85/15) to afford 2-bromo-N-(2,2-diethoxyethyl)-5,8-dihydro-4H-pyrazolo[1,5-d][1,4]diazepin-7-amine (295 mg, 80%) as a brown oil. LCMS (ESI) [M+H]$^+$=345.0.

Step 3: 8-bromo-5,6-dihydro-11H-imidazo[1,2-a]pyrazolo[1,5-d][1,4]diazepine

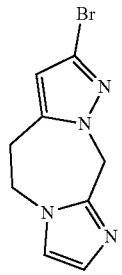

A solution of 2-bromo-N-(2,2-diethoxyethyl)-5,8-dihydro-4H-pyrazolo[1,5-d][1,4]diazepin-7-amine (228 mg, 0.66 mmol) and concentrated hydrochloric acid (0.17 mL, 0.66 mmol) in acetic acid (5 mL) was stirred at 80° C. for 1 h. The reaction was concentrated under vacuum. The residue was purified by reverse-phase column eluting with water (0.05% TFA)/ACN (85/15) to afford 8-bromo-5,6-dihydro-11H-imidazo[1,2-a]pyrazolo[1,5-d][1,4]diazepine (150 mg, 89.7%) as a brown oil. LCMS (ESI) [M+H]$^+$=253.0.

Step 4: tert-butyl N-tert-butoxycarbonyl-N-[5-[3-[(4,4-difluoro-6-methyl-7-oxo-5,8-dihydropyrazolo[1,5-d][1,4]diazepin-2-yl)amino]-7-fluoro-6-isoquinolyl]-4-methyl-3-pyridyl]carbamate

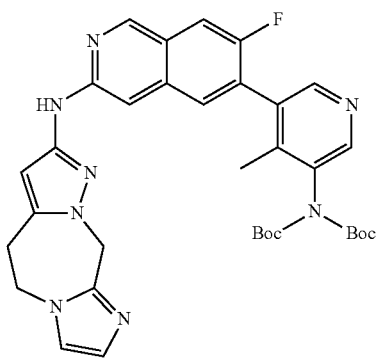 [SMILES: Cc1c(-c2cc3cc(Nc4cc5n(n4)Cc4nccn4CC5)ncc3cc2F)cncc1N(C(=O)OC(C)(C)C)C(=O)OC(C)(C)C]

A mixture of tert-butyl N-[5-(3-amino-7-fluoro-6-isoquinolyl)-4-methyl-3-pyridyl]-N-tert-butoxycarbonyl-carbamate (223.47 mg, 0.48 mmol), 4,4-difluoro-2-iodo-6-methyl-5,8-dihydropyrazolo[1,5-d][1,4]diazepin-7-one (130 mg, 0.40 mmol), tBuBrettphos Pd G3 (135.78 mg, 0.16 mmol), tBuBrettphos (96.39 mg, 0.20 mmol), and cesium carbonate (388.72 mg, 1.19 mmol) in 1,4-dioxane (20 mL) was stirred at 130° C. for 1 h. The reaction was concentrated under vacuum. The residue was purified by flash chromatography on silica gel eluting with dichloromethane/methanol (92/8) to afford tert-butyl N-tert-butoxycarbonyl-N-[5-[3-[(4,4-difluoro-6-methyl-7-oxo-5,8-dihydropyrazolo[1,5-d][1,4]diazepin-2-yl)amino]-7-fluoro-6-isoquinolyl]-4-methyl-3-pyridyl]carbamate (85 mg, 32%) as a brown solid. LCMS (ESI) [M+H]$^+$=641.3.

Step 5: N-(6-(5-amino-4-methylpyridin-3-yl)-7-fluoroisoquinolin-3-yl)-5,6-dihydro-11H-imidazo[1,2-a]pyrazolo[1,5-d][1,4]diazepin-8-amine

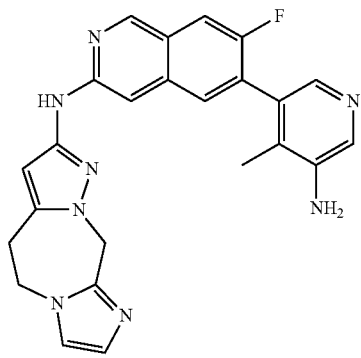 [SMILES: Cc1c(N)cncc1-c1cc2cc(Nc3cc4n(n3)Cc3nccn3CC4)ncc2cc1F]

To a mixture of tert-butyl N-tert-butoxycarbonyl-N-[5-[3-(6,11-dihydro-5H-imidazopyrazolo[1,4]diazepin-8-ylamino)-7-fluoro-6-isoquinolyl]-4-methyl-3-pyridyl]carbamate (80.0 mg, 0.12 mmol) in dichloromethane (5 mL) was added 2,2,2-trifluoroacetic acid (1.0 mL). The reaction was stirred at 25° C. for 1 h. The resulting solution was concentrated under vacuum. The residue was redissolved in methanol and the pH value was then adjusted to pH=8 with ammonia in methanol (7 M). After filtration, the filtrate was concentrated under vacuum The residue was purified by Prep-HPLC (Xbridge C18, 19*150 mm; water (10 mmol/L NH$_4$HCO$_3$): CH$_3$CN=17%-41% in 7 min) to afford N-(6-(5-amino-4-methylpyridin-3-yl)-7-fluoroisoquinolin-3-yl)-5,6-dihydro-11H-imidazo[1,2-a]pyrazolo[1,5-d][1,4]diazepin-8-amine (22 mg, 40%) as a yellow solid. LCMS (ESI) [M+H]$^+$=441; $^1$H NMR (300 MHz, DMSO-d$_6$) δ 9.29 (s, 1H), 8.99 (s, 1H), 8.02 (s, 1H), 7.94 (s, 1H), 7.81 (d, J=9.0 Hz, 1H), 7.72-7.70 (m, 2H), 7.21 (s, 1H), 6.84 (s, 1H), 6.06 (s, 1H), 5.42 (s, 2H), 5.27 (s, 2H), 4.35 (t, J=6.0 Hz, 2H), 3.24 (t, J=6.0 Hz, 2H), 1.92 (s, 3H).

Example 117

2-((6-(5-amino-4,6-dimethylpyridin-3-yl)-7-fluoroisoquinolin-3-yl)amino)-6-isopropyl-5,6-dihydro-4H-pyrazolo[1,5-d][1,4]diazepin-7(8H)-one (Compound 126) and 2-((6-(5-amino-4,6-dimethylpyridin-3-yl)-7-fluoro-8-hydroxyisoquinolin-3-yl)amino)-6-isopropyl-5,6-dihydro-4H-pyrazolo[1,5-d][1,4]diazepin-7(8H)-one (Compound 133)

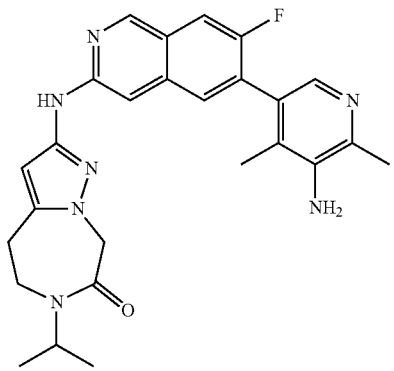

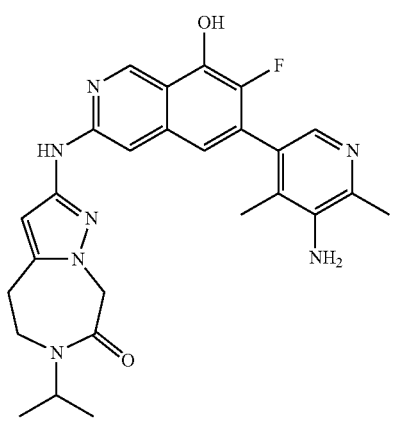

Step 1: Dimethyl 2-(5-bromo-2-methyl-3-nitropyridin-4-yl)malonate

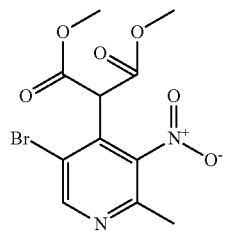

To an ice cold solution (0° C.) of dimethyl malonate (3.5 mL, 30 mmol) in DMF (100 mL) under nitrogen was added sodium hydride 60% in mineral oil (1.42 g, 35.5 mmol) as a solid with stirring. The mixture was stirred at 0° C. for 30 minutes, then 5-bromo-2-chloro-4-methyl-2-nitro-pyridine (5 g, 20 mmol) was added over 10 minutes. After stirring at 0° C. for 30 minutes, the mixture was heated at 40° C. overnight. The reaction was cooled to room temperature and concentrated under reduced pressure to give a red solid, which was dissolved in ethyl acetate (50 mL) and diluted with water (100 mL). The organic layer was collected, then the aqueous layer extracted once more with ethyl acetate (50 mL). The combined organic layers were washed with brine, then dried with anhydrous powdered magnesium sulfate, filtered and concentrated to give a red solid. The crude product was used directly in the next step without further purification. LCMS (ESI, m/z): 349 [M+H].

Step 2: 5-bromo-2,4-dimethyl-3-nitropyridine

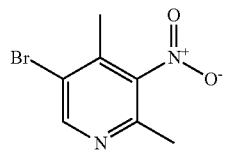

A solution of dimethyl 2-(5-bromo-2-methyl-3-nitropyridin-4-yl)malonate (8.2, 24 mmol) in 12 N HCl (50 mL, 609 mmol) was heated at 100° C. overnight. The reaction was then cooled to room temperature and concentrated under reduced pressure. The residue was then treated with 1 N NaOH solution to adjust the pH to 10, followed by extraction with ethyl acetate (3×100 mL). The combined organic layers were dried with magnesium sulfate, filtered and concentrated to give a brown oil. The residue was then purified by flash column using 0-100% isopropyl acetate in heptane to afford the product as a yellow solid (2.77 g, 12 mmol). LCMS (ESI, m/z): 233 [M+H]⁺.

Step 3: (4,6-dimethyl-5-nitropyridin-3-yl)boronic acid

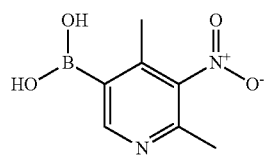

5-bromo-2,4-dimethyl-3-nitropyridine (2.75 g, 11.9 mmol), bis(pinacolato)diboron (6.42 g, 24.8 mmol), Pd₂(dppf)Cl₂·CH₂Cl₂ (2.06 g, 2.47 mmol) and potassium acetate (3.5 g, 35.7 mmol) was treated with 1,4 dioxane (50 mL) under nitrogen. The reaction was then heated at 90° C. overnight under nitrogen. After cooling to room temperature, the mixture was diluted with 50 mL ethyl acetate, then filtered through a celite/magnesium sulfate/celite plug. The filtrate was diluted with water and the organic layer was collected. The aqueous layer was extracted twice more with ethyl acetate (50 mL, 50 mL). The combined organic layers were dried with magnesium sulfate, filtered and concentrated to give a black oil, which was dissolved in ethyl acetate and filtered through a silica plug. The filtrate was then concentrated to give a brown oil that was purified by flash column using 0-100% isopropyl acetate in heptane to afford the product as a pale yellow solid. LCMS (ESI, m/z): 197 [M+H]⁺.

Step 4: 8-chloro-6-(4,6-dimethyl-5-nitropyridin-3-yl)-7-fluoroisoquinolin-3-amine

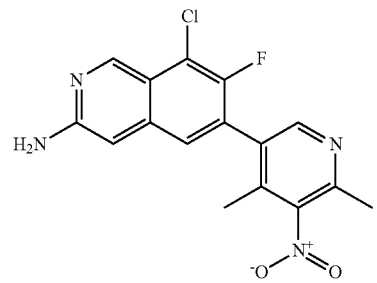

8-chloro-7-fluoro-6-iodo-isoquinolin-3-amine (2.84 g, 8.81 mmol), (4,6-dimethyl-5-nitropyridin-3-yl)boronic acid (2.86 g, 14.6 mmol), Pd(dppf)Cl₂·CH₂Cl₂ (980 mg, 1.18 mmol) and potassium carbonate (2.88 g, 20.8 mmol) were dissolved in 1,4 dioxane (41 mL) and water (3 mL) under nitrogen. The mixture was then heated at 120° C. overnight. The reaction was then cooled to room temperature and diluted with 50 mL of ethyl acetate. The mixture was then filtered through a celite/magnesium sulfate/celite plug. The silica plug was then further washed with 20 mL 5% MeOH in dichloromethane. The filtrate was then concentrated to give a black oil that was purified by flash column using 0-20% methanol in dichloromethane to obtain a black oil. The oil was then treated with heptane with small amounts of methanol to precipitate the product as a reddish yellow solid (2.2 g, 6.3 mmol). LCMS (ESI, m/z): 347 [M+H]⁺.

Step 5: 2-((6-(4,6-dimethyl-5-nitropyridin-3-yl)-7-fluoroisoquinolin-3-yl)amino)-6-isopropyl-5,6-dihydro-4H-pyrazolo[1,5-d][1,4]diazepin-7(8H)-one

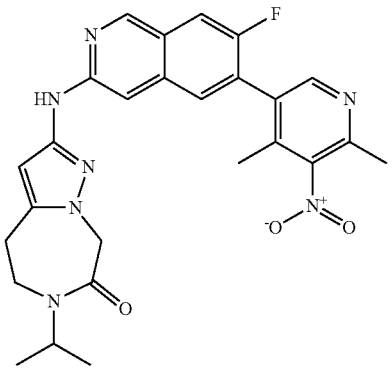

+

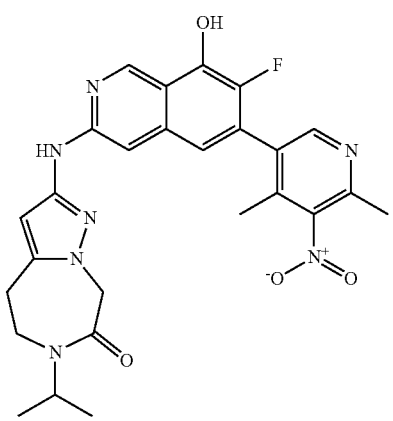

A mixture of 8-chloro-6-(4,6-dimethyl-5-nitropyridin-3-yl)-7-fluoroisoquinolin-3-amine (104.5 mg, 0.3 mmol), 2-bromo-6-isopropyl-5,6-dihydro-4H-pyrazolo[1,5-d][1,4]diazepin-7(8H)-one (100.6 mg, 0.37 mmol), tBuBrettPhos Pd G3 (62.2 mg, 0.07 mmol) and cesium carbonate (185 mg, 0.57 mmol) was dissolved in 1,4 dioxane (3 mL) under nitrogen, then heated to 120° C. overnight. The reaction was then cooled to room temperature and diluted with 25 mL ethyl acetate. The mixture was then filtered through celite. The filtrate was concentrated to give a black oil and purified by flash chromatography using 0-15% methanol in dichloromethane to obtain 2-((6-(4,6-dimethyl-5-nitropyridin-3-yl)-7-fluoroisoquinolin-3-yl)amino)-6-isopropyl-5,6-dihydro-4H-pyrazolo[1,5-d][1,4]diazepin-7(8H)-one (39.1 mg, 0.08 mmol), LCMS (ESI, m/z): 504 and 2-((6-chloro-(4,6-dimethyl-5-nitropyridin-3-yl)-7-fluoro-8-hydroxyisoquinolin-3-yl)amino)-6-isopropyl-5,6-dihydro-4H-pyrazolo[1,5-d][1,4]diazepin-7(8H)-one (30.4 mg, 0.06 mmol), LCMS (ESI, m/z): 521.

Step 6: 2-((6-(5-amino-4,6-dimethylpyridin-3-yl)-7-fluoroisoquinolin-3-yl)amino)-6-isopropyl-5,6-dihydro-4H-pyrazolo[1,5-d][1,4]diazepin-7(8H)-one (Compound 126)

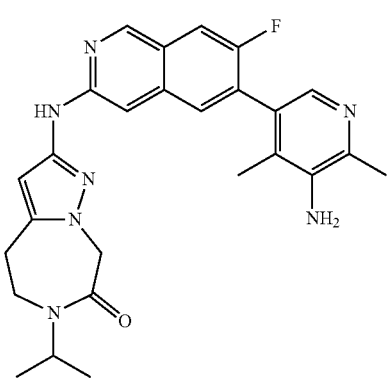 [SMILES: Cc1ncc(-c2cc3cc(Nc4cc5n(n4)CC(=O)N(C(C)C)CC5)ncc3cc2F)c(C)c1N]

A mixture of 2-((6-(4,6-dimethyl-5-nitropyridin-3-yl)-7-fluoroisoquinolin-3-yl)amino)-6-isopropyl-5,6-dihydro-4H-pyrazolo[1,5-d][1,4]diazepin-7(8H)-one (39.1 mg, 0.08 mmol) and Raney nickel (53 mg, 0.9 mmol) in methanol (3 mL) was stirred under an atmosphere of hydrogen using a balloon overnight at room temperature. The mixture was filtered through celite. The filtrate was concentrated and purified by reverse phase HPLC to afford 2-((6-(5-amino-4,6-dimethylpyridin-3-yl)-7-fluoroisoquinolin-3-yl)amino)-6-isopropyl-5,6-dihydro-4H-pyrazolo[1,5-d][1,4]diazepin-7(8H)-one (8.9 mg, 0.08 mmol). 1H NMR (400 MHz, DMSO-d6) δ 9.23 (s, 1H), 8.99 (s, 1H), 7.90 (s, 1H), 7.78 (d, J=10.1 Hz, 1H), 7.66 (d, J=7.2 Hz, 1H), 7.62 (s, 1H), 5.98 (s, 1H), 4.98 (s, 2H), 4.94 (s, 2H), 4.62-4.56 (m, 1H), 3.78 (t, J=5.9 Hz, 2H), 2.99 (t, J=5.9 Hz, 2H), 2.37 (s, 3H), 1.94 (d, J=1.9 Hz, 3H), 1.12 (d, J=6.8 Hz, 6H). Analytical HPLC retention time 3.174 min. Method N. LCMS (ESI, m/z): 474.1.

Step 7: 2-((6-(5-amino-4,6-dimethylpyridin-3-yl)-7-fluoro-8-hydroxyisoquinolin-3-yl)amino)-6-isopropyl-5,6-dihydro-4H-pyrazolo[1,5-d][1,4]diazepin-7(8H)-one (Compound 133)

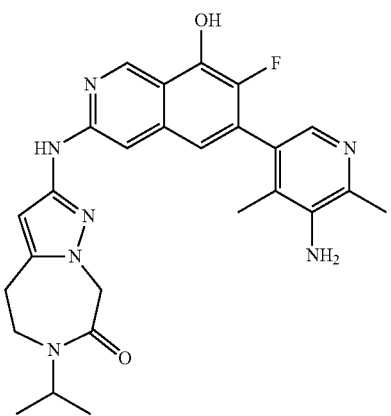 [SMILES: Cc1ncc(-c2cc3cc(Nc4cc5n(n4)CC(=O)N(C(C)C)CC5)ncc3c(O)c2F)c(C)c1N]

A mixture of 2-((6-chloro-(4,6-dimethyl-5-nitropyridin-3-yl)-7-fluoro-8-hydroxyisoquinolin-3-yl)amino)-6-isopropyl-5,6-dihydro-4H-pyrazolo[1,5-d][1,4]diazepin-7(8H)-one (95.1 mg, 0.18 mmol) and Raney nickel (126 mg, 2.14 mmol) in methanol (7 mL) was stirred under an atmosphere of hydrogen using a balloon overnight at room temperature. The mixture was then filtered. The filtrate was concentrated and purified by reverse phase HPLC to afford 2-((6-(5-amino-4,6-dimethylpyridin-3-yl)-7-fluoro-8-hydroxyisoquinolin-3-yl)amino)-6-isopropyl-5,6-dihydro-4H-pyrazolo[1,5-d][1,4]diazepin-7(8H)-one (16.7 mg, 0.03 mmol). 1H NMR (400 MHz, DMSO-d6) δ 10.54 (s, 1H), 9.17 (d, J=1.3 Hz, 2H), 7.77 (d, J=1.0 Hz, 1H), 7.62 (s, 1H), 7.04 (d, J=5.9 Hz, 1H), 5.98 (s, 1H), 4.95 (d, J=8.8 Hz, 4H), 4.61-4.56 (m, 1H), 3.77 (t, J=6.0 Hz, 2H), 2.98 (s, 2H), 2.37 (s, 3H), 1.96 (d, J=1.7 Hz, 3H), 1.12 (d, J=6.8 Hz, 6H). Analytical HPLC retention time. 2.829 min. Method N. LCMS (ESI, m/z): 490.2.

Example 118

2-[[6-(5-amino-4-methyl-3-pyridyl)-7-fluoro-3-isoquinolyl]amino]-4,4-difluoro-6-methyl-5,8-dihydropyrazolo[1,5-d][1,4]diazepin-7-one (Compound 127)

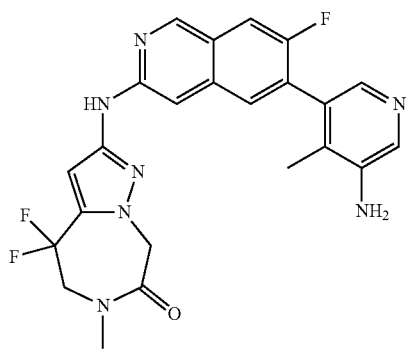 [SMILES: Cc1c(N)cncc1-c1cc2cc(Nc3cc4n(n3)CC(=O)N(C)CC4(F)F)ncc2cc1F]

Step 1: 2-amino-4,4-difluoro-6,8-dihydro-5H-pyrazolo[1,5-d][1,4]diazepin-7-one

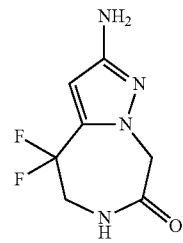

A mixture of 4,4-difluoro-2-nitro-6,8-dihydro-5H-pyrazolo[1,5-d][1,4]diazepin-7-one (100 mg, 0.43 mmol) and Pd/C (25.0 mg, 0.43 mmol) in methyl alcohol (10 mL) was stirred under 1 atm of hydrogen at 25° C. for 1 h. After filtration, the filtrate was concentrated under vacuum to afford 2-amino-4,4-difluoro-6,8-dihydro-5H-pyrazolo[1,5-d][1,4]diazepin-7-one (60 mg, 68.9%) as a yellow solid. LCMS(ESI) [M+H]⁺=203.1

Step 2: 4,4-difluoro-2-iodo-6,8-dihydro-5H-pyrazolo[1,5-d][1,4]diazepin-7-one

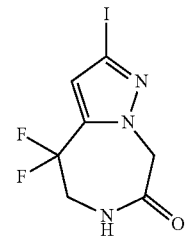

A mixture of 2-amino-4,4-difluoro-6,8-dihydro-5H-pyrazolo[1,5-d][1,4]diazepin-7-one (356 mg, 1.76 mmol), tert-butyl nitrite (544.14 mg, 5.28 mmol) and cuprous iodide (401.5 mg, 2.11 mmol) in acetonitrile (5 mL) was stirred for 1 h at room temperature. The residue was purified by reverse-phase column eluting with water (NH₄HCO₃ 10 mmol/L)/ACN (65/35) to afford 4,4-difluoro-2-iodo-6,8-dihydro-5H-pyrazolo[1,5-d][1,4]diazepin-7-one (320 mg, 58%) as a light yellow solid. LCMS (ESI) [M+H]⁺=314.0.

Step 3: 4,4-difluoro-2-iodo-6-methyl-5,8-dihydropyrazolo[1,5-d][1,4]diazepin-7-one

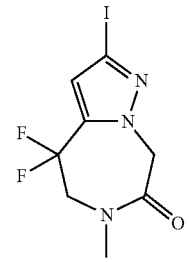

A mixture of 4,4-difluoro-2-iodo-6,8-dihydro-5H-pyrazolo[1,5-d][1,4]diazepin-7-one (100 mg, 0.32 mmol), potassium tert-butoxide (53.67 mg, 0.48 mmol) and iodomethane (68.04 mg, 0.48 mmol) in tetrahydrofuran (4 mL) was stirred at 25° C. for 2 h. The reaction was concentrated under vacuum and purified by flash chromatography on silica gel eluting with dichloromethane/methanol (96/4) to afford 4,4-difluoro-2-iodo-6-methyl-5,8-dihydropyrazolo[1,5-d][1,4] diazepin-7-one (65 mg, 62.2%) as a white solid. LCMS (ESI) [M+H]⁺=328.

Step 4: tert-butyl N-tert-butoxycarbonyl-N-[5-[3-[(4,4-difluoro-6-methyl-7-oxo-5,8-dihydropyrazolo[1,5-d][1,4]diazepin-2-yl)amino]-7-fluoro-6-isoquinolyl]-4-methyl-3-pyridyl]carbamate

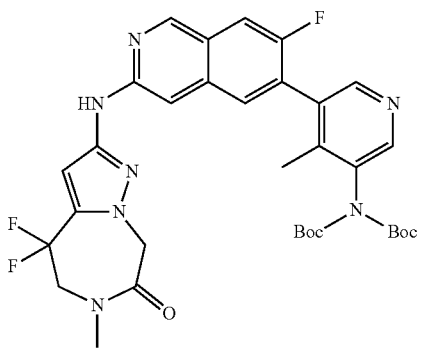 [SMILES: Cc1c(-c2cc3cc(Nc4cc5n(n4)CC(=O)N(C)CC5(F)F)ncc3cc2F)cncc1N(C(=O)OC(C)(C)C)C(=O)OC(C)(C)C]

A mixture of tert-butyl N-[5-(3-amino-7-fluoro-6-isoquinolyl)-4-methyl-3-pyridyl]-N-tert-butoxycarbonyl-carbamate (223.47 mg, 0.48 mmol), 4,4-difluoro-2-iodo-6-methyl-5,8-dihydropyrazolo[1,5-d][1,4]diazepin-7-one (130.0 mg, 0.40 mmol), tBuBrettphos Pd G3 (135.78 mg, 0.16 mmol), tBuBrettphos (96.39 mg, 0.20 mmol) and cesium carbonate (388.72 mg, 1.19 mmol) in 1,4-dioxane (20 mL) was stirred at 130° C. for 1 h. The reaction was concentrated under vacuum. The residue was purified by silica gel flash chromatography eluting with dichloromethane/methanol (92/8) to afford tert-butyl N-tert-butoxycarbonyl-N-[5-[3-[(4,4-difluoro-6-methyl-7-oxo-5,8-dihydropyrazolo[1,5-d][1,4]diazepin-2-yl)amino]-7-fluoro-6-isoquinolyl]-4-methyl-3-pyridyl]carbamate (85 mg, 32%) as a brown solid. LCMS (ESI) [M+H]$^+$=668.3.

Step 5: 2-[[6-(5-amino-4-methyl-3-pyridyl)-7-fluoro-3-isoquinolyl]amino]-4,4-difluoro-6-methyl-5,8-dihydropyrazolo[1,5-d][1,4]diazepin-7-one

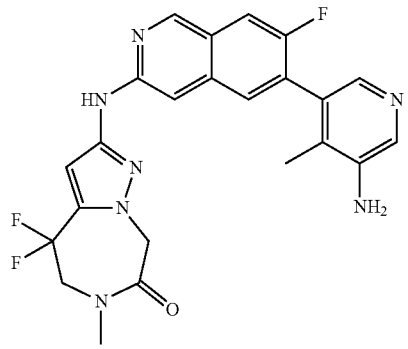 [SMILES: Cc1c(N)cncc1-c1cc2cc(Nc3cc4n(n3)CC(=O)N(C)CC4(F)F)ncc2cc1F]

To a mixture of tert-butyl N-tert-butoxycarbonyl-N-[5-[3-[(4,4-difluoro-6-methyl-7-oxo-5,8-dihydropyrazolo[1,5-d][1,4]diazepin-2-yl)amino]-7-fluoro-6-isoquinolyl]-4-methyl-3-pyridyl]carbamate (80 mg, 0.12 mmol) in dichloromethane (5 mL) was added 2,2,2-trifluoroacetic acid (1.0 mL). The reaction was stirred at 25° C. for 1 h and then concentrated under vacuum. The residue was redissolved in methanol and then the pH value was adjusted to pH=8 with ammonia in methanol (7 M). After filtration the filtrate was concentrated under vacuum. The residue was purified by Prep-HPLC (Atlantis HILIC OBD, 19*150 mm×5 um; water (10 mM NH$_4$HCO$_3$):CH$_3$CN=21%-42% in 10 min) to afford 2-[[6-(5-amino-4-methyl-3-pyridyl)-7-fluoro-3-isoquinolyl]amino]-4,4-difluoro-6-methyl-5,8-dihydropyrazolo[1,5-d][1,4]diazepin-7-one (18.8 mg, 33.6% yield) as a yellow solid. LCMS (ESI) [M+H]$^+$=468; $^1$H NMR (300 MHz, DMSO-d$_6$) δ 9.59 (s, 1H), 9.06 (s, 1H), 8.02 (s, 1H), 7.87 (s, 1H), 7.85 (d, J=9.0 Hz, 1H), 7.76 (d, J=9.0 Hz, 1H), 7.71 (s, 1H), 6.65 (s, 1H), 5.29 (s, 2H), 5.19 (s, 2H), 4.51 (t, J=12.0 Hz, 2H), 3.03 (s, 3H), 1.92 (s, 3H).

Example 119 tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (Compound 128)

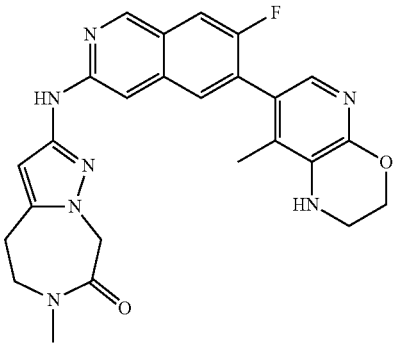 [SMILES: Cc1c(-c2cc3cc(Nc4cc5n(n4)CC(=O)N(C)CC5)ncc3cc2F)cnc2c1NCCO2]

Step 1: tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

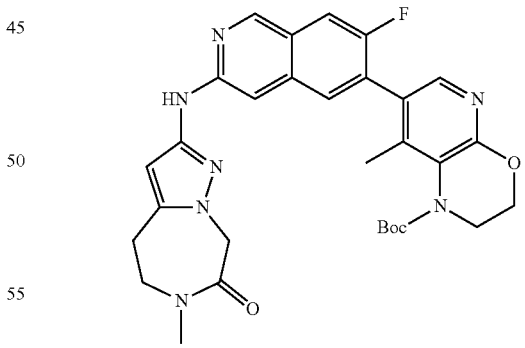

A mixture of 2-bromo-6-methyl-5,8-dihydro-4H-pyrazolo[1,5-d][1,4]diazepin-7-one (12.0 mg, 0.05 mmol), tert-butyl 7-(3-amino-7-fluoro-6-isoquinolyl)-8-methyl-2,3-dihydropyrido[2,3-b][1,4]oxazine-1-carboxylate (10.0 mg, 0.02 mmol), tBuBretphos G3 (41.98 mg, 0.05 mmol), tBu-Bretophos (23.84 mg, 0.05 mmol) and cesium carbonate (16.03 mg, 0.05 mmol) in 1,4-dioxane (1 mL) was stirred for 1 h at 120° C. The reaction mixture was concentrated under vacuum and purified by flash chromatography on silica gel eluting with dichloromethane/methanol (20/1) to afford tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (184 mg, 0.26 mmol) as a brown oil. LCMS (ESI) [M+H]+=573.6.

Step 2: tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

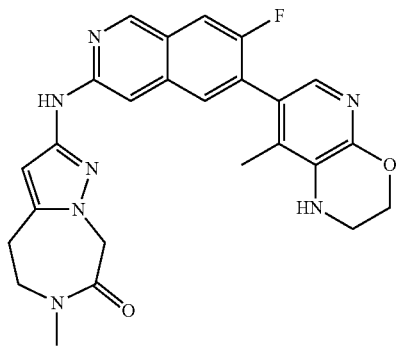

A mixture of tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (60.0 mg, 0.10 mmol) and 2,2,2-trifluoroacetic acid (1 mL) in dichloromethane (5 mL) was stirred for 1 h at 25° C. The resulting solution was concentrated under vacuum. The residue was redissolved in methanol and the pH value was then adjusted to pH=8 with ammonia in methanol (7 M). After filtration the filtrate was concentrated under vacuum and the residue was purified by Prep-HPLC (Atlantis HILIC OBD, 19*150 mm*5 um; Water (10 mmol/L NH$_4$HCO$_3$):CH$_3$CN=20%-43% in 7 min) to afford tert-butyl 7-[7-fluoro-3-[(6-methyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (60 mg, 0.10 mmol) as a yellow solid. LCMS (ESI) [M+H]+=473; $^1$H NMR (300 MHz, DMSO-d$_6$) δ 9.25 (s, 1H), 8.99 (s, 1H), 7.90 (s, 1H), 7.79 (d, J=10.2 Hz, 1H), 7.67 (d, J=7.2 Hz, 1H), 7.38 (s, 1H), 6.00 (s, 1H), 5.71 (s, 1H), 4.99 (s, 2H), 4.32-4.29 (m, 2H), 3.85-3.82 (m, 2H), 3.38-3.34 (m, 2H), 3.07-3.03 (m, 2H), 2.96 (s, 3H), 1.93 (d, J=1.9 Hz, 3H).

Example 120

2-[[6-(5-amino-4-methyl-3-pyridyl)-3-isoquinolyl]amino]-6-isopropyl-5,8-dihydro-4H-pyrazolo[1,5-d][1,4]diazepin-7-one Compound 129)

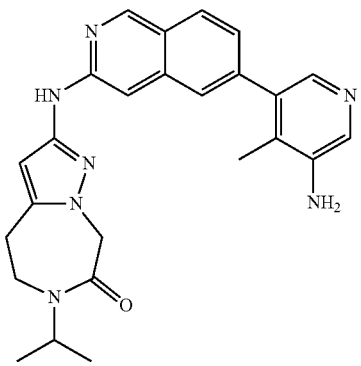 [SMILES: Cc1c(N)cncc1-c1ccc2cnc(Nc3cc4n(n3)CC(=O)N(C(C)C)CC4)cc2c1]

Step 1: tert-butyl N-[5-(3-amino-6-isoquinolyl)-4-methyl-3-pyridyl]-N-tert-butoxycarbonyl-carbamate

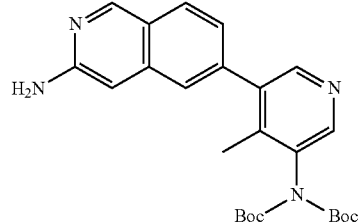 [SMILES: Cc1c(-c2ccc3cnc(N)cc3c2)cncc1N(C(=O)OC(C)(C)C)C(=O)OC(C)(C)C]

A mixture of 6-bromoisoquinolin-3-amine (500 mg, 2.24 mmol), tert-butyl N-tert-butoxycarbonyl-N-[4-methyl-5-(4,4,5,5-tetramethyl-1,3,2-dioxaborolan-2-yl)-3-pyridyl]carbamate (1265.59 mg, 2.91 mmol), [1,1'-bis(diphenylphosphino)ferrocene]dichloropalladium(II) (163.63 mg, 0.22 mmol), potassium carbonate (618.64 mg, 4.48 mmol) in 1,4-dioxane (15 mL), and water (1.5 mL) was stirred at 90° C. for 12 h. The reaction was concentrated under vacuum and purified by flash chromatography on silica gel eluting with dichloromethane/methanol (15/1) to afford tert-butyl N-[5-(3-amino-6-isoquinolyl)-4-methyl-3-pyridyl]-N-tert-butoxycarbonyl-carbamate (600 mg, 1.33 mmol) as a solid. LCMS (ESI) [M+H]+=451.

Step 2: tert-butyl N-tert-butoxycarbonyl-N-[5-[3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

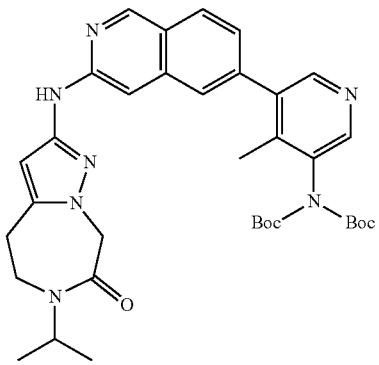 [SMILES: Cc1c(-c2ccc3cnc(Nc4cc5n(n4)CC(=O)N(C(C)C)CC5)cc3c2)cncc1N(C(=O)OC(C)(C)C)C(=O)OC(C)(C)C]

A mixture of 2-bromo-6-isopropyl-5,8-dihydro-4H-pyrazolo[1,5-d][1,4]diazepin-7-one (144.97 mg, 0.53 mmol), tert-butyl N-[5-(3-amino-6-isoquinolyl)-4-methyl-3-pyridyl]-N-tert-butoxycarbonyl-carbamate (160 mg, 0.36 mmol), tBuBrettphosG3 (121.31 mg, 0.14 mmol), tBuBrettphos (86.12 mg, 0.18 mmol) and cesium carbonate (347.32 mg, 1.07 mmol) in 1,4-dioxane (15 mL) was stirred at 120° C. for 1.5 h. The reaction was concentrated under vacuum and purified by flash chromatography on silica gel eluting with dichloromethane/methanol (15/1) to afford tert-butyl N-tert-butoxycarbonyl-N-[5-[3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (140 mg, 0.22 mmol) as a yellow solid. LCMS (ESI) [M+H]+=642.

Step 3: 2-[[6-(5-amino-4-methyl-3-pyridyl)-3-isoquinolyl]amino]-6-isopropyl-5,8-dihydro-4H-pyrazolo[1,5-d][1,4]diazepin-7-one

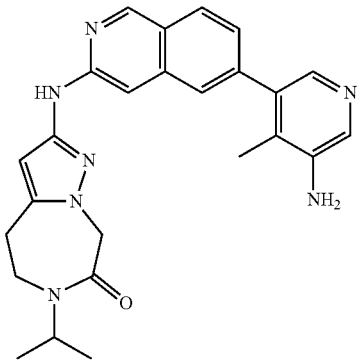 [SMILES: Cc1c(N)cncc1-c1ccc2cnc(Nc3cc4n(n3)CC(=O)N(C(C)C)CC4)cc2c1]

A mixture of tert-butyl N-tert-butoxycarbonyl-N-[5-[3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (100 mg, 0.16 mmol) and 2,2,2-trifluoroacetic acid (1 mL, 0.16 mmol) in dichloromethane (5 mL) was stirred at 20° C. for 1 h. The reaction was concentrated under vacuum The residue was redissolved in methanol and the pH value was then adjusted to pH=8 with ammonia in methanol (7 M). After filtration the filtrate was concentrated under vacuum. The residue was purified by reverse phase chromatography (acetonitrile 0-40%, 0.1% NH$_4$HCO$_3$ in water) to afford 2-[[6-(5-amino-4-methyl-3-pyridyl)-3-isoquinolyl]amino]-6-isopropyl-5,8-dihydro-4H-pyrazolo[1,5-d][1,4]diazepin-7-one (44.1 mg, 0.099 mmol) as a yellow solid.

LCMS (ESI) [M+H]$^+$=442; $^1$H NMR (300 MHz, DMSO-d$_6$) δ 9.25 (s, 1H), 8.99 (s, 1H), 7.90 (s, 1H), 7.79 (d, J=10.2 Hz, 1H), 7.67 (d, J=7.2 Hz, 1H), 7.38 (s, 1H), 6.00 (s, 1H), 5.71 (s, 1H), 4.99 (s, 2H), 4.30 (s, 2H), 3.84 (t, J=5.5 Hz, 2H), 3.4 (m, 2H), 3.10-3.00 (m, 2H), 2.96 (s, 3H), 1.93 (d, J=1.9 Hz, 3H).

Example 121

6-(5-amino-4-methyl-3-pyridyl)-3-[(6-isopropyl-7-oxo-5,8-dihydro-4H-pyrazolo[1,5-d][1,4]diazepin-2-yl)amino]-8-methyl-isoquinoline-7-carbonitrile (Compound 130)

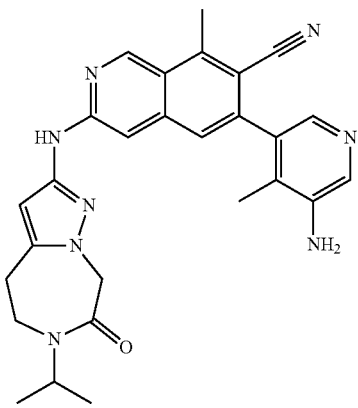 [SMILES: Cc1c(N)cncc1-c1cc2cc(Nc3cc4n(n3)CC(=O)N(C(C)C)CC4)ncc2c(C)c1C#N]

Step 1: tert-butyl N-[5-(3-amino-7-bromo-8-chloro-6-isoquinolyl)-4-methyl-3-pyridyl]-N-tert-butoxycarbonyl-carbamate

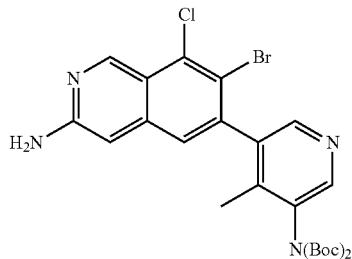

A mixture of 7-bromo-8-chloro-6-iodo-isoquinolin-3-amine (1.3 g, 3.39 mmol), tert-butyl N-tert-butoxycarbonyl-N-[4-methyl-5-(4,4,5,5-tetramethyl-1,3,2-dioxaborolan-2-yl)-3-pyridyl]carbamate (1.9 g, 4.41 mmol), [1,1'-bis(diphenylphosphino)ferrocene]dichloropalladium(II) (248.09 mg, 0.34 mmol) and sodium carbonate (840.88 mg, 6.78 mmol) in 1,4-dioxane (30 mL) and water (3 mL) was stirred at 80° C. for 16 hours. After filtration, the filtrate was concentrated under vacuum. The residue was purified by flash chromatography on silica gel eluting with PE/EA (2/1) to afford tert-butyl N-[5-(3-amino-7-bromo-8-chloro-6-isoquinolyl)-4-methyl-3-pyridyl]-N-tert-butoxycarbonyl-carbamate (1.38 g, 2.45 mmol) as a yellow solid. LCMS (ESI) [M+H]$^+$=563.1.

Step 2: tert-butyl N-[5-(3-amino-8-chloro-7-cyano-6-isoquinolyl)-4-methyl-3-pyridyl]carbamate

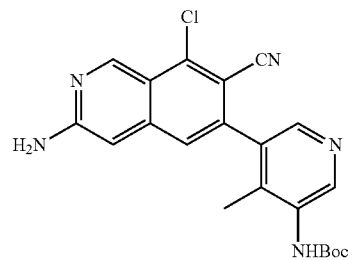 [SMILES: Cc1c(NC(=O)OC(C)(C)C)cncc1-c1cc2cc(N)ncc2c(Cl)c1C#N]

A mixture of tert-butyl N-[5-(3-amino-7-bromo-8-chloro-6-isoquinolyl)-4-methyl-3-pyridyl]-N-tert-butoxycarbonyl-carbamate (850 mg, 1.51 mmol), zinc cyanide (88.49 mg, 0.75 mmol) and tetrakis(triphenylphosphine)palladium (174.19 mg, 0.15 mmol) in 1-methyl-2-pyrrolidinone (30 mL) was stirred under a nitrogen atmosphere for 1.5 h at 130° C. After filtration, the filtrate was concentrated under vacuum. The residue was purified by reverse phase chromatography (acetonitrile 5-60% and 0.1% NH$_4$HCO$_3$ in water) to afford tert-butyl N-[5-(3-amino-8-chloro-7-cyano-6-isoquinolyl)-4-methyl-3-pyridyl]carbamate (326 mg, 0.79 mmol) as a yellow solid. LCMS (ESI) [M+H]$^+$=410.1.

Step 3: 6-(5-amino-4-methyl-3-pyridyl)-8-chloro-3-[(6-isopropyl-7-oxo-5,8-dihydro-4H-pyrazolo[1,5-d][1,4]diazepin-2-yl)amino]isoquinoline-7-carbonitrile

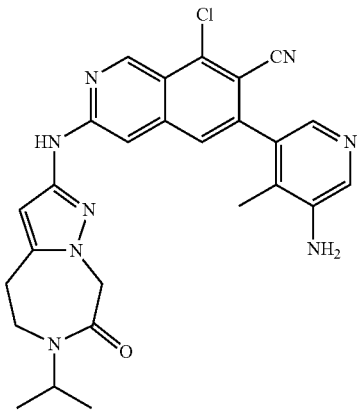 [SMILES: Cc1c(N)cncc1-c1cc2cc(Nc3cc4n(n3)CC(=O)N(C(C)C)CC4)ncc2c(Cl)c1C#N]

A mixture of 2-bromo-6-isopropyl-5,8-dihydro-4H-pyrazolo[1,5-d][1,4]diazepin-7-one (194.81 mg, 0.72 mmol), tert-butyl N-[5-(3-amino-8-chloro-7-cyano-6-isoquinolyl)-4-methyl-3-pyridyl]carbamate (326 mg, 0.48 mmol), 2-(di-tert-butylphosphino)-2',4',6'-triisopropyl-3,6-dimethoxy-1,1'-biphenyl (115.65 mg, 0.24 mmol), cesium carbonate (310.98 mg, 0.95 mmol) and t-BubrettPhos-Pd-G3 (163.02 mg, 0.19 mmol) in 1,4-dioxane (30 mL) was stirred for 2 h at 120° C. After filtration, the filtrate was concentrated under vacuum. The residue was purified by flash chromatography on silica gel eluting with dichloromethane/methanol (10:1) to afford 6-(5-amino-4-methyl-3-pyridyl)-8-chloro-3-[(6-isopropyl-7-oxo-5,8-dihydro-4H-pyrazolo[1,5-d][1,4]diazepin-2-yl)amino]isoquinoline-7-carbonitrile (200 mg, 0.40 mmol) as a yellow solid. LCMS (ESI) [M+H]$^+$=501.3.

Step 4: 6-(5-amino-4-methyl-3-pyridyl)-3-[(6-isopropyl-7-oxo-5,8-dihydro-4H-pyrazolo[1,5-d][1,4]diazepin-2-yl)amino]-8-methyl-isoquinoline-7-carbonitrile

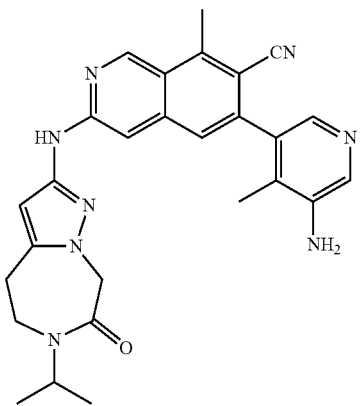 [SMILES: Cc1c(N)cncc1-c1cc2cc(Nc3cc4n(n3)CC(=O)N(C(C)C)CC4)ncc2c(C)c1C#N]

A mixture of 6-(5-amino-4-methyl-3-pyridyl)-8-chloro-3-[(6-isopropyl-7-oxo-5,8-dihydro-4H-pyrazolo[1,5-d][1,4]diazepin-2-yl)amino]isoquinoline-7-carbonitrile (200 mg, 0.40 mmol), potassium carbonate (165.28 mg, 1.2 mmol), trimethylboroxine (0.22 mL, 1.6 mmol) and terakis(triphenylphosphine)palladium (46.11 mg, 0.04 mmol) in 1,4-dioxane (18 mL) and water (4.5 mL) was stirred for 2 h at 100° C. After filtration, the filtrate was concentrated under vacuum. The residue was purified by Prep-HPLC (Sun Fire Prep C18 OBD, 19×150 mm, 5 um; water (10 mmol/L NH$_4$HCO$_3$):CH$_3$CN=22%-36% in 10 min) to afford product 6-(5-amino-4-methyl-3-pyridyl)-3-[(6-isopropyl-7-oxo-5,8-dihydro-4H-pyrazolo[1,5-d][1,4]diazepin-2-yl)amino]-8-methyl-isoquinoline-7-carbonitrile (19.7 mg, 0.041 mmol) as a yellow solid. LCMS (ESI) [M+H]$^+$=481.2; $^1$H NMR (400 MHz, DMSO-d$_6$) δ 9.68 (s, 1H), 9.30 (s, 1H), 8.02 (s, 1H), 7.88 (s, 1H), 7.66 (s, 1H), 7.56 (s, 1H), 6.04 (s, 1H), 5.31 (s, 2H), 5.00 (s, 2H), 4.63-4.43 (m, 1H), 3.78 (t, J=6.0 Hz, 2H), 3.05-2.98 (m, 3H), 2.97 (s, 2H), 1.92 (s, 3H), 1.12 (d, J=6.9 Hz, 6H).

Example 122

2-[[7-fluoro-6-(4-methyl-3-pyridyl)-3-isoquinolyl]amino]-6-isopropyl-5,8-dihydro-4H-pyrazolo[1,5-d][1,4]diazepin-7-one (Compound 131)

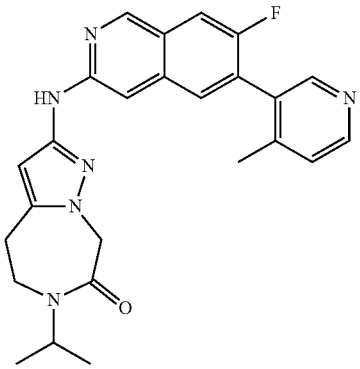 [SMILES: Cc1ccncc1-c1cc2cc(Nc3cc4n(n3)CC(=O)N(C(C)C)CC4)ncc2cc1F]

Step 1:
7-fluoro-6-(4-methyl-3-pyridyl)isoquinolin-3-amine

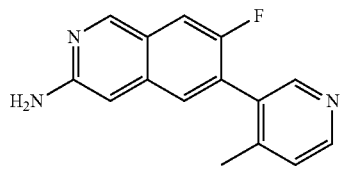 [SMILES: Cc1ccncc1-c1cc2cc(N)ncc2cc1F]

To a mixture of 7-fluoro-6-iodo-isoquinolin-3-amine (200 mg, 0.69 mmol), 4-methyl-3-(4,4,5,5-tetramethyl-1,3,2-dioxaborolan-2-yl)pyridine (228.17 mg, 1.04 mmol), and [1,1'-bis(diphenylphosphino)ferrocene]dichloropalladium(II) (50.75 mg, 0.070 mmol) in 1,4-dioxane (2 mL) and water (0.2 mL) was added potassium carbonate (210.79 mg, 1.53 mmol) at 25° C. The resulting solution was stirred for 2 h at 90° C. and then filtered. The filtrate was concentrated under vacuum. The residue was purified by flash chromatography on silica gel eluting with ethyl acetate/petroleum ether (4/1) to afford 7-fluoro-6-(4-methyl-3-pyridyl)isoquinolin-3-amine (150 mg, 0.59 mmol) as a yellow solid. LCMS (ESI) [M+H]$^+$=254.1.

Step 2: 2-[[7-fluoro-6-(4-methyl-3-pyridyl)-3-isoquinolyl]amino]-6-isopropyl-5,8-dihydro-4H-pyrazolo[1,5-d][1,4]diazepin-7-one

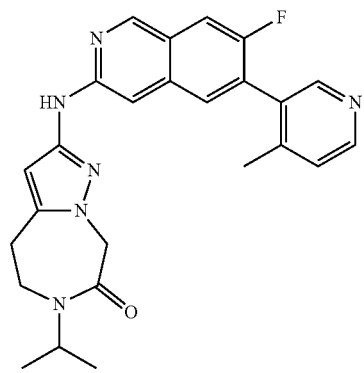 [SMILES: Cc1ccncc1-c1cc2cc(Nc3cc4n(n3)CC(=O)N(C(C)C)CC4)ncc2cc1F]

To a mixture of 7-fluoro-6-(4-methyl-3-pyridyl)isoquinolin-3-amine (100 mg, 0.39 mmol), 2-bromo-6-isopropyl-5,8-dihydro-4H-pyrazolo[1,5-d][1,4]diazepin-7-one (128.94 mg, 0.47 mmol), t-BuBrettphos Pd G3 (134.88 mg, 0.16 mmol) and t-BuBrettphos (95.55 mg, 0.20 mmol) in 1,4-dioxane (20 mL) was added cesium carbonate (643.58 mg, 1.97 mmol) at 25° C. The resulting solution was stirred for 1 h at 120° C. The resulting mixture was cooled to room temperature. After filtration, the filtrate was concentrated under vacuum. The residue was purified by reverse phase chromatography (acetonitrile 0-40/0.1% $NH_4HCO_3$ in water) to afford 2-[[7-fluoro-6-(4-methyl-3-pyridyl)-3-isoquinolyl]amino]-6-isopropyl-5,8-dihydro-4H-pyrazolo[1,5-d][1,4]diazepin-7-one (76.2 mg, 0.17 mmol) as a yellow solid. LCMS (ESI) [M+H]$^+$=445.2; $^1$H NMR (300 MHz, DMSO-d$_6$) δ 9.28 (s, 1H), 9.02 (s, 1H), 8.54 (d, J=5.2 Hz, 1H), 8.47 (s, 1H), 7.95 (s, 1H), 7.87-7.78 (m, 2H), 7.42 (d, J=5.2 Hz, 1H), 5.98 (s, 1H), 4.98 (s, 2H), 4.61-4.57 (m, 1H), 3.78 (t, J=5.9 Hz, 2H), 2.99 (t, J=5.7 Hz, 2H), 2.22 (s, 3H), 1.13 (d, J=6.9 Hz, 6H).

Example 123

2-[[7-fluoro-6-(8-methyl-2,3-dihydro-1H-pyrido[2,3-b][1,4]oxazin-7-yl)-3-isoquinolyl]amino]-6-(2-morpholinoethyl)-5,8-dihydro-4H-pyrazolo[1,5-d][1,4]diazepin-7-one (Compound 132)

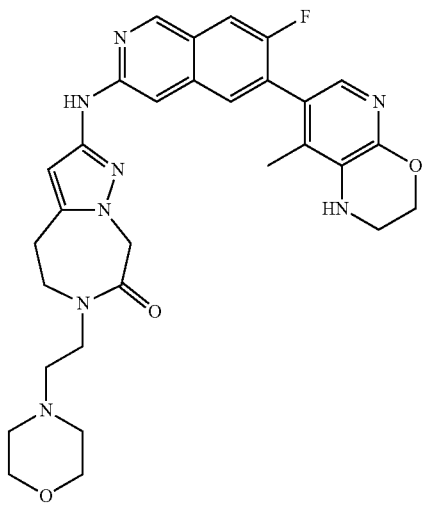 [SMILES: Cc1c(-c2cc3cc(Nc4cc5n(n4)CC(=O)N(CCN4CCOCC4)CC5)ncc3cc2F)cnc2c1NCCO2]

Step 1: 2-bromo-6-(2-morpholinoethyl)-5,8-dihydro-4H-pyrazolo[1,5-d][1,4]diazepin-7-one

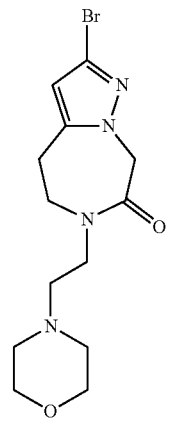 [SMILES: O=C1Cn2nc(Br)cc2CCN1CCN1CCOCC1]

A mixture of 2-bromo-4,5,6,8-tetrahydropyrazolo[1,5-d][1,4]diazepin-7-one (150 mg, 0.65 mmol) and sodium hydride (78.24 mg, 1.96 mmol, 60%) in N,N-dimethylformamide (3 mL) was stirred for 30 mins at 0° C. Then 4-(2-bromoethyl)morpholine (253.07 mg, 1.3 mmol) was added and stirred at 0° C. for 2 h. The reaction was quenched by adding water (1 mL). After filtration the filtrate was concentrated under vacuum. The residue was purified by reverse phase chromatography (acetonitrile 0-40%+0.05% TFA in water) to afford 2-bromo-6-(2-morpholinoethyl)-5,8-dihydro-4H-pyrazolo[1,5-d][1,4]diazepin-7-one (200 mg, 0.58 mmol) as a yellow oil. LCMS (ESI) [M+H]$^+$=343.

Step 2: tert-butyl 7-[7-fluoro-3-[[6-(2-morpholinoethyl)-7-oxo-5,8-dihydro-4H-pyrazolo[1,5-d][1,4]diazepin-2-yl]amino]-6-isoquinolyl]-8-methyl-2,3-dihydropyrido[2,3-b][1,4]oxazine-1-carboxylate

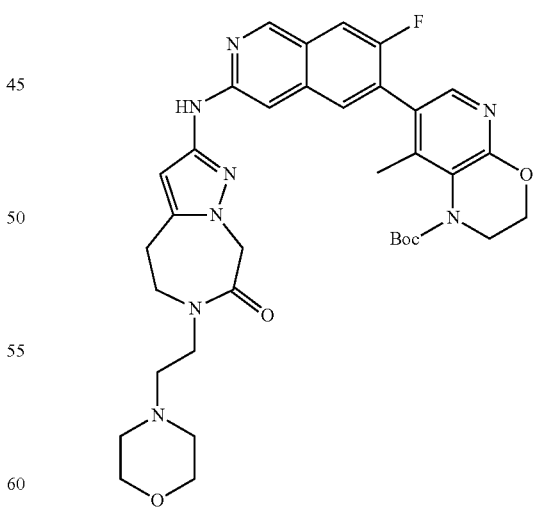

A mixture of 2-bromo-6-(2-morpholinoethyl)-5,8-dihydro-4H-pyrazolo[1,5-d][1,4]diazepin-7-one (100.35 mg, 0.29 mmol), tert-butyl 7-(3-amino-7-fluoro-6-isoquinolyl)-8-methyl-2,3-dihydropyrido[2,3-b][1,4]oxazine-1-carboxylate (100 mg, 0.24 mmol), t-BuBrettphos 3G Pd (83.23 mg, 0.10 mmol), t-BuBrettphos (58.96 mg, 0.12 mmol) and cesium carbonate (397.13 mg, 1.22 mmol) in 1,4-dioxane (10 mL) was stirred for 1 h at 120° C. The residue was purified by flash chromatography on silica gel eluting with dichloromethane/methanol (9/1) to afford tert-butyl 7-[7-fluoro-3-[[6-(2-morpholinoethyl)-7-oxo-5,8-dihydro-4H-pyrazolo[1,5-d][1,4]diazepin-2-yl]amino]-6-isoquinolyl]-8-methyl-2,3-dihydropyrido[2,3-b][1,4]oxazine-1-carboxylate (80 mg, 0.12 mmol) as a yellow solid. LCMS (ESI) [M+H]⁺=673.

Step 3: 2-[[7-fluoro-6-(8-methyl-2,3-dihydro-TH-pyrido[2,3-b][1,4]oxazin-7-yl)-3-isoquinolyl] amino]-6-(2-morpholinoethyl)-5,8-dihydro-4H-pyrazolo[1,5-d][1,4]diazepin-7-one.fomate

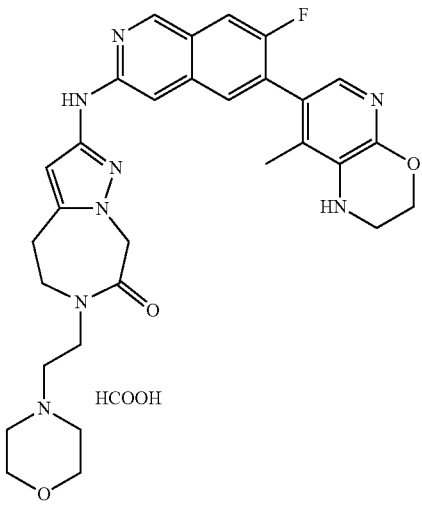 [SMILES: Cc1c(-c2cc3cc(Nc4cc5n(n4)CC(=O)N(CCN4CCOCC4)CC5)ncc3cc2F)cnc2c1NCCO2 ; "HCOOH"]

A solution of tert-butyl 7-[7-fluoro-3-[[6-(2-morpholinoethyl)-7-oxo-5,8-dihydro-4H-pyrazolo[1,5-d][1,4]diazepin-2-yl]amino]-6-isoquinolyl]-8-methyl-2,3-dihydropyrido[2,3-b][1,4]oxazine-1-carboxylate (80 mg, 0.12 mmol) in 1,2-dichloroethane (2.5 mL) and 2,2,2-trifluoroacetic acid (0.5 mL) was stirred for 2 h at 25° C. The solvent was concentrated under vacuum. The residue was redissolved in methanol and then the pH value was adjusted to pH=8 with ammonia in methanol (7 M). After filtration the filtrate was concentrated under vacuum. The residue was purified by Prep-HPLC (Atlantis HILIC OBD Column 19*150 mm*5 um; Water(0.1% FA):CH₃CN=5%-35% in 7 min) to afford 2-[[7-fluoro-6-(8-methyl-2,3-dihydro-1H-pyrido[2,3-b][1,4]oxazin-7-yl)-3-isoquinolyl]amino]-6-(2-morpholinoethyl)-5,8-dihydro-4H-pyrazolo[1,5-d][1,4]diazepin-7-one (57.3 mg, 0.10 mmol) as a yellow solid. LCMS (ESI) [M+H]⁺=573; $^1$H NMR (400 MHz, DMSO-$d_6$) δ 9.25 (s, 1H), 8.99 (s, 1H), 7.90 (s, 1H), 7.79 (d, J=10.2 Hz, 1H), 7.66 (d, J=7.1 Hz, 1H), 7.37 (s, 1H), 6.00 (s, 1H), 5.70 (s, 1H), 5.01 (s, 2H), 4.30 (t, J=4.4 Hz, 2H), 4.02-3.98 (m, 1H), 3.87-3.85 (m, 2H), 3.74-3.54 (m, 6H), 3.37-3.35 (m, 3H), 3.08-3.06 (m, 3H), 2.45-2.40 (m, 3H), 1.92 (s, 3H).

Example 124

2-((7-Fluoro-6-(4-hydroxy-5-methyl-3,4-dihydro-2H-pyrano[2,3-b]pyridine-6-yl)isoquinolin-3-yl) amino)-6-methyl-5,6-dihydro-4H-pyrazolo[1,5-d][1, 4]diazepin-7(8H)-one (Compound 180)

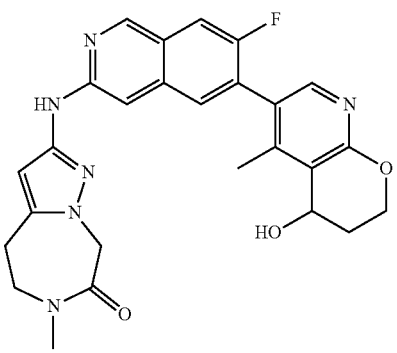 [SMILES: Cc1c(-c2cc3cc(Nc4cc5n(n4)CC(=O)N(C)CC5)ncc3cc2F)cnc2c1C(O)CCO2]

Step 1: 3,5-Dibromo-2-Methoxy-4-methylpyridine

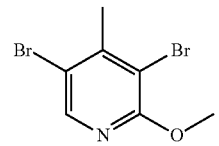

To a suspension of sodium acetate (9.86 g, 120 mmol) and 2-methoxy-4-methyl pyridine (5 g, 39 mmol) in acetic acid (40 mL) was added bromine (6.0 mL, 120 mmol). This was then heated at 80° C. for 12 hours. The reaction was cooled to room temperature and concentrated under reduced pressure. The residue was then treated with 10% sodium hydroxide in water (28 g, 698 mmol) and saturated sodium sulfite solution (15 g, 120 mmol). The resulting mixture was extracted with diethyl ether (3×100 mL). The combined organic layers were dried with anhydrous powdered magnesium sulfate, filtered, and concentrated to give a white solid which was purified by column chromatography (220 g silica column, 0-30% Isopropyl acetate in heptane in 12 minutes) to afford 3,5-Dibromo-2-methoxy-4-methylpyridine (10.02 g, 35.67 mmol) as a white solid. $^1$H NMR (400 MHz, Chloroform-d) δ 8.14 (s, 1H), 3.98 (s, 3H), 2.56 (s, 3H). LCMS (ESI, m/z): 280 [M+H]⁺.

Step 2: 1-(5-bromo-2-methoxy-4-methylpyridin-3-yl)prop-2-en-1-ol

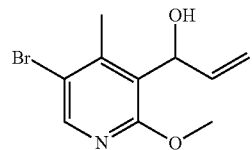

A solution of 3,5-Dibromo-2-methoxy-4-methylpyridine (7.6 g, 27 mmol) in diethyl ether (100 mL) was cooled to −65° C. under nitrogen. n-Butyl lithium (2.5 M in hexane, 12 mL, 29.7 mmol) was added dropwise with stirring while maintaining the temperature at −65° C. The reaction was cooled to −70° C. and stirred for 30 minutes under nitrogen, then warmed to room temperature overnight. The reaction was by addition of 30 ml saturated sodium bicarbonate solution. The resulting mixture was extracted with dichloromethane, dried with magnesium sulfate and filtered. The filtrate was concentrated to afford 1-(5-bromo-2-methoxy-4-methylpyridin-3-yl)prop-2-en-1-ol as a clear oil which was used directly in the next step without further purification. $^1$H NMR (400 MHz, Chloroform-d) δ 8.17 (s, 1H), 6.14-6.06 (m, 1H), 5.49-5.45 (m, 1H), 5.20 (t, J=1.4 Hz, 1H), 5.15 (dt, J=2.0, 1.1 Hz, 1H), 5.13 (t, J=1.4 Hz, 1H), 3.97 (s, 3H), 3.66 (d, J=10.3 Hz, 1H), 2.43 (s, 3H). LCMS (ESI, m/z): 260 [M+H]$^+$.

Step 3: 1-(5-bromo-2-methoxy-4-methylpyridin-3-yl)prop-2-en-1-one

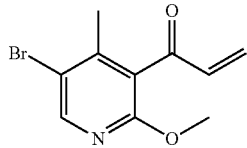

To a solution of 1-(5-bromo-2-methoxy-4-methylpyridin-3-yl)prop-2-en-1-ol (6.9 g, 26.7 mmol) in dichloromethane (100 mL) was added dess-martin periodinane (17.24 g, 39.4 mmol) at room temperature. The reaction was stirred at room temperature overnight, then quenched by addition of 200 ml saturated sodium bicarbonate solution slowly with stirring. The mixture was transferred to a seperatory funnel and the organic layer was collected. The aqueous layer was extracted twice more with dichloromethane. The combined organic layers were dried with magnesium sulfate, filtered, and concentrated to afford a yellow oil that purified by column chromatography (silica, 120 g, 0-50% isopropyl acetate in heptane in 25 minutes) to afford 1-(5-bromo-2-methoxy-4-methylpyridin-3-yl)prop-2-en-1-one as a clear oil (6.03 g, 23.5 mmol). $^1$H NMR (400 MHz, Chloroform-d) δ 8.26 (s, 1H), 6.59 (dd, J=17.6, 10.5 Hz, 1H), 6.13-5.94 (m, 2H), 3.89 (s, 3H), 2.24 (s, 3H). LCMS (ESI, m/z): 258 [M+H]$^+$.

Step 4: 6-bromo-5-methyl-2,3-dihydro-4H-pyrano[2,3-b]pyridin-4-one

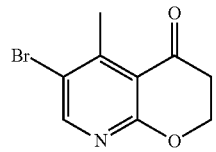

To a solution 1-(5-bromo-2-methoxy-4-methylpyridin-3-yl)prop-2-en-1-one (4.7 g, 18.24 mmol) in acetic acid (80 mL) was added hydrobromic acid (48% solution in water, 6.4 mL, 57 mmol). The reaction was heated to 100° C. for 45 minutes, then cooled to room temperature and extracted with ether (3×50 mL). The combined organic layers were washed with saturated sodium bicarbonate solution. The organic layer was collected, dried with magnesium sulfate, filtered, and concentrated to afford a yellow solid that was purified by column chromatography (silica, 220 g, 0-65% isopropyl acetate in heptane in 20 minutes) to afford 6-bromo-2-methy-2,3-dihydro-4H-pyranol[2,3-b]pyridin-4-one as a white solid (2.27 g, 9.4 mmol). $^1$H NMR (400 MHz, Chloroform-d) δ 8.46 (s, 1H), 4.59 (d, J=0.8 Hz, 2H), 2.87-2.84 (m, 2H), 2.81 (s, 3H). LCMS (ESI, m/z): 244 [M+H]$^+$.

Step 5: 6-bromo-5-methyl-3,4-dihydro-2H-pyrano[2,3-b]pyridin-4-ol

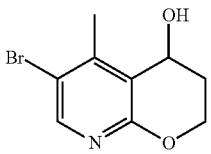

To a solution of 1-(5-bromo-2-methoxy-4-methylpyridin-3-yl)prop-2-en-1-one (468.3 mg, 1.9 mmol) in methanol (25 mL) was added sodium borohydride (167.6 mg, 4.43 mmol). The mixture was stirred overnight at room temperature, then quenched by addition of water and concentrated under reduced pressure. The residue was partitioned between water (50 mL) and ethyl acetate (30 mL). The organic layer was collected and the aqueous layer extracted twice more with ethyl acetate (2×30 mL). The combined organic layers was then dried with magnesium sulfate, filtered, and concentrated to give 6-bromo-5-methyl-3,4-dihydro-2H-pyrano[2,3-b]pyridin-4-ol as a white solid, which was used directly in the next step without further purification. LCMS (ESI, m/z): 246 [M+H]$^+$.

Step 6: 6-bromo-4-((tert-butyldimethylsilyl)oxy)-5-methyl-3,4-dihydro-2H-pyrano[2,3-b]pyridine

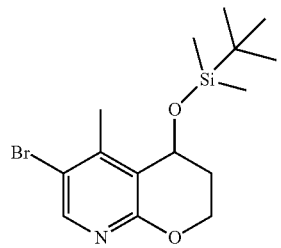 [SMILES: Cc1c(Br)cnc2c1C(O[Si](C)(C)C(C)(C)C)CCO2]

To a solution of 6-bromo-5-methyl-3,4-dihydro-2H-pyrano[2,3-b]pyridin-4-ol (507.2 mg, 2.1 mmol) in dichloromethane (12 mL) was added triethylamine (0.75 mL, 5.4 mmol). The mixture was cooled to 0° C. under nitrogen, then tert-butyldimethylsilyl trifluoromethane sulfonate (0.58 mL, 2.47 mmol) was added. The reaction was stirred at room temperature for 45 minutes, then quenched by addition of concentrated ammonium chloride solution. The mixture was extracted with dichloromethane and the organic layers were dried with sodium sulfate, filtered, and concentrated to give a clear oil that was purified by column chromatography (silica, 80 g, 0-50% isopropyl acetate in heptane in 18 minutes) to afford 6-bromo-4-((tert-butyldimethylsilyl)

oxy)-5-methyl-3,4-dihydro-2H-pyrano[2,3-b]pyridine as a white solid (640.8 mg, 1.79 mmol). LCMS (ESI, m/z): 360 [M+H]⁺.

Step 7: 6-bromo-4-((tert-butyldimethylsilyl)oxy)-5-methyl-6-(4,4,5,5-tetramethyl-1,3,2-dioxaborolan-2-yl)-3,4-dihydro-2H-pyranol[2,3-b]pyridine

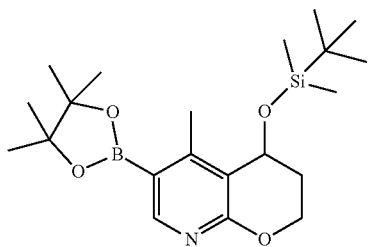 [SMILES: Cc1c(B2OC(C)(C)C(C)(C)O2)cnc2c1C(O[Si](C)(C)C(C)(C)C)CCO2]

6-bromo-4-((tert-butyldimethylsilyl)oxy)-5-methyl-3,4-dihydro-2H-pyranol[2,3-b]pyridine (441.5 mg, 1.2 mmol), Bis(pinacolato)diboron (500 mg, 1.93 mmol), Pd₂(dppf)Cl₂·CH₂Cl₂ (134.7 mg, 0.16 mmol) and potassium acetate (454.6 mg, 4.63 mmol) were dissolved in 1,4 dioxane (5 mL) under nitrogen, then heated to 90° C. overnight under nitrogen. The resulting mixture was cooled to room temperature, diluted with 20 mL ethyl acetate, and filtered. The filtrate was concentrated under reduced pressure to give 6-bromo-4-((tert-butyldimethylsilyl)oxy)-5-methyl-6-(4,4,5,5-tetramethyl-1,3,2-dioxaborolan-2-yl)-3,4-dihydro-2H-pyranol[2,3-b]pyridine as a black solid which was used directly in the next step without further purification. LCMS (ESI, m/z): 406 [M+H]⁺.

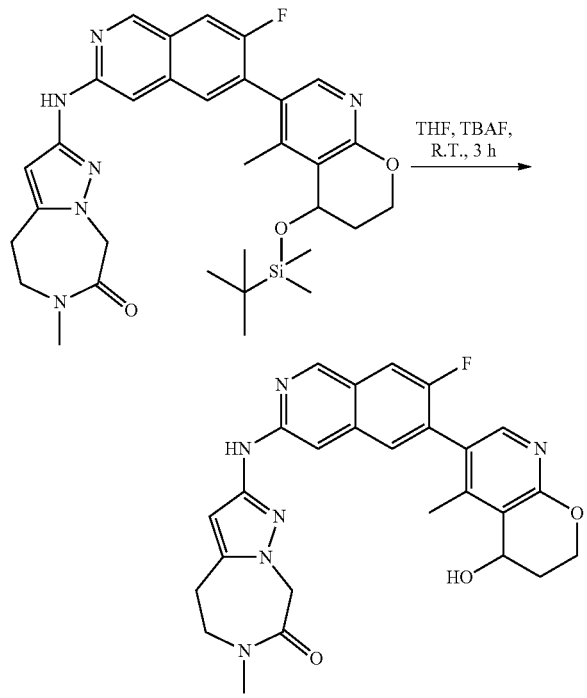

(S)-2-((7-Fluoro-6-(4-hydroxy-5-methyl-3,4-dihydro-2H-pyrano[2,3-b]pyridine-6-yl)isoquinolin-3-yl)amino)-6-methyl-5,6-dihydro-4H-pyrazolo[1,5-d][1,4]diazepin-7(8H)-one and (R)-2-((7-Fluoro-6-(4-hydroxy-5-methyl-3,4-dihydro-2H-pyrano[2,3-b]pyridine-6-yl)isoquinolin-3-yl)amino)-6-methyl-5,6-dihydro-4H-pyrazolo[1,5-d][1,4]diazepin-7(8H)-one

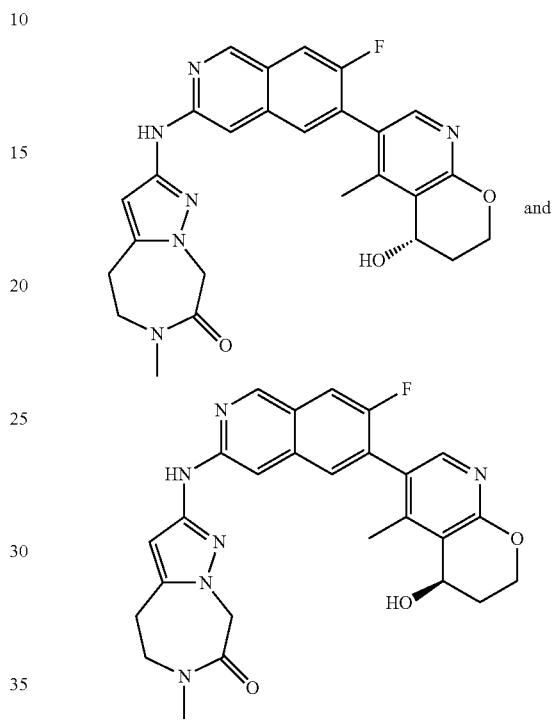

To a solution of 2-[[6-[tertbutyl(dimethyl)silyl]oxy-5-methyl-3,4-dihydro-2H-pyranol[2,3-b]pyridin-6-yl]-7-fluoror-3-isoquinolin]amino]-6-methyl-,8-dihydro-4H-pyrazolo[1,5-d][1,4]diazapin-7-one (110 mg, 0.19 mmol) in tetrahydrofuran (12 mL) at room temperature was added tetrabutylammonium fluoride (1.0 M in THF, 1 mL, 1 mmol). The reaction was stirred at room temperature for 3 hours, then quenched by addition of water. The resulting mixture was concentrated under reduced pressure. The residue was purified by reverse phase HPLC followed by Chiral SFC (Chiralpak IB-N, 150×21 mm, 5 M; 50% 0.1% ammonium hydroxide in MeOH in CO₂; flow rate=70 mL/min) to give 2-Fluoro-6-(4-hydroxy-5-methyl-3,4-dihydro-2H-pyranol[2,3-b]pyridine-6-yl)isoquinolin-3-yl)amino)-6-methyl-5,6-dihydro-4H-pyrazolo[1,5-d][1,4]diazapin-7(8H)-one (9.5 mg, 0.019 mmol) of each enantiomer.

Peak 1 (Compound 180a): cSFC retention time=1.4 min. ¹H NMR (400 MHz, DMSO-d6) δ 9.25 (s, 1H), 9.00 (s, 1H), 8.03 (s, 1H), 7.90 (s, 1H), 7.81 (d, J=10.2 Hz, 1H), 7.70 (d, J=7.2 Hz, 1H), 6.00 (s, 1H), 5.41 (d, J=5.6 Hz, 1H), 4.98 (s, 2H), 4.85 (d, J=5.5 Hz, 1H), 4.40-4.32 (m, 2H), 3.84-3.80 (m, 2H), 3.07-3.03 (m, 2H), 2.95 (s, 3H), 2.25 (d, J=1.7 Hz, 3H), 1.98 (dd, J=7.2, 3.8 Hz, 2H). Analytical HPLC retention time 3.667 min. Method N. LCMS (ESI, m/z): 489.3 [M+H]⁺.

Peak 2 (Compound 180b): cSFC retention time=1.84 min. ¹H NMR (400 MHz, DMSO-d6) δ 9.25 (s, 1H), 9.00 (s, 1H), 8.03 (s, 1H), 7.90 (s, 1H), 7.81 (d, J=10.1 Hz, 1H), 7.70 (d, J=7.2 Hz, 1H), 6.00 (s, 1H), 5.41 (d, J=5.7 Hz, 1H), 4.98 (s, 2H), 4.85 (d, J=4.4 Hz, 1H), 4.40-4.32 (m, 2H), 3.84-3.80 (m, 2H), 3.07-3.03 (m, 2H), 2.95 (s, 3H), 2.25 (d, J=1.6 Hz, 3H), 1.98 (dd, J=6.9, 3.7 Hz, 2H). Analytical HPLC retention time 3.666 min. Method N. LCMS (ESI, m/z): 489.2 [M+H]+.

Example 125

N-(7-fluoro-6-(4-methylpyridin-3-yl)isoquinolin-3-yl)-3,3-dimethyl-5,6-dihydro-3H,11H-[1,2,4]oxadiazolo[4,3-a]pyrazolo[1,5-d][1,4]diazepin-8-amine (Compound 134)

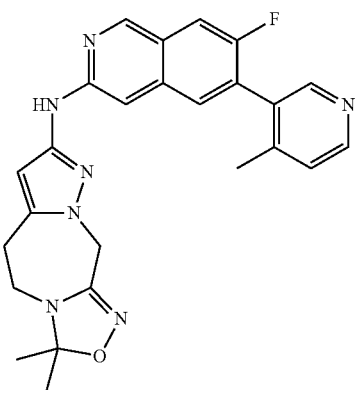 [SMILES: Cc1ccncc1-c1cc2cc(Nc3cc4n(n3)CC3=NOC(C)(C)N3CC4)ncc2cc1F]

Synthesized following procedures similar to those described above according to the general synthetic methods. ¹H NMR (300 MHz, CD₃OD) δ 8.99 (s, 1H), 8.53-8.51 (m, 1H), 8.47 (s, 1H), 7.89 (s, 1H), 7.77-7.72 (m, 2H), 7.51-7.49 (m, 1H), 6.13 (s, 1H), 5.06 (s, 2H), 3.47-3.43 (m, 2H), 3.25-3.21 (m, 2H), 2.34 (s, 3H), 1.45 (s, 6H). Analytical HPLC retention time 1.987 min. Method K. MS (ESI) [M+H]+=458.2.

Example 126

2-((7,8-difluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one (Compound 135)

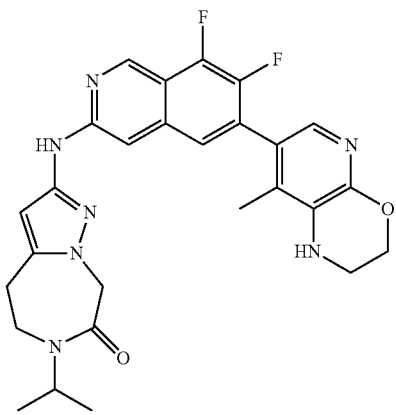

Synthesized following procedures similar to those described above according to the general synthetic methods. ¹H NMR (300 MHz, DMSO-d₆) δ 9.47 (s, 1H), 9.16 (s, 1H), 7.94 (s, 1H), 7.54 (d, J=6.0 Hz, 1H), 7.40 (s, 1H), 6.01 (s, 1H), 5.75 (s, 1H), 5.00 (s, 2H), 4.62-4.57 (m, 1H), 4.32-4.30 (s, 2H), 3.81-3.77 (m, 2H), 3.36-3.33 (m, 2H), 3.02-2.99 (m, 2H), 1.95 (s, 3H), 1.13 (d, J=6.9 Hz, 6H). Analytical HPLC retention time 2.316 min. Method K. MS (ESI) [M+H]+=520.2.

Example 127

2-((6-(5-amino-4-methylpyridin-3-yl)-7-fluoroisoquinolin-3-yl)amino)-6-(2-morpholinoethyl)-5,6-dihydro-4H-pyrazolo[1,5-d][1,4]diazepin-7(8H)-one (Compound 136)

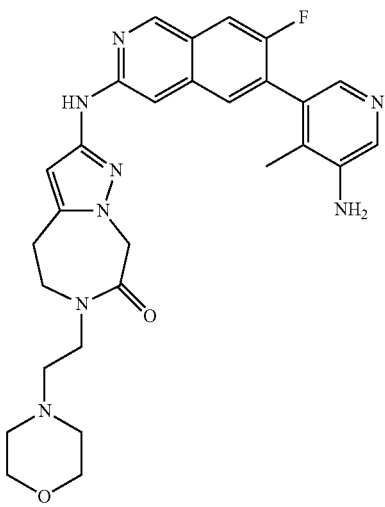 [SMILES: Cc1c(N)cncc1-c1cc2cc(Nc3cc4n(n3)CC(=O)N(CCN3CCOCC3)CC4)ncc2cc1F]

Synthesized following procedures similar to those described above according to the general synthetic methods. ¹H NMR (400 MHz, DMSO-d₆) δ 9.23 (s, 1H), 8.90 (s, 1H), 8.02 (s, 1H), 7.91 (s, 1H), 7.80 (d, J=7.5 Hz, 1H), 7.70-7.69 (m, 2H), 5.99 (s, 1H), 5.26 (s, 2H), 4.99 (s, 2H), 3.87-3.84 (m, 2H), 3.54-3.49 (m, 6H), 3.10-3.07 (m, 2H), 2.45-2.33 (m, 6H), 1.92 (s, 3H). Analytical HPLC retention time 1.541 min. Method K. MS (ESI) [M+H]+=531.2.

Example 128

2-((7-fluoro-6-(6-methoxy-4-methylpyridin-3-yl)isoquinolin-3-yl)amino)-6-methyl-5,6-dihydro-4H-pyrazolo[1,5-d][1,4]diazepin-7(8H)-one (Compound 137)

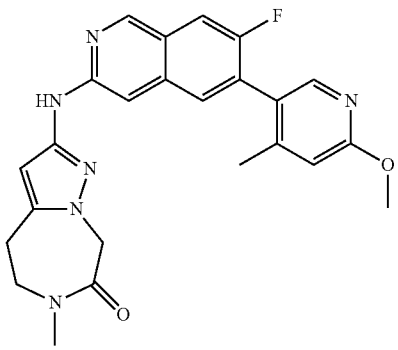 [SMILES: COc1cc(C)c(-c2cc3cc(Nc4cc5n(n4)CC(=O)N(C)CC5)ncc3cc2F)cn1]

Synthesized following procedures similar to those described above according to the general synthetic methods. $^1$H NMR (300 MHz, DMSO-d$_6$) δ 9.27 (s, 1H), 9.00 (s, 1H), 8.08 (s, 1H), 7.92 (s, 1H), 7.81 (d, J=10.2 Hz, 1H), 7.73 (d, J=7.2 Hz, 1H), 6.85 (s, 1H), 5.99 (s, 1H), 4.99 (s, 2H), 4.04 (s, 3H), 4.02-3.83 (m, 2H), 3.18-3.05 (m, 2H), 2.96 (s, 3H), 2.16 (s, 3H). Analytical HPLC retention time 1.878 min. Method M. MS (ESI) [M+H]$^+$=447.2.

Example 129

2-((7,8-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one (Compound 138)

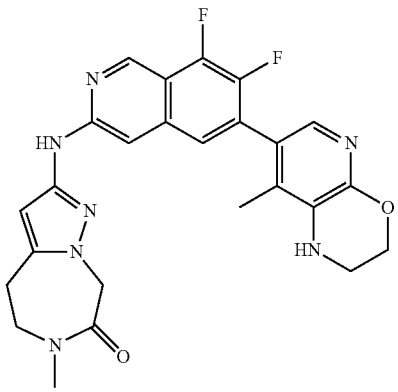 [SMILES: Cc1c(-c2cc3cc(Nc4cc5n(n4)CC(=O)N(C)CC5)ncc3c(F)c2F)cnc2c1NCCO2]

Synthesized following procedures similar to those described above according to the general synthetic methods. $^1$H NMR (300 MHz, DMSO-d$_6$) δ 9.50 (s, 1H), 9.17 (s, 1H), 7.93 (s, 1H), 7.54 (d, J=6.0 Hz, 1H), 7.40 (s, 1H), 6.02 (s, 1H), 5.76 (s, 1H), 5.01 (s, 2H), 4.31-4.29 (m, 2H), 3.85-8.83 (m, 2H), 3.34-3.13 (m, 2H), 3.07-3.05 (m, 2H), 2.96 (s, 3H), 1.95 (s, 3H). Analytical HPLC retention time 2.326 min. Method L. MS (ESI) [M+H]$^+$=492.1.

Example 130

N-(6-(5-amino-4-methylpyridin-3-yl)-7-fluoroisoquinolin-3-yl)-5,6-dihydro-11H-pyrazolo[1,5-d][1,2,4]triazolo[4,3-a][1,4]diazepin-8-amine (Compound 139)

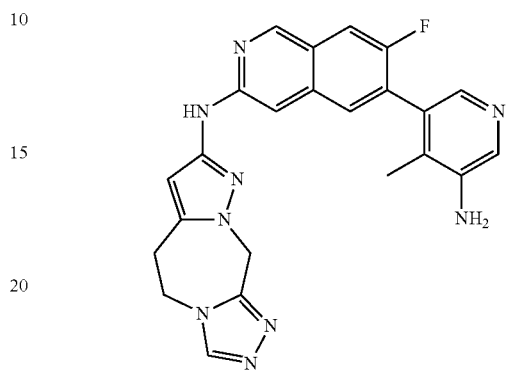

Synthesized following procedures similar to those described above according to the general synthetic methods. $^1$H NMR (300 MHz, DMSO-d$_6$) δ 9.35 (s, 1H), 9.00 (s, 1H), 8.52 (s, 1H), 8.02 (s, 1H), 7.96 (s, 1H), 7.81 (d, J=10.2 Hz, 1H), 7.71 (d, J=7.2 Hz, 1H), 7.70 (s, 1H), 6.12 (s, 1H), 5.57 (s, 2H), 5.28 (s, 2H), 4.40-4.36 (m, 2H), 3.32-3.28 (m, 2H), 1.92 (s, 3H). Analytical HPLC retention time 1.572 min. Method K. MS (ESI) [M+H]$^+$=442.2.

Example 131

2-((6-(5-amino-4-methylpyridin-3-yl)-7-chloroisoquinolin-3-yl)amino)-6-isopropyl-5,6-dihydro-4H-pyrazolo[1,5-d][1,4]diazepin-7(8H)-one (Compound 140)

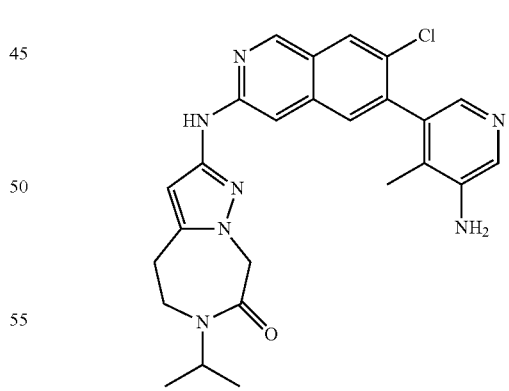

Synthesized following procedures similar to those described above according to the general synthetic methods. $^1$H NMR (300 MHz, DMSO-d$_6$) δ 9.37 (s, 1H), 9.01 (s, 1H), 8.15 (s, 1H), 7.99 (s, 1H), 7.89 (s, 1H), 7.67 (s, 1H), 7.60 (s, 1H), 5.99 (s, 2H), 5.25 (s, 2H), 4.98 (s, 2H), 4.61-4.56 (m, 1H), 3.80-3.76 (s, 1H), 3.00-2.98 (m, 2H), 1.84 (s, 3H), 1.12 (d, J=6.9 Hz, 6H). Analytical HPLC retention time 1.222 min. Method K. MS (ESI) [M+H]$^+$=476.2.

Example 132

(R)-2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diazepin-7(8H)-one (Compound 141a)

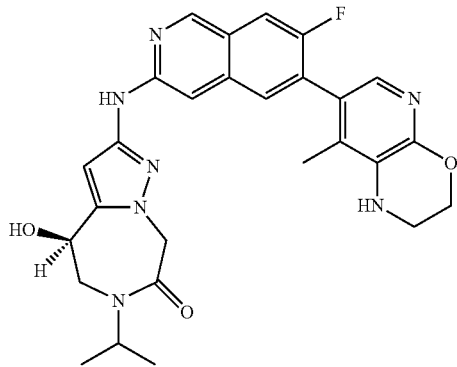 [SMILES: Cc1c(-c2cc3cc(Nc4cc5n(n4)CC(=O)N(C(C)C)C[C@H]5O)ncc3cc2F)cnc2c1NCCO2]

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 7.90 (s, 1H), 7.78 (d, J=10.2 Hz, 1H), 7.68 (d, J=7.2 Hz, 1H), 7.37 (s, 1H), 6.23 (s, 1H), 5.85 (d, J=6.0 Hz, 1H), 5.70 (s, 1H), 5.21 & 5.16 (s, 1H), 4.79-4.70 (m, 2H), 4.56-4.47 (m, 1H), 4.31-4.28 (m, 2H), 3.80-3.60 (m, 2H), 3.38 (s, 2H), 1.92 (s, 3H), 1.13-1.11 (m, 6H). Analytical HPLC retention time 1.903 min. Method K. MS (ESI) [M+H]$^+$=518.2.

(S)-2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diazepin-7(8H)-one (Compound 141b)

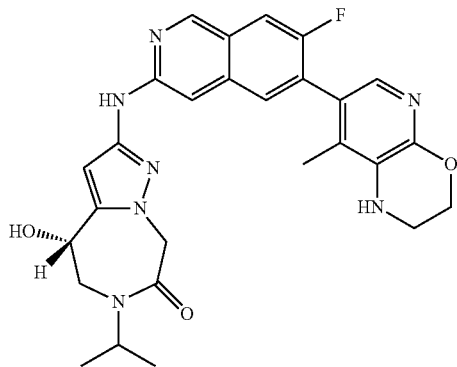

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 7.90 (s, 1H), 7.78 (d, J=10.2 Hz, 1H), 7.68 (d, J=7.2 Hz, 1H), 7.37 (s, 1H), 6.23 (s, 1H), 5.85 (d, J=6.0 Hz, 1H), 5.70 (s, 1H), 5.21 & 5.16 (s, 1H), 4.79-4.70 (m, 2H), 4.56-4.47 (m, 1H), 4.31-4.28 (m, 2H), 3.80-3.60 (m, 2H), 3.38 (s, 2H), 1.92 (s, 3H), 1.13-1.11 (m, 6H). Analytical HPLC retention time 1.903 min. Method K. MS (ESI) [M+H]$^+$=518.2.

Example 133

6-(7-fluoro-3-((6-isopropyl-7-oxo-5,6,7,8-tetrahydro-4H-pyrazolo[1,5-d][1,4]diazepin-2-yl)amino)isoquinolin-6-yl)-7-methyloxazolo[5,4-b]pyridin-2(1H)-one (Compound 142)

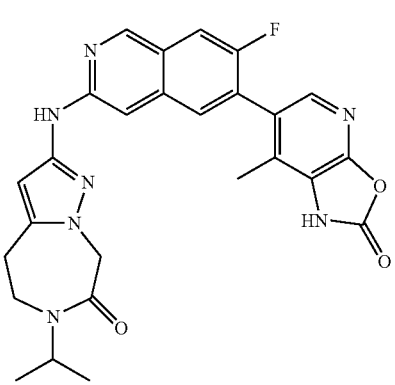 [SMILES: Cc1c(-c2cc3cc(Nc4cc5n(n4)CC(=O)N(C(C)C)CC5)ncc3cc2F)cnc2oc(=O)[nH]c12]

Synthesized following procedures similar to those described above according to the general synthetic methods. $^1$H NMR (400 MHz, DMSO-d$_6$) δ 12.23 (s, 1H), 9.28 (s, 1H), 9.02 (s, 1H), 7.93 (s, 1H), 7.88-7.83 (m, 2H), 7.77 (d, J=7.2 Hz, 1H), 5.98 (s, 1H), 4.98 (s, 2H), 4.61-4.57 (m, 1H), 3.78 (t, J=5.6 Hz, 2H), 2.99 (t, J=5.6 Hz, 2H), 2.18 (s, 3H), 1.12 (d, J=6.8 Hz, 6H). Analytical HPLC retention time 2.133 min. Method K. MS (ESI) [M+H]$^+$=502.2.

Example 134

N-(7-fluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine (Compound 143

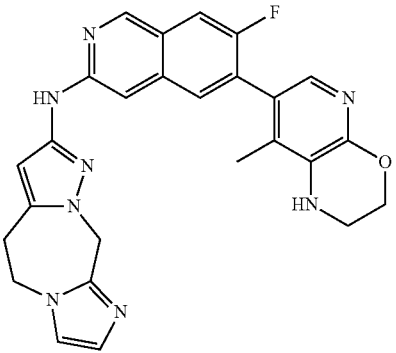 [SMILES: Cc1c(-c2cc3cc(Nc4cc5n(n4)Cc4nccn4CC5)ncc3cc2F)cnc2c1NCCO2]

Synthesized following procedures similar to those described above according to the general synthetic methods. $^1$H NMR (300 MHz, DMSO-d$_6$) δ 9.28 (s, 1H), 8.99 (s, 1H), 7.92 (s, 1H), 7.78 (d, J=10.2 Hz, 1H), 7.67 (d, J=7.2 Hz, 1H), 7.37 (s, 1H), 7.21 (s, 1H), 6.84 (s, 1H), 6.06 (s, 1H), 5.70 (s, 1H), 5.42 (s, 2H), 4.37-4.30 (m, 4H), 3.37-3.32 (m, 2H), 3.26-3.22 (m, 2H), 1.92 (s, 3H). Analytical HPLC retention time 1.017 min. Method K. MS (ESI) [M+H]$^+$=483.2.

Example 135

2-((6-(5-amino-4-methylpyridin-3-yl)-7-fluoroisoquinolin-3-yl)amino)-5,6-dihydro-4H-pyrazolo[1,5-d][1,4]diazepin-7(8H)-one (Compound 144)

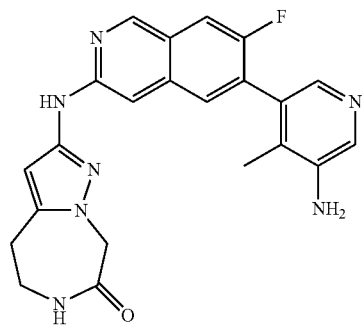 [SMILES: Cc1c(N)cncc1-c1cc2cc(Nc3cc4n(n3)CC(=O)NCC4)ncc2cc1F]

Synthesized following procedures similar to those described above according to the general synthetic methods. $^1$H NMR (300 MHz, DMSO-$d_6$) δ 9.26 (s, 1H), 8.99 (s, 1H), 8.17-8.13 (m, 1H), 8.01 (s, 1H), 7.91 (s, 1H), 7.80 (d, J=10.2 Hz, 1H), 7.71-7.69 (m, 2H), 5.99 (s, 1H), 5.27 (s, 2H), 4.90 (s, 2H), 3.54-3.50 (m, 2H), 2.99-2.95 (m, 2H), 1.91 (s, 3H). Analytical HPLC retention time 1.130 min. Method K. MS (ESI) [M+H]$^+$=418.2.

Example 136

2-((7-fluoro-6-(8-methyl-2,3-dihydro-1H-pyrido[2,3-b][1,4]oxazin-7-yl)isoquinolin-3-yl)amino)-6-(2-hydroxyethyl)-5,6-dihydro-4H-pyrazolo[1,5-d][1,4]diazepin-7(8H)-one (Compound 145)

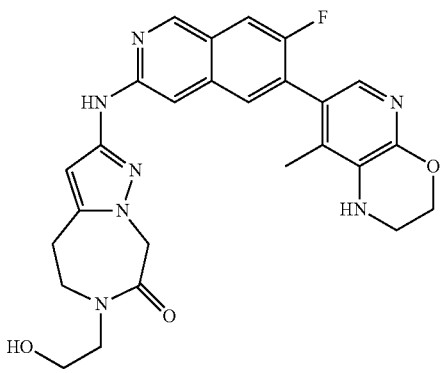 [SMILES: Cc1c(-c2cc3cc(Nc4cc5n(n4)CC(=O)N(CCO)CC5)ncc3cc2F)cnc2c1NCCO2]

Synthesized following procedures similar to those described above according to the general synthetic methods. $^1$H NMR (300 MHz, DMSO-$d_6$) δ 9.25 (s, 1H), 9.00 (s, 1H), 7.91 (s, 1H), 7.80 (d, J=10.2 Hz, 1H), 7.67 (d, 7.2 Hz, 1H), 7.38 (s, 1H), 5.99 (s, 1H), 5.71 (s, 1H), 5.00 (s, 2H), 7.81-4.79 (m, 1H), 4.32-4.30 (m, 2H), 3.90-3.88 (m, 2H), 3.51-3.46 (m, 6H), 3.09-3.06 (m, 2H), 1.94 (s, 3H). Analytical HPLC retention time 1.913 min. Method K. MS (ESI) [M+H]+=504.2.

Example 137

2-((5-fluoro-6-(8-methyl-2,3-dihydro-1H-pyrido[2,3-b][1,4]oxazin-7-yl)isoquinolin-3-yl)amino)-6-(2-hydroxyethyl)-5,6-dihydro-4H-pyrazolo[1,5-d][1,4]diazepin-7(8H)-one (Compound 146)

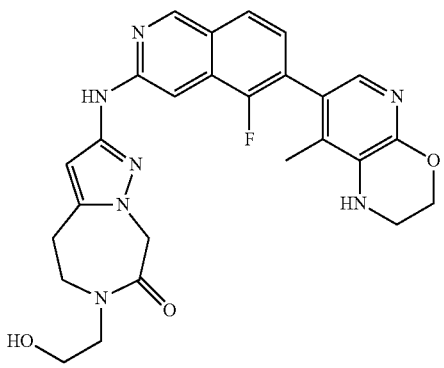 [SMILES: Cc1c(-c2ccc3cnc(Nc4cc5n(n4)CC(=O)N(CCO)CC5)cc3c2F)cnc2c1NCCO2]

Synthesized following procedures similar to those described above according to the general synthetic methods. $^1$H NMR (400 MHz, DMSO-$d_6$) δ 9.25 (s, 1H), 9.00 (s, 1H), 7.91 (s, 1H), 7.79 (d, J=10.2 Hz, 1H), 7.68 (d, J=7.2 Hz, 1H), 7.38 (s, 1H), 5.99 (s, 1H), 5.71 (s, 1H), 5.01 (s, 2H), 4.80 (t, J=5.0 Hz, 1H), 4.32-4.30 (m, 2H), 3.89-3.85 (m, 2H), 3.61-3.37 (m, 6H), 3.08-3.06 (m, 2H), 1.93 (s, 3H). Analytical HPLC retention time 1.915 min. Method K. MS (ESI) [M+H]$^+$=504.2.

Example 138

(S)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile (Compound 147a)

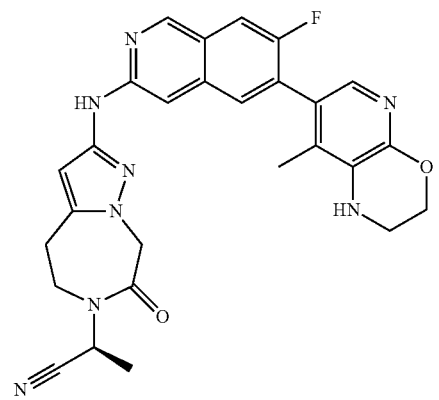 [SMILES: Cc1c(-c2cc3cc(Nc4cc5n(n4)CC(=O)N([C@@H](C)C#N)CC5)ncc3cc2F)cnc2c1NCCO2]

Synthesized following procedures similar to those described above according to the general synthetic methods. Absolute stereochemistry arbitrarily assigned. $^1$H NMR (400 MHz, DMSO-$d_6$) δ 9.30 (s, 1H), 9.00 (s, 1H), 7.92 (s, 1H), 7.79 (d, J=10.2 Hz, 1H), 7.68 (d, J=7.2 Hz, 1H), 7.38 (s, 1H), 6.03 (s, 1H), 5.71 (s, 1H), 5.47 (q, J=7.1 Hz, 1H), 5.24-4.96 (m, 2H), 4.31-4.29 (m, 2H), 4.03-4.00 (m, 2H), 3.38-3.35 (m, 2H), 3.10-3.08 (m, 2H), 1.93 (s, 3H), 1.53 (d, J=7.1 Hz, 3H). Analytical HPLC retention time 2.299 min. Method K. MS (ESI) [M+H]⁺=513.2.

(R)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile (Compound 147b)

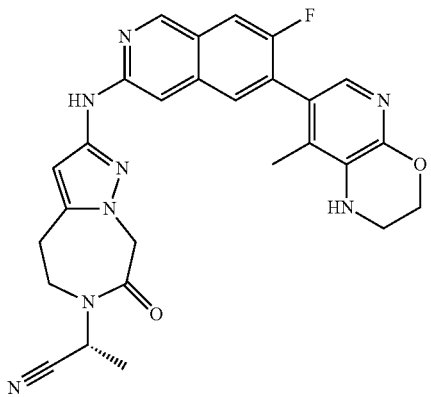 [SMILES: Cc1c(-c2cc3cc(Nc4cc5n(n4)CC(=O)N([C@H](C)C#N)CC5)ncc3cc2F)cnc2c1NCCO2]

Synthesized following procedures similar to those described above according to the general synthetic methods. Absolute stereochemistry arbitrarily assigned. ¹H NMR (400 MHz, DMSO-d₆) δ 9.30 (s, 1H), 9.00 (s, 1H), 7.92 (s, 1H), 7.79 (d, J=10.2 Hz, 1H), 7.68 (d, J=7.2 Hz, 1H), 7.38 (s, 1H), 6.03 (s, 1H), 5.71 (s, 1H), 5.47 (q, J=7.1 Hz, 1H), 5.24-4.96 (m, 2H), 4.31-4.29 (m, 2H), 4.03-4.00 (m, 2H), 3.38-3.35 (m, 2H), 3.10-3.08 (m, 2H), 1.93 (s, 3H), 1.53 (d, J=7.1 Hz, 3H). Analytical HPLC retention time 2.307 min. Method K. MS (ESI) [M+H]⁺=513.2.

Example 139

(S)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one (Compound 148a)

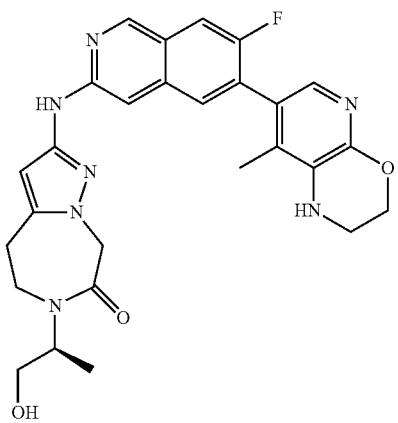 [SMILES: Cc1c(-c2cc3cc(Nc4cc5n(n4)CC(=O)N([C@@H](C)CO)CC5)ncc3cc2F)cnc2c1NCCO2]

Synthesized following procedures similar to those described above according to the general synthetic methods. Absolute stereochemistry arbitrarily assigned. ¹H NMR (300 MHz, DMSO-d₆) δ 9.24 (s, 1H), 8.99 (s, 1H), 7.91 (s, 1H), 7.79 (d, J=10.2 Hz, 1H), 7.67 (d, J=7.2 Hz, 1H), 7.38 (s, 1H), 5.97 (s, 1H), 5.70 (s, 1H), 5.00 (s, 2H), 4.78 (t, J=5.4 Hz, 1H), 4.47 (q, J=6.7 Hz, 1H), 4.31-4.30 (m, 2H), 3.81-3.79 (m, 2H), 3.48-3.40 (m, 4H), 3.11-2.96 (m, 2H), 1.93 (s, 3H), 1.08 (d, J=6.9 Hz, 3H). Analytical HPLC retention time 1.095 min. Method K. MS (ESI) [M+H]⁺=518.2.

(R)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one (Compound 148b)

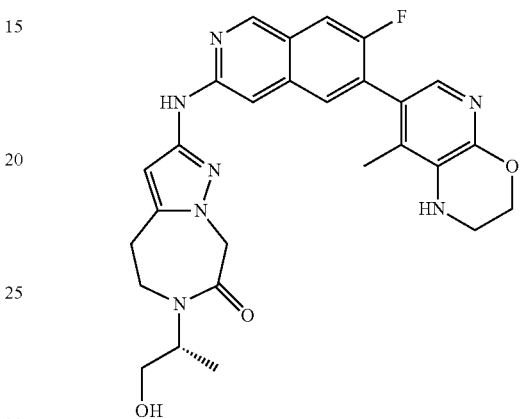

Synthesized following procedures similar to those described above according to the general synthetic methods. Absolute stereochemistry arbitrarily assigned. ¹H NMR (300 MHz, DMSO-d₆) δ 9.24 (s, 1H), 8.99 (s, 1H), 7.91 (s, 1H), 7.79 (d, J=10.2 Hz, 1H), 7.67 (d, J=7.2 Hz, 1H), 7.38 (s, 1H), 5.97 (s, 1H), 5.70 (s, 1H), 5.00 (s, 2H), 4.78 (t, J=5.4 Hz, 1H), 4.47 (q, J=6.7 Hz, 1H), 4.31-4.30 (m, 2H), 3.81-3.79 (m, 2H), 3.48-3.40 (m, 4H), 3.11-2.96 (m, 2H), 1.93 (s, 3H), 1.08 (d, J=6.9 Hz, 3H). Analytical HPLC retention time 1.095 min. Method K. MS (ESI) [M+H]⁺=518.2.

Example 140

(S)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one (Compound 149a)

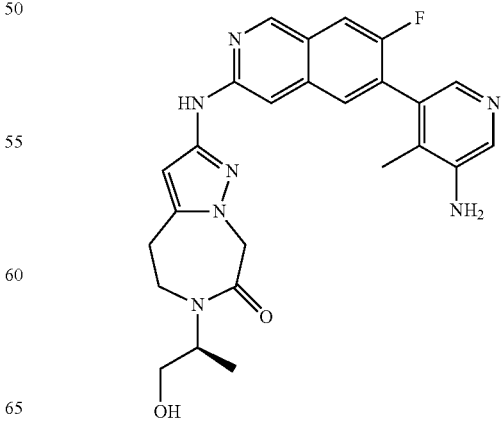

Synthesized following procedures similar to those described above according to the general synthetic methods. Absolute stereochemistry arbitrarily assigned. ¹H NMR (300 MHz, DMSO-d₆) δ 9.25 (s, 1H), 9.00 (s, 1H), 8.02 (s, 1H), 7.93 (s, 1H), 7.81 (d, J=10.1 Hz, 1H), 7.76-7.57 (m, 2H), 5.97 (s, 1H), 5.28 (s, 2H), 5.00 (d, J=2.8 Hz, 2H), 4.78 (t, J=5.4 Hz, 1H), 4.47 (q, J=6.6 Hz, 1H), 3.80 (t, J=5.9 Hz, 2H), 3.54-3.37 (m, 2H), 3.17-2.83 (m, 2H), 1.92 (s, 3H), 1.08 (d, J=6.9 Hz, 3H). Analytical HPLC retention time 1.020 min. Method K. MS (ESI) [M+H]⁺=476.2.

(R)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one (Compound 149b)

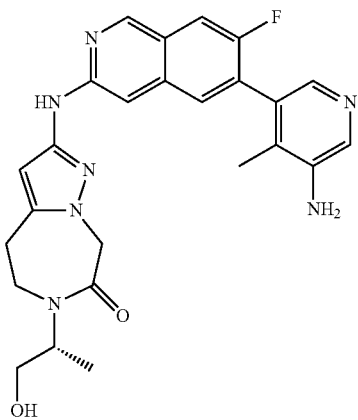 [SMILES: Cc1c(N)cncc1-c1cc2cc(Nc3cc4n(n3)CC(=O)N([C@H](C)CO)CC4)ncc2cc1F]

Synthesized following procedures similar to those described above according to the general synthetic methods. Absolute stereochemistry arbitrarily assigned. ¹H NMR (300 MHz, DMSO-d₆) δ 9.25 (s, 1H), 9.00 (s, 1H), 8.02 (s, 1H), 7.93 (s, 1H), 7.81 (d, J=10.1 Hz, 1H), 7.76-7.57 (m, 2H), 5.97 (s, 1H), 5.28 (s, 2H), 5.00 (d, J=2.8 Hz, 2H), 4.78 (t, J=5.4 Hz, 1H), 4.47 (q, J=6.6 Hz, 1H), 3.80 (t, J=5.9 Hz, 2H), 3.54-3.37 (m, 2H), 3.17-2.83 (m, 2H), 1.92 (s, 3H), 1.08 (d, J=6.9 Hz, 3H). Analytical HPLC retention time 1.728 min. Method K. MS (ESI) [M+H]⁺=476.2.

Example 141

N-(7-fluoro-6-(8-methyl-2,3-dihydro-1H-pyrido[2,3-b][1,4]oxazin-7-yl)isoquinolin-3-yl)-5,6-dihydro-11H-pyrazolo[1,5-d][1,2,4]triazolo[4,3-a][1,4]diazepin-8-amine (Compound 151)

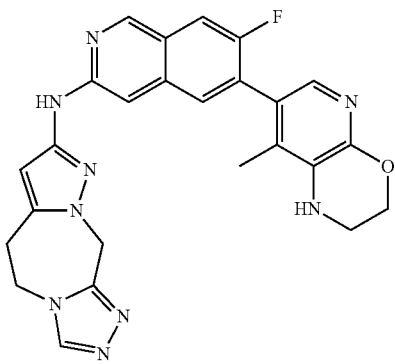 [SMILES: Cc1c(-c2cc3cc(Nc4cc5n(n4)Cc4nncn4CC5)ncc3cc2F)cnc2c1NCCO2]

Synthesized following procedures similar to those described above according to the general synthetic methods. ¹H NMR (300 MHz, DMSO-d₆) δ 9.37 (s, 1H), 9.01 (s, 1H), 8.56 (s, 1H), 7.95 (s, 1H), 7.81 (d, J=10.2 Hz, 1H), 7.70 (d, J=7.1 Hz, 1H), 7.41 (s, 1H), 6.12 (s, 1H), 5.59 (s, 2H), 4.52-4.22 (m, 4H), 3.90-3.62 (s, 3H), 3.49-3.24 (m, 2H), 1.95 (d, J=1.8 Hz, 3H). Analytical HPLC retention time 1.907 min. Method K. MS (ESI) [M+H]⁺=484.2.

Example 142

2-((6-(5-amino-4-methylpyridin-3-yl)-5-chloroisoquinolin-3-yl)amino)-6-isopropyl-5,6-dihydro-4H-pyrazolo[1,5-d][1,4]diazepin-7(8H)-one (Compound 152)

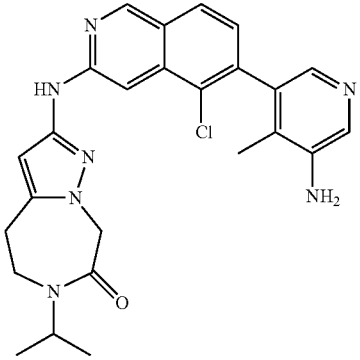 [SMILES: Cc1c(N)cncc1-c1ccc2cnc(Nc3cc4n(n3)CC(=O)N(C(C)C)CC4)cc2c1Cl]

Synthesized following procedures similar to those described above according to the general synthetic methods. ¹H NMR (400 MHz, DMSO-d₆) δ 9.56 (s, 1H), 9.09 (s, 1H), 8.16 (s, 1H), 8.05-7.92 (m, 2H), 7.60 (s, 1H), 7.16 (d, J=8.2 Hz, 1H), 6.06 (s, 1H), 5.28 (s, 2H), 4.98 (d, J=2.4 Hz, 2H), 4.65-4.50 (m, 1H), 3.85-3.68 (m, 2H), 3.01 (t, J=5.9 Hz, 2H), 1.83 (s, 3H), 1.13 (d, J=6.8 Hz, 6H). Analytical HPLC retention time 1.211 min. Method K. MS (ESI) [M+H]⁺=476.2.

Example 143

(R)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one (Compound 153a)

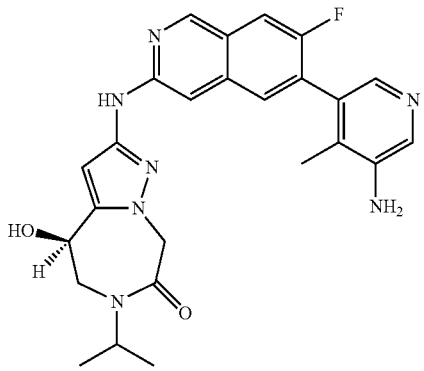 [SMILES: Cc1c(N)cncc1-c1cc2cc(Nc3cc4n(n3)CC(=O)N(C(C)C)C[C@H]4O)ncc2cc1F]

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 8.00 (s, 1H), 7.91 (s, 1H), 7.79 (d, J=10.1 Hz, 1H), 7.72-7.70 (m, 2H), 6.21 (s, 1H), 5.83 (d, J=6.2 Hz, 1H), 5.29-5.27 (m, 2H), 5.16 (d, J=15.0 Hz, 1H), 4.79-4.69 (m, 2H), 4.58-4.39 (m, 1H), 3.88-3.49 (m, 2H), 1.90 (s, 3H), 1.13-1.10 (m, 6H). Analytical HPLC retention time 1.074 min. Method K. MS (ESI) [M+H]$^+$=476.2.

(S)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one (Compound 153b)

Synthesized following procedures similar to those described above according to the general synthetic methods. Absolute stereochemistry arbitrarily assigned. $^1$H NMR (300 MHz, DMSO-d$_6$) δ 9.28 (s, 1H), 8.98 (s, 1H), 8.00 (s, 1H), 7.92 (s, 1H), 7.79 (d, J=10.1 Hz, 1H), 7.72-7.70 (m, 2H), 6.01 (s, 1H), 5.58-5.33 (m, 1H), 5.26 (s, 2H), 5.14-4.95 (m, 2H), 4.05-3.98 (m, 2H), 3.12-3.08 (m, 2H), 1.90 (s, 3H), 1.50 (d, J=7.2 Hz, 3H). Analytical HPLC retention time 1.120 min. Method K. MS (ESI) [M+H]$^+$=471.2.

(R)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile (Compound 154b)

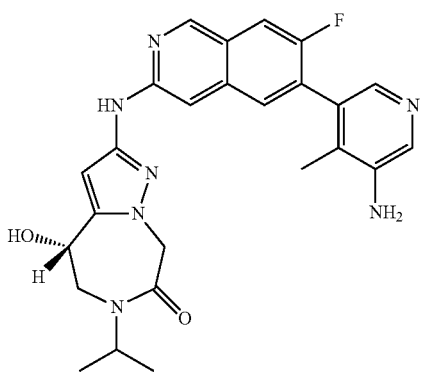 [SMILES: Cc1c(N)cncc1-c1cc2cc(Nc3cc4n(n3)CC(=O)N(C(C)C)C[C@@H]4O)ncc2cc1F]

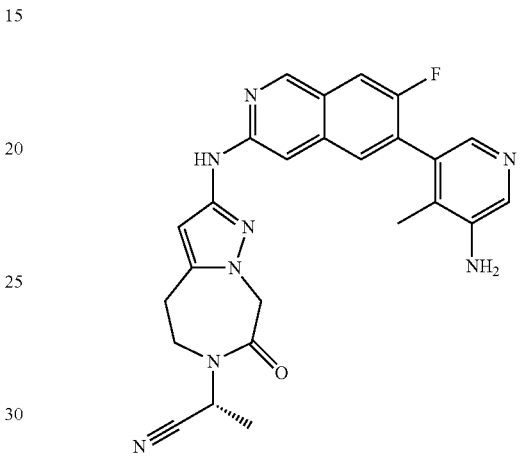

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 8.00 (s, 1H), 7.91 (s, 1H), 7.79 (d, J=10.1 Hz, 1H), 7.72-7.70 (m, 2H), 6.21 (s, 1H), 5.83 (d, J=6.2 Hz, 1H), 5.29-5.27 (m, 2H), 5.16 (d, J=15.0 Hz, 1H), 4.79-4.69 (m, 2H), 4.58-4.39 (m, 1H), 3.88-3.49 (m, 2H), 1.90 (s, 3H), 1.13-1.10 (m, 6H). Analytical HPLC retention time 1.074 min. Method K. MS (ESI) [M+H]$^+$=476.2.

Example 144

(S)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile (Compound 154a)

Synthesized following procedures similar to those described above according to the general synthetic methods. Absolute stereochemistry arbitrarily assigned. $^1$H NMR (300 MHz, DMSO-d$_6$) δ 9.28 (s, 1H), 8.98 (s, 1H), 8.00 (s, 1H), 7.92 (s, 1H), 7.79 (d, J=10.1 Hz, 1H), 7.72-7.70 (m, 2H), 6.01 (s, 1H), 5.58-5.33 (m, 1H), 5.26 (s, 2H), 5.14-4.95 (m, 2H), 4.05-3.98 (m, 2H), 3.12-3.08 (m, 2H), 1.90 (s, 3H), 1.50 (d, J=7.2 Hz, 3H). Analytical HPLC retention time 1.111 min. Method K. MS (ESI) [M+H]$^+$=471.2.

Example 145

2-((7-fluoro-6-(8-methyl-2,3-dihydro-1H-pyrido[2,3-b][1,4]oxazin-7-yl)isoquinolin-3-yl)amino)-6-(2-methoxyethyl)-5,6-dihydro-4H-pyrazolo[1,5-d][1,4]diazepin-7(8H)-one (Compound 155)

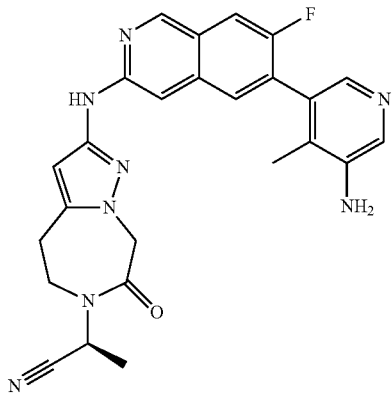 [SMILES: Cc1c(N)cncc1-c1cc2cc(Nc3cc4n(n3)CC(=O)N([C@@H](C)C#N)CC4)ncc2cc1F]

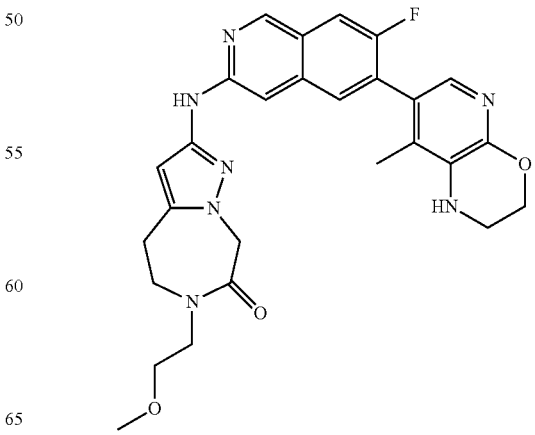

Synthesized following procedures similar to those described above according to the general synthetic methods. ¹H NMR (400 MHz, DMSO-d₆) δ 9.23 (s, 1H), 8.98 (s, 1H), 7.90 (s, 1H), 7.78 (d, J=10.1 Hz, 1H), 7.67 (d, J=7.2 Hz, 1H), 7.37 (s, 1H), 5.99 (s, 1H), 5.69 (s, 1H), 5.00 (s, 2H), 4.30 (t, J=4.4 Hz, 2H), 3.96-3.78 (m, 2H), 3.56 (t, J=5.4 Hz, 2H), 3.45 (t, J=5.4 Hz, 2H), 3.37-3.35 (m, 2H), 3.26 (s, 3H), 3.08-2.99 (m, 2H), 1.92 (s, 3H). Analytical HPLC retention time 2.095 min. Method K. MS (ESI) [M+H]⁺=518.2.

Example 146

2-((6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one (Compound 156)

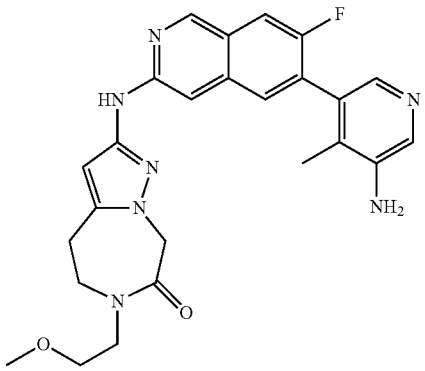 [SMILES: COCCN1CCc2cc(Nc3cc4cc(-c5cncc(N)c5C)c(F)cc4cn3)nn2CC1=O]

Synthesized following procedures similar to those described above according to the general synthetic methods. ¹H NMR (400 MHz, DMSO-d₆) δ 9.25 (s, 1H), 9.00 (s, 1H), 8.02 (s, 1H), 7.92 (s, 1H), 7.80 (d, J=10.0 Hz, 1H), 7.73-7.66 (m, 2H), 5.99 (s, 1H), 5.27 (s, 2H), 5.00 (s, 2H), 3.96-3.77 (m, 2H), 3.56 (t, J=5.4 Hz, 2H), 3.45 (t, J=5.4 Hz, 2H), 3.26 (s, 3H), 3.12-2.96 (m, 2H), 1.92 (s, 3H). Analytical HPLC retention time 1.090 min. Method K. MS (ESI) [M+H]⁺=476.2.

Example 147

N-(6-(5-amino-4-methylpyridin-3-yl)-7,8-difluoroisoquinolin-3-yl)-5,6-dihydro-11H-imidazo[1,2-a]pyrazolo[1,5-d][1,4]diazepin-8-amine (Compound 157)

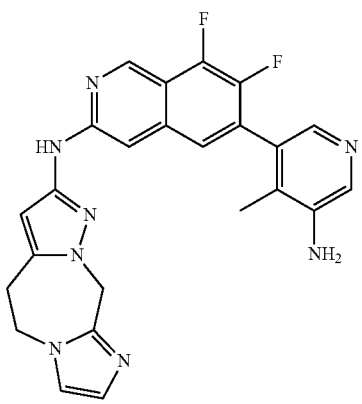 [SMILES: Cc1c(N)cncc1-c1cc2cc(Nc3cc4n(n3)Cc3nccn3CC4)ncc2c(F)c1F]

Synthesized following procedures similar to those described above according to the general synthetic methods. ¹H NMR (300 MHz, DMSO-d₆) δ 9.53 (s, 1H), 9.18 (s, 1H), 8.04 (s, 1H), 7.99 (s, 1H), 7.72 (s, 1H), 7.58 (d, J=6.0 Hz, 1H), 7.22 (s, 1H), 6.85 (s, 1H), 6.08 (s, 1H), 5.43 (s, 2H), 5.33 (s, 2H), 4.37-4.34 (m, 2H), 3.22-3.15 (m, 2H), 1.95 (s, 3H). Analytical HPLC retention time 1.803 min. Method K. MS (ESI) [M+H]⁺=459.2.

Example 148

2-((6-(5-amino-4-methylpyridin-3-yl)-7-fluoroisoquinolin-3-yl)amino)-6-(2-hydroxy-2-methylpropyl)-5,6-dihydro-4H-pyrazolo[1,5-d][1,4]diazepin-7(8H)-one (Compound 158)

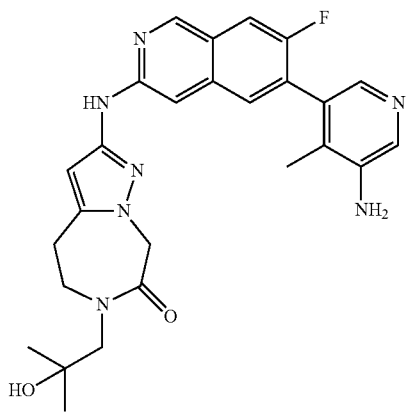 [SMILES: Cc1c(N)cncc1-c1cc2cc(Nc3cc4n(n3)CC(=O)N(CC(C)(C)O)CC4)ncc2cc1F]

Synthesized following procedures similar to those described above according to the general synthetic methods. ¹H NMR (300 MHz, CD₃OD) δ 8.95 (s, 1H), 8.04 (s, 1H), 7.83 (s, 1H), 7.77 (s, 1H), 7.67-7.64 (m, 2H), 6.07 (s, 1H), 5.12 (s, 2H), 4.27-3.95 (m, 2H), 3.52 (s, 2H), 3.26-3.24 (m, 2H), 2.06 (s, 3H), 1.20 (s, 6H). Analytical HPLC retention time 1.940 min. Method M. MS (ESI) [M+H]⁺=490.2.

Example 149

2-((6-(5-amino-4-methylpyridin-3-yl)-7-fluoroisoquinolin-3-yl)amino)-6-(2-hydroxyethyl)-5,6-dihydro-4H-pyrazolo[1,5-d][1,4]diazepin-7(8H)-one (Compound 159)

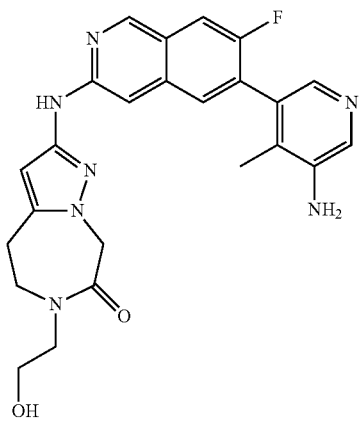 [SMILES: Cc1c(N)cncc1-c1cc2cc(Nc3cc4n(n3)CC(=O)N(CCO)CC4)ncc2cc1F]

Synthesized following procedures similar to those described above according to the general synthetic methods. ¹H NMR (400 MHz, DMSO-d₆) δ 9.26 (s, 1H), 9.00 (s, 1H), 8.02 (s, 1H), 7.93 (s, 1H), 7.81 (d, J=10.0 Hz, 1H), 7.72-7.70 (m, 2H), 5.99 (s, 1H), 5.28 (s, 2H), 4.99 (s, 2H), 4.79 (t, J=5.2 Hz, 1H), 3.88 (t, J=5.2 Hz, 2H), 3.54-3.46 (m, 4H), 3.07 (t, J=5.2 Hz, 2H), 1.92 (s, 3H). Analytical HPLC retention time 1.675 min. Method K. MS (ESI) [M+H]⁺=462.2.

Example 150

2-((7-fluoro-6-(8-methyl-2,3-dihydro-1H-pyrido[2,3-b][1,4]oxazin-7-yl)isoquinolin-3-yl)amino)-5,6-dihydro-4H-pyrazolo[1,5-d][1,4]diazepin-7(8H)-one (Compound 160)

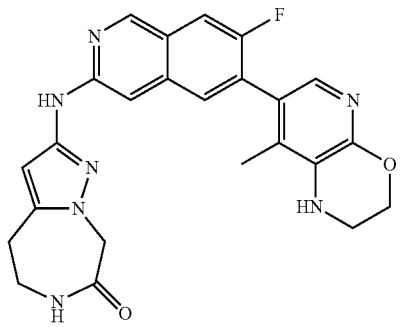 [SMILES: Cc1c(-c2cc3cc(Nc4cc5n(n4)CC(=O)NCC5)ncc3cc2F)cnc2c1NCCO2]

Synthesized following procedures similar to those described above according to the general synthetic methods. ¹H NMR (400 MHz, DMSO-d₆) δ 9.24 (s, 1H), 8.98 (s, 1H), 8.14 (t, J=6.0 Hz, 1H), 7.89 (s, 1H), 7.78 (d, J=10.4 Hz, 1H), 7.66 (d, J=7.2 Hz, 1H), 7.37 (s, 1H), 5.99 (s, 1H), 5.69 (s, 1H), 4.89 (s, 2H), 4.29 (t, J=4.0 Hz, 2H), 3.55-3.51 (m, 2H), 3.40-3.37 (m, 2H), 2.98-2.96 (m, 2H), 1.92 (s, 3H). Analytical HPLC retention time 1.782 min. Method K. MS (ESI) [M+H]⁺=460.1.

Example 151

N-(7,8-difluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine (Compound 161)

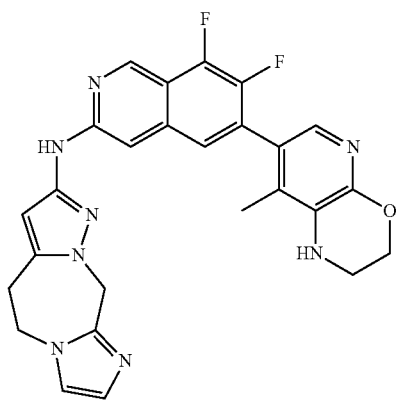 [SMILES: Cc1c(-c2cc3cc(Nc4cc5n(n4)Cc4nccn4CC5)ncc3c(F)c2F)cnc2c1NCCO2]

Synthesized following procedures similar to those described above according to the general synthetic methods. ¹H NMR (300 MHz, DMSO-d₆) δ 9.52 (s, 1H), 9.17 (s, 1H), 7.97 (s, 1H), 7.55 (d, J=5.7 Hz, 1H), 7.40 (s, 1H), 7.22 (s, 1H), 6.85 (s, 1H), 6.08 (s, 1H), 5.77-5.75 (m, 1H), 5.44 (s, 2H), 4.38-4.31 (m, 4H), 3.40-3.37 (m, 2H), 3.27-3.23 (m, 2H), 1.95 (s, 3H). Analytical HPLC retention time 1.710 min. Method K. MS (ESI) [M+H]⁺=501.2.

Example 152

2-((6-(1,8-dimethyl-2,3-dihydro-1H-pyrido[2,3-b][1,4]oxazin-7-yl)-7-fluoroisoquinolin-3-yl)amino)-6-methyl-5,6-dihydro-4H-pyrazolo[1,5-d][1,4]diazepin-7(8H)-one (Compound 162)

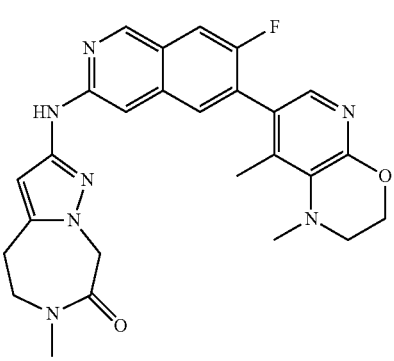 [SMILES: Cc1c(-c2cc3cc(Nc4cc5n(n4)CC(=O)N(C)CC5)ncc3cc2F)cnc2c1N(C)CCO2]

Synthesized following procedures similar to those described above according to the general synthetic methods. ¹H NMR (300 MHz, DMSO-d₆) δ 9.27 (s, 1H), 8.99 (s, 1H), 7.91 (s, 1H), 7.85-7.77 (m, 2H), 7.70 (d, J=6.0 Hz, 1H), 5.97 (s, 1H), 4.97 (s, 2H), 4.36-4.35 (m, 2H), 3.83-3.79 (m, 2H), 3.11-3.03 (m, 4H), 2.94 (s, 3H), 2.72 (s, 3H), 2.11 (s, 3H). Analytical HPLC retention time 1.556 min. Method K. MS (ESI) [M+H]⁺=488.2.

Example 153

N-(6-(5-amino-4-methylpyridin-3-yl)-7-fluoroisoquinolin-3-yl)-3-methyl-5,6-dihydro-11H-imidazo[1,2-a]pyrazolo[1,5-d][1,4]diazepin-8-amine (Compound 163)

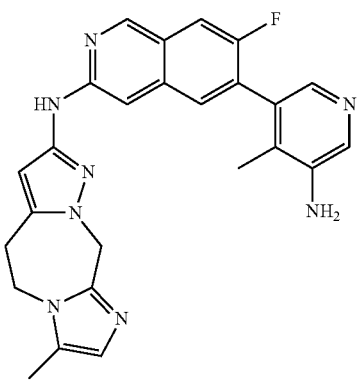 [SMILES: Cc1c(N)cncc1-c1cc2cc(Nc3cc4n(n3)Cc3ncc(C)n3CC4)ncc2cc1F]

Synthesized following procedures similar to those described above according to the general synthetic methods. ¹H NMR (400 MHz, CD₃OD) δ 8.94 (s, 1H), 8.04 (s, 1H), 7.82 (s, 1H), 7.76 (s, 1H), 7.68 (d, J=9.6 Hz, 1H), 7.64 (d, J=6.8 Hz, 1H), 6.67 (s, 1H), 6.13 (s, 1H), 5.44 (s, 2H), 4.28-4.25 (m, 2H), 3.36-3.32 (m, 2H), 2.25 (s, 3H), 2.06 (s, 3H). Analytical HPLC retention time 0.958. Method K. MS (ESI) [M+H]⁺=455.2.

Example 154

2-((6-(5-amino-4-methylpyridin-3-yl)-7-fluoroiso-quinolin-3-yl)amino)-6-(2-(3-fluoroazetidin-1-yl)ethyl)-5,6-dihydro-4H-pyrazolo[1,5-d][1,4]diazepin-7(8H)-one (Compound 164)

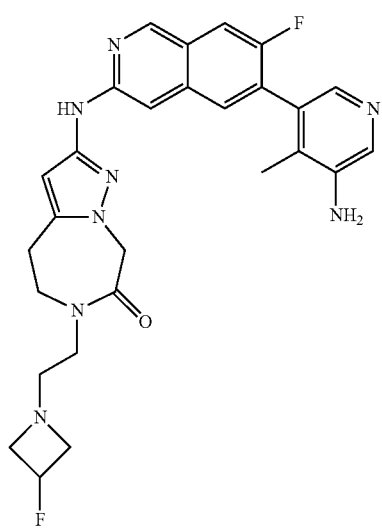 [SMILES: Cc1c(N)cncc1-c1cc2cc(Nc3cc4n(n3)CC(=O)N(CCN3CC(F)C3)CC4)ncc2cc1F]

Synthesized following procedures similar to those described above according to the general synthetic methods. ¹H NMR (400 MHz, DMSO-d₆) δ 9.26 (s, 1H), 9.00 (s, 1H), 8.02 (s, 1H), 7.92 (s, 1H), 7.81 (d, J=8.0 Hz, 1H), 7.71-7.70 (m, 2H), 5.99 (s, 1H), 5.28 (s, 2H), 5.24-5.04 (m, 1H), 4.99 (s, 2H), 3.83 (t, J=4.0 Hz, 2H), 3.62-3.54 (m, 2H), 3.36-3.33 (m, 2H), 3.16-3.04 (m, 4H), 2.59 (t, J=4.0 Hz, 2H), 1.92 (s, 3H). Analytical HPLC retention time 1.477 min. Method K. MS (ESI) [M+H]⁺=519.2.

Example 155

2-((6-(5-amino-4-methylpyridin-3-yl)-7-fluoroiso-quinolin-3-yl)amino)-6-(2-(3-hydroxyazetidin-1-yl)ethyl)-5,6-dihydro-4H-pyrazolo[1,5-d][1,4]diazepin-7(8H)-one (Compound 165)

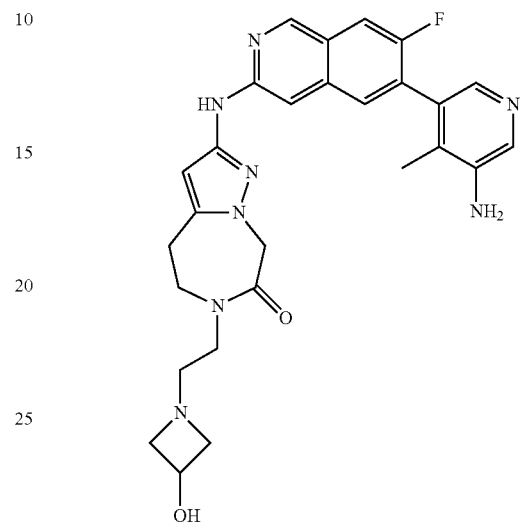

Synthesized following procedures similar to those described above according to the general synthetic methods. ¹H NMR (400 MHz, DMSO-d₆) δ 9.26 (s, 1H), 9.00 (s, 1H), 8.02 (s, 1H), 7.92 (s, 1H), 7.81 (d, J=10.1 Hz, 1H), 7.74-7.64 (m, 2H), 5.99 (s, 1H), 5.35-5.20 (m, 3H), 4.98 (s, 2H), 4.15-4.12 (m, 1H), 3.83 (t, J=6.0 Hz, 2H), 3.55-3.51 (m, 2H), 3.34-3.30 (m, 4H), 3.06 (t, J=6.0 Hz, 2H), 2.71-2.69 (m, 2H), 1.92 (s, 3H). Analytical HPLC retention time 0.921 min. Method K. MS (ESI) [M+H]⁺=259.2.

Example 156

N-(6-(5-amino-4-methylpyridin-3-yl)-7-fluoroiso-quinolin-3-yl)-3,3-dimethyl-5,6-dihydro-3H,11H-[1,2,4]oxadiazolo[4,3-a]pyrazolo[1,5-d][1,4]diazepin-8-amine (Compound 166)

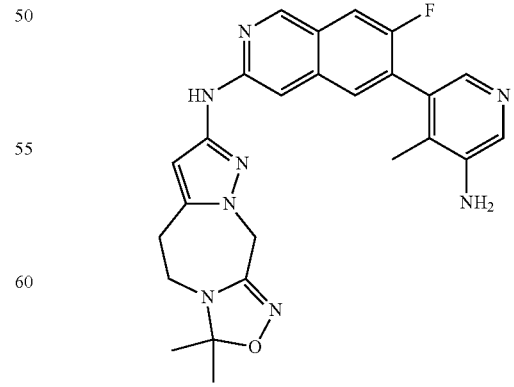

Synthesized following procedures similar to those described above according to the general synthetic methods.

¹H NMR (300 MHz, DMSO-d₆) δ 9.34 (s, 1H), 9.01 (s, 1H), 8.01 (s, 1H), 7.94 (s, 1H), 7.82 (d, J=12 Hz, 1H), 7.71-7.70 (m, 2H), 6.05 (s, 1H), 5.28 (s, 2H), 5.00 (s, 2H), 3.37-3.33 (m, 2H), 3.12 (t, J=6.0 Hz, 2H), 1.92 (s, 3H), 1.29 (s, 6H). Analytical HPLC retention time 2.202 min. Method K. MS (ESI) [M+H]⁺=473.2.

Example 157

(R)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one (Compound 167a)

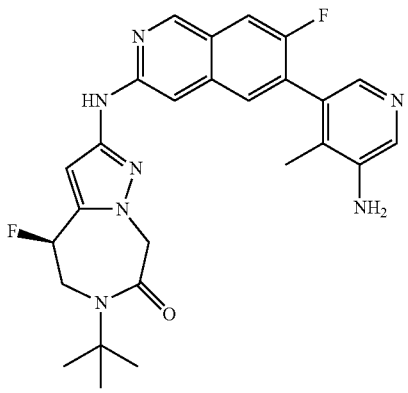 [SMILES: Cc1c(N)cncc1-c1cc2cc(Nc3cc4n(n3)CC(=O)N(C(C)(C)C)C[C@H]4F)ncc2cc1F]

Synthesized following procedures similar to those described above according to the general synthetic methods. Absolute stereochemistry arbitrarily assigned. ¹H NMR (300 MHz, DMSO-d₆) δ 9.44 (s, 1H), 9.04 (s, 1H), 8.03 (s, 1H), 7.90 (s, 1H), 7.83 (d, J=10.2 Hz, 1H), 7.75 (d, J=7.3 Hz, 1H), 7.72 (s, 1H), 6.41 (s, 1H), 5.92-5.76 (m, 1H), 5.29 (s, 2H), 5.22-4.85 (m, 2H), 4.26-4.12 (m, 2H), 1.93 (s, 3H), 1.40 (s, 9H). Analytical HPLC retention time 1.172 min. Method L. MS (ESI) [M+H]⁺=492.1.

(S)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one (Compound 167b)

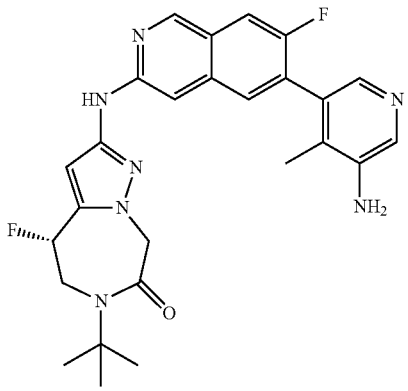 [SMILES: Cc1c(N)cncc1-c1cc2cc(Nc3cc4n(n3)CC(=O)N(C(C)(C)C)C[C@@H]4F)ncc2cc1F]

Synthesized following procedures similar to those described above according to the general synthetic methods. Absolute stereochemistry arbitrarily assigned. Absolute stereochemistry arbitrarily assigned. ¹H NMR (300 MHz, DMSO-d₆) δ 9.44 (s, 1H), 9.04 (s, 1H), 8.03 (s, 1H), 7.90 (s, 1H), 7.83 (d, J=10.2 Hz, 1H), 7.75 (d, J=7.3 Hz, 1H), 7.72 (s, 1H), 6.41 (s, 1H), 5.92-5.76 (m, 1H), 5.29 (s, 2H), 5.22-4.85 (m, 2H), 4.26-4.12 (m, 2H), 1.93 (s, 3H), 1.40 (s, 9H). Analytical HPLC retention time 1.177 min. Method L. MS (ESI) [M+H]⁺=492.1.

Example 158

N-(6-(5-amino-4-methylpyridin-3-yl)-8-fluoroisoquinolin-3-yl)-5,6-dihydro-1H-imidazo[1,2-a]pyrazolo[1,5-d][1,4]diazepin-8-amine (Compound 168)

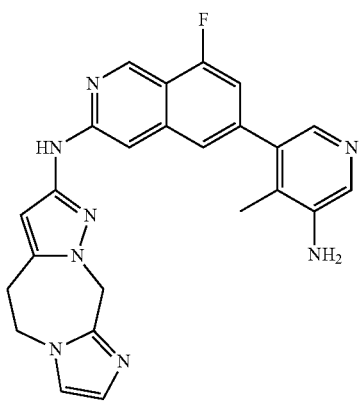 [SMILES: Cc1c(N)cncc1-c1cc(F)c2cnc(Nc3cc4n(n3)Cc3nccn3CC4)cc2c1]

Synthesized following procedures similar to those described above according to the general synthetic methods. ¹H NMR (300 MHz, DMSO-d₆) δ 9.52 (s, 1H), 9.14 (s, 1H), 7.99 (s, 1H), 7.94 (s, 1H), 7.72 (s, 1H), 7.49 (s, 1H), 7.22 (d, J=1.2 Hz, 1H), 7.04 (d, J=9.0 Hz, 1H), 6.85 (d, J=1.2 Hz, 1H), 6.11 (s, 1H), 5.44 (s, 2H), 5.28 (s, 2H), 4.36 (t, J=6.0 Hz, 2H), 3.25 (t, J=6.0 Hz, 2H), 2.03 (s, 3H). Analytical HPLC retention time 0.997 min. Method K. MS (ESI) [M+H]⁺=441.2.

Example 159

6-(5-amino-4-methylpyridin-3-yl)-3-((6-isopropyl-7-oxo-5,6,7,8-tetrahydro-4H-pyrazolo[1,5-d][1,4]diazepin-2-yl)amino)isoquinoline-7-carbonitrile (Compound 169)

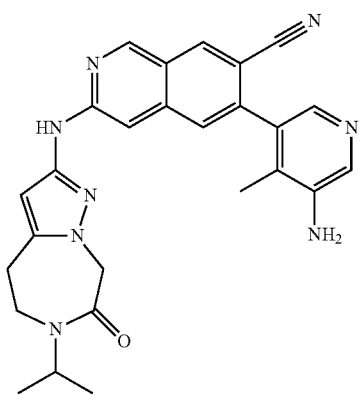 [SMILES: Cc1c(N)cncc1-c1cc2cc(Nc3cc4n(n3)CC(=O)N(C(C)C)CC4)ncc2cc1C#N]

Synthesized following procedures similar to those described above according to the general synthetic methods. ¹H NMR (300 MHz, DMSO-d₆) δ 9.74 (s, 1H), 9.13 (s, 1H), 8.62 (s, 1H), 8.04 (s, 1H), 7.92 (s, 1H), 7.74 (s, 1H), 7.68 (s, 1H), 6.04 (s, 1H), 5.35 (s, 2H), 5.01 (s, 2H), 4.62-4.57 (m, 1H), 3.79 (t, J=6.0 Hz, 2H), 3.00 (t, J=6.0 Hz, 2H), 1.93 (s, 3H), 1.12 (d, J=6.6 Hz, 6H). Analytical HPLC retention time 1.236 min. Method K. MS (ESI) [M+H]⁺=467.2.

Example 160

(+/−)-8-((6-(5-amino-4-methylpyridin-3-yl)-7,8-difluoroisoquinolin-3-yl)amino)-5,6-dihydro-11H-imidazo[1,2-a]pyrazolo[1,5-d][1,4]diazepin-6-ol (Compound 170)

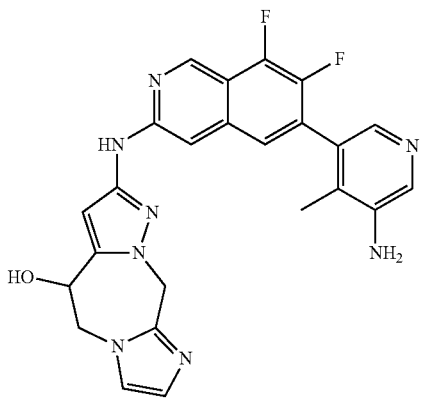 [SMILES: Cc1c(N)cncc1-c1cc2cc(Nc3cc4n(n3)Cc3nccn3CC4O)ncc2c(F)c1F]

Synthesized following procedures similar to those described above according to the general synthetic methods. ¹H NMR (300 MHz, DMSO-d₆) δ 9.58 (s, 1H), 9.19 (s, 1H), 8.04 (s, 1H), 8.00 (s, 1H), 7.73 (s, 1H), 7.59 (d, J=6.0 Hz, 1H), 7.24 (s, 1H), 6.84 (s, 1H), 6.24 (s, 1H), 5.99 (d, J=6.0 Hz, 1H), 5.43 (s, 2H), 5.33 (s, 2H), 5.05 (s, 1H), 4.50-4.34 (m, 2H), 1.95 (s, 3H). Analytical HPLC retention time 1.678 min. Method K. MS (ESI) [M+H]⁺=475.2.

Example 161

N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)acetamide (Compound 171)

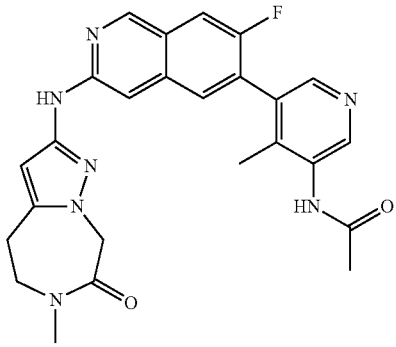 [SMILES: CC(=O)Nc1cncc(-c2cc3cc(Nc4cc5n(n4)CC(=O)N(C)CC5)ncc3cc2F)c1C]

Synthesized following procedures similar to those described above according to the general synthetic methods. ¹H NMR (300 MHz, DMSO-d₆) δ 9.66 (s, 1H), 9.28 (s, 1H), 9.02 (s, 1H), 8.62 (s, 1H), 8.31 (s, 1H), 7.94 (s, 1H), 7.85 (d, J=10.2 Hz, 1H), 7.79 (d, J=6.9 Hz, 1H), 6.00 (s, 1H), 4.99 (s, 2H), 3.83 (t, J=6.0 Hz, 2H), 3.05 (t, J=6.0 Hz, 2H), 2.95 (s, 3H), 2.12 (s, 3H), 2.08 (s, 3H). Analytical HPLC retention time 1.039 min. Method K. MS (ESI) [M+H]⁺=474.2

Example 162

N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)methanesulfonamide (Compound 172)

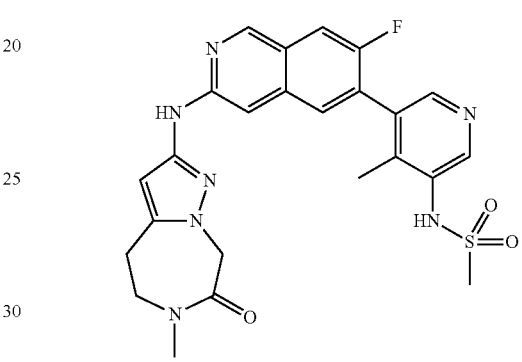

Synthesized following procedures similar to those described above according to the general synthetic methods. ¹H NMR (400 MHz, DMSO-d₆) δ 9.53 (s, 1H), 9.31 (s, 1H), 9.03 (s, 1H), 8.55 (s, 1H), 8.39 (s, 1H), 7.95 (s, 1H), 7.86 (d, J=10.4 Hz, 1H), 7.82 (d, J=8.0 Hz, 1H), 5.99 (s, 1H), 4.99 (s, 2H), 3.83 (t, J=5.6 Hz, 2H), 3.12 (s, 3H), 3.05 (t, J=5.6 Hz, 2H), 2.95 (s, 3H), 2.20 (s, 3H). Analytical HPLC retention time 1.117 min. Method K. MS (ESI) [M+H]⁺=510.2.

Example 163

6-(7-fluoro-3-((6-methyl-7-oxo-5,6,7,8-tetrahydro-4H-pyrazolo[1,5-d][1,4]diazepin-2-yl)amino)isoquinolin-6-yl)-5-methylbenzo[d]oxazol-2(3H)-one (Compound 173)

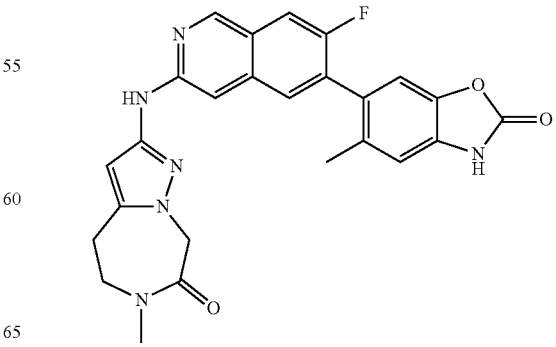

Synthesized following procedures similar to those described above according to the general synthetic methods. ¹H NMR (300 MHz, DMSO-d₆) δ 11.73 (s, 1H), 9.27 (s, 1H), 9.00 (s, 1H), 7.92 (s, 1H), 7.80 (d, J=12.0 Hz, 1H), 7.69 (d, J=6.0 Hz, 1H), 7.26 (s, 1H), 7.08 (s, 1H), 5.99 (s, 1H), 4.99 (s, 2H), 3.83 (t, J=6.0 Hz, 2H), 3.05 (t, J=6.0 Hz, 2H), 2.96 (s, 3H), 2.17 (s, 3H). Analytical HPLC retention time 1.299 min. Method K MS (ESI) [M+H]⁺=473.2.

Example 164

2-((5-fluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one (Compound 174)

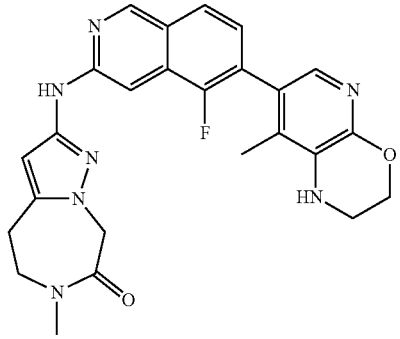 [SMILES: Cc1c(-c2ccc3cnc(Nc4cc5n(n4)CC(=O)N(C)CC5)cc3c2F)cnc2c1NCCO2]

Synthesized following procedures similar to those described above according to the general synthetic methods. ¹H NMR (400 MHz, DMSO-d₆) δ 9.49 (s, 1H), 9.08 (s, 1H), 7.92 (s, 1H), 7.81 (d, J=8.4 Hz, 1H), 7.38 (s, 1H), 7.16-7.12 (m, 1H), 6.04 (s, 1H), 4.97 (s, 2H), 4.31 (t, J=4.0 Hz, 2H), 3.83 (t, J=5.6 Hz, 2H), 3.37-3.35 (m, 2H), 3.06 (t, J=5.6 Hz, 2H), 2.96 (s, 3H), 1.94 (s, 3H). Analytical HPLC retention time 1.116 min. Method K. MS (ESI) [M+H]⁺=474.2.

Example 165

2-((7-fluoro-6-(7-methyl-1H-imidazo[4,5-b]pyridin-6-yl)isoquinolin-3-yl)amino)-6-methyl-5,6-dihydro-4H-pyrazolo[1,5-d][1,4]diazepin-7(8H)-one (Compound 175)

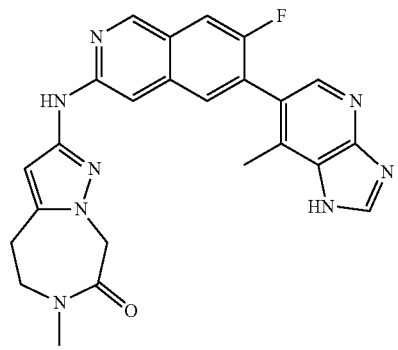 [SMILES: Cc1c(-c2cc3cc(Nc4cc5n(n4)CC(=O)N(C)CC5)ncc3cc2F)cnc2nc[nH]c12]

Synthesized following procedures similar to those escribed above according to the general synthetic methods.

¹H NMR (300 MHz, DMSO-d6) δ 12.79 (s, 1H), 8.99 (s, 1H), 8.81 (s, 1H), 8.37 (s, 1H), 8.24 (s, 1H), 7.84-7.69 (m, 3H), 6.05 (s, 1H), 4.95 (s, 2H), 3.85-3.75 (m, 2H), 3.10-3.02 (m, 2H), 3.00 (s, 3H), 2.45 (s, 3H). Analytical HPLC retention time 1.061 min.
Method K. MS (ESI) [M+H]⁺=457.2.

Example 166

2-((6-(3,3-difluoro-8-methyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one (Compound 176)

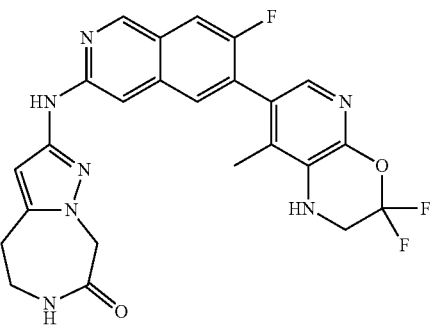 [SMILES: Cc1c(-c2cc3cc(Nc4cc5n(n4)CC(=O)NCC5)ncc3cc2F)cnc2c1NCC(F)(F)O2]

Synthesized following procedures similar to those described above according to the general synthetic methods. ¹H NMR (300 MHz, DMSO-d₆) δ 9.29 (s, 1H), 9.02 (s, 1H), 8.16 (t, J=5.9 Hz, 1H), 7.93 (s, 1H), 7.83 (d, J=10.1 Hz, 1H), 7.75 (d, J=7.1 Hz, 1H), 7.63 (s, 1H), 6.37 (s, 1H), 6.00 (s, 1H), 4.90 (s, 2H), 3.79-3.69 (s, 2H), 3.59-3.49 (m, 2H), 2.98 (t, J=5.7 Hz, 2H), 2.04 (d, J=1.7 Hz, 3H). Analytical HPLC retention time 2.120 min. Method K. MS (ESI) [M+H]⁺=496.2.

Example 167

2-((7-fluoro-6-(8-methyl-4,4-dioxido-2,3-dihydro-1H-pyrido[2,3-b][1,4]thiazin-7-yl)isoquinolin-3-yl)amino)-6-methyl-5,6-dihydro-4H-pyrazolo[1,5-d][1,4]diazepin-7(8H)-one (Compound 177)

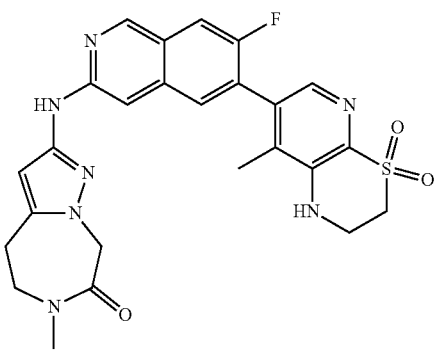 [SMILES: Cc1c(-c2cc3cc(Nc4cc5n(n4)CC(=O)N(C)CC5)ncc3cc2F)cnc2c1NCCS2(=O)=O]

Synthesized following procedures similar to those described above according to the general synthetic methods. ¹H NMR (300 MHz, DMSO-d₆) δ 9.29 (s, 1H), 9.02 (s, 1H), 7.93 (s, 1H), 7.90 (s, 1H), 7.87 (d, J=4.9 Hz, 1H), 7.80 (d, J=7.0 Hz, 1H). 6.37 (s, 1H), 6.00 (s, 1H), 4.90 (s, 2H), 3.87-3.77 (m, 4H), 3.60-3.54 (m, 2H), 3.08-3.02 (m, 2H), 2.98 (t, J=5.7 Hz, 3H), 2.04 (d, J=1.7 Hz, 3H). Analytical HPLC retention time 1.928 min. Method K. MS (ESI) [M+H]$^+$=522.2.

Example 168

2-((7-fluoro-6-(4-methyl-6-(S-methylsulfonimidoyl) pyridin-3-yl)isoquinolin-3-yl)amino)-6-methyl-5,6-dihydro-4H-pyrazolo[1,5-d][1,4]diazepin-7(8H)-one (Compound 178)

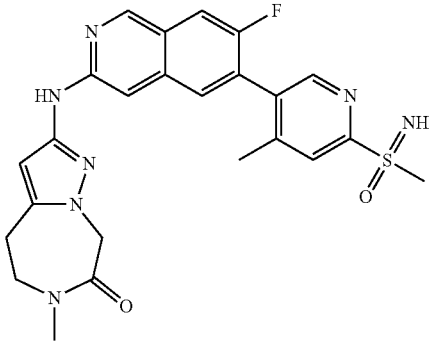 [SMILES: Cc1cc(S(C)(=N)=O)ncc1-c1cc2cc(Nc3cc4n(n3)CC(=O)N(C)CC4)ncc2cc1F]

$^1$H NMR (400 MHz, CD$_3$OD) δ 9.13 (s, 1H), 8.72 (s, 1H), 8.26 (s, 1H), 7.93-7.83 (m, 3H), 6.04 (s, 1H), 5.15 (s, 2H), 3.94 (dd, J=6.8, 4.9 Hz, 2H), 3.56 (s, 3H), 3.23-3.15 (m, 2H), 3.10 (s, 3H), 2.46 (d, J=1.1 Hz, 3H). Analytical HPLC retention time 2.251 min. Method K. MS (ESI) [M+H]$^+$=494.1.

Example 169

N-(6-(5-(azetidin-3-ylamino)-4-methylpyridin-3-yl)-7-fluoroisoquinolin-3-yl)-5,6-dihydro-11H-imidazo[1,2-a]pyrazolo[1,5-d][1,4]diazepin-8-amine (Compound 179)

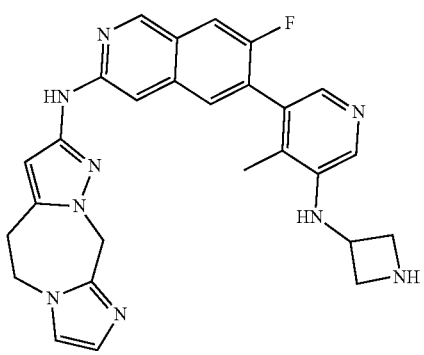 [SMILES: Cc1c(NC2CNC2)cncc1-c1cc2cc(Nc3cc4n(n3)Cc3nccn3CC4)ncc2cc1F]

Synthesized following procedures similar to those described above according to the general synthetic methods. $^1$H NMR (400 MHz, DMSO-d$_6$) δ 9.32 (s, 1H), 9.02 (s, 1H), 7.96 (s, 1H), 7.92 (s, 1H), 7.83 (t, J=5.1 Hz, 2H), 7.73 (d, J=7.1 Hz, 1H), 7.21 (d, J=1.3 Hz, 1H), 6.84 (d, J=1.2 Hz, 1H), 6.05 (s, 1H), 5.95 (s, 1H), 5.42 (s, 1H), 4.59-4.49 (m, 1H), 4.40-4.28 (m, 4H), 4.00 (t, J=8.5 Hz, 2H), 3.28-3.20 (m, 3H), 2.02 (d, J=1.7 Hz, 3H). Analytical HPLC retention time 1.476 min. Method K. MS (ESI) [M+H]$^+$=496.2.

Example 170

2-((7-fluoro-6-(4-methyl-5-(methylamino)pyridin-3-yl)isoquinolin-3-yl)amino)-5,6-dihydro-4H-pyrazolo[1,5-d][1,4]diazepin-7(8H)-one (Compound 181)

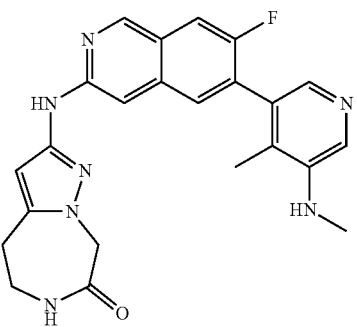 [SMILES: CNc1cncc(-c2cc3cc(Nc4cc5n(n4)CC(=O)NCC5)ncc3cc2F)c1C]

Synthesized following procedures similar to those described above according to the general synthetic methods. $^1$H NMR (300 MHz, DMSO-d$_6$) δ 9.26 (s, 1H), 8.99 (s, 1H), 8.14 (t, J=5.5 Hz, 1H), 7.90 (s, 2H), 7.80 (t, J=5.0 Hz, 2H), 7.70 (d, J=7.2 Hz, 1H), 5.97 (s, 1H), 5.49 (s, 1H), 4.88 (s, 2H), 3.56-3.47 (m, 2H), 2.95 (t, J=6.0 Hz, 2H), 2.84 (d, J=4.6 Hz, 3H), 1.93 (s, 3H). Analytical HPLC retention time 1.012 min. Method K. MS (ESI) [M+H]$^+$=432.2

Example 171

(+/−)-2-((6-(2,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one (Compound 182)

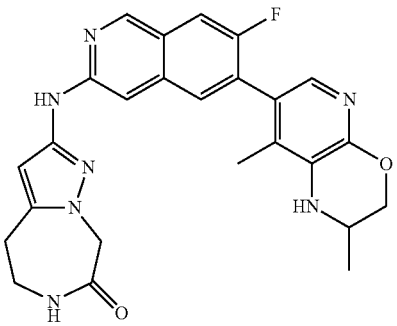 [SMILES: Cc1c(-c2cc3cc(Nc4cc5n(n4)CC(=O)NCC5)ncc3cc2F)cnc2c1NC(C)CO2]

Synthesized following procedures similar to those described above according to the general synthetic methods. $^1$H NMR (400 MHz, CDCl$_3$) δ 8.89 (s, 1H), 7.83 (s, 1H), 7.61 (d, J=5.0 Hz, 2H), 7.52 (d, J=9.6 Hz, 1H), 5.99 (s, 1H), 5.06 (s, 2H), 4.45-4.38 (m, 1H), 4.05-3.96 (m, 1H), 3.75-3.58 (m, 3H), 3.19-3.10 (m, 2H), 2.03 (s, 3H), 1.31 (d, J=6.4 Hz, 3H). Analytical HPLC retention time 1.124 min. Method K. MS (ESI) [M+H]$^+$=474.2.

Example 172

N-(7-fluoro-6-(9-methyl-1,2,3,4-tetrahydropyrido[2,3-b][1,4]oxazepin-8-yl)isoquinolin-3-yl)-5,6-dihydro-11H-imidazo[1,2-a]pyrazolo[1,5-d][1,4]diazepin-8-amine (Compound 183)

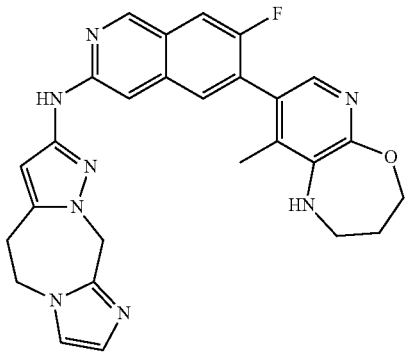 [SMILES: Cc1c(-c2cc3cc(Nc4cc5n(n4)Cc4nccn4CC5)ncc3cc2F)cnc2c1NCCCO2]

Synthesized following procedures similar to those described above according to the general synthetic methods. $^1$H NMR (300 MHz, DMSO-d$_6$) δ 9.29 (s, 1H), 8.98 (s, 1H), 7.91 (s, 1H), 7.78 (d, J=10.1 Hz, 1H), 7.68 (d, J=7.2 Hz, 1H), 7.44 (s, 1H), 7.20 (d, J=1.2 Hz, 1H), 6.83 (d, J=1.2 Hz, 1H), 6.04 (s, 1H), 5.40 (s, 2H), 5.14 (s, 1H), 4.32 (dd, J=14.3, 8.5 Hz, 4H), 3.27-3.17 (m, 2H), 3.42-3.33 (m, 2H), 1.96 (dd, J=6.7, 3.8 Hz, 5H). Analytical HPLC retention time 1.886 min. Method K. MS (ESI) [M+H]$^+$=497.2.

Example 173

(+/−)-2-((6-(3,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one (Compound 184)

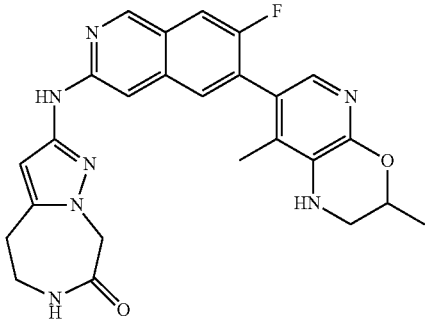 [SMILES: Cc1c(-c2cc3cc(Nc4cc5n(n4)CC(=O)NCC5)ncc3cc2F)cnc2c1NCC(C)O2]

Synthesized following procedures similar to those described above according to the general synthetic methods. $^1$H NMR (300 MHz, DMSO-d$_6$) δ 9.26 (s, 1H), 8.99 (s, 1H), 8.16 (t, J=5.9 Hz, 1H), 7.90 (s, 1H), 7.79 (d, J=10.2 Hz, 1H), 7.67 (d, J=7.2 Hz, 1H), 7.38 (s, 1H), 6.00 (s, 1H), 5.72 (s, 1H), 4.90 (s, 2H), 4.30 (t, J=6.1 Hz, 1H), 3.65-3.48 (m, 2H), 3.47-3.39 (m, 1H), 3.05-2.95 (m, 3H), 1.93 (d, J=1.9 Hz, 3H), 1.37 (d, J=6.2 Hz, 3H). Analytical HPLC retention time 1.107 min. Method K. MS (ESI) [M+H]$^+$=474.2.

Example 174

(R)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one (Compound 185a)

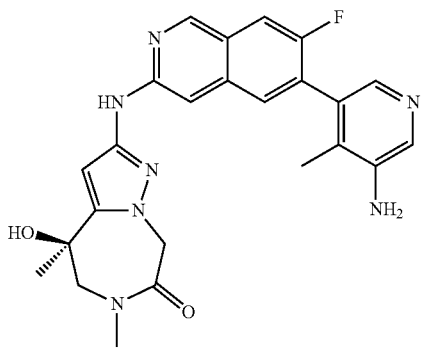 [SMILES: Cc1c(N)cncc1-c1cc2cc(Nc3cc4n(n3)CC(=O)N(C)C[C@@]4(C)O)ncc2cc1F]

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 8.00 (s, 1H), 7.90 (s, 1H), 7.79 (d, J=10.1 Hz, 1H), 7.69 (d, J=6.9 Hz, 2H), 6.24 (s, 1H), 5.71 (s, 1H), 5.26 (s, 2H), 5.10 (d, J=14.9 Hz, 1H), 4.82 (d, J=14.9 Hz, 1H), 3.96 (d, J=15.3 Hz, 1H), 3.56 (d, J=15.4 Hz, 1H), 2.98 (s, 3H), 1.90 (d, J=1.7 Hz, 3H), 1.45 (s, 3H). Analytical HPLC retention time 0.998 min. Method K. MS (ESI) [M+H]$^+$=462.2.

(S)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one (Compound 185b)

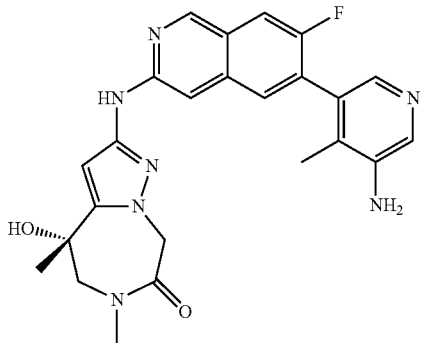 [SMILES: Cc1c(N)cncc1-c1cc2cc(Nc3cc4n(n3)CC(=O)N(C)C[C@]4(C)O)ncc2cc1F]

Synthesized following procedures similar to those described above according to the general synthetic methods. Absolute stereochemistry arbitrarily assigned. $^1$H NMR (300 MHz, DMSO-d$_6$) δ 9.31 (s, 1H), 8.99 (s, 1H), 8.00 (s, 1H), 7.91 (s, 1H), 7.79 (d, J=10.2 Hz, 1H), 7.69 (d, J=6.9 Hz, 2H), 6.24 (s, 1H), 5.71 (s, 1H), 5.27 (s, 2H), 5.10 (d, J=14.9 Hz, 1H), 4.82 (d, J=15.0 Hz, 1H), 3.96 (d, J=15.4 Hz, 1H), 3.56 (d, J=15.4 Hz, 1H), 2.98 (s, 3H), 1.90 (d, J=1.7 Hz, 3H), 1.45 (s, 3H). Analytical HPLC retention time 0.998 min. Method K. MS (ESI) [M+H]$^+$=462.2.

Example 175

2-((7-fluoro-6-(7-methyl-1H-pyrazolo[4,3-b]pyridin-6-yl)isoquinolin-3-yl)amino)-6-methyl-5,6-dihydro-4H-pyrazolo[1,5-d][1,4]diazepin-7(8H)-one (Compound 186)

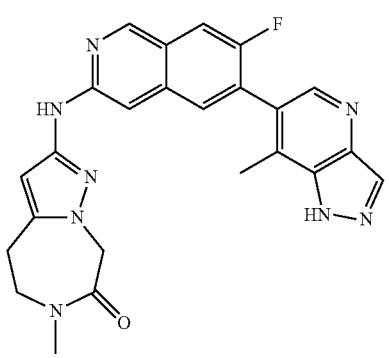 [SMILES: Cc1c(-c2cc3cc(Nc4cc5n(n4)CC(=O)N(C)CC5)ncc3cc2F)cnc2cn[nH]c12]

Synthesized following procedures similar to those described above according to the general synthetic methods. ¹H NMR (300 MHz, DMSO-d₆) δ 13.64 (s, 1H), 9.30 (s, 1H), 9.04 (s, 1H), 8.43 (s, 1H), 8.36 (d, J=1.3 Hz, 1H), 7.95 (s, 1H), 7.87 (dd, J=8.7, 6.4 Hz, 2H), 6.00 (s, 1H), 4.98 (s, 2H), 3.82 (t, J=5.7 Hz, 2H), 3.09-3.00 (m, 2H), 2.95 (s, 3H), 2.47 (d, J=1.3 Hz, 3H). Method K. Analytical HPLC retention time 2.522 min. Method K. MS (ESI) [M+H]⁺=457.2.

Example 176

7-(7-fluoro-3-((6-methyl-7-oxo-5,6,7,8-tetrahydro-4H-pyrazolo[1,5-d][1,4]diazepin-2-yl)amino)isoquinolin-6-yl)-3,8-dimethyl-2,3-dihydropyrido[3,2-d]pyrimidin-4(1H)-one (Compound 187)

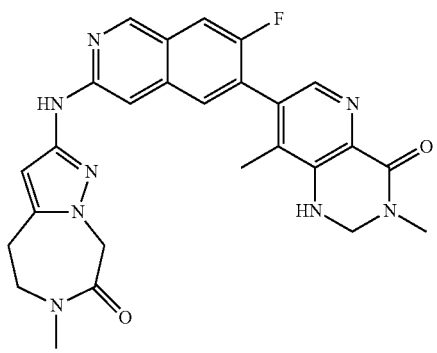 [SMILES: Cc1c(-c2cc3cc(Nc4cc5n(n4)CC(=O)N(C)CC5)ncc3cc2F)cnc2c1NCN(C)C2=O]

Synthesized following procedures similar to those described above according to the general synthetic methods. ¹H NMR (400 MHz, DMSO-d₆) δ 9.27 (s, 1H), 9.02 (s, 1H), 7.98 (s, 1H), 7.93 (s, 1H), 7.85 (d, J=10.1 Hz, 1H), 7.78 (d, J=7.1 Hz, 1H), 6.65 (d, J=2.9 Hz, 1H), 6.00 (s, 1H), 4.99 (s, 2H), 4.67 (d, J=2.7 Hz, 2H), 3.83 (t, J=5.7 Hz, 2H), 3.05 (t, J=5.7 Hz, 2H), 3.00 (s, 3H), 2.95 (s, 3H), 2.01 (d, J=1.6 Hz, 3H). Analytical HPLC retention time 1.052 min. Method K. MS (ESI) [M+H]⁺=501.2.

Example 177

(5-(3-((5,6-dihydro-11H-imidazo[1,2-a]pyrazolo[1,5-d][1,4]diazepin-8-yl)amino)-7-fluoroisoquinolin-6-yl)-4-methylpyridin-2-yl)(imino)(methyl)-16-sulfanone (Compound 188)

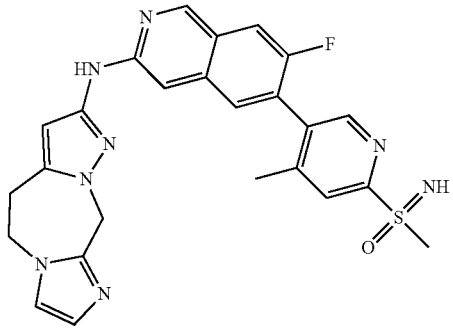 [SMILES: Cc1cc(S(C)(=N)=O)ncc1-c1cc2cc(Nc3cc4n(n3)Cc3nccn3CC4)ncc2cc1F]

Synthesized following procedures similar to those described above according to the general synthetic methods. ¹H NMR (400 MHz, Methanol-d₄) δ 9.01 (s, 1H), 8.63 (s, 1H), 8.18 (s, 1H), 7.90 (s, 1H), 7.77 (dd, J=16.6, 8.4 Hz, 2H), 7.54 (d, J=1.9 Hz, 1H), 7.47 (d, J=1.9 Hz, 1H), 6.22 (s, 1H), 5.72 (s, 2H), 4.62-4.55 (m, 2H), 3.51-3.43 (m, 2H), 3.36 (s, 3H), 2.42 (s, 3H). Analytical HPLC retention time 1.982 min. Method M. MS (ESI) [M+H]⁺=503.3.

Example 178

(+/−)-7-(3-((5,6-dihydro-11H-imidazo[1,2-a]pyrazolo[1,5-d][1,4]diazepin-8-yl)amino)-7-fluoroisoquinolin-6-yl)-8-methyl-2,3-dihydro-1H-pyrido[2,3-b][1,4]thiazine 4-oxide (Compound 189)

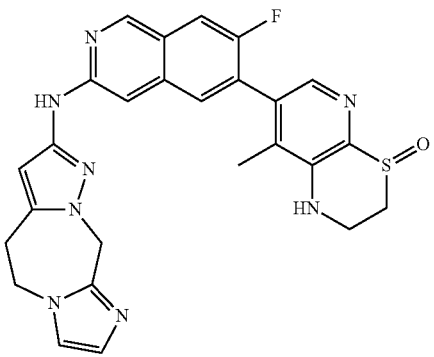 [SMILES: Cc1c(-c2cc3cc(Nc4cc5n(n4)Cc4nccn4CC5)ncc3cc2F)cnc2c1NCCS2=O]

Synthesized following procedures similar to those described above according to the general synthetic methods. ¹H NMR (400 MHz, CD₃OD) δ 8.96 (s, 1H), 7.90 (s, 1H), 7.87 (d, J=7.4 Hz, 1H), 7.71 (t, J=9.1 Hz, 2H), 7.17 (d, J=1.4 Hz, 1H), 6.94 (d, J=1.4 Hz, 1H), 6.13 (s, 1H), 5.49 (s, 2H), 4.47-4.40 (m, 2H), 3.86-3.79 (m, 2H), 3.39-3.29 (m, 3H), 2.95 (s, 1H), 2.10 (d, J=1.6 Hz, 3H). Analytical HPLC retention time 1.037 min. Method K. MS (ESI) [M+H]⁺=515.5.

Example 179

Exemplary compounds were synthesized according to the General Synthetic Methods described herein and following procedures similar to those described above. The Compound (also abbreviated as "Cpd." or "Compd.") No. structure, name, HPLC analytical method, retention time (RT) and MS m/z are provided in Table A1.

TABLE A1

| Cpd. No. | Structure | Name | LCMS m/z Method RT (min) |
|---|---|---|---|
| 101 | 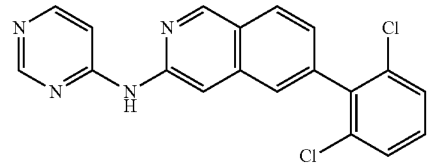 | 6-(2,6-dichlorophenyl)-N-(pyrimidin-4-yl)isoquinolin-3-amine | 367.0 N 4.23 |
| 102 | 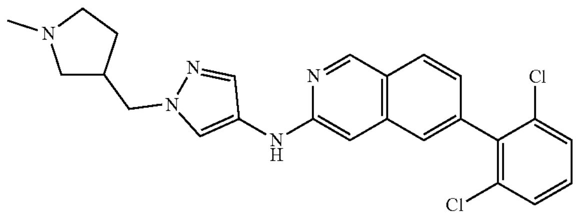 [SMILES: CN1CCC(Cn2cc(Nc3cc4cc(-c5c(Cl)cccc5Cl)ccc4cn3)cn2)C1] | (+/-)-6-(2,6-dichlorophenyl)-N-(1-((1-methylpyrrolidin-3-yl)methyl)-1H-pyrazol-4-yl)isoquinolin-3-amine | 452.1 N 3.913 |
| 103 | 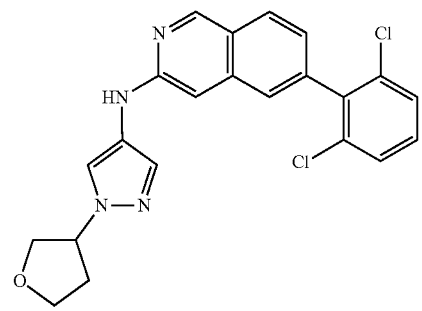 [SMILES: Clc1cccc(Cl)c1-c1ccc2cnc(Nc3cnn(C4CCOC4)c3)cc2c1] | (+/-)-6-(2,6-dichlorophenyl)-N-(1-(tetrahydrofuran-3-yl)-1H-pyrazol-4-yl)isoquinolin-3-amine | 425.0 N 4.54 |
| 104 | 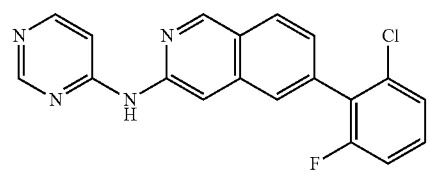 [SMILES: Fc1cccc(Cl)c1-c1ccc2cnc(Nc3ccncn3)cc2c1] | 6-(2-chloro-6-fluorophenyl)-N-(pyrimidin-4-yl)isoquinolin-3-amine | 351.0 N 4.11 |
| 105 | 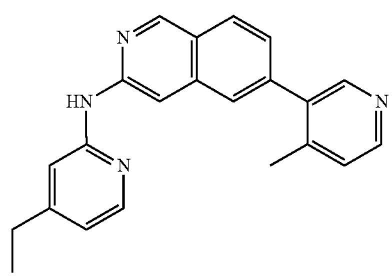 [SMILES: CCc1ccnc(Nc2cc3cc(-c4cnccc4C)ccc3cn2)c1] | N-(4-ethylpyridin-2-yl)-6-(4-methylpyridin-3-yl)isoquinolin-3-amine | 342.0 O 1.51 |
| 106 | 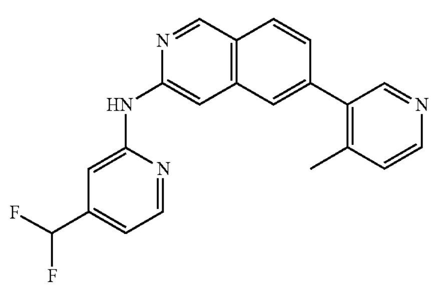 [SMILES: Cc1ccncc1-c1ccc2cnc(Nc3cc(C(F)F)ccn3)cc2c1] | N-(4-(difluoromethyl)pyridin-2-yl)-6-(4-methylpyridin-3-yl)isoquinolin-3-amine | 363.13 N 1.48 |

TABLE A1-continued

| Cpd. No. | Structure | Name | LCMS m/z Method RT (min) |
|---|---|---|---|
| 107 | 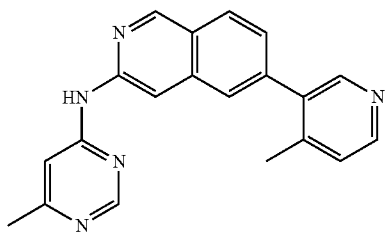 [SMILES: Cc1cc(Nc2cc3cc(-c4cnccc4C)ccc3cn2)ncn1] | 6-(4-methylpyridin-3-yl)-N-(6-methylpyrimidin-4-yl)isoquinolin-3-amine | 328.1 N 1.18 |
| 108 | 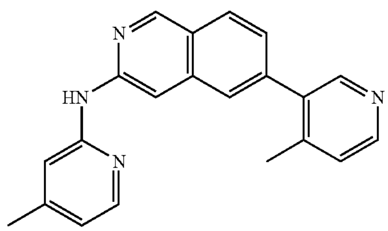 [SMILES: Cc1ccnc(Nc2cc3cc(-c4cnccc4C)ccc3cn2)c1] | N-(4-methylpyridin-2-yl)-6-(4-methylpyridin-3-yl)isoquinolin-3-amine | 327.15 N 1.36 |
| 109a | 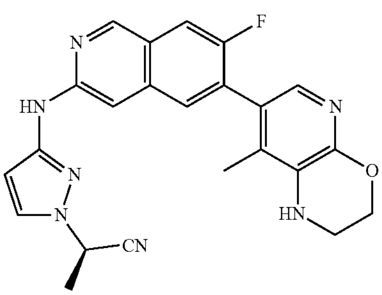 [SMILES: Cc1c(-c2cc3cc(Nc4ccn([C@H](C)C#N)n4)ncc3cc2F)cnc2c1NCCO2] | 2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile (absolute stereochemistry arbitrarily assigned) | 430.2 K 1.969 |
| 109b | 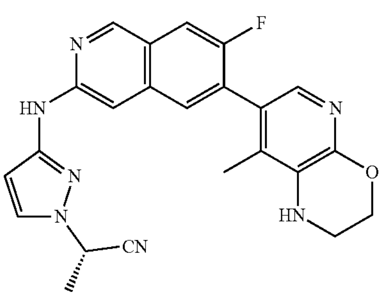 [SMILES: Cc1c(-c2cc3cc(Nc4ccn([C@@H](C)C#N)n4)ncc3cc2F)cnc2c1NCCO2] | 2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile (absolute stereochemistry arbitrarily assigned) | 430.0 L 2.073 |
| 150 | 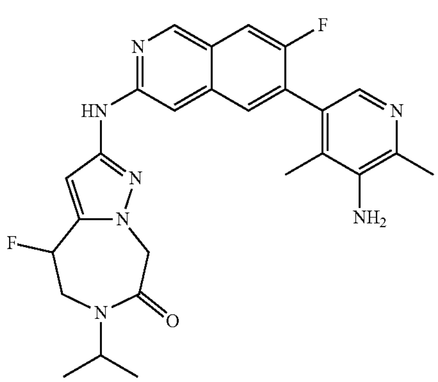 [SMILES: Cc1ncc(-c2cc3cc(Nc4cc5n(n4)CC(=O)N(C(C)C)CC5F)ncc3cc2F)c(C)c1N] | (+/-)-2-((6-(5-amino-4,6-dimethylpyridin-3-yl)-7-fluoroisoquinolin-3-yl)amino)-4-fluoro-6-isopropyl-5,6-dihydro-4H-pyrazolo[1,5-d][1,4]diazepin-7(8H)-one | 492.2 N 3.320 |

TABLE A1-continued

| Cpd. No. | Structure | Name | LCMS m/z Method RT (min) |
|---|---|---|---|
| 190 | 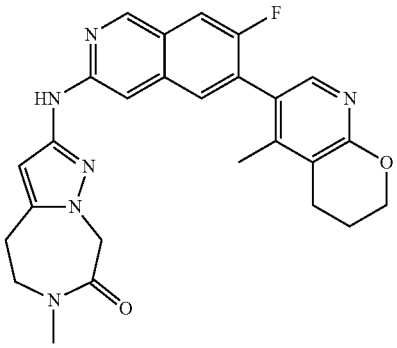 [SMILES: Cc1c(-c2cc3cc(Nc4cc5n(n4)CC(=O)N(C)CC5)ncc3cc2F)cnc2c1CCCO2] | 2-((7-fluoro-6-(5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one | 473.2 N 3.957 |
| 191 | 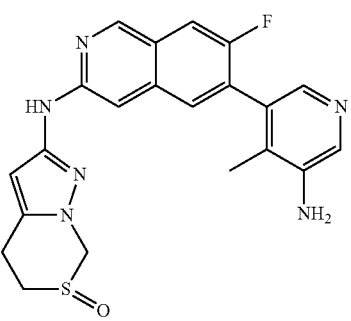 [SMILES: Cc1c(N)cncc1-c1cc2cc(Nc3cc4n(n3)CS(=O)CC4)ncc2cc1F] | (+/-)-2-((6-(5-amino-4-methylpyridin-3-yl)-7-fluoroisoquinolin-3-yl)amino)-4,5-dihydro-7H-pyrazolo[1,5-c][1,3]thiazine 6-oxide | 423.1 M 2.318 |
| 192 | 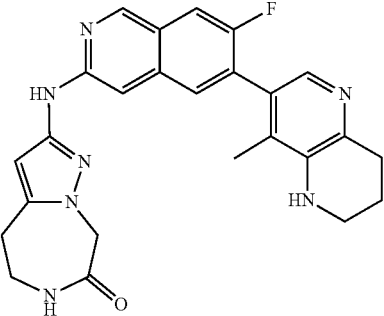 [SMILES: Cc1c(-c2cc3cc(Nc4cc5n(n4)CC(=O)NCC5)ncc3cc2F)cnc2c1NCCC2] | 2-((7-fluoro-6-(4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one | 458.2 K 1.837 |
| 193 | 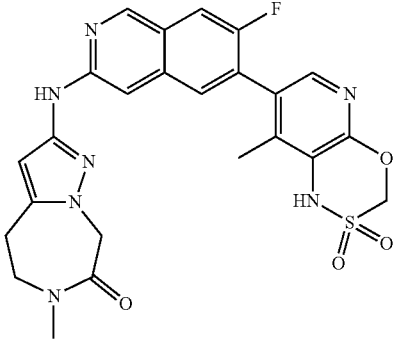 [SMILES: Cc1c(-c2cc3cc(Nc4cc5n(n4)CC(=O)N(C)CC5)ncc3cc2F)cnc2c1NS(=O)(=O)CO2] | 2-((7-fluoro-6-(8-methyl-2,2-dioxido-1H,3H-pyrido[3,2-e][1,3,4]oxathiazin-7-yl)isoquinolin-3-yl)amino)-6-methyl-5,6-dihydro-4H-pyrazolo[1,5-d][1,4]diazepin-7(8H)-one | 524.1 K 2.181 |

TABLE A1-continued

| Cpd. No. | Structure | Name | LCMS m/z Method RT (min) |
|---|---|---|---|
| 194 | 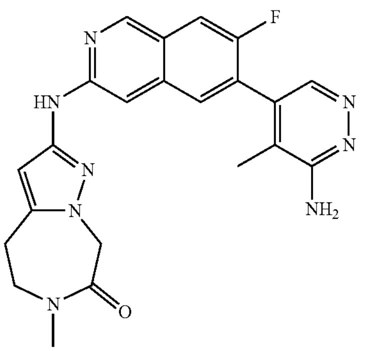 [SMILES: Cc1c(-c2cc3cc(Nc4cc5n(n4)CC(=O)N(C)CC5)ncc3cc2F)cnnc1N] | 2-((6-(6-amino-5-methylpyridazin-4-yl)-7-fluoroisoquinolin-3-yl)amino)-6-methyl-5,6-dihydro-4H-pyrazolo[1,5-d][1,4]diazepin-7(8H)-one | 433.2 M 2.015 |
| 195 | 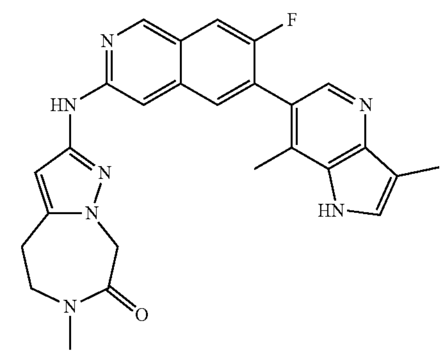 [SMILES: Cc1c[nH]c2c(C)c(-c3cc4cc(Nc5cc6n(n5)CC(=O)N(C)CC6)ncc4cc3F)cnc12] | 2-((6-(3,7-dimethyl-1H-pyrrolo[3,2-b]pyridin-6-yl)-7-fluoroisoquinolin-3-yl)amino)-6-methyl-5,6-dihydro-4H-pyrazolo[1,5-d] [1,4]diazepin-7(8H)-one | 470.2 M 1.682 |
| 196 | 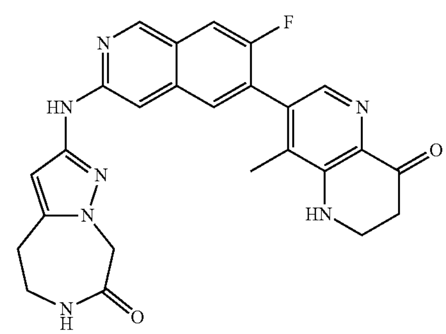 [SMILES: Cc1c(-c2cc3cc(Nc4cc5n(n4)CC(=O)NCC5)ncc3cc2F)cnc2c1NCCC2=O] | 2-((7-fluoro-6-(4-methyl-8-oxo-5,6,7,8-tetrahydro-1,5-naphthyridin-3-yl)isoquinolin-3-yl)amino)-5,6-dihydro-4H-pyrazolo[1,5-d][1,4]diazepin-7(8H)-one | 471.7 K 0.993 |
| 197 | 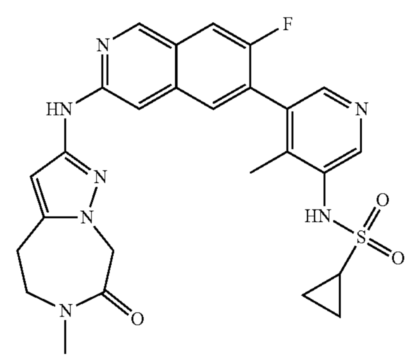 [SMILES: Cc1c(NS(=O)(=O)C2CC2)cncc1-c1cc2cc(Nc3cc4n(n3)CC(=O)N(C)CC4)ncc2cc1F] | N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)cyclopropanesulfonamide | 536.2 M 2.651 |

TABLE A1-continued

| Cpd. No. | Structure | Name | LCMS m/z Method RT (min) |
|---|---|---|---|
| 198 | 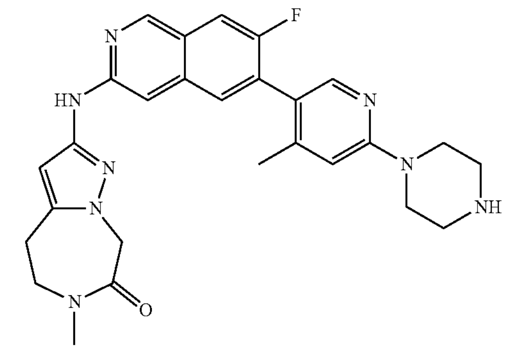 [SMILES: Cc1cc(N2CCNCC2)ncc1-c1cc2cc(Nc3cc4n(n3)CC(=O)N(C)CC4)ncc2cc1F] | 2-((7-fluoro-6-(4-methyl-6-(piperazin-1-yl)pyridin-3-yl)isoquinolin-3-yl)amino)-6-methyl-5,6-dihydro-4H-pyrazolo[1,5-d][1,4]diazepin-7(8H)-one | 501.2 K 1.063 |
| 199 | 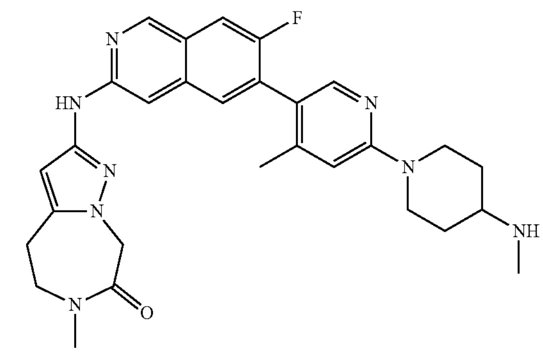 [SMILES: CNC1CCN(c2cc(C)c(-c3cc4cc(Nc5cc6n(n5)CC(=O)N(C)CC6)ncc4cc3F)cn2)CC1] | 2-((7-fluoro-6-(4-methyl-6-(4-(methylamino)piperidin-1-yl)pyridin-3-yl)isoquinolin-3-yl)amino)-6-methyl-5,6-dihydro-4H-pyrazolo[1,5-d][1,4]diazepin-7(8H)-one | 529.3 K 1.725 |
| 200 | 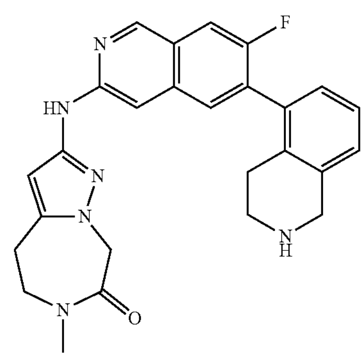 [SMILES: CN1CCc2cc(Nc3cc4cc(-c5cccc6c5CCNC6)c(F)cc4cn3)nn2CC1=O] | 2-((7'-fluoro-1,2,3,4-tetrahydro-[5,6'-biisoquinolin]-3'-yl)amino)-6-methyl-5,6-dihydro-4H-pyrazolo[1,5-d][1,4]diazepin-7(8H)-one | 457.3 N 3.169 |
| 201 | 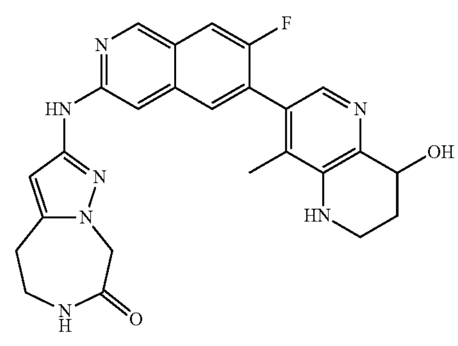 [SMILES: Cc1c(-c2cc3cc(Nc4cc5n(n4)CC(=O)NCC5)ncc3cc2F)cnc2c1NCCC2O] | (+/-)-2-((7-fluoro-6-(8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one formate salt | 474.2 P 1.348 |

TABLE A1-continued

| Cpd. No. | Structure | Name | LCMS m/z Method RT (min) |
|---|---|---|---|
| 202 | 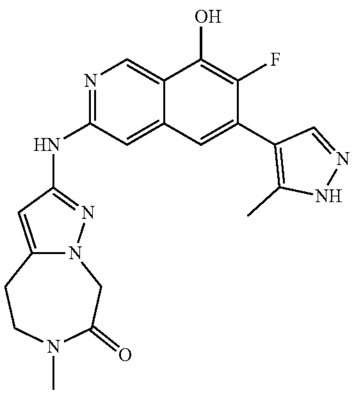 [SMILES: Cc1[nH]ncc1-c1cc2cc(Nc3cc4n(n3)CC(=O)N(C)CC4)ncc2c(O)c1F] | 2-((7-fluoro-8-hydroxy-6-(5-methyl-1H-pyrazol-4-yl)isoquinolin-3-yl)amino)-6-methyl-5,6-dihydro-4H-pyrazolo[1,5-d][1,4]diazepin-7(8H)-one | 422.2 N 2.849 |
| 203 | 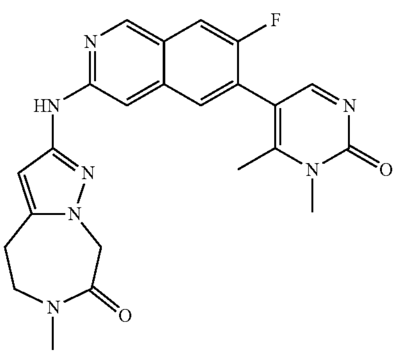 [SMILES: Cc1c(-c2cc3cc(Nc4cc5n(n4)CC(=O)N(C)CC5)ncc3cc2F)cnc(=O)n1C] | 2-((6-(1,6-dimethyl-2-oxo-1,2-dihydropyrimidin-5-yl)-7-fluoroisoquinolin-3-yl)amino)-6-methyl-5,6-dihydro-4H-pyrazolo[1,5-d][1,4]diazepin-7(8H)-one | 448.2 P 2.046 |
| 204 | 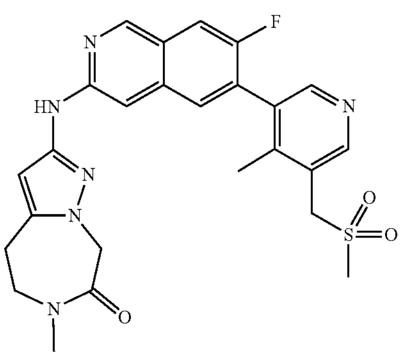 [SMILES: Cc1c(CS(C)(=O)=O)cncc1-c1cc2cc(Nc3cc4n(n3)CC(=O)N(C)CC4)ncc2cc1F] | 2-((7-fluoro-6-(4-methyl-5-((methylsulfonyl)methyl)pyridin-3-yl)isoquinolin-3-yl)amino)-6-methyl-5,6-dihydro-4H-pyrazolo[1,5-d][1,4]diazepin-7(8H)-one | 509.2 K 1.105 |
| 205a | 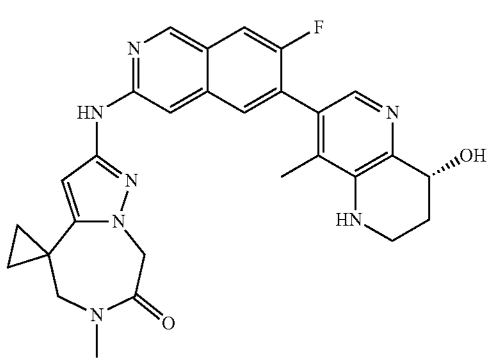 [SMILES: Cc1c(-c2cc3cc(Nc4cc5n(n4)CC(=O)N(C)CC54CC4)ncc3cc2F)cnc2c1NCC[C@H]2O] | (R)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 514.2 K 1.139 |

TABLE A1-continued

| Cpd. No. | Structure | Name | LCMS m/z Method RT (min) |
|---|---|---|---|
| 205b | 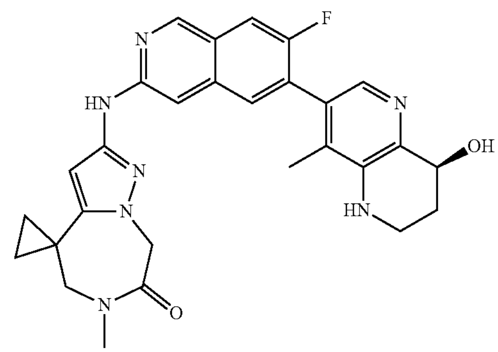 [SMILES: Cc1c(-c2cc3cc(Nc4cc5n(n4)CC(=O)N(C)CC54CC4)ncc3cc2F)cnc2c1NCC[C@@H]2O] | (S)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 514.2 K 1.142 |
| 206a | 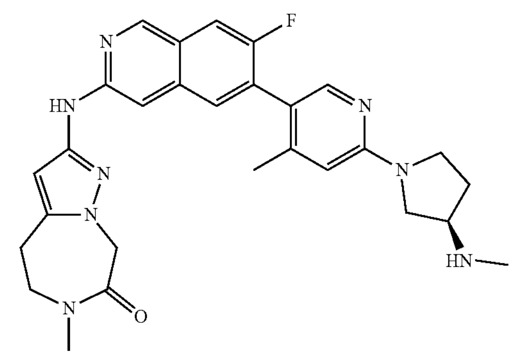 [SMILES: CN[C@@H]1CCN(c2cc(C)c(-c3cc4cc(Nc5cc6n(n5)CC(=O)N(C)CC6)ncc4cc3F)cn2)C1] | (R)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 515.3 K 1.482 |
| 206b | 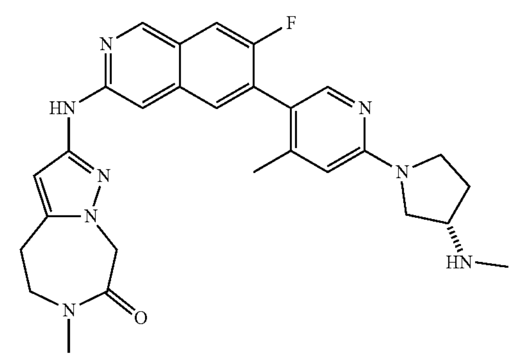 [SMILES: CN[C@H]1CCN(c2cc(C)c(-c3cc4cc(Nc5cc6n(n5)CC(=O)N(C)CC6)ncc4cc3F)cn2)C1] | (S)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 515.3 K 1.482 |
| 207 | 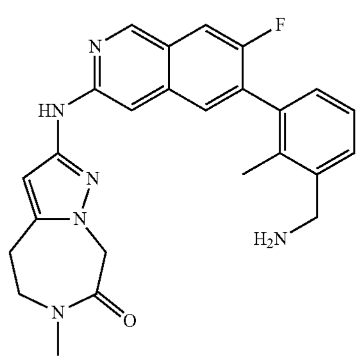 [SMILES: Cc1c(CN)cccc1-c1cc2cc(Nc3cc4n(n3)CC(=O)N(C)CC4)ncc2cc1F] | 2-((6-(3-(aminomethyl)-2-methylphenyl)-7-fluoroisoquinolin-3-yl)amino)-6-methyl-5,6-dihydro-4H-pyrazolo[1,5-d][1,4]diazepin-7(8H)-one | 445.2 P 2.411 |

TABLE A1-continued

| Cpd. No. | Structure | Name | LCMS m/z Method RT (min) |
|---|---|---|---|
| 208 | 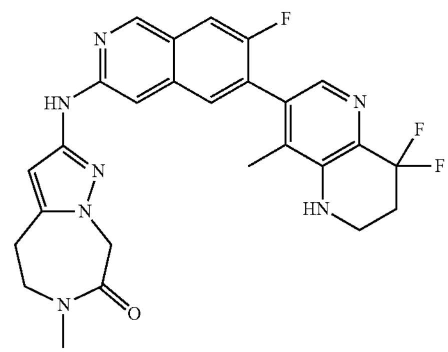 [SMILES: Cc1c(-c2cc3cc(Nc4cc5n(n4)CC(=O)N(C)CC5)ncc3cc2F)cnc2c1NCCC2(F)F] | 2-((6-(8,8-difluoro-4-methyl-5,6,7,8-tetrahydro-1,5-naphthyridin-3-yl)-7-fluoroisoquinolin-3-yl)amino)-6-methyl-5,6-dihydro-4H-pyrazolo[1,5-d][1,4]diazepin-7(8H)-one | 508.2 K 2.202 |
| 209 | 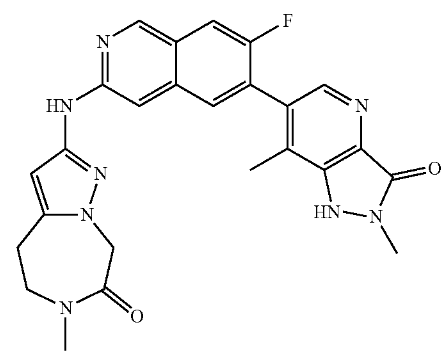 [SMILES: Cc1c(-c2cc3cc(Nc4cc5n(n4)CC(=O)N(C)CC5)ncc3cc2F)cnc2c(=O)n(C)[nH]c12] | 2-((6-(2,7-dimethyl-3-oxo-2,3-dihydro-1H-pyrazolo[4,3-b]pyridin-6-yl)-7-fluoroisoquinolin-3-yl)amino)-6-methyl-5,6-dihydro-4H-pyrazolo[1,5-d][1,4]diazepin-7(8H)-one | 487.2 K 1.772 |
| 210 | 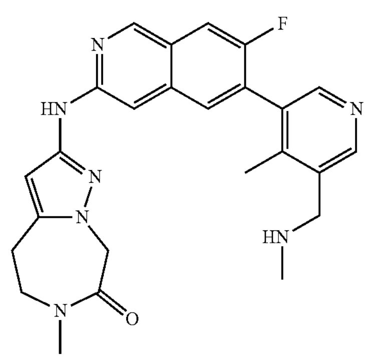 [SMILES: CNCc1cncc(-c2cc3cc(Nc4cc5n(n4)CC(=O)N(C)CC5)ncc3cc2F)c1C] | 2-((7-fluoro-6-(4-methyl-5-((methylamino)methyl)pyridin-3-yl)isoquinolin-3-yl)amino)-6-methyl-5,6-dihydro-4H-pyrazolo[1,5-d][1,4]diazepin-7(8H)-one | 460.2 K 1.223 |
| 211 | 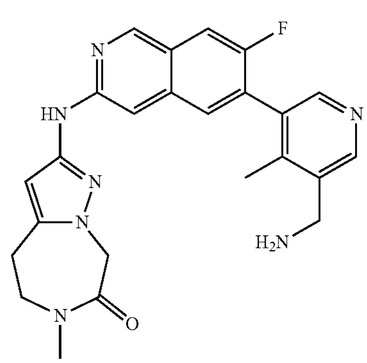 [SMILES: Cc1c(CN)cncc1-c1cc2cc(Nc3cc4n(n3)CC(=O)N(C)CC4)ncc2cc1F] | 2-((6-(5-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one | 446.2 K 1.190 |

TABLE A1-continued

| Cpd. No. | Structure | Name | LCMS m/z Method RT (min) |
|---|---|---|---|
| 212 | 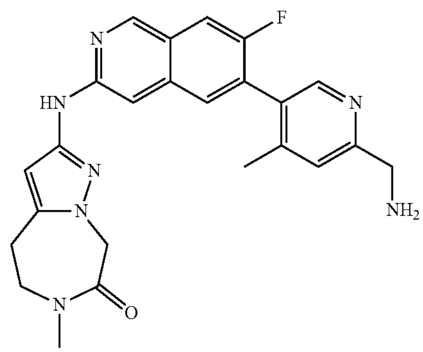 [SMILES: Cc1cc(CN)ncc1-c1cc2cc(Nc3cc4n(n3)CC(=O)N(C)CC4)ncc2cc1F] | 2-((6-(6-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one | 446.2 K 1.332 |
| 213 | 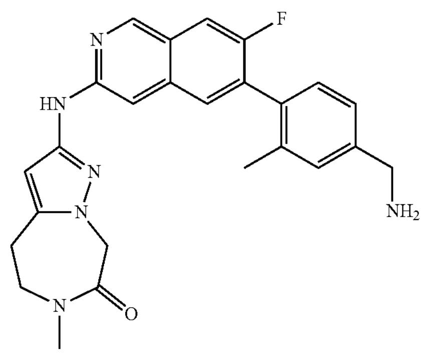 [SMILES: Cc1cc(CN)ccc1-c1cc2cc(Nc3cc4n(n3)CC(=O)N(C)CC4)ncc2cc1F] | 2-((6-(4-(aminomethyl)-2-methylphenyl)-7-fluoroisoquinolin-3-yl)amino)-6-methyl-5,6-dihydro-4H-pyrazolo[1,5-d][1,4]diazepin-7(8H)-one | 445.2 K 1.078 |
| 214 | 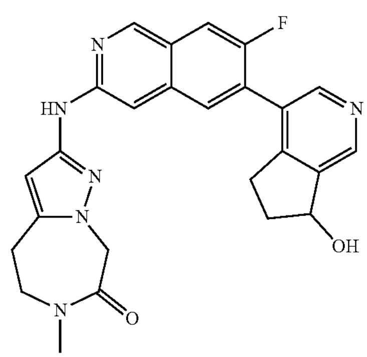 [SMILES: CN1CCc2cc(Nc3cc4cc(-c5cncc6c5CCC6O)c(F)cc4cn3)nn2CC1=O] | (+/-)-2-((7-fluoro-6-(7-hydroxy-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one | 459.2 K 1.271 |
| 215 | 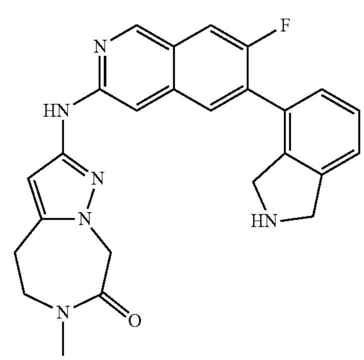 [SMILES: CN1CCc2cc(Nc3cc4cc(-c5cccc6c5CNC6)c(F)cc4cn3)nn2CC1=O] | 2-((7-fluoro-6-(isoindolin-4-yl)isoquinolin-3-yl)amino)-6-methyl-5,6-dihydro-4H-pyrazolo[1,5-d][1,4]diazepin-7(8H)-one | 443.2 K 1.101 |

TABLE A1-continued

| Cpd. No. | Structure | Name | LCMS m/z Method RT (min) |
|---|---|---|---|
| 216 | 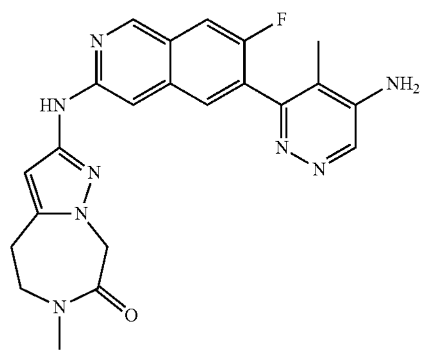 [SMILES: Cc1c(N)cnnc1-c1cc2cc(Nc3cc4n(n3)CC(=O)N(C)CC4)ncc2cc1F] | 2-((6-(5-amino-4-methylpyridazin-3-yl)-7-fluoroisoquinolin-3-yl)amino)-6-methyl-5,6-dihydro-4H-pyrazolo[1,5-d][1,4]diazepin-7(8H)-one | 433.2 K 1.749 |
| 217 | 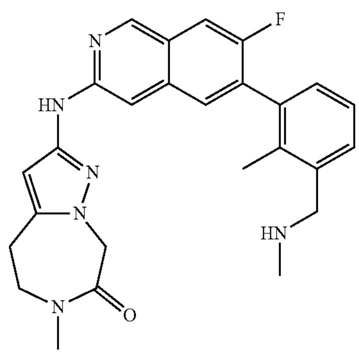 [SMILES: CNCc1cccc(-c2cc3cc(Nc4cc5n(n4)CC(=O)N(C)CC5)ncc3cc2F)c1C] | 2-((7-fluoro-6-(2-methyl-3-((methylamino)methyl)phenyl)isoquinolin-3-yl)amino)-6-methyl-5,6-dihydro-4H-pyrazolo[1,5-d][1,4]diazepin-7(8H)-one | 459.4 K 1.149 |
| 218 | 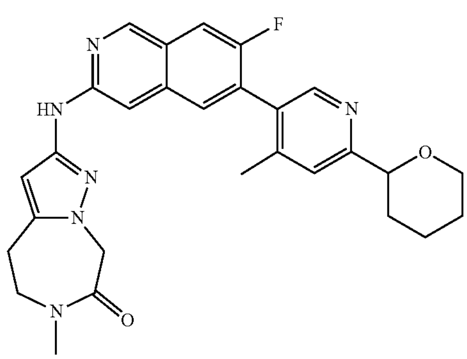 [SMILES: Cc1cc(C2CCCCO2)ncc1-c1cc2cc(Nc3cc4n(n3)CC(=O)N(C)CC4)ncc2cc1F] | (+/-)-2-((7-fluoro-6-(4-methyl-6-(tetrahydro-2H-pyran-2-yl)pyridin-3-yl)isoquinolin-3-yl)amino)-6-methyl-5,6-dihydro-4H-pyrazolo[1,5-d][1,4]diazepin-7(8H)-one | 501.2 K 1.270 |
| 219 | 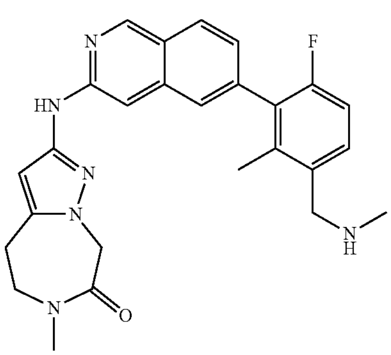 [SMILES: CNCc1ccc(F)c(-c2ccc3cnc(Nc4cc5n(n4)CC(=O)N(C)CC5)cc3c2)c1C] | 2-((6-(6-fluoro-2-methyl-3-((methylamino)methyl)phenyl)isoquinolin-3-yl)amino)-6-methyl-5,6-dihydro-4H-pyrazolo[1,5-d][1,4]diazepin-7(8H)-one | 459.2 K 2.023 |

TABLE A1-continued

| Cpd. No. | Structure | Name | LCMS m/z Method RT (min) |
|---|---|---|---|
| 220 | 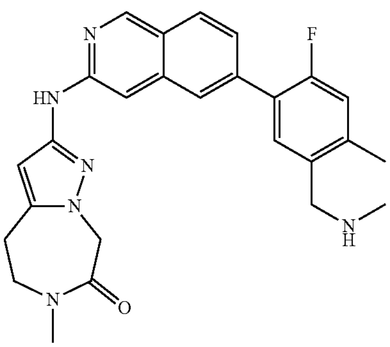 [SMILES: CNCc1cc(-c2ccc3cnc(Nc4cc5n(n4)CC(=O)N(C)CC5)cc3c2)c(F)cc1C] | 2-((6-(2-fluoro-4-methyl-5-((methylamino)methyl)phenyl)isoquinolin-3-yl)amino)-6-methyl-5,6-dihydro-4H-pyrazolo[1,5-d][1,4]diazepin-7(8H)-one | 459.2 K 2.24 |
| 221 | 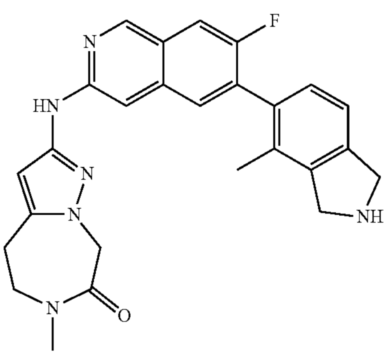 [SMILES: Cc1c(-c2cc3cc(Nc4cc5n(n4)CC(=O)N(C)CC5)ncc3cc2F)ccc2c1CNC2] | 2-((7-fluoro-6-(4-methylisoindolin-5-yl)isoquinolin-3-yl)amino)-6-methyl-5,6-dihydro-4H-pyrazolo[1,5-d][1,4]diazepin-7(8H)-one | 457.2 K 2.334 |
| 222 | 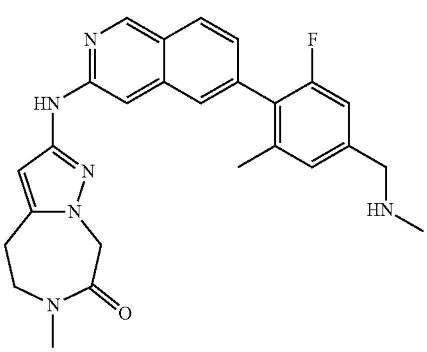 [SMILES: CNCc1cc(C)c(-c2ccc3cnc(Nc4cc5n(n4)CC(=O)N(C)CC5)cc3c2)c(F)c1] | 2-((6-(2-fluoro-6-methyl-4-((methylamino)methyl)phenyl)isoquinolin-3-yl)amino)-6-methyl-5,6-dihydro-4H-pyrazolo[1,5-d][1,4]diazepin-7(8H)-one | 459.2 K 1.983 |
| 223 | 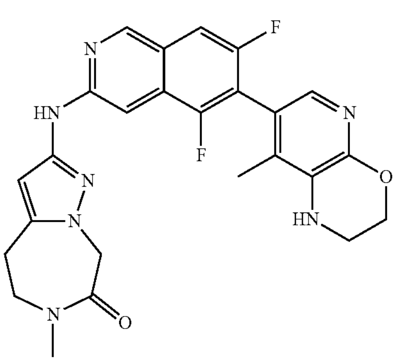 [SMILES: Cc1c(-c2c(F)cc3cnc(Nc4cc5n(n4)CC(=O)N(C)CC5)cc3c2F)cnc2c1NCCO2] | 2-((5,7-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one | 492.2 K 2.113 |

TABLE A1-continued

| Cpd. No. | Structure | Name | LCMS m/z Method RT (min) |
|---|---|---|---|
| 224 | 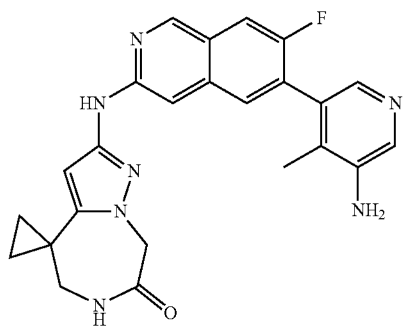 [SMILES: Cc1c(N)cncc1-c1cc2cc(Nc3cc4n(n3)CC(=O)NCC43CC3)ncc2cc1F] | 2'-((6-(5-amino-4-methylpyridin-3-yl)-7-fluoroisoquinolin-3-yl)amino)-5',6'-dihydrospiro[cyclopropane-1,4'-pyrazolo[1,5-d][1,4]diazepin]-7'(8'H)-one | 444.2 K 1.061 |
| 225 | 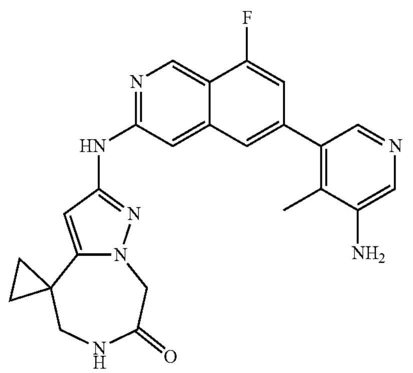 [SMILES: Cc1c(N)cncc1-c1cc(F)c2cnc(Nc3cc4n(n3)CC(=O)NCC43CC3)cc2c1] | 2'-((6-(5-amino-4-methylpyridin-3-yl)-8-fluoroisoquinolin-3-yl)amino)-5',6'-dihydrospiro[cyclopropane-1,4'-pyrazolo[1,5-d][1,4]diazepin]-7'(8'H)-one | 444.2 M 2.18 |
| 226a | 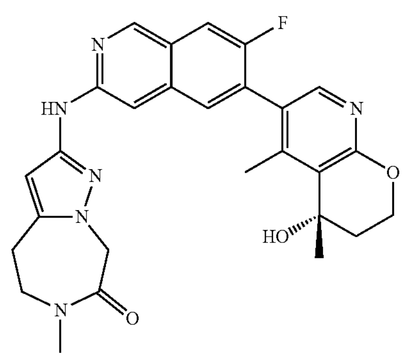 [SMILES: Cc1c(-c2cc3cc(Nc4cc5n(n4)CC(=O)N(C)CC5)ncc3cc2F)cnc2c1[C@@](C)(O)CCO2] | (S)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (absolute stereochemistry arbitrarily assigned) | 503.3 N 3.521 |
| 226b | 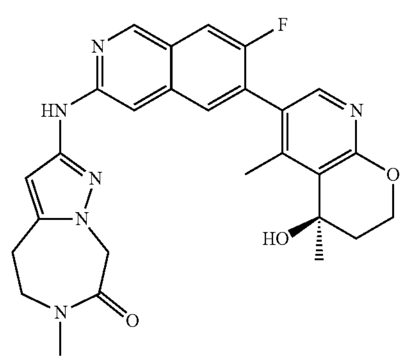 [SMILES: Cc1c(-c2cc3cc(Nc4cc5n(n4)CC(=O)N(C)CC5)ncc3cc2F)cnc2c1[C@](C)(O)CCO2] | (R)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (absolute stereochemistry arbitrarily assigned) | 503.3 N 3.522 |

TABLE A1-continued

| Cpd. No. | Structure | Name | LCMS m/z Method RT (min) |
|---|---|---|---|
| 227 | 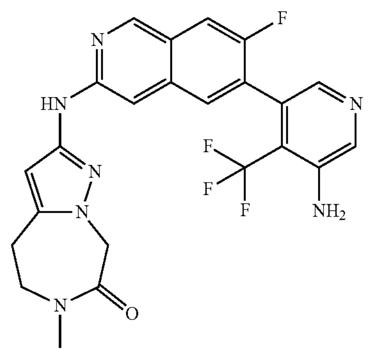 [SMILES: CN1CCc2cc(Nc3cc4cc(-c5cncc(N)c5C(F)(F)F)c(F)cc4cn3)nn2CC1=O] | 2-((6-(5-amino-4-(trifluoromethyl)pyridin-3-yl)-7-fluoroisoquinolin-3-yl)amino)-6-methyl-5,6-dihydro-4H-pyrazolo[1,5-d][1,4]diazepin-7(8H)-one | 486.2 K 1.276 |
| 228a | 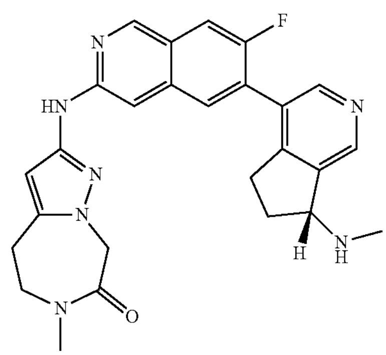 [SMILES: CN[C@@H]1CCc2c(-c3cc4cc(Nc5cc6n(n5)CC(=O)N(C)CC6)ncc4cc3F)cncc21] | (R)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one (absolute stereochemistry arbitrarily assigned) | 472.2 K 0.975 |
| 228b | 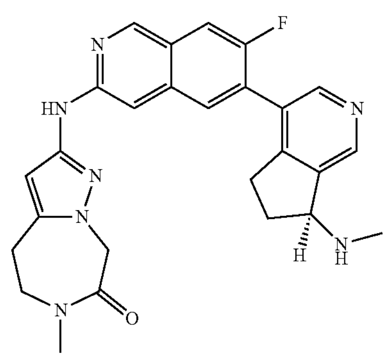 [SMILES: CN[C@H]1CCc2c(-c3cc4cc(Nc5cc6n(n5)CC(=O)N(C)CC6)ncc4cc3F)cncc21] | (S)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one (absolute stereochemistry arbitrarily assigned) | 472.2 K 0.974 |
| 229a | 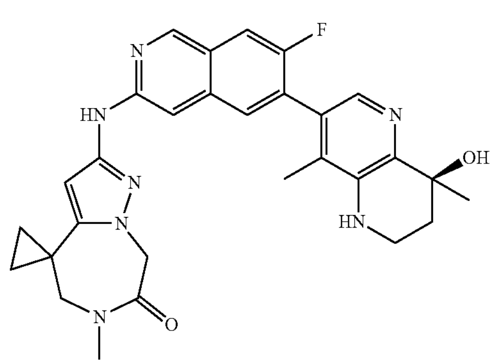 [SMILES: Cc1c(-c2cc3cc(Nc4cc5n(n4)CC(=O)N(C)CC54CC4)ncc3cc2F)cnc2c1NCC[C@]2(C)O] | (S)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 528.2 M 2.471 |

TABLE A1-continued

| Cpd. No. | Structure | Name | LCMS m/z Method RT (min) |
|---|---|---|---|
| 229b | 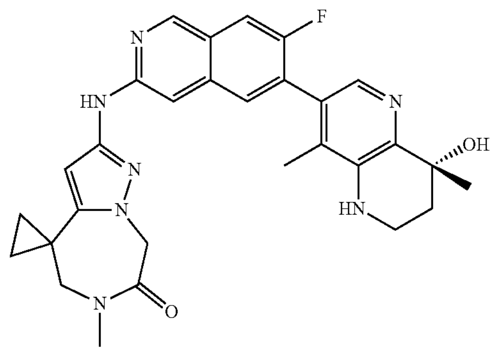 [SMILES: Cc1c(-c2cc3cc(Nc4cc5n(n4)CC(=O)N(C)CC54CC4)ncc3cc2F)cnc2c1NCC[C@@]2(C)O] | (R)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 528.3 L 0.808 |
| 230 | 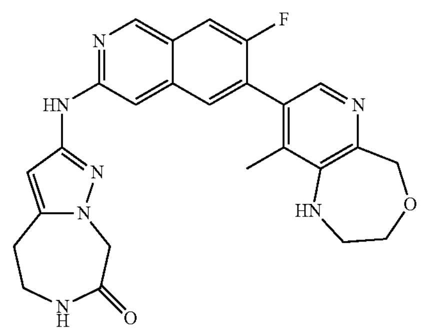 [SMILES: Cc1c(-c2cc3cc(Nc4cc5n(n4)CC(=O)NCC5)ncc3cc2F)cnc2c1NCCOC2] | 2-((7-fluoro-6-(9-methyl-1,2,3,5-tetrahydropyrido[3,2-e][1,4]oxazepin-8-yl)isoquinolin-3-yl)amino)-5,6-dihydro-4H-pyrazolo[1,5-d][1,4]diazepin-7(8H)-one | 474.2 K 1.801 |
| 231a | 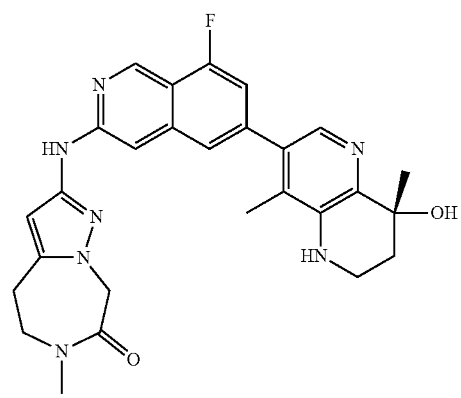 [SMILES: Cc1c(-c2cc(F)c3cnc(Nc4cc5n(n4)CC(=O)N(C)CC5)cc3c2)cnc2c1NCC[C@@]2(C)O] | (R)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 502.2 M 2.395 |
| 231b | 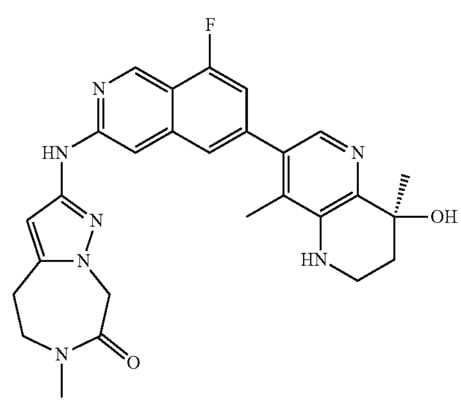 [SMILES: Cc1c(-c2cc(F)c3cnc(Nc4cc5n(n4)CC(=O)N(C)CC5)cc3c2)cnc2c1NCC[C@]2(C)O] | (S)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 502.2 M 2.394 |

TABLE A1-continued

| Cpd. No. | Structure | Name | LCMS m/z Method RT (min) |
|---|---|---|---|
| 232 | 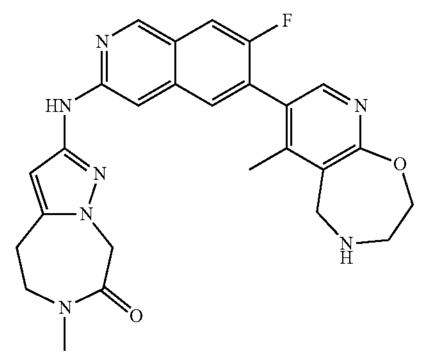 [SMILES: Cc1c(-c2cc3cc(Nc4cc5n(n4)CC(=O)N(C)CC5)ncc3cc2F)cnc2c1CNCCO2] | 2-((7-fluoro-6-(6-methyl-2,3,4,5-tetrahydropyrido[3,2-f][1,4]oxazepin-7-yl)isoquinolin-3-yl)amino)-6-methyl-5,6-dihydro-4H-pyrazolo[1,5-d][1,4]diazepin-7(8H)-one | 488.2 K 1.008 |
| 233 | 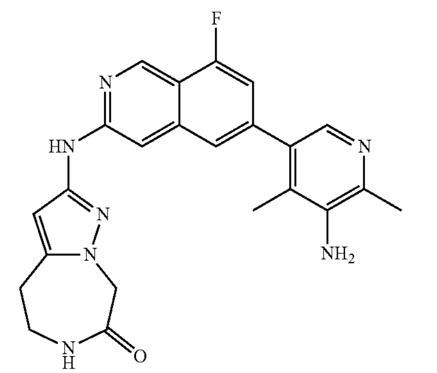 [SMILES: Cc1ncc(-c2cc(F)c3cnc(Nc4cc5n(n4)CC(=O)NCC5)cc3c2)c(C)c1N] | 2-((6-(5-amino-4,6-dimethylpyridin-3-yl)-8-fluoroisoquinolin-3-yl)amino)-5,6-dihydro-4H-pyrazolo[1,5-d][1,4]diazepin-7(8H)-one | 432.2 M 2.074 |
| 234a | 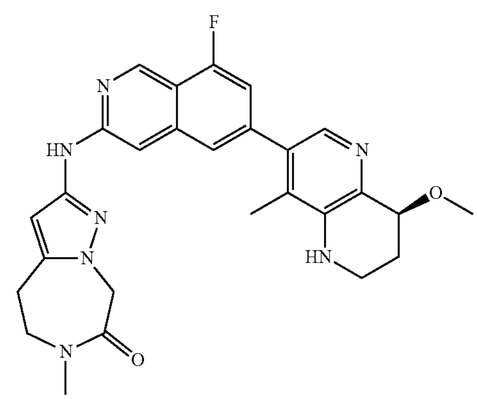 [SMILES: CO[C@H]1CCNc2c1ncc(-c1cc(F)c3cnc(Nc4cc5n(n4)CC(=O)N(C)CC5)cc3c1)c2C] | (S)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 502.2 K 1.181 |
| 234b | 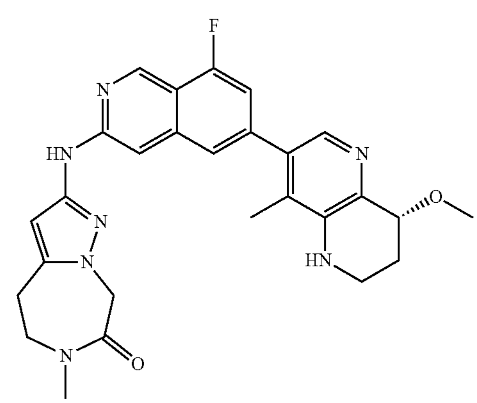 [SMILES: CO[C@@H]1CCNc2c1ncc(-c1cc(F)c3cnc(Nc4cc5n(n4)CC(=O)N(C)CC5)cc3c1)c2C] | (R)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 502.3 K 1.184 |

TABLE A1-continued

| Cpd. No. | Structure | Name | LCMS m/z Method RT (min) |
|---|---|---|---|
| 235a | 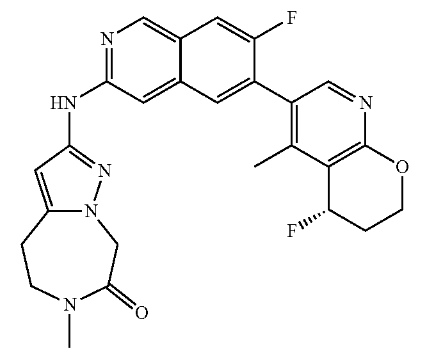 [SMILES: Cc1c(-c2cc3cc(Nc4cc5n(n4)CC(=O)N(C)CC5)ncc3cc2F)cnc2c1[C@@H](F)CCO2] | (S)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (absolute stereochemistry arbitrarily assigned) | 491.2 N 4.180 |
| 235b | 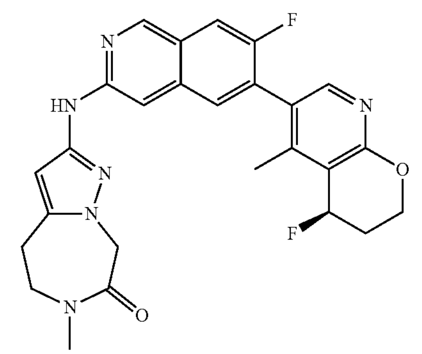 [SMILES: Cc1c(-c2cc3cc(Nc4cc5n(n4)CC(=O)N(C)CC5)ncc3cc2F)cnc2c1[C@H](F)CCO2] | (R)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one (absolute stereochemistry arbitrarily assigned) | 491.2 N 4.181 |
| 236a | 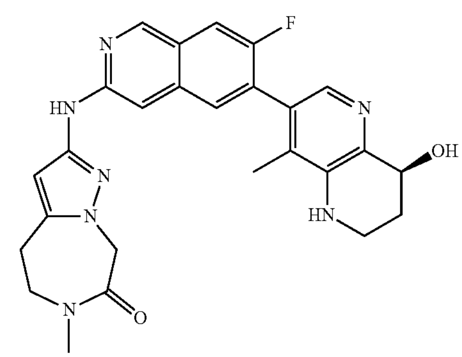 [SMILES: Cc1c(-c2cc3cc(Nc4cc5n(n4)CC(=O)N(C)CC5)ncc3cc2F)cnc2c1NCC[C@@H]2O] | (S)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 488.2 K 1.056 |
| 236b | 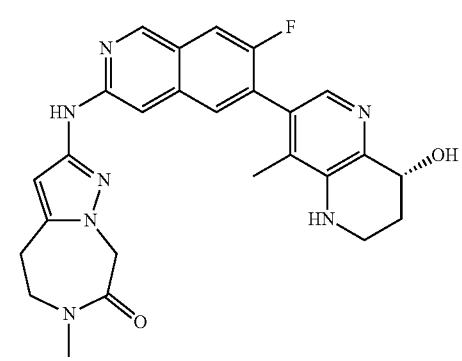 | (R)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 488.2 K 1.056 |

TABLE A1-continued

| Cpd. No. | Structure | Name | LCMS m/z Method RT (min) |
|---|---|---|---|
| 237a | 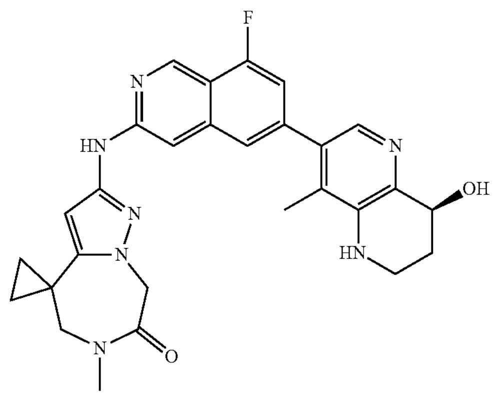 [SMILES: Cc1c(-c2cc(F)c3cnc(Nc4cc5n(n4)CC(=O)N(C)CC54CC4)cc3c2)cnc2c1NCC[C@@H]2O] | (S)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 514.2 M 2.379 |
| 237b | 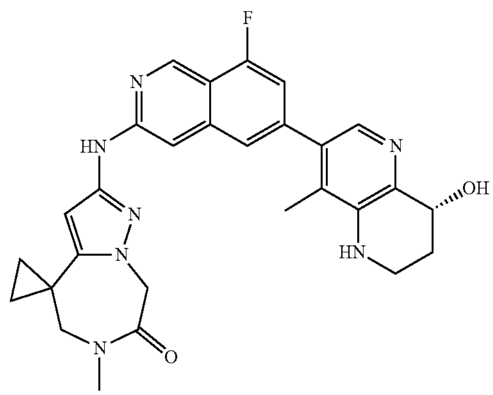 [SMILES: Cc1c(-c2cc(F)c3cnc(Nc4cc5n(n4)CC(=O)N(C)CC54CC4)cc3c2)cnc2c1NCC[C@H]2O] | (R)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (absolute stereochemistry arbitrarily assigned) | 514.2 M 2.379 |
| 238 | 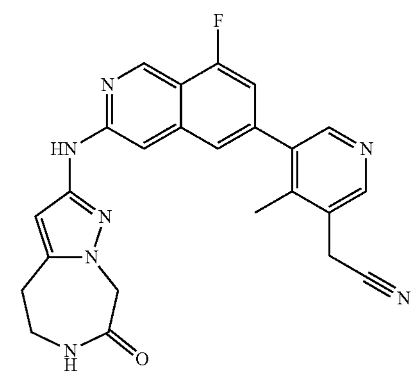 [SMILES: Cc1c(CC#N)cncc1-c1cc(F)c2cnc(Nc3cc4n(n3)CC(=O)NCC4)cc2c1] | 2-(5-(8-fluoro-3-((7-oxo-5,6,7,8-tetrahydro-4H-pyrazolo[1,5-d][1,4]diazepin-2-yl)amino)isoquinolin-6-yl)-4-methylpyridin-3-yl)acetonitrile | 442.1 K 1.920 |
| 239 | 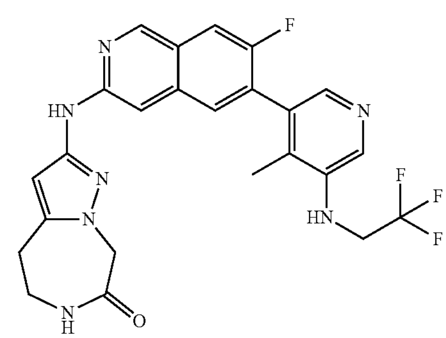 [SMILES: Cc1c(NCC(F)(F)F)cncc1-c1cc2cc(Nc3cc4n(n3)CC(=O)NCC4)ncc2cc1F] | 2-((7-fluoro-6-(4-methyl-5-((2,2,2-trifluoroethyl)amino)pyridin-3-yl)isoquinolin-3-yl)amino)-5,6-dihydro-4H-pyrazolo[1,5-d][1,4]diazepin-7(8H)-one | 500.2 M 2.215 |

TABLE A1-continued

| Cpd. No. | Structure | Name | LCMS m/z Method RT (min) |
|---|---|---|---|
| 240 | 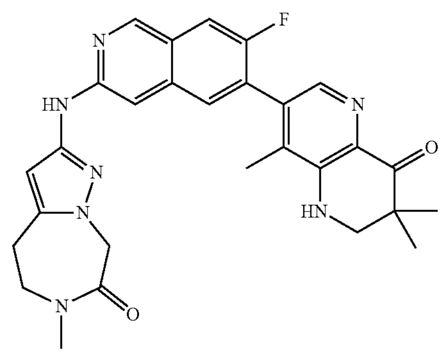 [SMILES: Cc1c(-c2cc3cc(Nc4cc5n(n4)CC(=O)N(C)CC5)ncc3cc2F)cnc2c1NCC(C)(C)C2=O] | 2-((7-fluoro-6-(4,7,7-trimethyl-8-oxo-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one | 514.2 K 1.966 |
| 241a | 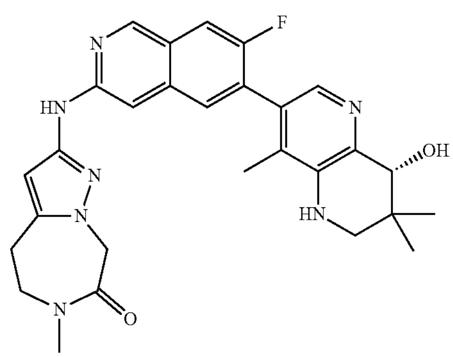 | (R)-2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 516.2 K 2.057 |
| 241b | 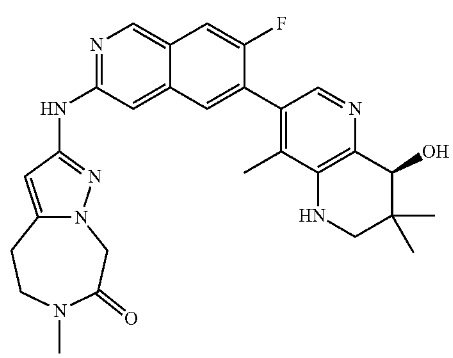 [SMILES: Cc1c(-c2cc3cc(Nc4cc5n(n4)CC(=O)N(C)CC5)ncc3cc2F)cnc2c1NCC(C)(C)[C@@H]2O] | (S)-2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one (absolute stereochemistry arbitrarily assigned) | 516.3 K 2.055 |
| 242a | 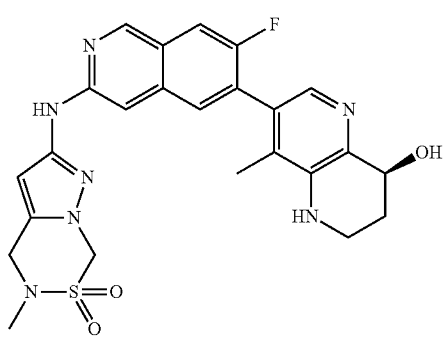 [SMILES: Cc1c(-c2cc3cc(Nc4cc5n(n4)CS(=O)(=O)N(C)C5)ncc3cc2F)cnc2c1NCC[C@@H]2O] | (S)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide(absolute stereochemistry arbitrarily assigned) | 510.1 K 2.029 |

TABLE A1-continued

| Cpd. No. | Structure | Name | LCMS m/z Method RT (min) |
|---|---|---|---|
| 242b | 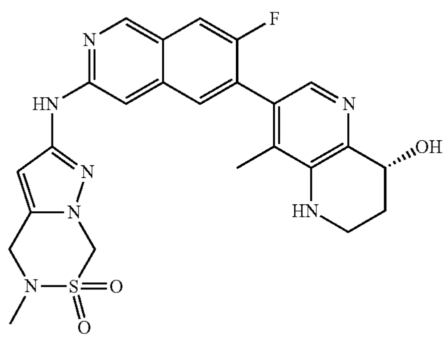 [SMILES: Cc1c(-c2cc3cc(Nc4cc5n(n4)CS(=O)(=O)N(C)C5)ncc3cc2F)cnc2c1NCC[C@H]2O] | (R)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide (absolute stereochemistry arbitrarily assigned) | 510.2 K 2.027 |
| 243a | 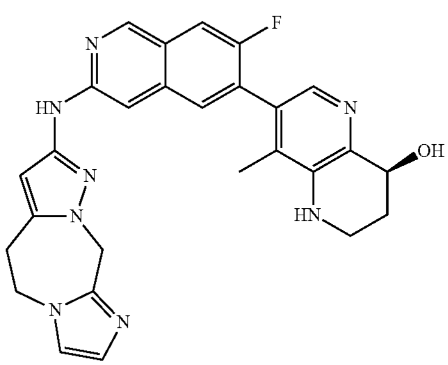 [SMILES: Cc1c(-c2cc3cc(Nc4cc5n(n4)Cc4nccn4CC5)ncc3cc2F)cnc2c1NCC[C@@H]2O] | (S)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol (absolute stereochemistry arbitrarily assigned) | 497.3 K 1.672 |
| 243b | 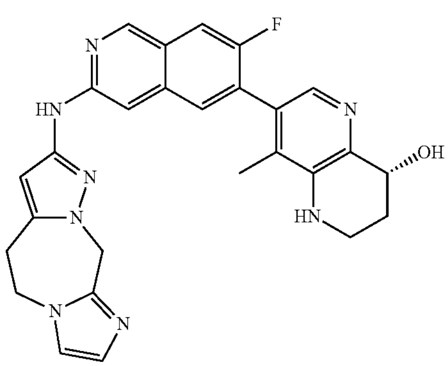 [SMILES: Cc1c(-c2cc3cc(Nc4cc5n(n4)Cc4nccn4CC5)ncc3cc2F)cnc2c1NCC[C@H]2O] | (R)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol (absolute stereochemistry arbitrarily assigned) | 497.2 K 1.361 |
| 244 | 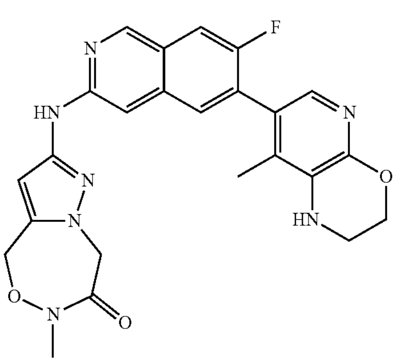 | 2-((7-fluoro-6-(8-methyl-2,3-dihydro-1H-pyrido[2,3-b][1,4]oxazin-7-yl)isoquinolin-3-yl)amino)-6-methyl-4H,6H-pyrazolo[1,5-e][1,2,5]oxadiazepin-7(8H)-one | 476.2 K 1.190 |

BIOLOGICAL EXAMPLE

Exemplary compounds of Formula (I) were tested to assess compound inhibition of HPK-1. The $K_i$ for each exemplary compound was determined

Example B1: HPK1-FL HTRF Enzymatic Assay ("HTRF")

Assay Principle:
HPK-FL enzyme phosphorylates Biotin-SLP-76 substrate in the presence of ATP at 1 mM and varying concentrations of test compound. Product is detected by FRET using Eu-anti-pSLP76 Ab and SA-XL665. Also see www.cisbio.com/HTRF for additional HTRF technology information.

Instrumentation:
Echo555 compound dispenser
Agilent Bravo
Perkin Elmer Envision

Final Assay Conditions:

| | |
|---|---|
| HPK full length, T165E S171E: | 0.125 nM |
| Biotin-SLP76: | 100 nM |
| ATP: | 1 mM (ATP Km = 20 μM) |
| Eu-anti-pSLP76: | 2 nM |
| SA-XL665: | 8.3 nM |
| Preincubation time: | 30 min |
| Kinase reaction time: | 60 min |
| Temperature: | ambient |
| Total volume: | 12 μl |
| $ATP^{app}$ Km: | 17.7 μM |

Materials:
Assay plate: White ProxiPlate 384 F (PerkinElmer cat #6008289)
Kinase: HPK full length double mutant
Substrate: Biotin-SLP76
ATP: 100 mM ATP
BSG: 2% BSG
DMSO: DMSO (Sigma cat #34869-100ML)
Reaction Buffer: $H_2O$/50 mM HEPES, pH 7.5/10 mM $MgCl_2$/2 mM TCEP/0.01% Brij-35/0.01% BSG
Detection mix:Eu-anti-pSLP76/SA-XL665 (Cisbio, #610SAXAC)

Assay Procedure Ki determination:
To a 384 well Proxiplate with 80 nL compound or DMSO spotted on was added 4 μl/well kinase mix. The mixture was preincubated for 30 minutes and then 4 μl/well substrate mix was added. The solution was incubated for 60 min and then 4 μl/well detection mix was added. The solution was incubated for another 60 min. The plates were then loaded onto a Perkin Elmer Envision and the TR-FRET signal was measured at 615 and 665 nm. A ratio of 665/620 was used to calculate the % activity at each concentration of compound.

Example B2: HPK1 Lantha Binding Assay ("Lanth")

Materials:

| Reagent | Vender-Cat# |
|---|---|
| white ProxiPlate 384 F(assay plate) | PerkinElmer-6008289 |
| 384-well Microplate(compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |
| Assay Buffer | 2 mM DTT(Sigma-43815), 0.01% BRIJ-35(Sigma-B4184), 10 mM $MgCl_2$, 50 mM HEPES(Invitrogen-15630130 ) |

Procedure:
I. Compound Dilution:
The compounds to be tested were diluted by preparing 12.5 uL/well of 5 mM compound (100×) in columns 2 and 13 and 10 ul/well of DMSO in columns 3-12, 14-23, and wells A1-H1 and I24-P24 of the compound plate using a Bravo liquid handling platform. For the reference compound, the top concentration was 1 mM. To the plate was added 10 ul 2 mM staurosporine in wells J1-P1 and A24-H24. A 11 point 5-fold compound serial dilution was performed using the Bravo liquid handling platform. From the plate were transferred 2.5 ul of the solutions from column 2 and column 13 to the 10 ul of DMSO in columns 3 and 14 & so on. The compound plate was centrifuged at 2500 rpm for 1 min. From the compound plate was transferred 80 nl of the compounds into an assay plate using the Echo liquid handler system. One compound plate makes two assay plates. Each assay plate is sealed and stored in an $N_2$ cabinet.

II. Assay Condition:
The following assay concentrations and times were used: 2 nM HPK1, 2 nM Eu-Anti-GST Ab, and 15 nM Tracer222, with 60 min incubation time.

III. HPK Lantha Binding Assay:
For the binding assay, 4 ul 2X HPK1 and Eu-anti-GST antibody were added to each well of the assay plate using a Multidrop reagent dispenser. The solutions were incubated in a 23 C incubator for 1 h. To each well of the assay plate was added 4 ul 2× Tracer-222 using a Multidrop reagent dispenser. The solutions were again incubated in a 23 C incubator for 1 h. The results of the assay were read using an Envision plate reader with the following parameters: TR_FRET, 340ex/615 and 665em; 100 usec Delay; and 200 usec integration.

IV. Analysis:
Compound Ki was analyzed using Morrison ki fit model in XL-fit
a. fit=$(1-(((((E+x)+(Ki*(1+(S/Kd))))-(((((E+x)+(Ki*(1+(S/Kd))))^2)-((4*E)*x))^0.5))/(2*E)))$
res=(y-fit)
b. Parameters:
E=enzyme concentration
S=Tracer222 concentration, Kd=Tracer222 Kd
All measurements reported using the same units (uM)
Exemplary compounds were tested in the binding assays. The Ki values determined are listed in Table B1.

TABLE B1

| Compound No. | HPK1 Ki (nM) L = Lanth; H = HTRF |
|---|---|
| 101 | 110, L |
| 102 | 68, L |
| 103 | 180, L |
| 104 | 57, L |
| 105 | 6, L |

TABLE B1-continued

| Compound No. | HPK1 Ki (nM) L = Lanth; H = HTRF |
|---|---|
| 106 | 6.6, L |
| 107 | 9, L |
| 108 | 4.4, L |
| 109a | 2.17, H |
| 109b | 1.19, H |
| 110 | 4.6, H |
| 111 | 0.01, H |
| 113 | 1.2, H |
| 114 | 75, H |
| 115 | 0.2, H |
| 116 | 0.014, H |
| 117 | 0.64, H |
| 118 | 0.065, H |
| 119 | 0.050, H |
| 120 | 0.04, H |
| 121 | 0.08, H |
| 122 | 1.0, H |
| 123 | 0.11, H |
| 124 | 63, H |
| 125 | 0.03, H |
| 126 | 0.148, H |
| 127 | 0.04, H |
| 128 | 0.01, H |
| 129 | 0.04, H |
| 130 | 0.068, H |
| 131 | 2.5, H |
| 132 | 0.02, H |
| 133 | 3.7, H |
| 134 | 3.4, H |
| 135 | 0.038, H |
| 136 | 0.028, H |
| 137 | 2.2, H |
| 138 | 0.013, H |
| 139 | 0.076, H |
| 140 | 0.086, H |
| 141a | 0.033, H |
| 141b | 0.018, H |
| 142 | 1.9, H |
| 143 | 0.013, H |
| 144 | 0.062, H |
| 145 | 0.013, H |
| 146 | 0.034, H |
| 147a | 0.014, H |
| 147b | 0.013, H |
| 148a | 0.013, H |
| 148b | 0.013, H |
| 149a | 0.043, H |
| 149b | 0.019, H |
| 150 | 0.15, H |
| 151 | 0.013, H |
| 152 | 0.028, H |
| 153a | 0.064, H |
| 153b | 0.075, H |
| 154a | 0.014, H |
| 154b | 0.032, H |
| 155 | 0.013, H |
| 156 | 0.017, H |
| 157 | 0.014, H |
| 158 | 0.023, H |
| 159 | 0.015, H |
| 160 | 0.013, H |
| 161 | 0.014, H |
| 162 | 0.43, H |
| 163 | 0.013, H |
| 164 | 0.013, H |
| 165 | 0.013, H |
| 166 | 0.12, H |
| 167a | 0.128, H |
| 167b | 0.013, H |
| 168 | 0.028, H |
| 169 | 0.39, H |
| 170 | 0.035, H |
| 171 | 1.78, H |
| 172 | 0.46, H |
| 174 | 0.026. H |
| 175 | 0.14, H |
| 176 | 0.161, H |
| 177 | 0.277, H |
| 178 | 23.7, H |
| 179 | 0.50, H |
| 180a | 0.050, H |
| 180b | 4.82, H |
| 181 | 0.026, H |
| 182 | 0.073, H |
| 183 | 0.013, H |
| 184 | 0.018, H |
| 185a | 0.169, H |
| 185b | 0.037, H |
| 186 | 0.120, H |
| 187 | 0.25, H |
| 189 | 0.48, H |
| 190 | 0.24, H |
| 191 | 2.6, H |
| 192 | 0.018, H |
| 193 | 23, H |
| 194 | 0.83, H |
| 195 | 0.26, H |
| 196 | 0.1, H |
| 197 | 4.1, H |
| 198 | 4.2, H |
| 199 | 5, H |
| 200 | 127, H |
| 201 | 0.11, H |
| 202 | 119, H |
| 203 | 97, H |
| 204 | 0.18, H |
| 205a | 0.013, H |
| 205b | 0.013, H |
| 206a | 6.7, H |
| 206b | 6.2, H |
| 207 | 22, H |
| 208 | 0.02, H |
| 209 | 1.9, H |
| 210 | 37, H |
| 211 | 19, H |
| 212 | 50, H |
| 213 | 25, H |
| 214 | 9, H |
| 215 | 364, H |
| 216 | 2.3, H |
| 217 | 64, H |
| 218 | 9, H |
| 219 | 7, H |
| 220 | 176, H |
| 221 | 97, H |
| 222 | 5.2, H |
| 223 | 0.04, H |
| 224 | 0.013, H |
| 225 | 0.013, H |
| 226a | 18, H |
| 226b | 1.9, H |
| 227 | 0.29, H |
| 228a | 8.3, H |
| 228b | 446, H |
| 229a | 0.09, H |
| 229b | 0.016, H |
| 230 | 0.793, H |
| 231a | 1.3, H |
| 231b | 0.38, H |
| 232 | 11, H |
| 233 | 0.155, H |
| 234a | 0.46, H |
| 234b | 2.1, H |
| 235a | 2.1, H |
| 235b | 0.127, H |
| 236a | 0.076, H |
| 236b | 0.062, H |
| 237a | 0.332, H |
| 237b | 0.319, H |
| 238 | 0.076, H |
| 239 | 0.062, H |
| 240 | 0.014, H |
| 241a | 0.11, H |
| 241b | 0.265, H |

TABLE B1-continued

| Compound No. | HPK1 Ki (nM) L = Lanth; H = HTRF |
|---|---|
| 242a | 0.457, H |
| 242b | 1.7, H |
| 243a | 0.013, H |
| 243b | 0.020, H |
| 244 | 0.013, H |

Example B3: Human T-cell IL2 Induction Assay

Assay Principle:

Anti-CD3 and anti-CD28 activates TCR signaling in primary human pan T cells leading to IL-2 promoter induction. Secreted IL-2 in cell culture supernatant is detected by electrochemiluminescence using a capture antibody against IL-2 and an anti-IL-2 antibody labeled with SULFO-tag.

Literature:

See www.mesoscale.com for additional electrochemiluminescence technology information.

Assay Procedure:

Incubate primary human pan T cells with varying concentrations of test compounds for 30 minutes in a humidified incubator at 37° C. and 5% $CO_2$. Transfer cells to a plate pre-coated with a fixed concentration of anti-human CD3 (determined separately for each donor lot) and add soluble anti-human CD28 (final concentration=1 µg/ml). Stimulate cells in a humidified incubator at 37° C. and 5% $CO_2$ for 4 hours. Transfer 25 µl of supernatant to a MSD single spot plate pre-coated with an anti-human IL-2 antibody. Incubate MSD plate overnight at 4° C. with gentle shaking. Wash MSD plate 4× with wash buffer. Add SULFO-tagged detection antibody at a 1:50 dilution and incubate at room temperature shaking for 2 hours. Wash MSD plate 4× with wash buffer and add 150 µl 2×MSD read buffer. Read on an MSD instrument. Normalize data to stimulated/untreated controls to calculate % activity at each concentration of compound.

Materials:
Frozen Primary Human Pan-T Cells (StemCell Technologies #70024)
anti-human CD3 (OKT3 clone) (eBioscience #16-0037-81)
anti-human CD28 (CD28.2 clone) (BD #555725)
96-well Human IL-2 tissue culture kit (MSD #K151AHB-4)

Instrumentation:
Biomek FX for liquid handling (Beckman Coulter)
MSD SECTOR S 600 (Meso Scale Discovery)

Exemplary compounds of Formula (I) were tested in the human T-cell IL-2 induction assays. The % increase measured for IL-2 in cells treated by the test compounds relative to untreated cells are provided in Table B2 for certain compounds.

TABLE B2

| Compound No. | % IL-2 increase relative to untreated cells | Assayed concentration (µM) |
|---|---|---|
| 118 | 400% | 0.31 |
| 119 | 542% | 0.10 |
| 130 | 308% | 0.10 |
| 139 | 154% | 0.31 |

TABLE B2-continued

| Compound No. | % IL-2 increase relative to untreated cells | Assayed concentration (µM) |
|---|---|---|
| 140 | 304% | 0.10 |
| 141b | 350% | 0.31 |

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.10% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A compound of Formula (I)

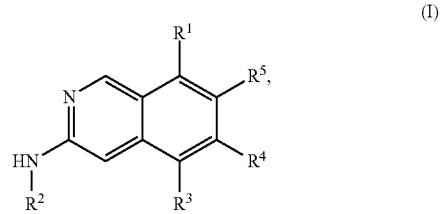

or a pharmaceutically acceptable salt thereof, wherein:
$R^1$ is hydrogen, halogen, hydroxyl, $C_{1-6}$ alkyl optionally substituted with halogen, $C_{3-4}$ cycloalkyl, or —O($C_{1-6}$ alkyl) optionally substituted with halogen;
$R^2$ is (i) or (ii):
(i) a monocyclic 5- or 6-membered heteroaryl optionally substituted with 1, 2, 3 or 4 substituents independently selected from $R^{10}$; or
(ii) a polycyclic heteroaryl having the formula (a) or (b):

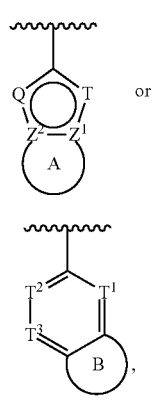

wherein the wavy line represents the attachment point to the parent structure,
Q is $CR^{20}$, $NR^{21}$, N, O or S;
T is N or $CR^{22}$;
$Z^1$ and $Z^2$ are independently N or C, provided at least one of $Z^1$ and $Z^2$ is C;
$T^1$, $T^2$ and $T^3$ are independently N or $CR^{23}$;
ring A and ring B are independently a $C_{5-8}$ cycloalkyl or a 5- to 8-membered heterocycle having at least 3 ring-forming carbon atoms and 1, 2 or 3 ring-forming heteroatoms independently selected from the group consisting of N, P, O and S; wherein the $C_{5-8}$ cycloalkyl and the 5- to 8-membered heterocycle are independently optionally substituted with 1, 2, 3, 4 or 5 substituents independently selected from $R^{10}$; and wherein two substituents of the $C_{5-8}$ cycloalkyl or the 5- to 8-membered heterocycle, where present, optionally taken together form a spiro, fused or bridged cycloalkyl optionally substituted with 1, 2, 3 or 4 substituents independently selected from $R^{10}$ or a sprio, fused or bridged heterocyclyl optionally substituted with 1, 2, 3 or 4 substituents independently selected from $R^{10}$;
$R^{20}$, $R^{21}$, $R^{22}$ and $R^{23}$ are each independently hydrogen or $R^{10}$;
$R^3$ is hydrogen or halogen; cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;
$R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl or halogen, cyano, —C(O)$R^6$, —C(O)$OR^7$, —C(O)$NR^{8a}R^{8b}$, —$OR^7$, —OC(O)$R^6$, —OC(O)$NR^{8a}R^{8b}$, —$SR^7$, —S(O)$R^9$, —S(O)$_2R^9$, —S(O)$_2NR^{8a}R^{8b}$, —P(O)$R^{9a}R^{9b}$, —$NR^{8a}R^{8b}$, —N($R^8$)C(O)$R^6$, —N($R^8$)C(O)$OR^7$, —N($R^8$)C(O)$NR^{8a}R^{8b}$, —N($R^8$)S(O)$_2R^9$, or —N($R^8$)S(O)$_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$;
$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, halogen, cyano, —C(O)$R^6$, —C(O)$OR^7$, —C(O)$NR^{8a}R^{8b}$, —$OR^7$, —OC(O)$R^6$, —OC(O)$NR^{8a}R^{8b}$, —$SR^7$, —S(O)$R^9$, —S(O)$_2R^9$, —S(O)$_2NR^{8a}R^{8b}$, —P(O)$R^{9a}R^{9b}$, —$NR^{8a}R^{8b}$, —N($R^8$)C(O)$R^6$, —N($R^8$)C(O)$OR^7$, —N($R^8$)C(O)$NR^{8a}R^{8b}$, —N($R^8$)S(O)$_2R^9$, or —N($R^8$)S(O)$_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;
each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;
each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;
each $R^8$ is independently hydrogen or $C_{1-6}$ alkyl;
each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;
or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;
each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;
each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;
or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR, —C(O)NR$^c$R$^d$, —OR, —OC(O)R$^a$, —OC(O)NR$^c$R$^d$, —SR$^b$, —S(O)R, —S(O)$_2$R$^e$, —S(O)(=NH)R$^c$, —S(O)$_2$NR$^c$R$^d$, —NR$^c$R$^d$, —N(R$^f$)C(O)R$^a$, —N(R$^f$)C(O)OR, —N(R$^f$)C(O)NR$^c$R$^d$, —N(R$^f$)S(O)$_2$R$^e$, —N(R$^f$)S(O)$_2$NR$^c$R$^d$, or —P(O)R$^g$R$^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)R$^{a1}$, —C(O)OR$^{b1}$, —C(O)NR$^{c1}$R$^{d1}$, —OR$^{b1}$, —OC(O)Rai, —OC(O)NR$^{c1}$R$^{d1}$, —SR$^{b1}$, —S(O)R$^{e1}$, —S(O)$_2$R$^{e1}$, —S(O)$_2$NR$^{c1}$R$^{d1}$, —NR$^{c1}$R$^{d1}$, —N(R$^{f1}$)C(O)R$^{a1}$, —N(R$^{f1}$)C(O)OR$^{f1}$, —N(R$^{f1}$)C(O)NR$^{c1}$R$^{d1}$, —N(R$^{f1}$)S(O)$_2$R$^{e1}$, —N(R$^{f1}$)S(O)$_2$NR$^{c1}$R$^{d1}$, or —P(O)R$^{g1}$R$^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of R are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)R$^{a2}$, —C(O)OR$^2$, —C(O)NR$^{c2}$R$^2$, —OR$^2$, —OC(O)R$^{a2}$, —OC(O)NR$^{c2}$R$^{d2}$, —S(O)$_2$R$^{e2}$, —S(O)$_2$NR$^{c2}$R$^{d2}$, —NR$^{c2}$R$^{d2}$, —N(R$^{f2}$)C(O)R$^{a2}$, —N(R$^{f2}$)C(O)OR$^{f2}$, —N(R$^{f2}$)C(O)NR$^{c2}$R$^{d2}$, —N(R$^{f2}$)S(O)$_2$R$^{e2}$, —N(R$^{f2}$)S(O)$_2$NR$^{c2}$R$^{d2}$, or —P(O)R$^{g2}$R$^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^2$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than
1H-Pyrazole-1-ethanol, 4-[3-[[2-methoxy-6-(4-morpholinyl)-3-pyridinyl]amino]-6-isoquinolinyl]-α,α-dimethyl-;
1H-Pyrazole-1-ethanol, 4-[3-[[5-(1,2-dimethyl-1H-imidazol-5-yl)-3-methoxy-2-pyridinyl]amino]-6-isoquinolinyl]-α,α-dimethyl-;
1H-Pyrazole-1-ethanol, 4-[3-[[6-(1,2-dimethyl-1H-imidazol-5-yl)-2-methoxy-3-pyridinyl]amino]-6-isoquinolinyl]-α,α-dimethyl-; and
3-Isoquinolinamine, 6-(1H-pyrazol-4-yl)-N-[4-(1-pyrrolidinylmethyl)-2-pyridinyl]-; and
salts thereof.

2. The compound of claim 1, wherein $R^1$ is hydrogen, fluoro, chloro, cyano or $C_{1-6}$ alkyl.

3. The compound of claim 1, wherein $R^3$ is hydrogen.

4. The compound of claim 1, wherein R is hydrogen, fluoro, chloro.

5. The compound of claim 1, wherein $R^4$ is —C(O)$R^6$, $C_{3-8}$ cycloalkyl, $C_{6-14}$ aryl, 5- to 14-membered heteroaryl or 3- to 14-membered heterocyclyl; wherein the $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

6. The compound of claim 1, wherein $R^4$ is $C_{6-10}$ aryl, 5- to 10-membered heteroaryl or 5- to 6-membered heterocyclyl; wherein the $C_{6-10}$ aryl, 5- to 10-membered heteroaryl and 5- to 6-membered heterocyclyl of $R^4$ are each optionally substituted with 1, 2, 3, 4 or 5 substituents independently selected from $R^{10}$.

7. The compound of claim 6, wherein $R^4$ is

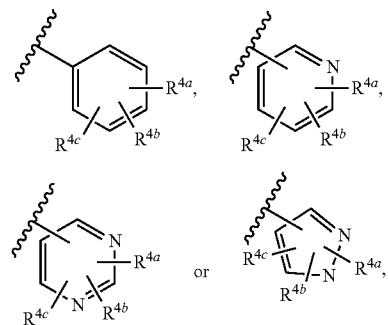

wherein the wavy line represents the attachment point to the parent structure, $R^{4a}$, $R^{4b}$ and $R^{4c}$ are each independently hydrogen or $R^{10}$, or two vicinal $R^{4(a-c)}$ are taken together with the atoms to which they are attached form a fused 5- or 6-membered heteroaryl optionally substituted with 1, 2, 3 or 4 substituents independently selected from $R^{10}$ or a fused 5- or 6-membered heterocyclyl optionally substituted with 1, 2, 3 or 4 substituents independently selected from $R^{10}$.

8. The compound of claim 6, wherein $R^4$ is selected from the group consisting of

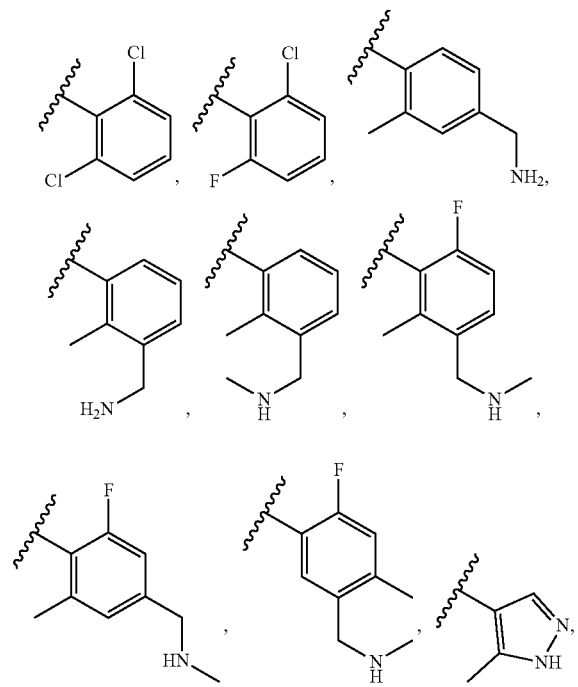

-continued
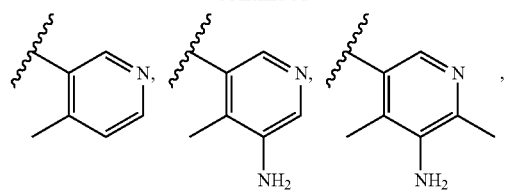
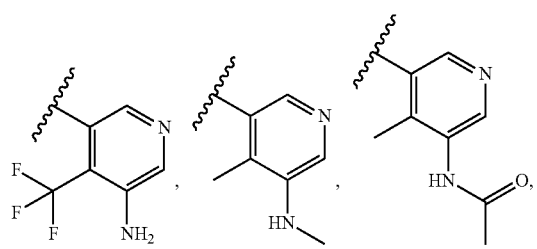
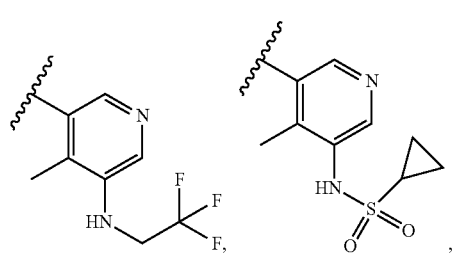
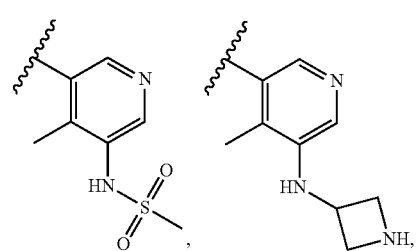
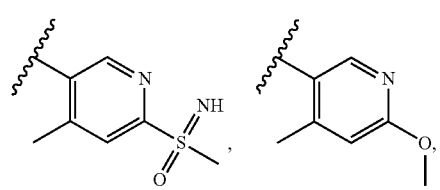
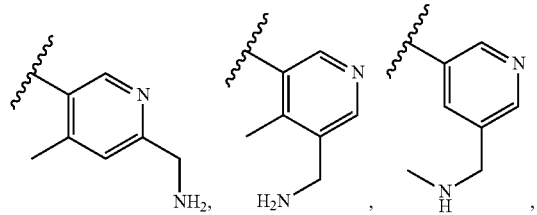
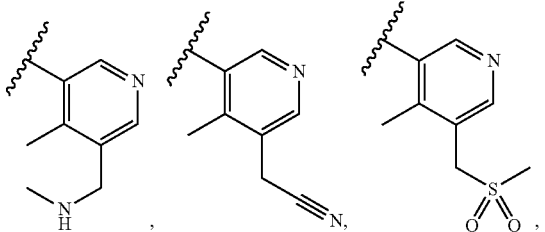
-continued
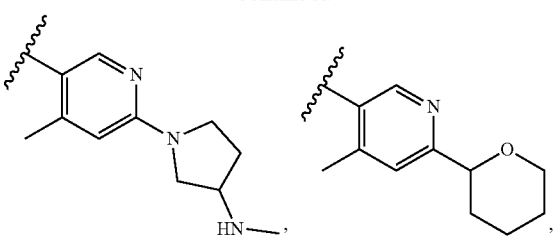
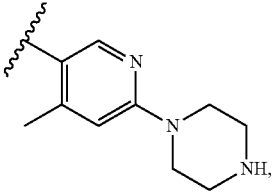
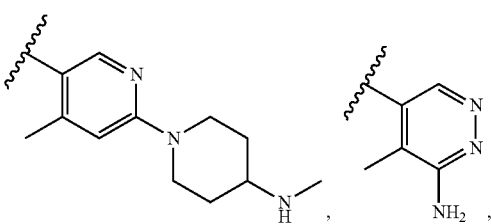
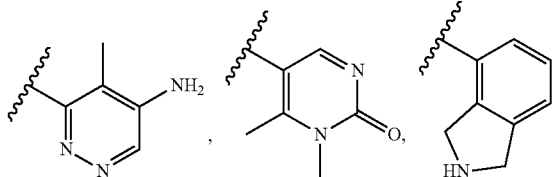
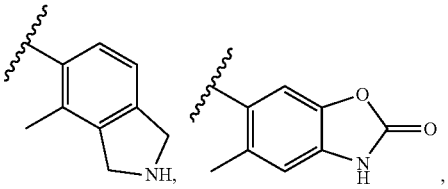
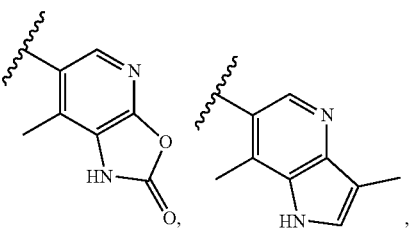
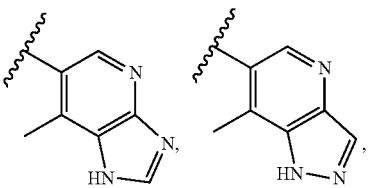
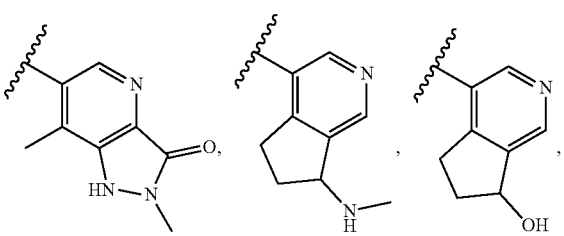

-continued
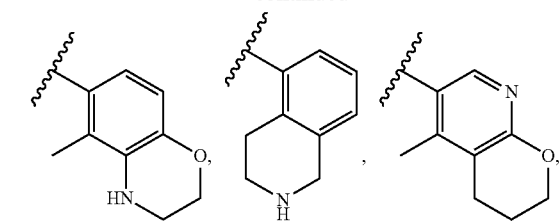
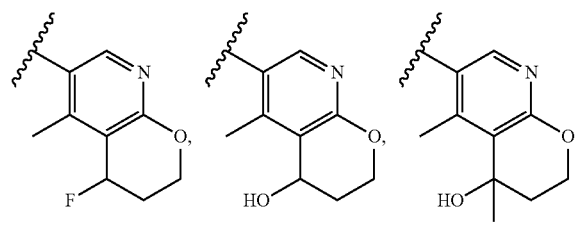
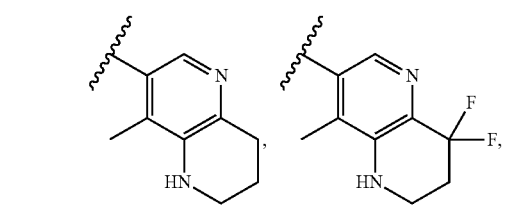
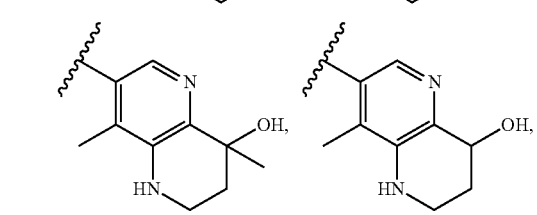
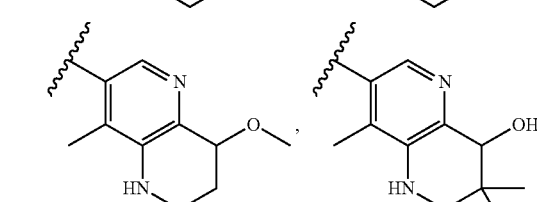
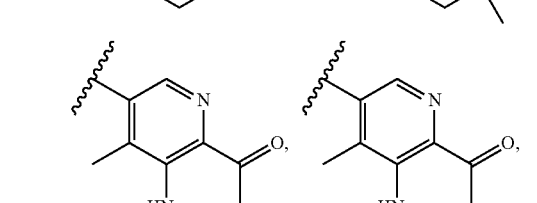
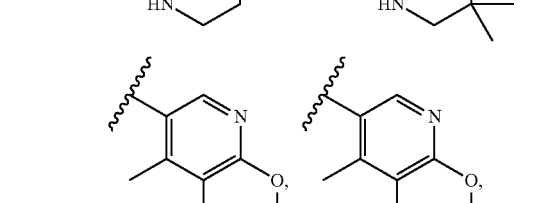
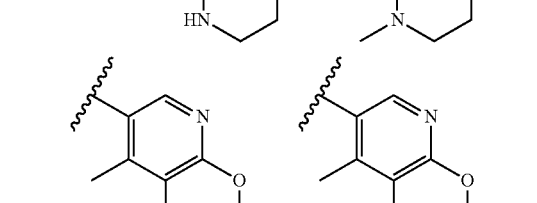
-continued
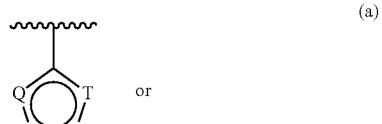
and
9. The compound of claim 1, wherein $R^2$ is a polycyclic heteroaryl having the formula (a) or (b):
(a)
(b)
10. The compound of claim 9, wherein $R^2$ is a polycyclic heteroaryl having the formula (a):

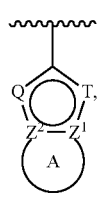

(a)

wherein Q, T, $Z^1$, $Z^2$ and ring A are as defined in claim 1.

11. The compound of claim 10, wherein $R^2$ is

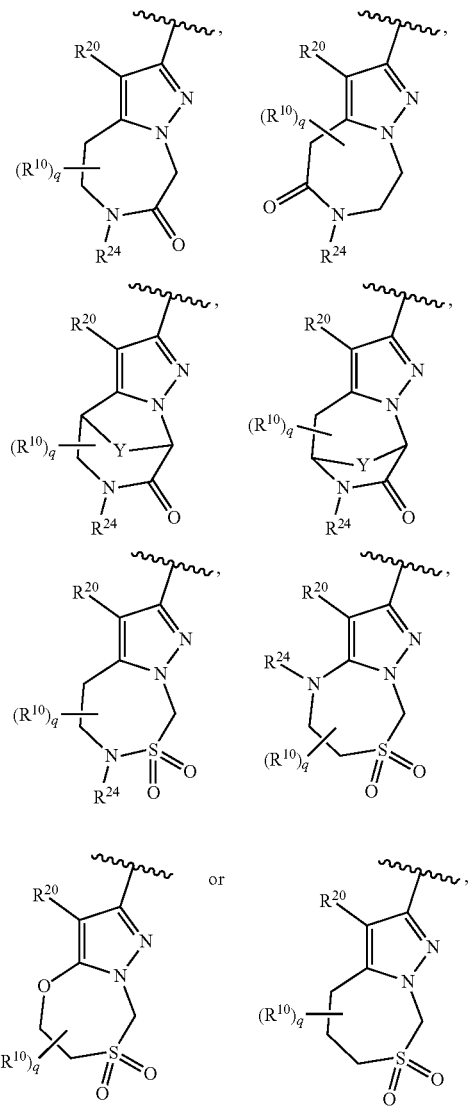

wherein q is 0, 1, 2, 3, 4, 5 or 6;
Y is $C_{1-4}$ alkylene wherein optionally one or more of the carbon atoms of the $C_{1-4}$ alkylene are replaced by a heteroatom selected from oxygen, sulfur and nitrogen, and the $C_{1-4}$ alkylene is optionally substituted with $R^{10}$;
$R^{24}$ is independently hydrogen or $R^{10}$; and
$R^{10}$ and $R^{20}$ are as defined in claim 1.

12. The compound of claim 10, wherein $R^2$ is

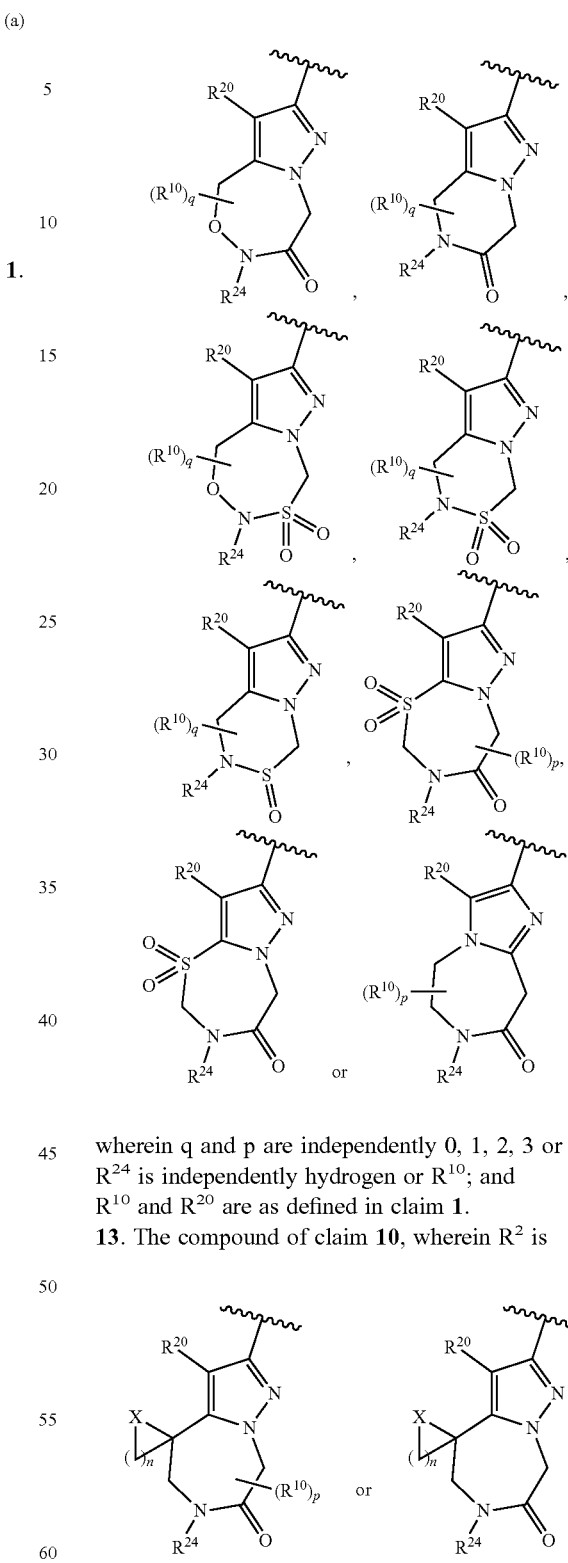

wherein q and p are independently 0, 1, 2, 3 or 4;
$R^{24}$ is independently hydrogen or $R^{10}$; and
$R^{10}$ and $R^{20}$ are as defined in claim 1.

13. The compound of claim 10, wherein $R^2$ is wherein X is $CH_2$, N, O or S;
n is 1, 2, 3 or 4;
p is 0, 1, 2, 3 or 4;
$R^{24}$ is hydrogen or $R^{10}$; and
$R^{10}$ and $R^{20}$ are as defined in claim 1.

14. The compound of claim 10, wherein $R^2$ is

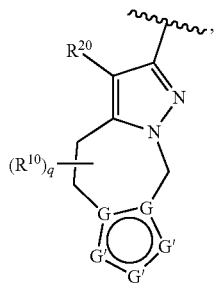

wherein q is 0, 1, 2, 3, 4, 5 or 6;

G is independently C or N;

G' is independently N, $NR^{28}$, $CR^{29}$, S or O;

$R^{28}$ and $R^{29}$ are independently hydrogen or $R^{11}$; or two vicinal groups $R^{28}$ and $R^{29}$ are taken together to form a 5- to 6-membered heterocyclyl; and $R^{10}$, $R^{11}$ and $R^{20}$ are as defined in claim 1.

15. The compound of claim 10, wherein $R^2$ is selected from the group consisting of

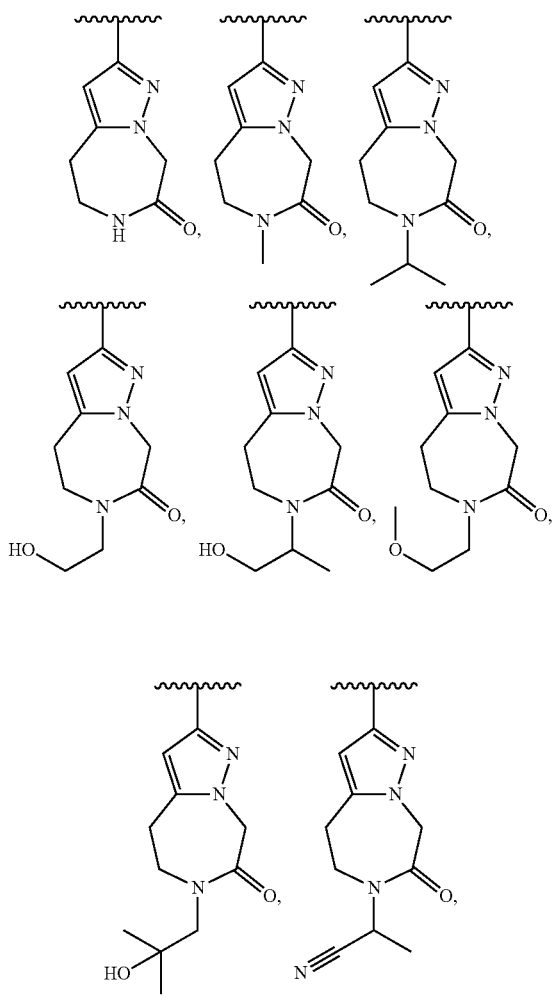

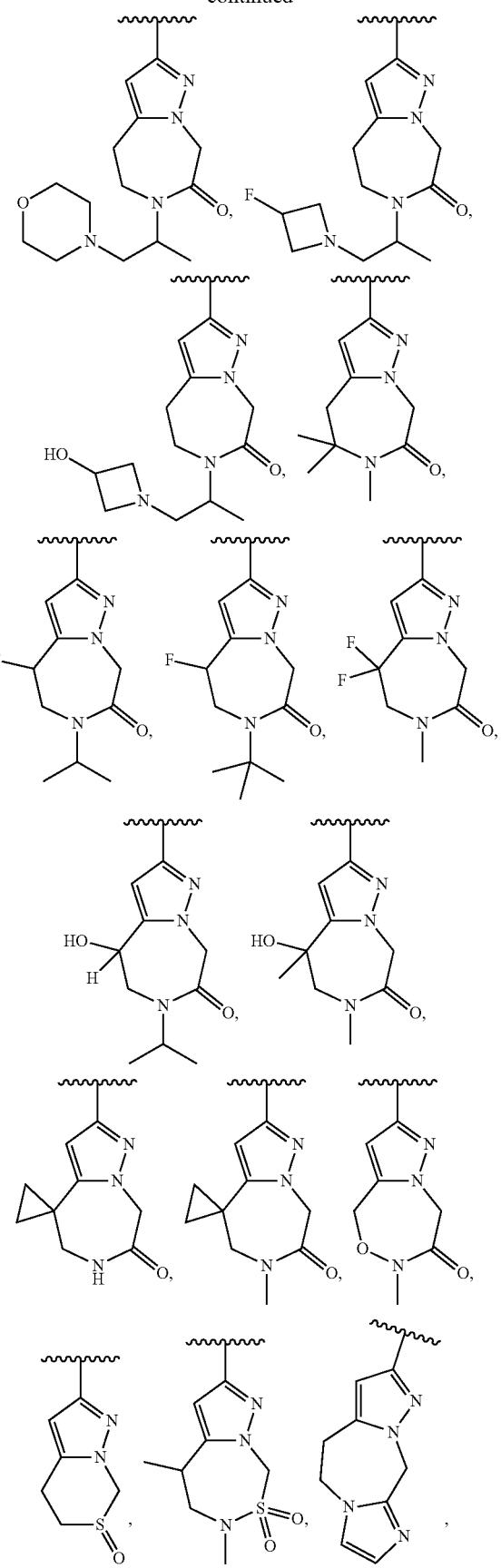

-continued

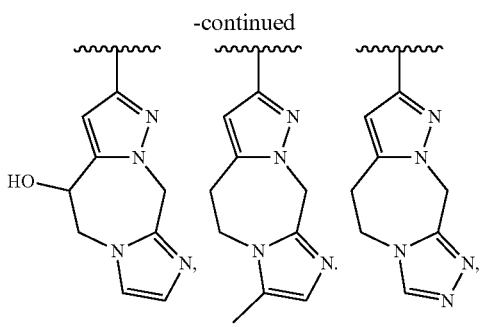

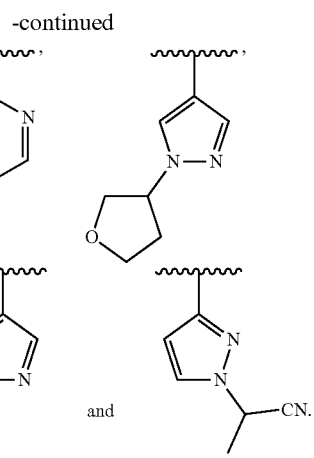

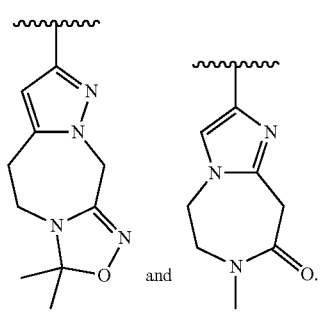

and

16. The compound of claim 1, wherein $R^2$ is a monocyclic 5- or 6-membered heteroaryl optionally substituted with 1, 2, 3 or 4 substituents independently selected from $R^{10}$.

17. The compound of claim 16, wherein $R^2$ is

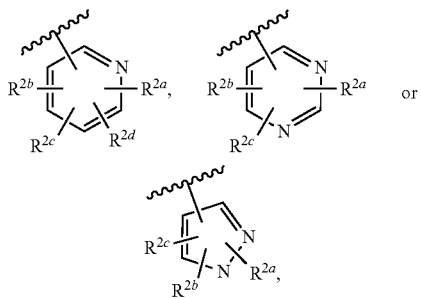

wherein the wavy line represents the attachment point to the parent structure, $R^{2a}$, $R^{2b}$, $R^{2c}$ and $R^{2d}$ are each independently hydrogen or $R^{10}$.

18. The compound of claim 16, wherein $R^2$ is selected from the group consisting of

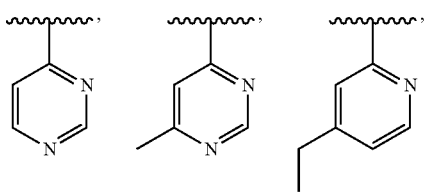

19. The compound of claim 16, wherein $R^4$ is $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, cyano, $-C(O)R^6$, $-OC(O)R^6$, $-OC(O)NR^{8a}R^{8b}$, $-SR^7$, $-S(O)R^9$, $-S(O)_2R^9$, $-S(O)_2NR^{8a}R^{8b}$, $-NR^{8a}R^{8b}$, $-N(R^8)C(O)R^6$, $-N(R)C(O)OR^7$, $-N(R^8)C(O)NR^{8a}R^{8b}$, $-N(R^8)S(O)_2R^9$, or $-N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^4$ are each optionally substituted with 1, 2, 3, 4 or 5 substituents independently selected from $R^{10}$.

20. The compound of claim 1, wherein the compound is selected from the group consisting of:
  6-(2,6-dichlorophenyl)-N-(pyrimidin-4-yl)isoquinolin-3-amine;
  6-(2,6-dichlorophenyl)-N-(1-((1-methylpyrrolidin-3-yl)methyl)-1H-pyrazol-4-yl)isoquinolin-3-amine;
  6-(2,6-dichlorophenyl)-N-(1-(tetrahydrofuran-3-yl)-1H-pyrazol-4-yl)isoquinolin-3-amine;
  6-(2-chloro-6-fluorophenyl)-N-(pyrimidin-4-yl)isoquinolin-3-amine;
  N-(4-ethylpyridin-2-yl)-6-(4-methylpyridin-3-yl)isoquinolin-3-amine;
  N-(4-(difluoromethyl)pyridin-2-yl)-6-(4-methylpyridin-3-yl)isoquinolin-3-amine;
  6-(4-methylpyridin-3-yl)-N-(6-methylpyrimidin-4-yl)isoquinolin-3-amine;
  N-(4-methylpyridin-2-yl)-6-(4-methylpyridin-3-yl)isoquinolin-3-amine;
  2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile;
  (R)-2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile;
  (S)-2-(3-((7-fluoro-6-(8-methyl-2,3-dihydro-1H-pyrido[2,3-b][1,4]oxazin-7-yl)isoquinolin-3-yl)amino)-1H-pyrazol-1-yl)propanenitrile;
  2-[[8-Chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one;
  2-[[6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one;
  2-[[6-(5-amino-4-methyl-3-pyridyl)-8-chloro-7-fluoro-3-isoquinolyl]amino]-6-methyl-spiro[5,8-dihydropyrazolo[1,5-d][1,4]diazepine-4,1'-cyclopropane]-7-one;

2-((6-(5-amino-4-methylpyridin-3-yl)-7-fluoroisoquino-lin-3-yl)amino)-4,6-dimethyl-5,6-dihydro-4H,8H-pyrazolo[5,1-e][1,2,6]thiadiazepine 7,7-dioxide;

2-((8-chloro-7-fluoro-6-(4-methylpyridin-3-yl)isoquino-lin-3-yl)amino)-7-methyl-6,7-dihydro-5H-imidazo[1,2-d][1,4]diazepin-8(9H)-one;

2-((8-chloro-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one;

2-((7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one;

2-((6-(5-amino-4-methylpyridin-3-yl)-8-chloroisoquino-lin-3-yl)amino)-6-isopropyl-5,6-dihydro-4H-pyrazolo[1,5-d][1,4]diazepin-7(8H)-one;

2-((6-(5-amino-4-methylpyridin-3-yl)-7,8-difluoroiso-quinolin-3-yl)amino)-6-isopropyl-5,6-dihydro-4H-pyrazolo[1,5-d][1,4]diazepin-7(8H)-one;

2-((6-(5-amino-4-methylpyridin-3-yl)-7-fluoroisoquino-lin-3-yl)amino)-6-isopropyl-5,6-dihydro-4H-pyrazolo[1,5-d][1,4]diazepin-7(8H)-one;

2-((6-(5-amino-4-methylpyridin-3-yl)-7-fluoroisoquino-lin-3-yl)amino)-5,5,6-trimethyl-5,6-dihydro-4H-pyra-zolo[1,5-d][1,4]diazepin-7(8H)-one;

2-((6-(5-amino-4-methylpyridin-3-yl)-7-fluoro-8-methyl-isoquinolin-3-yl)amino)-6-isopropyl-5,6-dihydro-4H-pyrazolo[1,5-d][1,4]diazepin-7(8H)-one;

6-isopropyl-2-[[6-(4-methyl-3-pyridyl)-3-isoquinolyl]amino]-5,8-dihydro-4H-pyrazolo[1,5-d][1,4]diazepin-7-one;

7-[7-fluoro-3-[(6-isopropyl-7-oxo-5,8-dihydro-4H-pyra-zolo[1,5-d][1,4]diazepin-2-yl)amino]-6-isoquinolyl]-8-methyl-1H-pyrido[2,3-b][1,4]oxazin-2-one;

2-((7-fluoro-6-(4-methylpiperazine-1-carbonyl)isoquino-lin-3-yl)amino)-6-isopropyl-5,6-dihydro-4H-pyrazolo[1,5-d][1,4]diazepin-7(8H)-one;

N-(6-(5-amino-4-methylpyridin-3-yl)-7-fluoroisoquino-lin-3-yl)-5,6-dihydro-11H-imidazo[1,2-a]pyrazolo[1,5-d][1,4]diazepin-8-amine;

2-((6-(5-amino-4,6-dimethylpyridin-3-yl)-7-fluoroiso-quinolin-3-yl)amino)-6-isopropyl-5,6-dihydro-4H-pyrazolo[1,5-d][1,4]diazepin-7(8H)-one;

2-[[6-(5-amino-4-methyl-3-pyridyl)-7-fluoro-3-isoqui-nolyl]amino]-4,4-difluoro-6-methyl-5,8-dihydropyra-zolo[1,5-d][1,4]diazepin-7-one;

tert-butyl 7-[7-fluoro-3-[(6-methyl-7-oxo-5,8-dihydro-4H-pyrazolo[1,5-d][1,4]diazepin-2-yl)amino]-6-iso-quinolyl]-8-methyl-2,3-dihydropyrido[2,3-b][1,4]oxazine-1-carboxylate;

2-[[6-(5-amino-4-methyl-3-pyridyl)-3-isoquinolyl]amino]-6-isopropyl-5,8-dihydro-4H-pyrazolo[1,5-d][1,4]diazepin-7-one;

6-(5-amino-4-methyl-3-pyridyl)-3-[(6-isopropyl-7-oxo-5,8-dihydro-4H-pyrazolo[1,5-d][1,4]diazepin-2-yl)amino]-8-methyl-isoquinoline-7-carbonitrile;

2-[[7-fluoro-6-(4-methyl-3-pyridyl)-3-isoquinolyl]amino]-6-isopropyl-5,8-dihydro-4H-pyrazolo[1,5-d][1,4]diazepin-7-one;

2-[[7-fluoro-6-(8-methyl-2,3-dihydro-1H-pyrido[2,3-b][1,4]oxazin-7-yl)-3-isoquinolyl]amino]-6-(2-mor-pholinoethyl)-5,8-dihydro-4H-pyrazolo[1,5-d][1,4]di-azepin-7-one;

2-((6-(5-amino-4,6-dimethylpyridin-3-yl)-7-fluoro-8-hy-droxyisoquinolin-3-yl)amino)-6-isopropyl-5,6-di-hydro-4H-pyrazolo[1,5-d][1,4]diazepin-7(8H)-one;

N-(7-fluoro-6-(4-methylpyridin-3-yl)isoquinolin-3-yl)-3,3-dimethyl-5,6-dihydro-3H,11H-[1,2,4]oxadiazolo[4,3-a]pyrazolo[1,5-d][1,4]diazepin-8-amine;

2-((7,8-difluoro-6-(8-methyl-2,3-dihydro-1H-pyrido[2,3-b][1,4]oxazin-7-yl)isoquinolin-3-yl)amino)-6-isopro-pyl-5,6-dihydro-4H-pyrazolo[1,5-d][1,4]diazepin-7(8H)-one;

2-((6-(5-amino-4-methylpyridin-3-yl)-7-fluoroisoquino-lin-3-yl)amino)-6-(2-morpholinoethyl)-5,6-dihydro-4H-pyrazolo [1,5-d][1,4]diazepin-7(8H)-one;

2-((7-fluoro-6-(6-methoxy-4-methylpyridin-3-yl)isoqui-nolin-3-yl)amino)-6-methyl-5,6-dihydro-4H-pyrazolo[1,5-d][1,4]diazepin-7(8H)-one;

2-((7,8-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one;

N-(6-(5-amino-4-methylpyridin-3-yl)-7-fluoroisoquino-lin-3-yl)-5,6-dihydro-11H-pyrazolo[1,5-d][1,2,4]tri-azolo[4,3-a][1,4]diazepin-8-amine;

2-((6-(5-amino-4-methylpyridin-3-yl)-7-chloroisoquino-lin-3-yl)amino)-6-isopropyl-5,6-dihydro-4H-pyrazolo[1,5-d][1,4]diazepin-7(8H)-one;

2-((7-fluoro-6-(8-methyl-2,3-dihydro-1H-pyrido[2,3-b][1,4]oxazin-7-yl)isoquinolin-3-yl)amino)-4-hydroxy-6-isopropyl-5,6-dihydro-4H-pyrazolo[1,5-d][1,4]diaz-epin-7(8H)-one;

(R)-2-((7-fluoro-6-(8-methyl-2,3-dihydro-1H-pyrido[2,3-b][1,4]oxazin-7-yl)isoquinolin-3-yl)amino)-4-hy-droxy-6-isopropyl-5,6-dihydro-4H-pyrazolo[1,5-d][1,4]diazepin-7(8H)-one;

(S)-2-((7-fluoro-6-(8-methyl-2,3-dihydro-1H-pyrido[2,3-b][1,4]oxazin-7-yl)isoquinolin-3-yl)amino)-4-hy-droxy-6-isopropyl-5,6-dihydro-4H-pyrazolo[1,5-d][1,4]diazepin-7(8H)-one;

6-(7-fluoro-3-((6-isopropyl-7-oxo-5,6,7,8-tetrahydro-4H-pyrazolo[1,5-d][1,4]diazepin-2-yl)amino)isoquinolin-6-yl)-7-methyloxazolo[5,4-b]pyridin-2(1H)-one;

N-(7-fluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine;

2-((6-(5-amino-4-methylpyridin-3-yl)-7-fluoroisoquino-lin-3-yl)amino)-5,6-dihydro-4H-pyrazolo[1,5-d][1,4]diazepin-7(8H)-one;

2-((7-fluoro-6-(8-methyl-2,3-dihydro-1H-pyrido[2,3-b][1,4]oxazin-7-yl)isoquinolin-3-yl)amino)-6-(2-hy-droxyethyl)-5,6-dihydro-4H-pyrazolo[1,5-d][1,4]diaz-epin-7(8H)-one;

2-((5-fluoro-6-(8-methyl-2,3-dihydro-1H-pyrido[2,3-b][1,4]oxazin-7-yl)isoquinolin-3-yl)amino)-6-(2-hy-droxyethyl)-5,6-dihydro-4H-pyrazolo[1,5-d][1,4]diaz-epin-7(8H)-one;

2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diazepin-6-yl)propanenitrile;

(S)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diaz-epin-6-yl)propanenitrile;

(R)-2-(2-((7-fluoro-6-(8-methyl-2,3-dihydro-1H-pyrido[2,3-b][1,4]oxazin-7-yl)isoquinolin-3-yl)amino)-7-oxo-4,5,7,8-tetrahydro-6H-pyrazolo[1,5-d][1,4]diaz-epin-6-yl)propanenitrile;

2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one;

(S)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one;

(R)-2-((7-fluoro-6-(8-methyl-2,3-dihydro-1H-pyrido[2,3-b][1,4]oxazin-7-yl)isoquinolin-3-yl)amino)-6-(1-hydroxypropan-2-yl)-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one;

(S)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one;

(R)-2-((6-(5-amino-4-methylpyridin-3-yl)-7-fluoroisoquinolin-3-yl)amino)-6-(1-hydroxypropan-2-yl)-5,6-dihydro-4H-pyrazolo[1,5-d][1,4]diazepin-7(8H)-one;

2-((6-(5-amino-4,6-dimethylpyridin-3-yl)-7-fluoroisoquinolin-3-yl)amino)-4-fluoro-6-isopropyl-5,6-dihydro-4H-pyrazolo[1,5-d][1,4]diazepin-7(8H)-one;

N-(7-fluoro-6-(8-methyl-2,3-dihydro-1H-pyrido[2,3-b][1,4]oxazin-7-yl)isoquinolin-3-yl)-5,6-dihydro-11H-pyrazolo[1,5-d][1,2,4]triazolo[4,3-a][1,4]diazepin-8-amine;

2-((6-(5-amino-4-methylpyridin-3-yl)-5-chloroisoquinolin-3-yl)amino)-6-isopropyl-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one;

(R)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one;

(S)-2-((6-(5-amino-4-methylpyridin-3-yl)-7-fluoroisoquinolin-3-yl)amino)-4-hydroxy-6-isopropyl-5,6-dihydro-4H-pyrazolo[1,5-d][1,4]diazepin-7(8H)-one;

2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile;

(S)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile;

(R)-2-(2-((6-(5-amino-4-methylpyridin-3-yl)-7-fluoroisoquinolin-3-yl)amino)-7-oxo-4,5,7,8-tetrahydro-6H-pyrazolo[1,5-d][1,4]diazepin-6-yl)propanenitrile;

2-((7-fluoro-6-(8-methyl-2,3-dihydro-1H-pyrido[2,3-b][1,4]oxazin-7-yl)isoquinolin-3-yl)amino)-6-(2-methoxyethyl)-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one;

N-(6-(5-amino-4-methylpyridin-3-yl)-7,8-difluoroisoquinolin-3-yl)-5,6-dihydro-11H-imidazo[1,2-a]pyrazolo[1,5-d][1,4]diazepin-8-amine;

2-((6-(5-amino-4-methylpyridin-3-yl)-7-fluoroisoquinolin-3-yl)amino)-6-(2-hydroxy-2-methylpropyl)-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-6-(2-hydroxyethyl)-5,6-dihydro-4H-pyrazolo[1,5-d][1,4]diazepin-7(8H)-one;

2-((7-fluoro-6-(8-methyl-2,3-dihydro-1H-pyrido[2,3-b][1,4]oxazin-7-yl)isoquinolin-3-yl)amino)-5,6-dihydro-4H-pyrazolo[1,5-d][1,4]diazepin-7(8H)-one;

N-(7,8-difluoro-6-(8-methyl-2,3-dihydro-1H-pyrido[2,3-b][1,4]oxazin-7-yl)isoquinolin-3-yl)-5,6-dihydro-11H-imidazo[1,2-a]pyrazolo[1,5-d][1,4]diazepin-8-amine;

2-((6-(1,8-dimethyl-2,3-dihydro-1H-pyrido[2,3-b][1,4]oxazin-7-yl)-7-fluoroisoquinolin-3-yl)amino)-6-methyl-5,6-dihydro-4H-pyrazolo[1,5-d][1,4]diazepin-7(8H)-one;

N-(6-(5-amino-4-methylpyridin-3-yl)-7-fluoroisoquinolin-3-yl)-3-methyl-5,6-dihydro-11H-imidazo[1,2-a]pyrazolo[1,5-d][1,4]diazepin-8-amine;

2-((6-(5-amino-4-methylpyridin-3-yl)-7-fluoroisoquinolin-3-yl)amino)-6-(2-(3-fluoroazetidin-1-yl)ethyl)-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-6-(2-(3-hydroxyazetidin-1-yl)ethyl)-5,6-dihydro-4H-pyrazolo[1,5-d][1,4]diazepin-7(8H)-one;

N-(6-(5-amino-4-methylpyridin-3-yl)-7-fluoroisoquinolin-3-yl)-3,3-dimethyl-5,6-dihydro-3H,11H-[1,2,4]oxadiazolo[4,3-a]pyrazolo[1,5-d][1,4]diazepin-8-amine;

2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one;

(R)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one;

(S)-2-((6-(5-amino-4-methylpyridin-3-yl)-7-fluoroisoquinolin-3-yl)amino)-6-(tert-butyl)-4-fluoro-5,6-dihydro-4H-pyrazolo[1,5-d][1,4]diazepin-7(8H)-one;

N-(6-(5-amino-4-methylpyridin-3-yl)-8-fluoroisoquinolin-3-yl)-5,6-dihydro-11H-imidazo[1,2-a]pyrazolo[1,5-d][1,4]diazepin-8-amine;

6-(5-amino-4-methylpyridin-3-yl)-3-((6-isopropyl-7-oxo-5,6,7,8-tetrahydro-4H-pyrazolo[1,5-d][1,4]diazepin-2-yl)amino)isoquinoline-7-carbonitrile;

8-((6-(5-amino-4-methylpyridin-3-yl)-7,8-difluoroisoquinolin-3-yl)amino)-5,6-dihydro-11H-imidazo[1,2-a]pyrazolo[1,5-d][1,4]diazepin-6-ol;

N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)acetamide;

N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)methanesulfonamide;

6-(7-fluoro-3-((6-methyl-7-oxo-5,6,7,8-tetrahydro-4H-pyrazolo[1,5-d][1,4]diazepin-2-yl)amino)isoquinolin-6-yl)-5-methylbenzo[d]oxazol-2(3H)-one;

2-((5-fluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one;

2-((7-fluoro-6-(7-methyl-1H-imidazo[4,5-b]pyridin-6-yl)isoquinolin-3-yl)amino)-6-methyl-5,6-dihydro-4H-pyrazolo[1,5-d][1,4]diazepin-7(8H)-one;

2-((6-(3,3-difluoro-8-methyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one;

2-((7-fluoro-6-(8-methyl-4,4-dioxido-2,3-dihydro-1H-pyrido[2,3-b][1,4]thiazin-7-yl)isoquinolin-3-yl)amino)-6-methyl-5,6-dihydro-4H-pyrazolo[1,5-d][1,4]diazepin-7(8H)-one;

2-((7-fluoro-6-(4-methyl-6-(S-methylsulfonimidoyl)pyridin-3-yl)isoquinolin-3-yl)amino)-6-methyl-5,6-dihydro-4H-pyrazolo[1,5-d][1,4]diazepin-7(8H)-one;

N-(6-(5-(azetidin-3-ylamino)-4-methylpyridin-3-yl)-7-fluoroisoquinolin-3-yl)-5,6-dihydro-11H-imidazo[1,2-a]pyrazolo[1,5-d][1,4]diazepin-8-amine;

2-((7-fluoro-6-(4-hydroxy-5-methyl-3,4-dihydro-2H-pyrano [2,3-b]pyridin-6-yl)isoquinolin-3-yl)amino)-6-methyl-5,6-dihydro-4H-pyrazolo[1,5-d][1,4]diazepin-7(8H)-one;

(S)-2-((7-fluoro-6-(4-hydroxy-5-methyl-3,4-dihydro-2H-pyran[2,3-b]pyridin-6-yl)isoquinolin-3-yl)amino)-6-methyl-5,6-dihydro-4H-pyrazolo[1,5-d][1,4]diazepin-7(8H)-one;

(R)-2-((7-fluoro-6-(4-hydroxy-5-methyl-3,4-dihydro-2H-pyran[2,3-b]pyridin-6-yl)isoquinolin-3-yl)amino)-6-methyl-5,6-dihydro-4H-pyrazolo[1,5-d][1,4]diazepin-7(8H)-one;

2-((7-fluoro-6-(4-methyl-5-(methylamino)pyridin-3-yl)isoquinolin-3-yl)amino)-5,6-dihydro-4H-pyrazolo[1,5-d][1,4]diazepin-7(8H)-one;

2-((6-(2,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one;

N-(7-fluoro-6-(9-methyl-1,2,3,4-tetrahydropyrido[2,3-b][1,4]oxazepin-8-yl)isoquinolin-3-yl)-5,6-dihydro-11H-imidazo[1,2-a]pyrazolo[1,5-d][1,4]diazepin-8-amine;

2-((6-(3,8-dimethyl-2,3-dihydro-1H-pyrido[2,3-b][1,4]oxazin-7-yl)-7-fluoroisoquinolin-3-yl)amino)-5,6-dihydro-4H-pyrazolo[1,5-d][1,4]diazepin-7(8H)-one;

2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one;

(R)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one;

(S)-2-((6-(5-amino-4-methylpyridin-3-yl)-7-fluoroisoquinolin-3-yl)amino)-4-hydroxy-4,6-dimethyl-5,6-dihydro-4H-pyrazolo[1,5-d][1,4]diazepin-7(8H)-one;

2-((7-fluoro-6-(7-methyl-1H-pyrazolo[4,3-b]pyridin-6-yl)isoquinolin-3-yl)amino)-6-methyl-5,6-dihydro-4H-pyrazolo[1,5-d][1,4]diazepin-7(8H)-one;

7-(7-fluoro-3-((6-methyl-7-oxo-5,6,7,8-tetrahydro-4H-pyrazolo[1,5-d][1,4]diazepin-2-yl)amino)isoquinolin-6-yl)-3,8-dimethyl-2,3-dihydropyrido[3,2-d]pyrimidin-4(1H)-one;

(5-(3-((5,6-dihydro-1H-imidazo[1,2-a]pyrazolo[1,5-d][1,4]diazepin-8-yl)amino)-7-fluoroisoquinolin-6-yl)-4-methylpyridin-2-yl)(imino)(methyl)-16-sulfanone;

7-(3-((5,6-dihydro-11H-imidazo[1,2-a]pyrazolo[1,5-d][1,4]diazepin-8-yl)amino)-7-fluoroisoquinolin-6-yl)-8-methyl-2,3-dihydro-1H-pyrido[2,3-b][1,4]thiazine 4-oxide;

2-((7-fluoro-6-(5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

(+/−)-2-((6-(5-amino-4-methylpyridin-3-yl)-7-fluoroisoquinolin-3-yl)amino)-4,5-dihydro-7H-pyrazolo[1,5-c][1,3]thiazine 6-oxide;

2-((7-fluoro-6-(4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one;

2-((7-fluoro-6-(8-methyl-2,2-dioxido-1H,3H-pyrido[3,2-e][1,3,4]oxathiazin-7-yl)isoquinolin-3-yl)amino)-6-methyl-5,6-dihydro-4H-pyrazolo[1,5-d][1,4]diazepin-7(8H)-one;

2-((6-(6-amino-5-methylpyridazin-4-yl)-7-fluoroisoquinolin-3-yl)amino)-6-methyl-5,6-dihydro-4H-pyrazolo[1,5-d][1,4]diazepin-7(8H)-one;

2-((6-(3,7-dimethyl-1H-pyrrolo[3,2-b]pyridin-6-yl)-7-fluoroisoquinolin-3-yl)amino)-6-methyl-5,6-dihydro-4H-pyrazolo[1,5-d][1,4]diazepin-7(8H)-one;

2-((7-fluoro-6-(4-methyl-8-oxo-5,6,7,8-tetrahydro-1,5-naphthyridin-3-yl)isoquinolin-3-yl)amino)-5,6-dihydro-4H-pyrazolo[1,5-d][1,4]diazepin-7(8H)-one;

N-(5-(7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)cyclopropanesulfonamide;

2-((7-fluoro-6-(4-methyl-6-(piperazin-1-yl)pyridin-3-yl)isoquinolin-3-yl)amino)-6-methyl-5,6-dihydro-4H-pyrazolo[1,5-d][1,4]diazepin-7(8H)-one;

2-((7-fluoro-6-(4-methyl-6-(4-(methylamino)piperidin-1-yl)pyridin-3-yl)isoquinolin-3-yl)amino)-6-methyl-5,6-dihydro-4H-pyrazolo[1,5-d][1,4]diazepin-7(8H)-one;

2-((7'-fluoro-1,2,3,4-tetrahydro-[5,6'-biisoquinolin]-3'-yl)amino)-6-methyl-5,6-dihydro-4H-pyrazolo[1,5-d][1,4]diazepin-7(8H)-one;

2-((7-fluoro-6-(8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one;

2-((7-fluoro-6-((8R)-8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one;

2-((7-fluoro-6-((8S)-8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one;

2-((7-fluoro-8-hydroxy-6-(5-methyl-1H-pyrazol-4-yl)isoquinolin-3-yl)amino)-6-methyl-5,6-dihydro-4H-pyrazolo[1,5-d][1,4]diazepin-7(8H)-one;

2-((6-(1,6-dimethyl-2-oxo-1,2-dihydropyrimidin-5-yl)-7-fluoroisoquinolin-3-yl)amino)-6-methyl-5,6-dihydro-4H-pyrazolo[1,5-d][1,4]diazepin-7(8H)-one;

2-((7-fluoro-6-(4-methyl-5-((methylsulfonyl)methyl)pyridin-3-yl)isoquinolin-3-yl)amino)-6-methyl-5,6-dihydro-4H-pyrazolo[1,5-d][1,4]diazepin-7(8H)-one;

2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(R)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(S)-2'-((7-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one;

(R)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one;

(S)-2-((7-fluoro-6-(4-methyl-6-(3-(methylamino)pyrrolidin-1-yl)pyridin-3-yl)isoquinolin-3-yl)amino)-6-methyl-5,6-dihydro-4H-pyrazolo[1,5-d][1,4]diazepin-7(8H)-one;

2-((6-(3-(aminomethyl)-2-methylphenyl)-7-fluoroisoquinolin-3-yl)amino)-6-methyl-5,6-dihydro-4H-pyrazolo[1,5-d][1,4]diazepin-7(8H)-one;

2-((6-(8,8-difluoro-4-methyl-5,6,7,8-tetrahydro-1,5-naphthyridin-3-yl)-7-fluoroisoquinolin-3-yl)amino)-6-methyl-5,6-dihydro-4H-pyrazolo[1,5-d][1,4]diazepin-7(8H)-one;

2-((6-(2,7-dimethyl-3-oxo-2,3-dihydro-1H-pyrazolo[4,3-b]pyridin-6-yl)-7-fluoroisoquinolin-3-yl)amino)-6-methyl-5,6-dihydro-4H-pyrazolo[1,5-d][1,4]diazepin-7(8H)-one;

2-((7-fluoro-6-(4-methyl-5-((methylamino)methyl)pyridin-3-yl)isoquinolin-3-yl)amino)-6-methyl-5,6-dihydro-4H-pyrazolo[1,5-d][1,4]diazepin-7(8H)-one;

2-((6-(5-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one;

2-((6-(6-(aminomethyl)-4-methylpyridin-3-yl)-7-fluoroisoquinolin-3-yl)amino)-6-methyl-5,6-dihydro-4H-pyrazolo[1,5-d][1,4]diazepin-7(8H)-one;

2-((6-(4-(aminomethyl)-2-methylphenyl)-7-fluoroisoquinolin-3-yl)amino)-6-methyl-5,6-dihydro-4H-pyrazolo[1,5-d][1,4]diazepin-7(8H)-one;

(+/−)-2-((7-fluoro-6-(7-hydroxy-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one;

2-((7-fluoro-6-(isoindolin-4-yl)isoquinolin-3-yl)amino)-6-methyl-5,6-dihydro-4H-pyrazolo[1,5-d][1,4]diazepin-7(8H)-one;

2-((6-(5-amino-4-methylpyridazin-3-yl)-7-fluoroisoquinolin-3-yl)amino)-6-methyl-5,6-dihydro-4H-pyrazolo[1,5-d][1,4]diazepin-7(8H)-one;

2-((7-fluoro-6-(2-methyl-3-((methylamino)methyl)phenyl)isoquinolin-3-yl)amino)-6-methyl-5,6-dihydro-4H-pyrazolo[1,5-d][1,4]diazepin-7(8H)-one;

(+/−)-2-((7-fluoro-6-(4-methyl-6-(tetrahydro-2H-pyran-2-yl)pyridin-3-yl)isoquinolin-3-yl)amino)-6-methyl-5,6-dihydro-4H-pyrazolo[1,5-d][1,4]diazepin-7(8H)-one;

2-((6-(6-fluoro-2-methyl-3-((methylamino)methyl)phenyl)isoquinolin-3-yl)amino)-6-methyl-5,6-dihydro-4H-pyrazolo[1,5-d][1,4]diazepin-7(8H)-one;

2-((6-(2-fluoro-4-methyl-5-((methylamino)methyl)phenyl)isoquinolin-3-yl)amino)-6-methyl-5,6-dihydro-4H-pyrazolo[1,5-d][1,4]diazepin-7(8H)-one;

2-((7-fluoro-6-(4-methylisoindolin-5-yl)isoquinolin-3-yl)amino)-6-methyl-5,6-dihydro-4H-pyrazolo[1,5-d][1,4]diazepin-7(8H)-one;

2-((6-(2-fluoro-6-methyl-4-((methylamino)methyl)phenyl)isoquinolin-3-yl)amino)-6-methyl-5,6-dihydro-4H-pyrazolo[1,5-d][1,4]diazepin-7(8H)-one;

2-((5,7-difluoro-6-(8-methyl-2,3-dihydro-1H-pyrido[2,3-b][1,4]oxazin-7-yl)isoquinolin-3-yl)amino)-6-methyl-5,6-dihydro-4H-pyrazolo[1,5-d][1,4]diazepin-7(8H)-one;

2'-((6-(5-amino-4-methylpyridin-3-yl)-7-fluoroisoquinolin-3-yl)amino)-5',6'-dihydrospiro[cyclopropane-1,4'-pyrazolo[1,5-d][1,4]diazepin]-7'(8'H)-one;

2'-((6-(5-amino-4-methylpyridin-3-yl)-8-fluoroisoquinolin-3-yl)amino)-5',6'-dihydrospiro[cyclopropane-1,4'-pyrazolo[1,5-d][1,4]diazepin]-7'(8'H)-one;

2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

(S)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

(R)-2-((7-fluoro-6-(4-hydroxy-4,5-dimethyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

2-((6-(5-amino-4-(trifluoromethyl)pyridin-3-yl)-7-fluoroisoquinolin-3-yl)amino)-6-methyl-5,6-dihydro-4H-pyrazolo[1,5-d][1,4]diazepin-7(8H)-one;

2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one;

(R)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one;

(S)-2-((7-fluoro-6-(7-(methylamino)-6,7-dihydro-5H-cyclopenta[c]pyridin-4-yl)isoquinolin-3-yl)amino)-6-methyl-5,6-dihydro-4H-pyrazolo[1,5-d][1,4]diazepin-7(8H)-one;

2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(S)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(R)-2'-((7-fluoro-6-(8-hydroxy-4,8-dimethyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

2-((7-fluoro-6-(9-methyl-1,2,3,5-tetrahydropyrido[3,2-e][1,4]oxazepin-8-yl)isoquinolin-3-yl)amino)-5,6-dihydro-4H-pyrazolo[1,5-d][1,4]diazepin-7(8H)-one;

2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(R)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(S)-2-((8-fluoro-6-(8-hydroxy-4,8-dimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

2-((7-fluoro-6-(6-methyl-2,3,4,5-tetrahydropyrido[3,2-f][1,4]oxazepin-7-yl)isoquinolin-3-yl)amino)-6-methyl-5,6-dihydro-4H-pyrazolo[1,5-d][1,4]diazepin-7(8H)-one;

2-((6-(5-amino-4,6-dimethylpyridin-3-yl)-8-fluoroisoquinolin-3-yl)amino)-5,6-dihydro-4H-pyrazolo[1,5-d][1,4]diazepin-7(8H)-one;

2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(S)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(R)-2-((8-fluoro-6-(8-methoxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

(S)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

(R)-2-((7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one;

2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(S)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(R)-2-((7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(S)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

(R)-2'-((8-fluoro-6-(8-hydroxy-4-methyl-5,6,7,8-tetrahydro-1,5-naphthyridin-3-yl)isoquinolin-3-yl)amino)-6'-methyl-5',6'-dihydrospiro[cyclopropane-1,4'-pyrazolo[1,5-d][1,4]diazepin]-7'(8'H)-one;

2-(5-(8-fluoro-3-((7-oxo-5,6,7,8-tetrahydro-4H-pyrazolo[1,5-d][1,4]diazepin-2-yl)amino)isoquinolin-6-yl)-4-methylpyridin-3-yl)acetonitrile;

2-((7-fluoro-6-(4-methyl-5-((2,2,2-trifluoroethyl)amino)pyridin-3-yl)isoquinolin-3-yl)amino)-5,6-dihydro-4H-pyrazolo[1,5-d][1,4]diazepin-7(8H)-one;

2-((7-fluoro-6-(4,7,7-trimethyl-8-oxo-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

(S)-2-((7-fluoro-6-(8-hydroxy-4,7,7-trimethyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one;

2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide;

(S)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide;

(R)-2-((7-fluoro-6-(8-hydroxy-4-methyl-5,6,7,8-tetrahydro-1,5-naphthyridin-3-yl)isoquinolin-3-yl)amino)-5-methyl-4,5-dihydro-7H-pyrazolo[5,1-d][1,2,5]thiadiazine 6,6-dioxide;

7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol;

(S)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol;

(R)-7-(3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol; and 2-((7-fluoro-6-(8-methyl-2,3-dihydro-1H-pyrido[2,3-b][1,4]oxazin-7-yl)isoquinolin-3-yl)amino)-6-methyl-4H,6H-pyrazolo[1,5-e][1,2,5]oxadiazepin-7(8H)-one;

or a pharmaceutically acceptable salt thereof.

21. A pharmaceutical composition comprising the compound of claim 1, or a pharmaceutically acceptable salt thereof, and a pharmaceutically acceptable excipient.

22. A method of inhibiting HPK1, said method comprising contacting HPK1 in a subject with an effective amount of the compound of claim 1, or a pharmaceutically acceptable salt thereof.

23. A method for enhancing an immune response in a subject in need thereof, wherein the method comprises administering to said subject an effective amount of the compound of claim 1, or a pharmaceutically acceptable salt thereof.

24. A method for treating a HPK1-dependent disorder, said method comprising administering to a subject in need thereof an effective amount of the compound of claim 1, or a pharmaceutically acceptable salt thereof.

25. The method of claim 24, wherein said HPK1-dependent disorder is a cancer.

* * * * *